US007294760B2

(12) United States Patent
Ruezinsky

(10) Patent No.: US 7,294,760 B2
(45) Date of Patent: Nov. 13, 2007

(54) PLANT PROMOTERS FOR USE IN EARLY SEED DEVELOPMENT

(75) Inventor: Diane M. Ruezinsky, Woodland, CA (US)

(73) Assignee: Monsanto Technology LLC, St. Louis, MO (US)

( * ) Notice: Subject to any disclaimer, the term of this patent is extended or adjusted under 35 U.S.C. 154(b) by 156 days.

(21) Appl. No.: 10/810,788

(22) Filed: Mar. 26, 2004

(65) Prior Publication Data

US 2004/0216184 A1 Oct. 28, 2004

Related U.S. Application Data

(60) Provisional application No. 60/458,828, filed on Mar. 28, 2003.

(51) Int. Cl.
*C12N 15/82* (2006.01)
*A01H 5/10* (2006.01)
*A01H 5/00* (2006.01)

(52) U.S. Cl. ...................... 800/281; 800/278; 800/295; 800/298; 435/320.1; 536/24.1

(58) Field of Classification Search ..................... None
See application file for complete search history.

(56) References Cited

U.S. PATENT DOCUMENTS 5,850,026 A * 12/1998 DeBonte et al. ............ 800/281
6,207,879 B1 * 3/2001 McElroy et al. ............ 800/278
6,426,447 B1 7/2002 Knauf et al. ................ 800/281

FOREIGN PATENT DOCUMENTS

WO WO 96/38573 5/1996

OTHER PUBLICATIONS

Kim et al., A 20 nucleotide upstream element is essential for the nopaline synthase (nos) promoter activity. (1994) Plant Molecular Biology 24:105-117, e.g., p. 108.*

Dolferus et al., Differential Interactions of Promoter Elements in Stress Responses of the *Arabidopsis* Adh gene. (1994) Plant Physiology 105:1075-1087, e.g., pp. 1080-1082.*

Johnson-Hopson et al., Genomic sequence for *Arabidopsis thaliana* BAC T25N20 from chromosome I. GenBank Accession AC005106, direct submission. Jun. 28, 2000.*

Bevan et al., "Transcriptional Control of Plant Storage Protein Genes", Phil. Trans. Royal Soc. Lond. Biol. Sci., 342:209-215 (1993).

Devic et al., "The BANYULS gene encodes a DFR-like protein and is a marker of early seed coat development", The Plant Journal, 19(4):387-398 (1999).

Satos et al., Database NCBI, Accession No. BAA97167 (2000).

Satos et al., Database NCBI, Accession No. AB18117 (2000).

Devic et al., Database NCBI, Accession No. AF092912 (1999).

Federspiel et al., Database NCBI, Accession No. AC005882 (1999).

Benfey et al. "The Cauliflower Mosaic Virus 35S promoter: Combinatorial regulation of transcription in plants," *Science*, 250:959-966, 1990.

* cited by examiner

*Primary Examiner*—Anne Kubelik
*Assistant Examiner*—Brent T Page
(74) *Attorney, Agent, or Firm*—Sonnenschein Nath & Rosenthal LLP

(57) ABSTRACT

The present invention relates to DNA molecules that encode transcription regulatory regions. Furthermore, this present invention relates to nucleotide sequences encoding transcription regulatory regions that promote early seed enhanced or seed coat enhanced transcription of contiguous nucleotide sequences.

12 Claims, 7 Drawing Sheets

PLANT PROMOTERS FOR USE IN EARLY SEED DEVELOPMENT

This application claims the benefit of U.S. Provisional Application 60/458,828 filed Mar. 28, 2003, which is incorporated herein by reference.

FIELD OF THE INVENTION

The present invention relates to the field of plant genetics. More specifically, the present invention relates to early seed development gene expression. The present invention provides promoters capable of transcribing heterologous nucleic acid sequences in seeds, and methods of modifying, producing, and using the same. The compositions comprise novel nucleotide sequences for plant promoters, more particularly the seed coat promoter from *Arabidopsis*, pBAN; and the early seed promoters from *Arabidopsis*, p26, p63, and p63tr that are useful for expression of transgenes of agronomic importance in crop plants.

BACKGROUND OF THE INVENTION

A large number of genes are known which are expressed only in developing seeds, or are expressed in developing seeds at much higher levels than in any other organ or tissue type. Much of the information about seed-specific gene expression has been derived from studies of genes encoding storage proteins (reviewed by Bevan et al., *Phil. Trans. Royal Soc. Lond. Biol. Sci*., 342:209-215 (1993)). For instance, DNA sequences that confer embryo-specific expression by the soybean conglycinin promoter in transgenic plants have been identified (Chen et al., *EMBO J*., 6:3559-3564 (1988)). Similarly, the storage protein napin is one of the major protein components of *Brassica napus* L. (oilseed rape) seeds. The 5' regulatory region from napin has been published (Kridl et al., *Seed Sci. Res*., 1:209-219 (1991)). A 152 bp fragment from the napin promoter directed strong expression of the β-glucuronidase reporter gene in mature tobacco seeds (Stalberg et al., *Transgenic Research*, 7(3):165-172 (1998)). The napin promoter has been used to control expression of genes in transgenic plants designed to produce novel fatty acids (e.g., Voelker et al., *Plant Journal*, 9:229-241 (1996)). However, because storage lipid accumulation begins substantially before the maximal level of expression of the napin or other storage protein genes is reached (Post-Beittenmiller et al., in *Control of Plant Gene Expression*. Verma, D. P. (ed.) Telford Press, pp. 157-174 (1992)), the promoters of storage protein genes may not always be preferred for controlling expression of genes related to oil accumulation in plant seeds.

Current technology permits the transformation of plants with heterologous genes. The expression of these genes is either ubiquitous if the promoter is constitutive, or is regulated in a temporal or spatial manner if the promoter is stage- or tissue-specific. Continuous expression precludes production at particular stages or in specific tissues, and can adversely affect yield due to increased energy demands associated with prolonged synthesis of the product. Tissue- or stage-specific expression permits greater control over the temporal and spatial accumulation of desired products. Thus, promoter sequences that control the expression of desired genes in a tissue-specific, stage-specific manner that can be employed in recombinant constructs for the transformation of plants, and that would facilitate greater control over the location, timing, and duration of expression of introduced genes and reduce the possibility of deleterious effects on overall plant growth, are highly desirable.

For production of transgenic plants with various desired characteristics, it would be advantageous to have a variety of promoters to provide gene expression such that a gene is transcribed efficiently in the amount necessary to produce the desired effect. The commercial development of genetically improved germplasm has also advanced to the stage of introducing multiple traits into crop plants, often referred to as a gene stacking approach. In this approach, multiple genes conferring different characteristics of interest can be introduced into a plant. It is often desired when introducing multiple genes into a plant that each gene is modulated or controlled for optimal expression, leading to a requirement for diverse regulatory elements. In light of these and other considerations, it is apparent that optimal control of gene expression and regulatory element diversity are important in plant biotechnology.

SUMMARY OF THE INVENTION

In the present invention, we provide DNA molecules that encode transcription regulatory regions useful in driving expression of selected polynucleotide molecules at specific times and in specific tissues in plant cells.

The present invention provides and describes compositions and methods for regulating expression of heterologous polynucleotide molecules in a plant. The compositions comprise novel nucleotide sequences for plant promoters, more particularly the seed coat promoter from *Arabidopsis*, pBAN; and the early seed promoters from *Arabidopsis*, p26, p63 and p63tr.

In one embodiment, the present invention provides a promoter comprising a polynucleotide sequence selected from the group of polynucleotide sequences consisting of: a polynucleotide sequence from the group of polynucleotide sequences consisting essentially of SEQ ID NO: 1 and SEQ ID NO: 4, a polynucleotide sequence substantially homologous to SEQ ID NO: 2 or any fragments or regions thereof, and a polynucleotide sequence comprising SEQ ID NO: 3.

In another embodiment, the present invention provides a plant expression construct comprising a promoter comprising a polynucleotide sequence selected from the group of polynucleotide sequences consisting of: a polynucleotide sequence from the group of polynucleotide sequences consisting essentially of SEQ ID NO: 1 and SEQ ID NO: 4, a polynucleotide sequence substantially homologous to SEQ ID NO: 2 or any fragments or regions thereof, and a polynucleotide sequence comprising SEQ ID NO: 3, wherein said promoter is operably linked to a transcribable polynucleotide molecule. In a preferred embodiment, the transcribable polynucleotide molecule is a gene of agrinomic interest. In a preferred embodiment, the transcribable polynucleotide molecule is a marker gene.

In yet another embodiment, the present invention provides a transgenic seed-producing dicotyledonous plant stably transformed with a plant expression construct comprising a promoter comprising a polynucleotide sequence selected from the group of polynucleotide sequences consisting of: a polynucleotide sequence from the group consisting essentially of SEQ ID NO: 1 and SEQ ID NO: 4, a polynucleotide sequence substantially homologous to SEQ ID NO: 2 or any fragments or regions thereof, and a polynucleotide sequence comprising SEQ ID NO: 3, wherein said promoter is operably linked to a transcribable polynucleotide molecule operably linked to a 3' transcription termination polynucleotide molecule. In a preferred embodiment, the dicotyledonous plant is selected from the group consisting of tobacco, tomato, potato, peanut, soybean, cotton, canola, rapeseed, safflower, flax, sugarbeet, *Arabidopsis, Brassica*, sunflower and alfalfa. In a more preferred embodiment, the transgenic dicotyledonous plant has seed with altered protein content. In a more preferred embodiment, the transgenic dicotyledonous plant has seed with altered oil content. In a more preferred embodiment, the transgenic dicotyledonous plant has seed with altered micronutrient content. In a more preferred embodiment, the present invention provides seed, oil, or meal of a transgenic dicotyledonous plant.

In another embodiment, the present invention provides a method of making a vegetable oil and meal, comprising the steps of incorporating into the genome of a dicotyledonous seed-producing plant a promoter of the present invention operably linked to a transcribable polynucleotide molecule conferring altered oil content, growing the dicotyledonous plant to produce seed, and extracting the oil from the seed to produce extracted oil and meal.

The foregoing and other aspects of the present invention will become more apparent from the following detailed description and accompanying drawings.

BRIEF DESCRIPTION OF THE SEQUENCE LISTING

SEQ ID NO: 1 represents a nucleic acid molecule encoding a pBAN promoter.

SEQ ID NO: 2 represents a nucleic acid molecule encoding a p26 promoter.

SEQ ID NO: 3 represents a nucleic acid molecule encoding a p63 promoter.

SEQ ID NO: 4 represents a nucleic acid molecule encoding a p63tr promoter.

SEQ ID NO: 5 represents the P1 clone: MQL5gi|3702735|dbj|AB018117.1| from chromosome 5 of *Arabidopsis thaliana.*

SEQ ID NO: 6 represents the BAC clone T13M11.

SEQ ID NO: 7 is a primer sequence for PCR amplification identified as Clone 26 GSP1.

SEQ ID NO: 8 is a primer sequence for PCR amplification identified as Clone 26 GSP2.

SEQ ID NO: 9 is a primer sequence for PCR amplification identified as BAN+1500.

SEQ ID NO: 10 is a primer sequence for PCR amplification identified as pBAN GSP1.

SEQ ID NO: 11 is a primer sequence for PCR amplification identified as BAN-Nco.

SEQ ID NO: 12 is a primer sequence for PCR amplification identified as p63-Nco.

SEQ ID NO: 13 is a primer sequence for PCR amplification identified as p63-fwd3.

SEQ ID NO: 14 is a primer sequence for PCR amplification identified as GUS 5'.

SEQ ID NO: 15 is a primer sequence for PCR amplification identified as GUS 3'.

SEQ ID NO: 16 is a primer sequence for PCR amplification identified as CP4-Dra.

SEQ ID NO: 17 is a primer sequence for PCR amplification identified as CP4-Kpn.

DETAILED DESCRIPTION OF THE INVENTION

Figure 1:
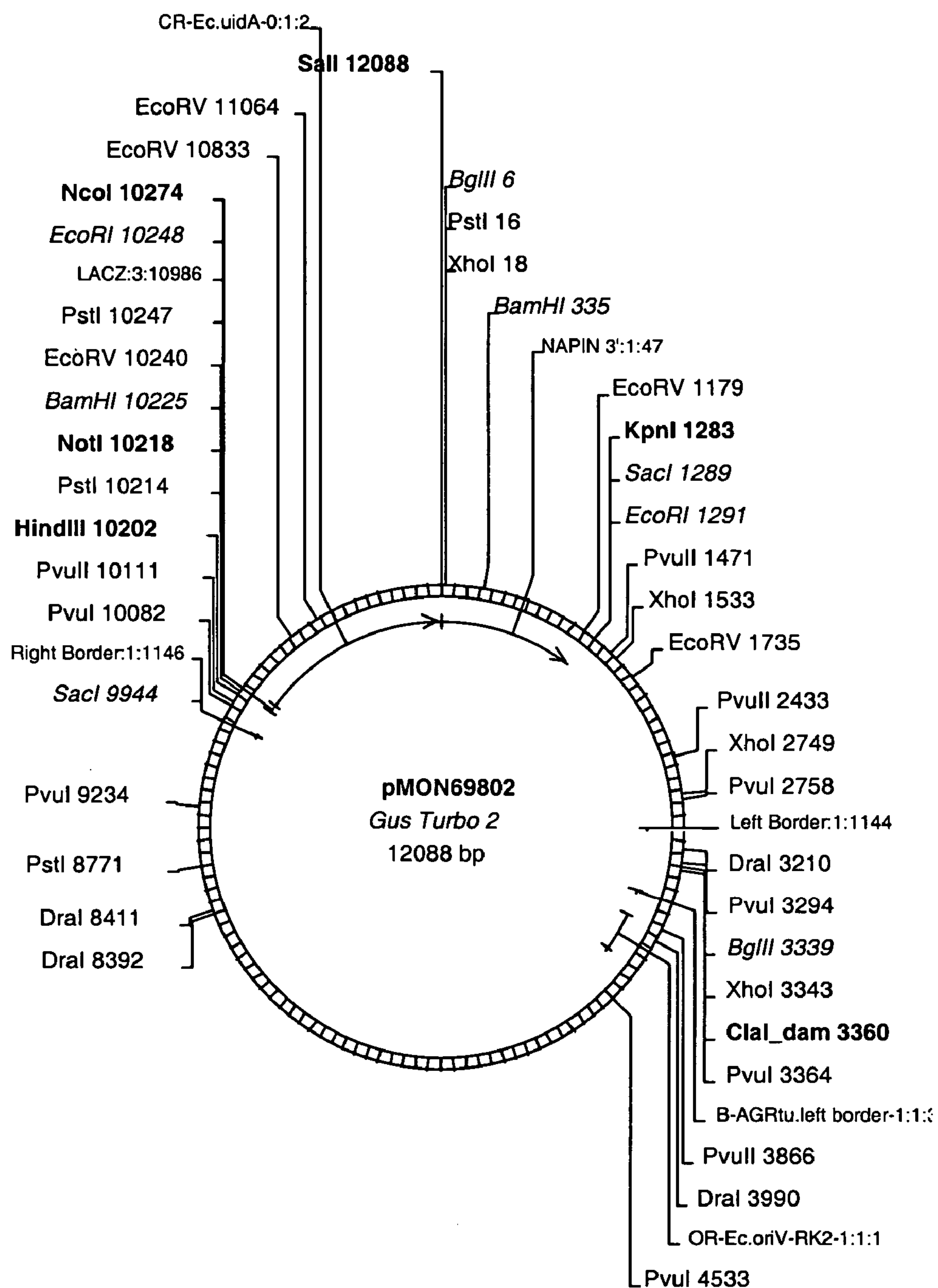
FIG. 1 is a schematic representation of pMON69802.

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the phrase "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the phrase "polynucleotide sequence" refers to the sequence of a polynucleotide molecule. The nomenclature for DNA bases as set forth at 37 CFR § 1.822 is used.

As used herein "heterologous" DNA is any polynucleotide sequence which is not naturally found next to the adjacent DNA. Heterologous DNA is often found in a DNA construct used for transformation. A p26 promoter operably linked to a reporter gene is an example of a heterologous DNA as the p26 promoter is naturally and normally associated with a p26 gene.

Promoters

As used herein, the term "promoter" refers to a polynucleotide molecule that in its native state is located upstream or 5' to a translational start codon of an open reading frame (or protein-coding region) and that is involved in recognition and binding of RNA polymerase II and other proteins (trans-acting transcription factors) to initiate transcription. A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters comprising at least one cis-element of SEQ ID NOs: 1, 2, 3, or 4 for modulating the expression of operably linked polynucleotide sequences is encompassed by the present invention.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

In one embodiment, the promoters of the present invention comprise multiple cis-elements each of which confers a different aspect to the overall control of gene expression. In a preferred embodiment, cis-elements from the polynucleotide molecules of SEQ ID NOs: 1, 2, 3, and 4 are identified using computer programs designed specifically to identify cis-element, domains, or motifs within sequences. Cis-elements may either positively or negatively regulate gene expression, depending on the conditions. The present invention therefore encompasses cis-elements of the disclosed promoters.

As used herein, the phrase "substantially homologous" refers to polynucleotide molecules that generally demonstrate a substantial percent sequence identity with the promoters provided herein. Of particular interest are polynucleotide molecules wherein the polynucleotide molecules function in plants to direct transcription and have at least about 70% sequence identity, at least about 80% sequence identity, at least about 90% sequence identity, or even greater sequence identity, such as 98% or 99% sequence identity with the polynucleotide sequences of the promoters described herein. Polynucleotide molecules that are capable of regulating transcription of operably linked transcribable polynucleotide molecules and are substantially homologous to the polynucleotide sequences of the promoters provided herein are encompassed within the scope of this present invention.

As used herein, the phrase "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20% of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules, e.g., promoters that have similar function may have homologous cis-elements. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology. The phrase "stringent conditions" is functionally defined with regard to the hybridization of a nucleic-acid probe to a target nucleic acid (i.e., to a particular nucleic-acid sequence of interest) by the specific hybridization procedure discussed in *Molecular Cloning: A Laboratory Manual*, 3rd *edition Volumes* 1, 2, *and* 3. J. F. Sambrook, D. W. Russell, and N. Irwin, Cold Spring Harbor Laboratory Press, 2000 (referred to herein as Sambrook, et al.). Accordingly, the nucleotide sequences of the present invention may be used for their ability to selectively form duplex molecules with complementary stretches of polynucleotide molecule fragments. Depending on the application envisioned one would desire to employ varying conditions of hybridization to achieve varying degrees of selectivity of probe towards target sequence. For applications requiring high selectivity, one will typically desire to employ relatively high stringent conditions to form the hybrids, e.g., one will select relatively low salt and/or high temperature conditions, such as provided by about 0.02 M to about 0.15 M NaCl at temperatures of about 50° C. to about 70° C. A high stringent condition, for example, is to wash the hybridization filter at least twice with high-stringency wash buffer (0.2×SSC, 0.1% SDS, 65° C.). Appropriate moderate stringency conditions that promote DNA hybridization, for example, 6.0× sodium chloride/sodium citrate (SSC) at about 45° C., followed by a wash of 2.0×SSC at 50° C., are known to those skilled in the art. Additionally, the salt concentration in the wash step can be selected from a low stringency of about 2.0×SSC at 50° C. to a high stringency of about 0.2×SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of polynucleotide molecules via hybridization is well known to those of skill in the art, and the teachings of U.S. Pat. Nos. 4,965,188 and 5,176,995 are exemplary of the methods of hybridization analyses.

Homology can also be determined by computer programs that align polynucleotide sequences and estimate the ability of polynucleotide molecules to form duplex molecules under certain stringency conditions. Polynucleotide molecules from different sources that share a high degree of homology are referred to as "homologues".

Methods well known to one skilled in the art may be used to identify promoters of interest having activity similar to the promoters described herein. For example, cDNA libraries may be constructed using cells or tissues of interest and screened to identify genes having an expression pattern similar to that of the promoters described herein. The cDNA sequence for the identified gene may then be used to isolate the gene's promoter for further characterization. See, for example, U.S. Pat. Nos. 6,096,950; 5,589,583; and 5,898,096; incorporated herein by reference. Alternately, transcriptional profiling or electronic northern techniques may be used to identify genes having an expression pattern similar to that of the promoters described herein. Once these genes have been identified, their promoters may be isolated for further characterization. See, for example, U.S. Pat. Nos. 6,506,565 and 6,448,387, incorporated herein by reference. The electronic northern technique refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a population of labeled cDNA probes prepared from RNA samples of different cell or tissue types, allowing direct comparative analysis of expression. This approach may be used for the isolation of regulatory sequences such as promoters associated with those genes.

In another embodiment, the promoter disclosed herein can be modified. Those skilled in the art can create promoters that have variations in the polynucleotide sequence. The polynucleotide sequences of the promoters of the present invention as shown in SEQ ID NOs: 1, 2, 3, or 4 may be modified or altered to enhance their control characteristics. One preferred method of alteration of a polynucleotide sequence is to use PCR to modify selected nucleotides or regions of sequences. These methods are well known to those of skill in the art. Sequences can be modified, for example by insertion, deletion, or replacement of template sequences in a PCR-based DNA modification approach. A "variant" is a promoter containing changes in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted, deleted, or substituted internally to a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. Many promoters contain cis-elements that activate, enhance, or define the strength and/or specificity of the promoter. For example, promoters may contain "TATA" boxes defining the site of transcription initiation and other cis-elements located upstream of the transcription initiation site that modulate transcription levels. For example, a chimeric promoter may be produced by fusing a first promoter fragment containing the activator cis-element from one promoter to a second promoter fragment containing the activator cis-element from another promoter; the resultant chimeric promoter may cause an increase in expression of an operably linked transcribable polynucleotide molecule. Promoters can be constructed such that promoter fragments or elements are operably linked, for example, by placing such a fragment upstream of a minimal promoter. The cis-elements and fragments of the present invention can be used for the construction of such chimeric promoters. Methods for construction of chimeric and variant promoters of the present invention include, but are not limited to, combining control elements of different promoters or duplicating portions or regions of a promoter (see, for example, U.S. Pat. Nos. 4,990,607; 5,110,732; and 5,097,025, all of which are herein incorporated by reference). Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

In another embodiment, a promoter comprising the polynucleotide sequence shown in SEQ ID NO: 2 includes any length of said polynucleotide sequence that is capable of regulating an operably linked transcribable polynucleotide molecule. For example, the promoters as disclosed in SEQ ID NO: 2 may be truncated or portions deleted and still be capable of regulating transcription of an operably linked polynucleotide molecule. In a related embodiment, a cis-element of the disclosed promoters may confer a particular specificity such as conferring enhanced expression of operably linked polynucleotide molecules in certain tissues and therefore is also capable of regulating transcription of operably linked polynucleotide molecules. Consequently, any fragments, portions, or regions of the promoters comprising the polynucleotide sequence shown in SEQ ID NO: 2 can be used as regulatory polynucleotide molecules, including but not limited to cis-elements or motifs of the disclosed polynucleotide molecules. Substitutions, deletions, insertions, or any combination thereof can be combined to produce a final construct.

Polynucleotide Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner.

As used herein, the phrase "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the phrase "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional MRNA molecule that is translated and therefore expressed as a protein product. Constructs may also be constructed for transcription of antisense RNA molecules or other similar inhibitory RNA in order to inhibit expression of a specific RNA molecule of interest in a target host cell. For the practice of the present invention, conventional compositions and methods for preparing and using constructs and host cells are well known to one skilled in the art, see, for example, Sambrook, et al.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an MRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see, for example, U.S. Pat. Nos. 5,659,122 and 5,362,865, herein incorporated by reference). These additional upstream and downstream regulatory polynucleotide molecules may be derived from a source that is native or heterologous with respect to the other elements present on the promoter construct.

Thus, constructs of the present invention comprise promoters such as those provided in SEQ ID NOs: 1, 2, 3, or 4 modified as described above, operatively linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or DNA molecule that is introduced into a recipient cell. The type of DNA included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

The promoters of the present invention can be incorporated into a construct using marker genes as described and tested in transient analyses that provide an indication of gene expression in stable plant systems. As used herein the phrase "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Preferred marker genes for transient analyses of the promoters or promoter fragments of the present invention include a GUS gene (U.S. Pat. No. 5,599,670, herein incorporated by reference) or a GFP gene (U.S. Pat. No. 5,491,084, herein incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NOs: 1, 2, 3, or 4 or fragments, variants, or derivatives thereof is incorporated into a construct such that a promoter of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep), and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061; 5,633,435; and 6,040,497; and aroA described in U.S. Pat. No. 5,094, 945 for glyphosate tolerance; a polynucleotide molecule encoding bromoxynil nitrilase (Bxn) described in U.S. Pat.

No. 4,810,648 for Bromoxynil tolerance; a polynucleotide molecule encoding phytoene desaturase (crtI) described in Misawa et al., *Plant J.*, 4:833-840 (1993) and Misawa et al., *Plant J.*, 6:481-489 (1994) for norflurazon tolerance; a polynucleotide molecule encoding acetohydroxyacid synthase (AHAS, aka ALS) described in Sathasiivan et al., *Nucl. Acids Res.*, 18:2188-2193 (1990) for tolerance to sulfonylurea herbicides; and the bar gene described in DeBlock, et al., *EMBO J.*, 6:2513-2519 (1987) for glufosinate and bialaphos tolerance.

In one preferred embodiment, a polynucleotide molecule of the present invention as shown in SEQ ID NOs: 1, 2, 3, or 4 or fragments, variants, or derivatives thereof is incorporated into a construct such that a promoter of the present invention is operably linked to a transcribable polynucleotide molecule that is a gene of agronomic interest. As used herein, the phrase "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648), low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

Useful nucleic acid sequences that can be combined with the promoter nucleic acid sequence of the present invention and provide improved end-product traits include, without limitation, those encoding seed storage proteins, fatty acid pathway enzymes, tocopherol biosynthetic enzymes, amino acid biosynthetic enzymes, and starch branching enzymes. A discussion of exemplary heterologous DNAs useful for the modification of plant phenotypes may be found in, for example, U.S. Pat. Nos. 6,194,636; 6,207,879; 6,232,526; 6,426,446; 6,429,357; 6,433,252; 6,437,217; 6,515,201; and 6,583,338 and PCT Publication WO 02/057471, each of which is specifically incorporated herein by reference in its entirety.

Preferred seed storage proteins include zeins (U.S. Pat. Nos. 4,886,878; 4,885,357; 5,215,912; 5,589,616; 5,508,468; 5,939,599; 5,633,436; and 5,990,384; PCT Publications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576,203), brazil nut protein (U.S. Pat. No. 5,850,024), phenylalanine free proteins (PCT Publication WO 96/17064), albumin (PCT Publication WO 97/35023), b-conglycinin (PCT Publication WO 00/19839), 11S (U.S. Pat. No. 6,107,051), alpha-hordothionin (U.S. Pat. Nos. 5,885,802 and 5,88,5801), arcelin seed storage proteins (U.S. Pat. No. 5,270,200), lectins (U.S. Pat. No. 6,110,891), and glutenin (U.S. Pat. Nos. 5,990,389 and 5,914,450) all of which are incorporated herein by reference.

Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), diacylglycerol acyltransferases (U.S. Patent Publications 20030115632A1 and 20030028923A1), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249) all of which are incorporated herein by reference.

Preferred tocopherol biosynthetic enzymes include tyrA, slr1736, ATPT2, dxs, dxr, GGPPS, HPPD, GMT, MT1, tMT2, AANT1, slr 1737, and an antisense construct for homogentisic acid dioxygenase (Kridl et al., *Seed Sci. Res.*, 1:209:219 (1991); Keegstra, *Cell*, 56(2):247-53 (1989); Nawrath et al., *Proc. Natl. Acad. Sci. USA*, 91:12760-12764 (1994); Xia et al., *J. Gen. Microbiol.*, 138:1309-1316 (1992); Lois et al., *Proc. Natl. Acad. Sci. USA*, 95 (5):2105-2110 (1998); Takahashi et al., *Proc. Natl. Acad. Sci. USA*, 95(17):9879-9884 (1998); Norris et al., *Plant Physiol.*, 117:1317-1323 (1998); Bartley and Scolnik, *Plant Physiol.*, 104:1469-1470 (1994); Smith et al., *Plant J.*, 11:83-92 (1997); WO 00/32757; WO 00/10380; Saint Guily et al., *Plant Physiol.*, 100(2):1069-1071 (1992); Sato et al., *J. DNA Res.,* 7(1):31-63 (2000)) all of which are incorporated herein by reference.

Preferred amino acid biosynthetic enzymes include anthranilate synthase (U.S. Pat. No. 5,965,727 and PCT Publications WO 97/26366, WO 99/11800, WO 99/49058), tryptophan decarboxylase (PCT Publication WO 99/06581), threonine decarboxylase (U.S. Pat. Nos. 5,534,421 and 5,942,660; PCT Publication WO 95/19442), threonine deaminase (PCT Publications WO 99/02656 and WO 98/55601), dihydrodipicolinic acid synthase (U.S. Pat. No. 5,258,300), and aspartate kinase (U.S. Pat. Nos. 5,367,110; 5,858,749; and 6,040,160) all of which are incorporated herein by reference.

Preferred starch branching enzymes include those set forth in U.S. Pat. Nos. 6,232,122 and 6,147,279; and PCT Publication WO 97/22703, all of which are incorporated herein by reference.

Alternatively, a transcribable polynucleotide may be designed to down-regulate a specific nucleic acid sequence. This is typically accomplished by operably linking with a promoter, such as a promoter of the present invention, an exogenous DNA in an antisense orientation or a DNA designed such that a hairpin-forming RNA molecule is generated upon transcription. Gene suppression may be effective against a native plant gene associated with a trait, e.g., to provide plants with reduced levels of a protein encoded by the native gene or with enhanced or reduced levels of an affected metabolite. For example, a promoter of the present invention may be operably linked to a heterologous DNA designed such that a hairpin-shaped RNA is formed for suppression of a native gene in dicotyledonous seed. The RNA could also be a catalytic RNA molecule (i.e., a ribozyme) engineered to cleave a desired endogenous mRNA product. Thus, any polynucleotide molecule that encodes a protein or MRNA that expresses a phenotype or morphology change of interest is useful for the practice of the present invention.

As used herein "gene suppression" means any of the well-known methods for suppressing an RNA transcript or production of protein translated from an RNA transcript, including post-transcriptional gene suppression and transcriptional suppression. Post-transcriptional gene suppression is mediated by double-stranded RNA having homology to a gene targeted for suppression. Gene suppression by RNA transcribed from an exogenous DNA construct comprising an inverted repeat of at least part of a transcription unit is a common feature of gene suppression methods known as anti-sense suppression, co-suppression, and RNA interference. Transcriptional suppression can be mediated by a transcribed double-stranded RNA having homology to promoter DNA sequence to effect what is called promoter trans-suppression.

More particularly, post transcriptional gene suppression by inserting an exogenous DNA construct with anti-sense oriented DNA to regulate gene expression in plant cells is disclosed in U.S. Pat. Nos. 5,107,065 and 5,759,829, each of which is incorporated herein by reference in its entirety. Transgenic plants transformed using such anti-sense oriented DNA constructs for gene suppression can comprise DNA arranged as an inverted repeat, as disclosed by Redenbaugh et al., in "Safety Assessment of Genetically Engineered Flavr Savr™ Tomato, CRC Press, Inc. (1992). Inverted repeat insertions can comprise a part or all of a T-DNA construct, e.g., an inverted repeat of transcription terminator sequence.

Post transcriptional gene suppression by inserting an exogneous DNA construct with sense-oriented DNA to regulate gene expression in plants is disclosed in U.S. Pat. Nos. 5,283,184 and 5,231,020, each of which is incorporated herein by reference.

Different types of exogenous DNA arrangements resulting in gene suppression are known to those of skill in the art and include but are not limited to the following. PCT Publication WO 94/01550 discloses DNA constructs where the anti-sense RNA was stabilized with a self-complementary 3' segment. Other double-stranded hairpin-forming elements in transcribed RNA are disclosed in PCT Publication No. 98/05770 where the anti-sense RNA is stabilized by hairpin forming repeats of poly(CG) nucleotides and U.S. Application Publication No. 2002/0048814A1 describes sense or anti-sense RNA stabilized by a poly(T)-poly(A) tail. U.S. Application Publication No. 2003/0018993A1 discloses sense or anti-sense RNA is stabilized by an inverted repeat of a subsequence of 3' untranslated region of the NOS gene. U.S. Application Publication No. 2003/0036197A1 describes an RNA stabilized by two complementary RNA regions having homology to a target sequence.

Gene silencing can also be effected by transcribing RNA from both a sense and an anti-sense oriented DNA, e.g., as disclosed in U.S. Pat. No. 5,107,065 and other examples as follows. U.S. Pat. No. 6,326,193 discloses gene targeted DNA which is operably linked to opposing promoters. Sijen et al., *The Plant Cell*, 8:2277-2294 (1996) discloses the use of constructs carrying inverted repeats of a cowpea mosaic virus gene in transgenic plants to mediate virus resistance. Such constructs for post transcriptional gene suppression in plants by double-stranded RNA are also disclosed in PCT Publication Nos. WO 99/53050, WO 99/49029, and U.S. Application Publication No. 2003/0175965A1, U.S. application Ser. No. 10/465,800, and U.S. Pat. No. 6,506,559. See, also, U.S. application Ser. No. 10/393,347 which discloses constructs and methods for simultaneously expressing one or more recombinant genes while simultaneously suppressing one or more native genes in a transgenic plant. See, also, U.S. Pat. No. 6,448,473 which discloses multigene suppression vectors for use in plants. All of the above-described patents, applications and international publications disclosing materials and methods for post transcriptional gene suppression in plants are incorporated herein by reference.

Transcriptional suppression such as promoter trans suppression can be effected by expressing a DNA construct comprising a promoter operably linked to inverted repeats of promoter DNA for a target gene. Constructs useful for such gene suppression mediated by promoter trans suppression are disclosed by Mette et al., *The EMBO Journal*, 18(1): 241-248, 1999 and by Mette et al., *The EMBO Journal*, 19(19):5194-5201, 2000), both of which are incorporated herein by reference.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this present invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; *Agrobacterium*-mediated transformation as illustrated in U.S. Pat. Nos. 5,824,877; 5,591,616; 5,981,840; and 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this present invention can be harvested from fertile transgenic plants and be used to grow progeny generations of transformed plants of this present invention including hybrid plant lines comprising the construct of this present invention and expressing a gene of agronomic interest.

The present invention also provides for parts of the plants of the present invention. Plant parts, without limitation, include seed, endosperm, ovule, and pollen. In a particularly preferred embodiment of the present invention, the plant part is a seed. It is understood that even after separation or isolation from other plant parts, the isolated or separated plant part may be contaminated with other plant parts. In a preferred aspect, the separated plant part is greater than 50% (w/w) of the separated material, more preferably, greater than 75% (w/w) of the separated material, and even more preferably greater than 90% (w/w) of the separated material. Plants or plant parts of the present invention generated by such methods may be processed into products using known techniques. Preferred products are meal, feedstock, and oil.

In another embodiment, the present invention provides a method of making a vegetable oil, comprising the steps of incorporating into the genome of an oilseed plant a promoter of the present invention operably linked to a transcribable polynucleotide molecule conferring altered oil content, growing the oilseed plant to produce oilseeds, and extracting the oil from the oilseed.

In another embodiment, the present invention provides a method of making a meal, comprising the steps of incorporating into the genome of an oilseed plant a promoter of the present invention operably linked to a transcribable polynucleotide molecule conferring altered protein and/or micronutrient content, growing the oilseed plant to produce oilseeds, and producing the meal from the oilseed.

Methods to produce feed, meal, protein, and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than about 5% w/v, more preferably greater than about 10% w/v, and even more preferably greater than about 15% w/v. In a preferred oil preparation, the oil preparation is a high oil preparation with an oil content derived from a plant or part thereof of the present invention of greater than about 5% w/v, more preferably greater than about 10% w/v, and even more preferably greater than about 15% w/v. In a preferred embodiment the oil preparation is a liquid and of a volume greater than 1, 5, 10, or 50 liters. The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than about 0.5%, about 1%, about 5%, about 10%, about 25%, about 50%, about 75%, or about 90% by volume or weight of the oil component of any product. In another embodiment, the oil preparation may be blended and can constitute greater than about 10%, about 25%, about 35%, about 50%, or about 75% of the blend by volume. Oil produced from a plant of the present invention can be admixed with one or more organic solvents or petroleum distillates.

In a further embodiment, meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

The phrase "micronutrient content" means the amount of micronutrients, i.e., vitamins A, E, K, tocopherols, tocotrienols, or carotenoids, within a seed expressed on a per weight basis.

The phrase "oil content" means oil level, which may be determined, for example, by low-resolution $^{1}$H nuclear magnetic resonance (NMR) (Tiwari et al., *JAOCS*, 51:104-109, 1974 or Rubel, *JAOCS*, 71:1057-1062, 1994) or near infrared transmittance (NIT) spectroscopy (Orman et al., *JAOCS*, 69(10): 1036-1038, 1992 and Patrick et al., *JAOCS*, 74(3):273-276, 1997).

The phrase "protein quality" means the level of one or more essential amino acids, whether free or incorporated in protein, namely histidine, isoleucine, leucine, lysine, methionine, cysteine, phenylalanine, tyrosine, threonine, tryptophan, and valine.

The following examples are included to demonstrate preferred embodiments of the present invention. It should be appreciated by those of skill in the art that the techniques disclosed in the examples that follow represent techniques discovered by the inventors to function well in the practice of the present invention. However, those of skill in the art should, in light of the present disclosure, appreciate that many changes can be made in the specific embodiments that are disclosed and still obtain a like or similar result without departing from the spirit and scope of the present invention, therefore all matter set forth or shown in the accompanying drawings is to be interpreted as illustrative and not in a limiting sense.

EXAMPLE 1

This example sets forth the isolation and characterization of the nucleic acid sequences for the plant promoters p26, p63, p63tr and pBAN.

p26

A cDNA clone, designated clone 26, was identified from *Arabidopsis thaliana* using a cDNA-AFLP procedure. Briefly, SMART cDNA libraries were prepared from mRNA isolated from *Arabidopsis* according to manufacturer's instructions (Clontech Laboratories, Palo Alto, Calif.). The MRNA was isolated from open flowers (inflorescence), stem, whole seedling, and developing seed harvested at 4, 7, 10, 13, or 18 days after flowering (DAF). Five hundred micrograms of amplified SMART cDNA was used for AFLP analysis using the Gibco-BRL small genome AFLP II Kit (Invitrogen, Carlsbad, Calif.) according to manufacturer's instructions. The resulting bands were visualized after electrophoresis through 6% acrylamide/8M Urea sequencing gels. A single band, designated band 26, visible only in the lane derived from cDNA from 4 DAF developing seed tissue, was extracted from the gel. The DNA was eluted by placing the acrylamide band in 50 μl of TE (10 mM Tris-HCl (pH 8.0); 1 mM EDTA) and allowing the band to elute at ambient temperature overnight. After a brief centrifugation, 0.75 μl of supernatant was used as a template source for a PCR amplification. Twenty microliters of Preamp primer mix 2 (Gibco-BRL small genome AFLP II Kit, Invitrogen), 2.5 μl 10×PCR buffer with 15 mM MgCl (PE Applied Biosystems Foster City, Calif., 2.5 units AmpliTaq DNA Polymerase (PE Applied Biosystems), and 2 μl water were added to the DNA template. Amplification conditions were as follows: 25 cycles of 94° C. for 30 seconds, 56° C. for 60 seconds, and 72° C. for 2 minutes followed by 1 cycle of 72° C. for 2 minutes. The resulting DNA fragment was subcloned into pCR2.1Topo (Invitrogen) according to manufacturers' instructions. This cDNA clone 26 was hybridized to virtual Northerns that were prepared from SMART cDNA libraries, according to the manufacturer's instructions, using the SMART PCR cDNA Synthesis Kit (BD Biosciences, Clontech, Palo Alto, Calif.) Clone 26 was characterized as being expressed in early stages of seed development. The sequence of clone 26 was determined using standard sequencing methodologies as set forth by PE Applied Biosystems BigDye terminator v.3.0 (PE Applied Biosystems, Foster City, Calif.).

The entire sequence of clone 26 was then used as a query for a BLAST search against public and proprietary genomic DNA databases. A single EST clone, LIB3176-P1-K1-C12, was identified from the search. The clone had homology to a palmitoyl-protein thioesterase in *Arabidopsis thaliana* (GenBank protein_id BAA97167; gi:8809616). The entire genomic sequence of clone 26 was contained within the P1 clone MQL5 (SEQ ID NO: 5, GenBank Accession AB018117; gi:3702735).

To prepare a genomic library from *Arabidopsis*, genomic DNA was isolated using a modification of a genomic DNA isolation protocol (Dellaporta et al., *Plant Molecular Biology Reporter*, 1:19-21, 1983). Soil or plate grown *Arabidopsis* seedlings were harvested and kept frozen in liquid nitrogen until extraction. The tissue was ground to a fine powder using a mortar and pestle while keeping the tissue frozen with liquid nitrogen. The ground tissue was transferred to a Waring blender containing 200 ml of cold (0° C.) DNA extraction buffer (350 mM sorbitol; 100 mM Tris; 5 mM EDTA; pH to 7.5 with HCl; sodium bisulfite (3.8 mg/ml) added just before use, and homogenized at high speed for 30-60 seconds. The homogenate was filtered through a layer of cheesecloth and collected in a centrifuge bottle. The samples were centrifuged at 2500×g for 20 minutes. The supernatant and any loose green material was discarded. The pellet was then resuspended in 1.25 ml DNA extraction buffer and transferred to a 50 ml polypropylene tube. Then 1.75 ml nuclei lysis buffer (200 mM Tris; 50 mM EDTA; 2 M NaCl; 2% CTAB (Hexadecyltrimethyl-Ammonium Bromide, Sigma, St. Louis, Mo.); pH to 7.5 with HCl), and 0.6 ml of 5% (w/v) sarkosyl was added. The tubes were mixed gently, and the samples were incubated at 65° C. for 20 minutes. An equal volume of chloroform:isoamyl alcohol (24:1) was added and the tubes were mixed gently. The tubes were then centrifuged at 2500×g for 15 minutes, and the resulting supernatant was transferred to a clean tube. An equal volume of ice-cold isopropanol was poured onto the sample, and the sample was inverted several times until a precipitate formed. The precipitate was removed from the solution using a glass pipette and residual alcohol removed by allowing the precipitate to air dry for 2-5 minutes. The precipitate was resuspended in 400 μl TE buffer (10 mM Tris-HCl pH 8.0, 1 mM EDTA).

*Arabidopsis* genomic DNA as prepared above was used to prepare Genome Walker libraries (Clontech) according to the manufacturer's instructions. The p26 promoter sequence (SEQ ID NO: 2) was isolated from the libraries according to the manufacturer's instructions. Primers were designed based upon the sequence of the P1 clone MQL5 (SEQ ID NO: 5). The following were used as the primers for the PCR reaction:

```
Clone 26 GSP1
5'-ATCGGCAACTCCATTTCCAATTTCTC-3'     (SEQ ID NO: 7)

and Clone 26 GSP2
5'-TAGCATCCCTAGCATTAGAACATTGAG-3'.   (SEQ ID NO: 8)
```

After an initial PCR using the Genome Walker libraries as template and primers GSP1 and AP1 (supplied by the manufacturer), a second amplification was performed using the first round amplification product as template and primers GSP2 and AP2 (supplied by the manufacturer).

The product of the PCR reaction was purified according to standard methodology well known in the art and cloned into pCR2.1 Topo (Invitrogen) according to manufacturer's instructions. The resulting plasmid was named pMON69803 and contained the sequence of the promoter p26 (SEQ ID NO: 2). The sequence of this clone was determined using standard sequencing methodologies as set forth by PE Applied Biosystems, (Foster City, Calif.).

pBAN

The promoter sequence for pBAN was identified from a BLAST search of the coding region of the BANYULS gene (GenBank AF092912, Devic etal., *The Plant Journal*, 19(4): 387-398, 1999) against an *Arabidopsis* database in GenBank, the NIH genetic sequence database containing an annotated collection of all publicly available DNA sequences (*Nucleic Acids Research*, 30(1):17-20, 2002). The search identified BAC clone T13M11 (GenBank AC005882, [SEQ ID NO: 6]) that contains the BANYULS coding region in antisense orientation. The following primers were designed to amplify the sequences corresponding to T12M11 base pairs 44629-45570 from *Arabidopsis* genomic DNA prepared as described above.

BAN+1500
5'-GTTTGATAACTCGTCTCTTG-3' (SEQ ID NO: 9)

and BAN GSP1
5'-GGTGTGTGTAAGAGTCTGGTCC-3' (SEQ ID NO: 10)

The reaction conditions for the PCR followed a protocol recommended by the enzyme manufacturer (PE Applied Biosystems, Foster City, Calif.). The Banyuls promoter was isolated from *Arabidopsis* genomic DNA using 30 nanomoles each of primers Ban+1500 and Ban GSP1, 10 micromoles each of dATP, dCTP, dGTP, and TTP, 2.5 units of AmpliTaq Gold in 1×Opti-Prime™ Buffer 3 (Stratagene, La Jolla, Calif.). After an initial incubation at 95° C. for 10 minutes, 30 cycles of PCR were performed with 92° C. for 30 seconds, 56° C. for 30 seconds, and 72° C. for 2 minutes followed by 1 cycle of 72° C. for 7 minutes.

The product of the PCR reaction was purified according to standard methodology well known in the art and cloned into pCR2.1 Topo (Invitrogen) according to manufacturer's instructions. The resulting plasmid was named pBAN1.

To add an NcoI site at the predicted ATG start codon of the Banyuls gene an additional PCR reaction was performed. pBAN1 was used as template DNA with the following primers:

Ban-Nco
5'-CCATGGTTGTACTTTTGAAATTACAGAG-3' (SEQ ID NO: 11)

and Ban+1500
5'-GTTTGATAACTCGTCTCTTG-3' (SEQ ID NO: 9)

The reaction conditions for the second PCR reaction followed a protocol recommended by the enzyme manufacturer (PE Applied Biosystems, Foster City, Calif.). Approximately 10 nanograms of pBAN1 is amplified using 30 nanomoles each of primers Ban+1500 and Ban-Nco, 10 micromoles each of dATP, dCTP, dGTP, and TTP, 2.5 units of AmpliTaq Gold in 1×Opti-Prime™ Buffer 3 (Stratagene). After an initial incubation at 95° C. for 10 minutes, 30 cycles of PCR were performed with 92° C. for 30 seconds, 56° C. for 30 seconds, and 72° C. for 2 minutes followed by 1 cycle of 72° C. for 7 minutes.

The product of the PCR reaction was purified according to standard methodology well known in the art and cloned into pCR2.1 Topo (Invitrogen) according to manufacturer's instructions. The resulting plasmid was named pMON69809 and contained the sequence of the promoter pBAN (SEQ ID NO: 1). The sequence of this clone was determined using standard sequencing methodologies as set forth by PE Applied Biosystems.

p63

A cDNA clone, designated clone 63, was identified from *Arabidopsis thaliana* using cDNA-AFLP. SMART cDNA libraries were prepared from mRNA isolated from *Arabidopsis* open flowers (inflorescence), stem, whole seedling, and developing seed harvested at 4, 7, 10, 13, or 18 days after flowering (DAF), according to manufacturer's instructions (Clontech). Five hundred micrograms of amplified SMART cDNA was used for AFLP analysis using the Gibco-BRL small genome AFLP II kit and following manufacturer's instructions (Invitrogen). The resulting bands were visualized after electrophoresis through 6% acrylamide/8M Urea sequencing gels. A single band, designated band 63, visible only in the lane derived from cDNA from 4 DAF developing seed tissue, was extracted from the gel. The DNA was eluted by placing the acrylamide band in 50 µl of TE (10 mM Tris-HCl (pH 8.0); 1 mM EDTA) and allowing the band to elute at ambient temperature overnight. After a brief centrifugation, 0.75 µl of supernatant was used as the template source for a PCR amplification. Twenty microliters of Preamp primer mix 2 (from the Gibco-BRL small genome AFLP II Kit), 2.5 µl 10×PCR buffer with 15 mM $MgCl_2$ (PE Applied Biosystems), 2.5 units AmpliTaq DNA Polymerase (PE Applied Biosystems), and 2 µl water were added to the DNA template. Amplification conditions were as follows: 25 cycles of 94° C. for 30 seconds, 56° C. for 60 seconds, and 72° C. for 2 minutes followed by 1 cycle of 72° C. for 2 minutes. The resulting DNA fragment was subcloned into pCR2.1 Topo (Invitrogen) according to manufacturers' instructions. This cDNA clone 63 was hybridized to virtual Northerns that were prepared from SMART cDNA libraries, according to the manufacturer's instructions, using the SMART PCR cDNA Synthesis Kit (BD Biosciences, Clontech, Palo Alto, Calif.). Clone 63 was characterized as being expressed in early stages of seed development. The sequence of clone 63 was determined using standard sequencing methodologies as set forth by PE Applied Biosystems BigDye terminator v.3.0 (PE Applied Biosystems, Foster City, Calif.).

The entire sequence of the clone 63 was used as a query for a BLAST search against public and proprietary databases. Public database searches indicated that clone 63 was annotated as a putative protein. The entire genomic sequence of clone 63 was contained within the BAC clone T25N20 (Choi et al., *Weeds World*, 2:17-20, 1995), which was then obtained from the Arabidopsis Biological Resource Center (Columbus, Ohio).

An overnight culture of *E. coli* containing the BAC clone T25N20 was grown from a single colony in LB broth (10% bacto-tryptone, 5% yeast extract, and 10% NaCl with kanamycin (25 mg/L) and ampicillin (100 mg/L)), containing 12.5 mg/liter chloramphenicol at 37° C. with vigorous shaking until late exponential or early stationary phase. Clone 63 (p63) was then isolated from the BAC clone T25N20. The cells were collected via centrifugation resulting pellet was resuspended in 0.2 ml buffer (50 mM glucose; 10 mM EDTA; 25 mM Tris pH 8.0; 5 mg/ml lysozyme) and incubated on ice for 5 minutes, followed by the addition of 0.4 ml of 0.2 N NaOH; 1% SDS solution. The tube was mixed gently and incubated on ice for 5 minutes, followed by the addition of 0.3 ml of 3 M potassium acetate. The tube was mixed gently and then frozen at minus 80° C. for 15 minutes. The debris was pelleted by centrifugation at 20,000×g for 15 minutes, and 0.75 ml of the resulting supernatant was transferred to a new tube. Isopropanol (0.45 ml) was added and the mixture was incubated at minus 80° C. for 15 minutes. DNA was pelleted by centrifugation at 20,000×g for 5 minutes. The pellet was rinsed with 1 ml of cold 70% ethanol, then dried on the bench for at least 15 minutes prior to being resuspended in 40 µl TE buffer.

The following primers were used to PCR amplify p63 from BAC T25N20:

p63-Nco
5'-CCATGGTTATTCAAGTGACCACAG-3' (SEQ ID NO: 12)

and p63-fwd3
5'-CGTGTTGAGGTGAGAGG-3' (SEQ ID NO: 13)

The conditions for the PCR reaction followed a protocol recommended by the enzyme manufacturer (PE Applied Biosystems, Foster City, Calif.). The p63 sequence was amplified using 1.5 μl of T25N20 as template, 30 nanomoles each of the primers p63-Nco and p63-fwd3, 10 micromoles each of dATP, dCTP, dGTP, and TTP, 2.5 units of AmpliTaq Gold (PE Applied Biosystems) in 1×Opti-Prime™ Buffer 3 (Stratagene). After an initial incubation at 95° C. for 10 minutes, 28 cycles of PCR were performed with 94° C. for 15 seconds, 62° C. for 10 seconds, 52° C. for 10 seconds, and 72° C. for 3 minutes followed by 1 cycle of 72° C. for 7 minutes.

The product of the PCR reaction was purified according to standard methodology well known in the art and cloned into pCR2.1 Topo (Invitrogen) according to manufacturer's instructions. The resulting plasmid was named pMON69811 and contained the sequence of the promoter p63 (SEQ ID NO: 3). The sequence of this clone was determined using standard sequencing methodologies as set forth by PE Applied Biosystems.

EXAMPLE 2

This example describes the construction of the vectors used for *Arabidopsis* transformation.

pMON69802

An 1861 base pair (bp) fragment containing the *E. coli* uidA gene (GUS) was removed from the donor plasmid pCGN10906 by digestion with EcoRI. The fragment was isolated from an agarose gel using the QiaGel Purification kit (Qiagen) according to the manufacturer's instructions. The purified DNA was eluted from the column using 30 μl of Buffer EB (10 mM Tris-Cl pH 8.5). New restriction endonuclease sites were added to the *E. coli* uidA gene using primers:

```
Gus 5'
5'-AGGCGGCGCCTAAACCATGGTCCGTCCTGTAGAAACCCC-3'   (SEQ ID NO: 14)

and Gus 3'
5'-AGTCGACTCATTGTTTGCCTCCCTGCTGCGGTTTTTCAC-3'.  (SEQ ID NO: 15)
```

The purified fragment (0.5 μl) was used as the template for the following PCR amplification. Thirty nanomoles each of primers Gus 5' (SEQ ID NO: 14) and GUS 3' (SEQ ID NO: 15), 10 micromoles each of dATP, dCTP, dGTP, and TTP, 2.5 units of AmpliTaq Gold (PE Applied Biosystems) in 1×Opti-Prime™ Buffer 3 (Stratagene) were added to the DNA template. Amplification conditions were as follows: 25 cycles of 94° C. for 30 seconds, 56° C. for 60 seconds, and 72° C. for 2 minutes followed by 1 cycle of 72° C. for 2 minutes. The product of the PCR reaction was purified according to standard methodology well known in the art and cloned into pCR2.1 Topo (Invitrogen) according to manufacturer's instructions. The resulting plasmid was named pMON65400. The sequence of this clone was determined using standard sequencing methodologies as set forth by PE Applied Biosystems.

A 1278 bp fragment containing the napin 3' UTR was removed from the vector pCGN 7770 by digestion with SalI and Asp718I. An 1861 base pair fragment, containing the *E. coli* uidA gene, was removed from the vector pMON65400 by sequential digestion with BstXI and SalI. Prior to SalI digestion and gel purification, the BstXI overhang was blunt ended using Pfu polymerase according to the manufacturer's instructions (Stratagene). Both fragments were ligated into the vector pCGN8541, which had been digested with Asp718I and SwaI. The resulting plasmid, containing the *E. coli* uidA gene and the napin 3' UTR, was named pMON69802 (FIG. 1). The nucleic acid sequence was determined using known methodology and confirmed the integrity of the cloning junctions.

pMON69804 (p26::GUS)

Figure 2:
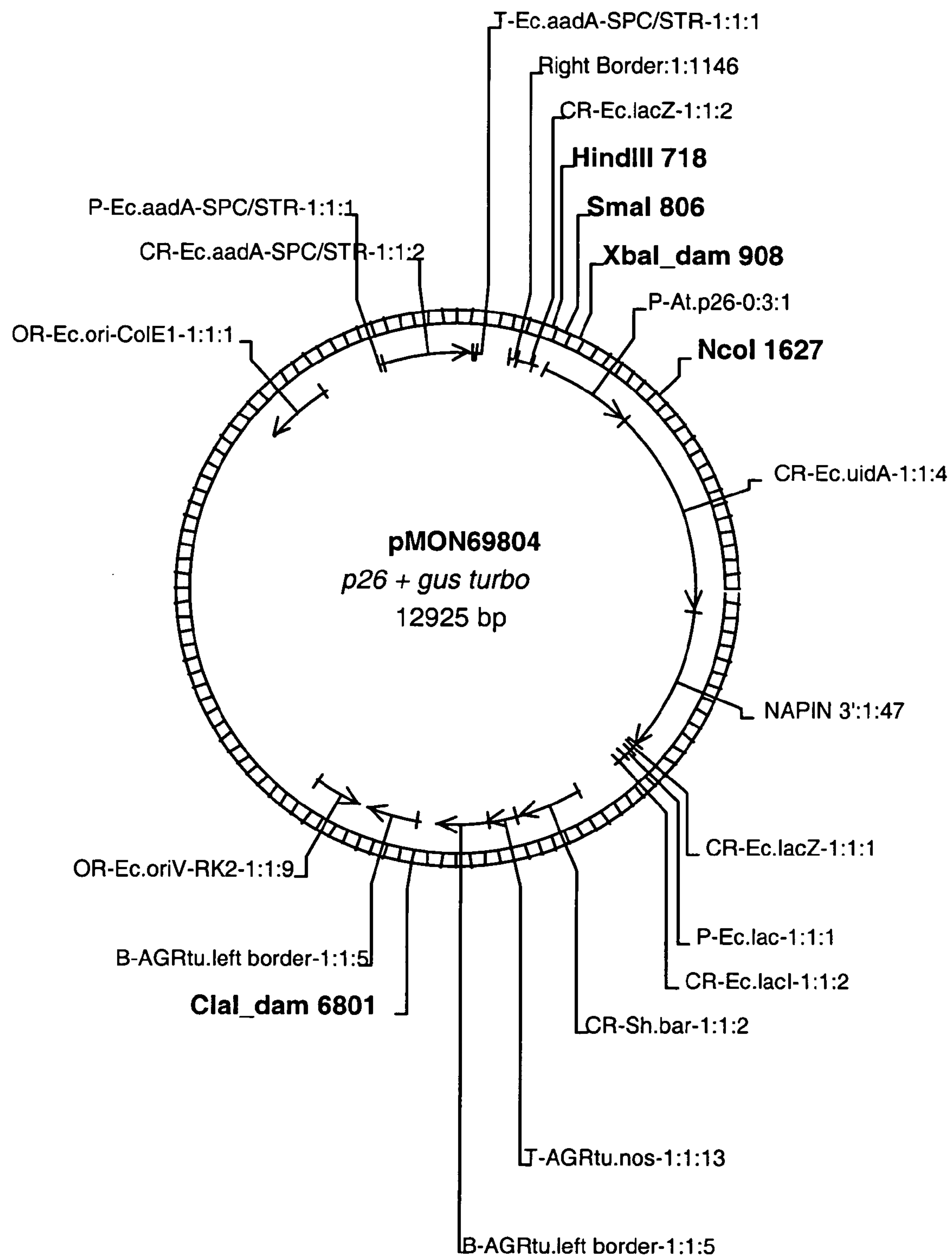
FIG. 2 is a schematic representation of pMON69804.

A 1007 bp fragment containing the p26 sequence was removed from pMON69803 by digestion with HindIII and NcoI. The fragment was ligated into pMON69802, which had also been digested with HindIII and NcoI. The resulting plasmid, containing the p26 promoter driving the *E. coli* uidA gene and with the napin 3' UTR was named pMON69804 (FIG. 2). The nucleic acid sequence was determined using known methodology and confirmed the integrity of the cloning junctions. This vector was used in the subsequent transformation of *Arabidopsis*.

pMON69815 (pBAN::GUS)

Figure 3:
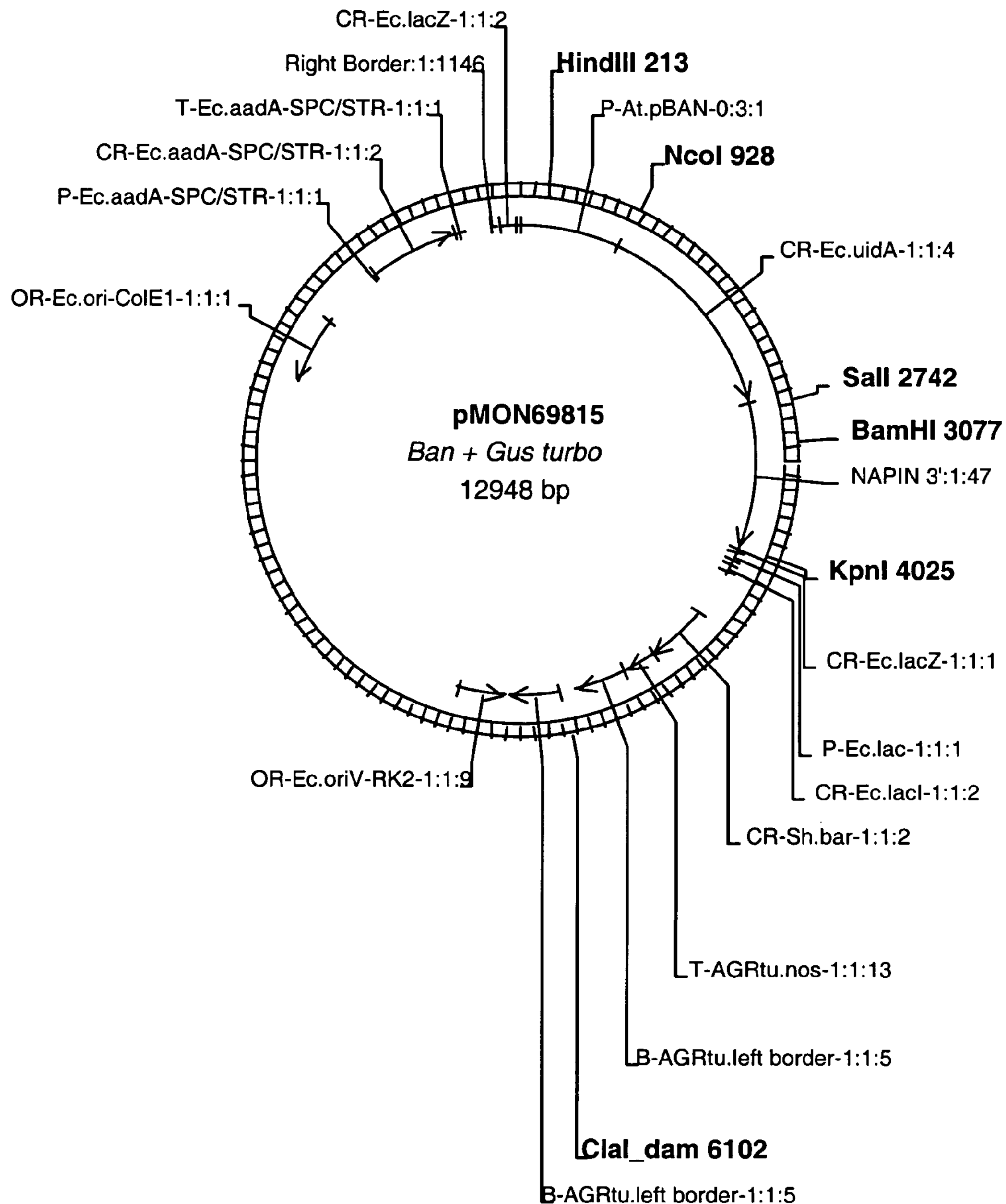
FIG. 3 is a schematic representation of pMON69815.

A 947bp BstXI-NcoI fragment containing the pBAN promoter sequence was removed from pMON69809 by sequential digestion with BstXI followed by and NcoI. Prior to NcoI digestion and gel purification, the BstXI overhang was blunt ended using Pfu polymerase according to the manufacturer's instructions (Stratagene). The fragment was ligated into pMON69802, which had been sequentially digested with HindIf and NcoI. Prior to NcoI digestion and gel purification, the HindHI overhang from pMON69802 was blunt ended using Pfu polymerase according to the manufacturer's instructions (Stratagene). The resulting plasmid, containing the pBAN promoter driving the *E. coli* uidA gene and with the napin 3' UTR, was named pMON69815 (FIG. 3). The nucleic acid sequence was determined using known methodology and confirmed the integrity of the cloning junctions. This vector was used in the subsequent transformation of *Arabidopsis*.

pMON69812 (p63::GUS)

Figure 4:
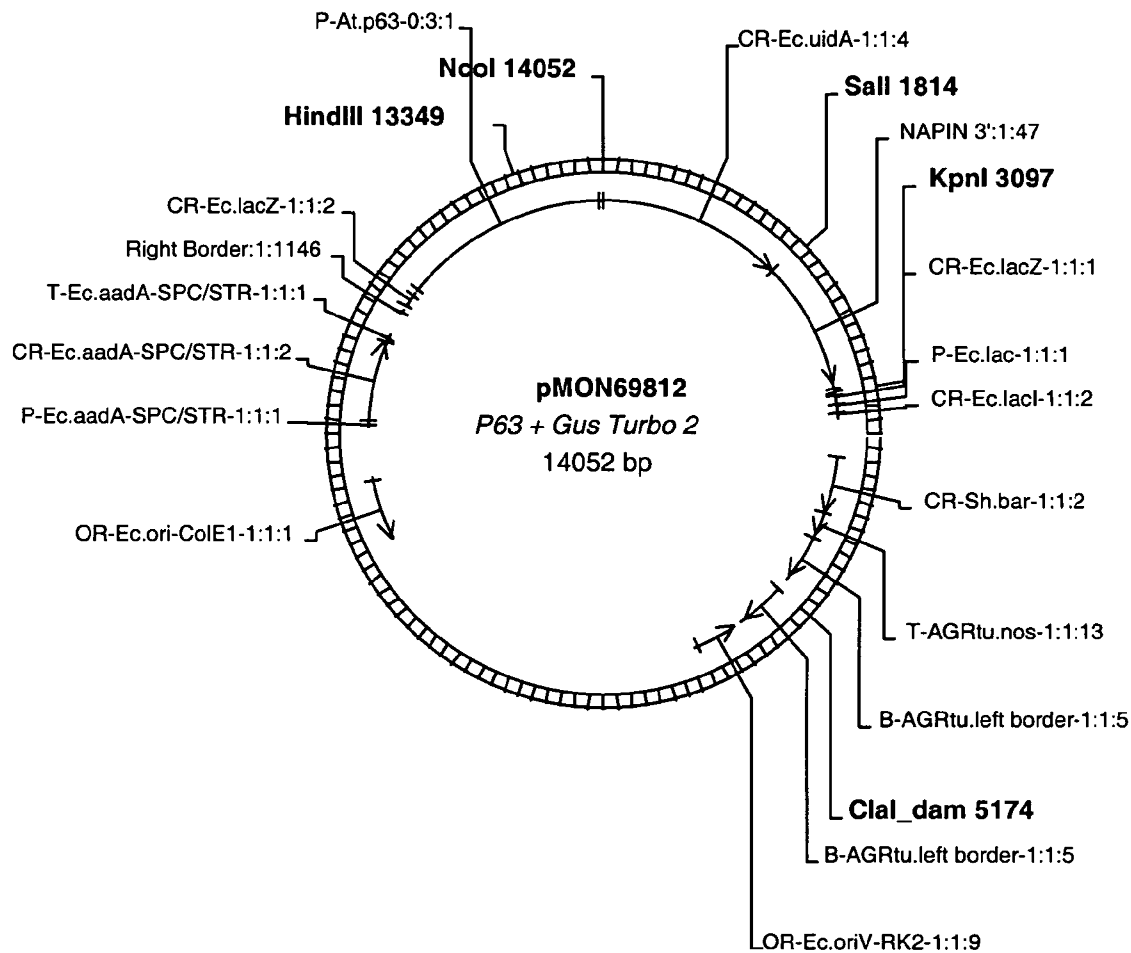
FIG. 4 is a schematic representation of pMON69812.

A 2031 base pair fragment containing the p63 sequence was cut out of pMON69811 by sequential digestion with BstXI and NcoI. Prior to NcoI digestion and gel purification, the BsatXI overhang was blunt ended using Pfu polymerase according to manufacturer's instructions (Stratagene). The fragment was ligated into pMON69802, which had been digested with Hindlil, and also had the resulting overhang blunt ended with Pfu polymerase. The resulting plasmid, containing the p63 promoter driving the *E. coli* uidA gene and with the napin 3' UTR was named pMON69812 (FIG. 4). The nucleic acid sequence was determined using known methodology and confirmed the integrity of the cloning junctions. This vector was used in the subsequent transformation of *Arabidopsis*.

EXAMPLE 3

This example describes the transformation and subsequent regeneration of transgenic *Arabidopsis* plants expressing a heterologous gene of interest.

*Arabidopsis* plants were grown by sowing seeds onto 4 inch pots containing reverse osmosis water (ROW) saturated MetroMix 200 (The Scotts Company, Columbus, Ohio). The plants were vernalized by placing the pots in a covered flat, in a growth chamber at 4-7° C., 8 hours light/day for 4-7 days. The flats were transferred to a growth chamber at 22° C., 55% relative humidity, and 16 hours light/day at an average intensity of 160-200 μEinstein/s/$m^2$. The cover was lifted and slid back 1 inch after germination, and then was removed when the true leaves had formed. The plants were bottom watered, as needed, with ROW until 2-3 weeks after germination. Plants were then bottom watered, as needed, with Plantex 15-15-18 solution (Plantex Corporation Ottawa, Canada) at 50 ppm $N_2$. Pots were thinned so that 1 plant remained per pot at 2-3 weeks after germination. Once the plants began to bolt, the primary inflorescence was trimmed to encourage the growth of axillary bolts.

Transgenic *Arabidopsis thaliana* plants were obtained as described by Bent et al., *Science*, 265:1856-1860, 1994 or Bechtold et al., *C.R.Acad.Sci, Life Sciences*, 316:1194-1199, 1993. Cultures of *Agrobacterium tumefaciens* strain ABI containing one of the transformation vectors pMON69804, pMON69812, or pMON69815 were grown overnight in LB (10% bacto-tryptone, 5% yeast extract, and 10% NaCl with kanamycin (75 mg/L), chloramphenicol (25 mg/L), and spectinomycin (100 mg/L)). The bacterial culture was centrifuged and resuspended in 5% sucrose+0.05% Silwet-77 solution. The aerial portions of whole *Arabidopsis thaliana* plants (at about 5-7 weeks of age) were immersed in the resulting solution for 2-3 seconds. The excess solution was removed by blotting the plants on paper towels. The dipped plants were placed on their side in a covered flat and transferred to a growth chamber at 19° C. After 16 to 24 hours the dome was removed and the plants were set upright. When plants had reached maturity, water was withheld for 2-7 days prior to seed harvest. Harvested seed was passed through a stainless steel mesh screen (40 holes/inch) to remove debris. The harvested seed was stored in paper coin envelopes at room temperature until analysis.

The harvested seeds described above were sown onto flats containing ROW saturated MetroMix 200 (The Scotts Company). The plants were vernalized and germinated as described above. After true leaves had emerged, the aerial portion of the seedlings were sprayed with a solution containing a 1:200 dilution of Finale herbicide (The Scotts Company). Approximately 1 week after the first application, the plants were sprayed a second time. Up to 16 Finale resistant seedlings were transplanted to 2¼ inch pots, one seedling per pot, containing MetroMix 200 and were grown under the conditions described above until the initial siliques that had formed began to desiccate. Tissue (rosette leaf, cauline leaf, stem, flowers, floral buds, and developing siliques) was removed from each T1 plant for subsequent histochemical staining.

EXAMPLE 4

Expression of β-glucuronidase was analyzed in *Arabidopsis thaliana* plants transformed with pMON69815, pMON69812, or pMON69804 using histochemical staining. Tissues, prepared as described in Example 3, were incubated for approximately 24 hours at 37° C. in a solution containing 50 mM $NaPO_4$ (pH 7.2); 100 μM potassium ferricyanide; 100 μM potassium ferrocyanide, 0.03% Triton X-100; 20% methanol and 2.5 mg/ml 5-bromo-4-chloro-3-indoyl glucuronic acid (X-gluc). In some cases the potassium ferricyanide, potassium ferrocyanide, and methanol were omitted from the staining solution. The stained tissue was cleared of chlorophyll by an overnight incubation in 70% ethanol/30% $H_2O$ at 37° C. Stained tissues were photographed immediately or transferred to a solution of 70% ethanol/30% glycerol (v/v) and stored at 4° C. until photographed. The results, summarized in Table 1 below, show that 4 out of the 11 individual T1 plants tested from pMON69804, (p26::GUS), showed GUS expression in the seed. For pMON69812, (p63::GUS), 13 of the 15 lines tested had expression in the seed. For pMON69815, (pBAN::GUS), 12 out of 12 lines tested had expression in the seed.

TABLE 1

| Construct | Promoter | # of Lines Tested | Lines with Seed Expression |
|---|---|---|---|
| pMON69804 | p26 | 11 | 4 |
| pMON69815 | pBan | 12 | 12 |
| pMON69812 | p63 | 15 | 13 |

To examine the developmental stage at which the promoters were active, seeds from the independent lines that were positive for GUS expression in the T1 generation (described above) were sown onto pots containing ROW saturated MetroMix 200. The plants were vernalized, in a growth chamber, at 4-7° C. and 8 hours of light/day for 4-7 days. The plants were transferred to a growth chamber at 22° C., 55% relative humidity, and 16 hours of light/day at an average intensity of 160-200 μEinstein/s/$m^2$. The plants were bottom watered, as needed, with ROW until well established, generally 2-3 weeks after germination. Plants were then bottom watered, as needed, with Plantex 15-15-18 at 50 ppm $N_2$. Pots were thinned so that 1 plant remained per 2¼ inch pot at 2-3 weeks after germination. At least 10 plants from each line were stained, as described above, at each time point. Visual observations of the GUS expression patterns were recorded. Qualitative expression was compared to the positive control plants containing a pNapin::GUS construct (labeled as 10908) and to the null segregants which served as the negative control plants. The results are shown in Table 2.

Expression driven by the napin promoter is detected from 7-18 days after flowering (daf). Expression driven by the p26 promoter, pBAN promoter, and the p63 promoter, was detected from 5-10, 1-14, and 4-14 daf, respectively. Hence, expression of all three promoters was detected earlier than that of the napin promoter.

TABLE 2

| | | Day after flowering | | | | | | | | | | | | |
|---|---|---|---|---|---|---|---|---|---|---|---|---|---|---|
| Line | promoter | 0 | 1 | 2 | 3 | 4 | 5 | 6 | 7 | 8 | 10 | 13 | 14 | 18 |
| 10908-7 | napin | – | – | ND | ND | ND | – | ND | + | ND | + | ND | + | + |
| 10908-10 | napin | – | – | – | ND | ND | – | ND | + | ND | + | ND | + | ND |
| 10908-16 | napin | – | – | – | – | ND | – | – | – | ND | + | ND | – | – |
| 69804-13 | p26 | – | – | – | – | – | ND | ND | + | ND | – | ND | – | – |

TABLE 2-continued

| | | Day after flowering | | | | | | | | | | | | |
|---|---|---|---|---|---|---|---|---|---|---|---|---|---|---|
| Line | promoter | 0 | 1 | 2 | 3 | 4 | 5 | 6 | 7 | 8 | 10 | 13 | 14 | 18 |
| 69804-14 | p26 | – | – | – | – | – | + | ND | + | + | + | ND | – | – |
| 69804-7 | p26 | – | – | – | ND | ND | + | ND | + | ND | – | ND | – | – |
| 69815-2 | pBan | – | + | + | + | ND | + | ND | + | ND | + | + | ND | – |
| 69815-9 | pBan | – | + | + | + | ND | + | ND | + | ND | + | ND | ND | – |
| 69815-14 | pBan | – | + | + | + | ND | + | ND | + | ND | + | ND | + | – |
| 69812-4 | p63 | – | – | – | – | – | + | ND | + | ND | + | ND | + | – |
| 69812-9 | p63 | – | – | – | – | ND | – | ND | – | ND | + | ND | + | – |
| 69812-16 | p63 | – | – | – | – | ND | – | ND | – | ND | + | ND | + | – |
| 69812-13 | p63 | ND | ND | ND | ND | + | + | ND | ND | ND | ND | ND | ND | ND |

ND: Not Determined

EXAMPLE 5

This example describes the vector construction and transformation of soy plants with reporter genes driven by promoters of the present invention.

Vector Construction pMON82350 (p63::GUS)

Figure 5:
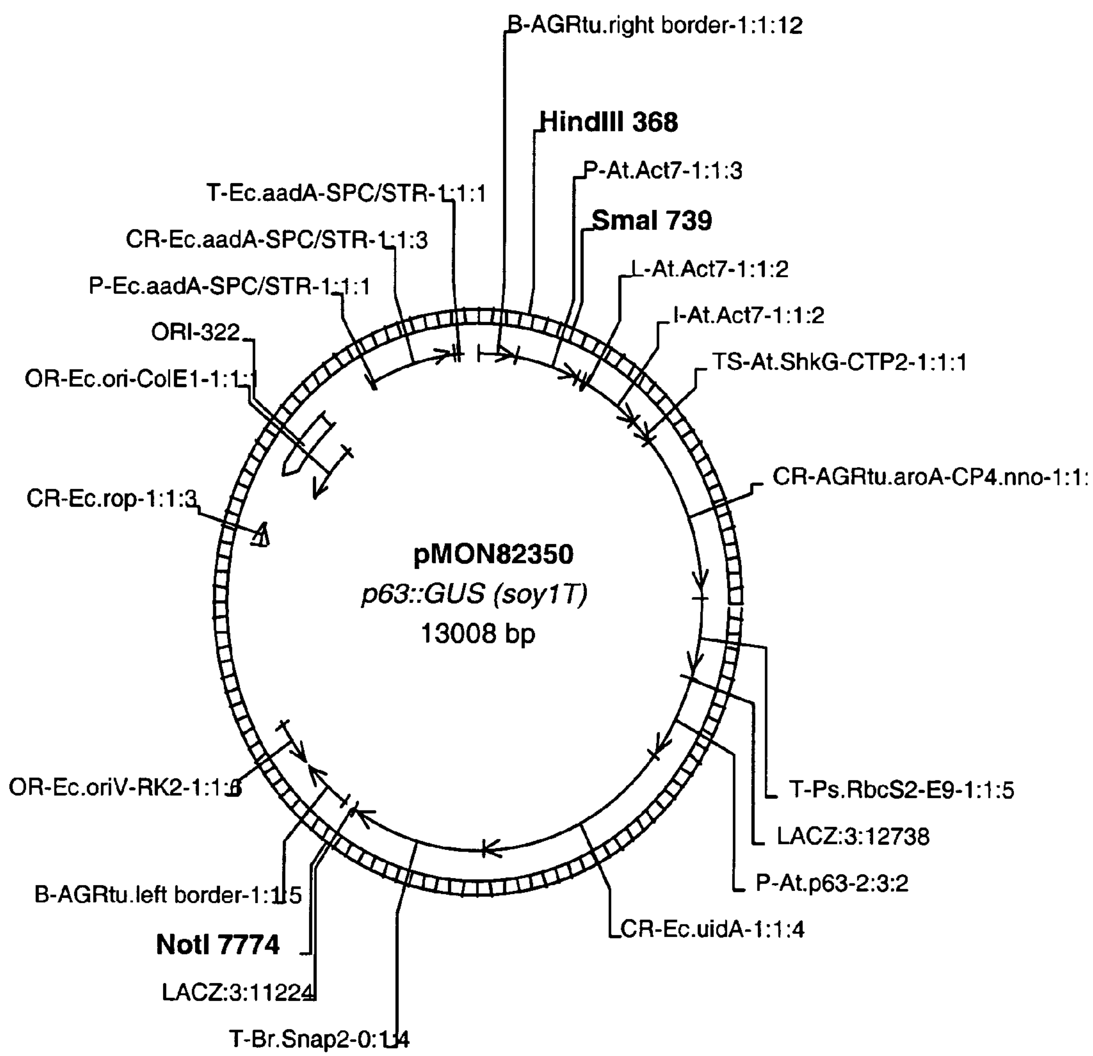
FIG. 5 is a schematic representation of pMON82350.
Figure 6:
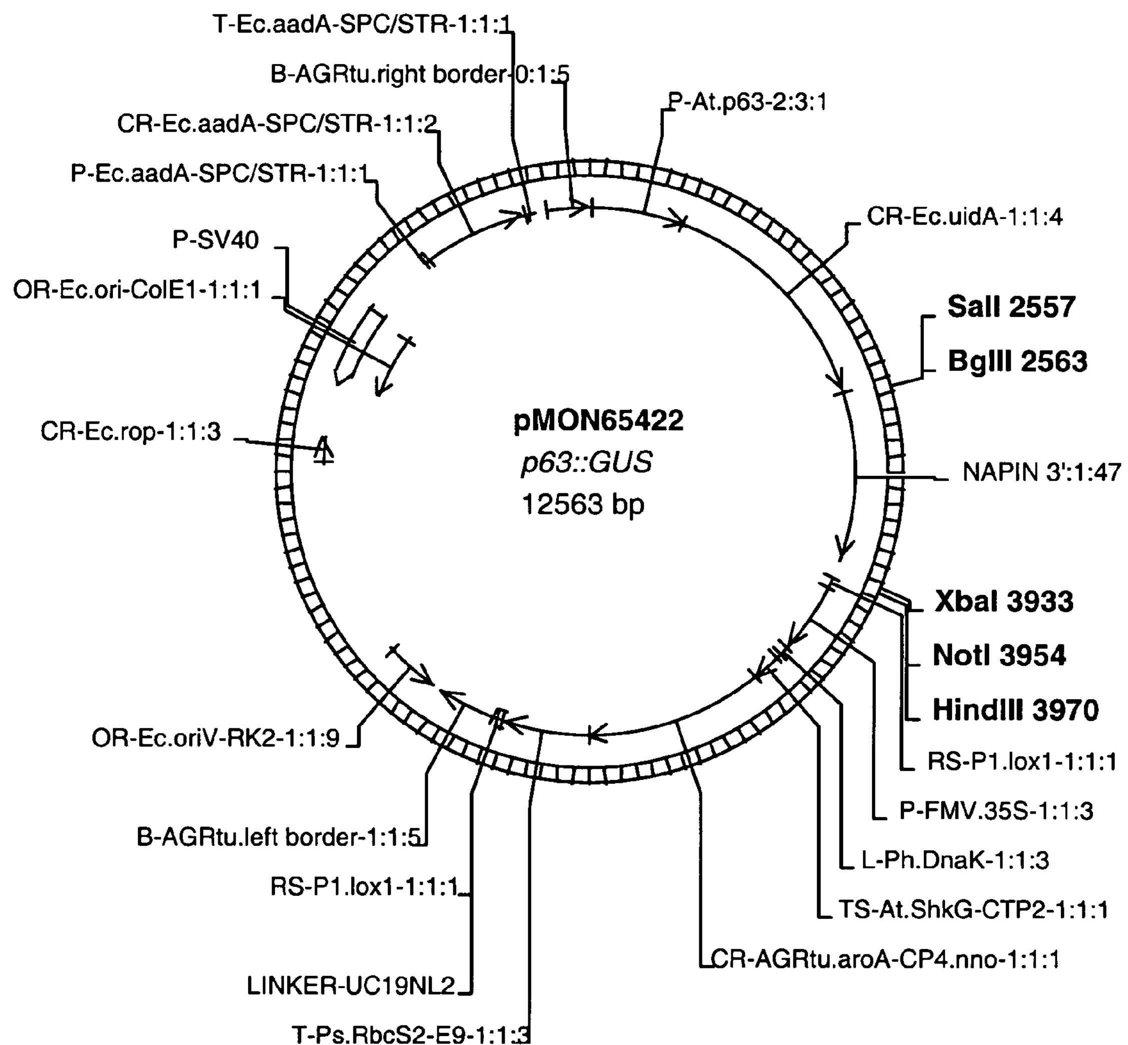
FIG. 6 is a schematic representation of pMON65422.

A 3859-base pair fragment containing p63 (SEQ ID NO: 3), the *Escherichia coli* uidA gene and the napin 3' UTR was removed from the vector pMON65415 by digestion with NotI and Sse83871. The fragment was ligated in between the 3' UTR from the pea rbsc E9 gene and octopine T-DNA left border sequence in the vector pMON65448, which had been digested with NotI and Sse8387I. The vector pMON65448 contains a nopaline T-DNA right border sequence and octopine T-DNA left border sequence, in between which are the promoter, 5' UTR and first intron from the *Arabidopsis* act7 gene driving the expression of a CP4 EPSP synthase gene containing a CTP, linked to a synthetic EPSP synthase coding region and the 3' UTR from the pea rbsc E9 gene. The resulting plasmid was named pMON82350 (FIG. 5). The nucleic acid sequence was determined using standard sequencing methodology and confirmed the integrity of the cloning junctions.

pMON82350 was transformed into soy via *Agrobacterium*-mediated transformation as described by Martinell et al., U.S. Pat. No. 6,384,301. Transformed plant tissues are collected and stained as described in Example 4. Gus expression is detected in the seed.

EXAMPLE 6

This example describes the transformation and regeneration of canola plants with the heterologous gene of interest.

Vector Construction a. pMON65422

To analyze the expression of p63 in Canola, a binary vector was constructed. A 3796 base pair fragment containing 703 base pairs of the p63 promoter (p63tr) (SEQ ID NO: 4), the *E. coli* uidA gene and the napin 3' untranslated region (UTR) was removed from pMON69812 by digestion with HindIII and Asp718I. Prior to gel purification the HindIII and the Asp718I overhangs were blunt ended using Pfu polymerase (Stratagene). The fragment was ligated into a Pmel digested pMON70650 backbone. The vector pMON70650 contains a nopaline T-DNA right border sequence and octopine T-DNA left border sequence, with a 35S promoter from the Figwort Mosaic Virus (FMV) between the two T-DNA borders, driving the expression of a chimeric EPSP synthase gene containing a chloroplast targeting sequence from the *Arabidopsis* EPSP synthase gene (GenBank identifier number gi:16272) linked to a synthetic EPSP synthase coding region (U.S. Pat. No. 5,633,435) and the 3' untranslated region from the pea rbcS E9 gene. Additionally, pMON70650 contains recognition sites for cre recombinase. The recombinase sites are 5' of the FMV promoter and 3' of the E9 3'. The resulting plasmid was designated pMON65422. DNA sequence analysis confirmed the integrity of the cloning junctions.

b. pMON65428

To analyze expression of p26 in Canola, a binary vector was derived from the vector pCGN11123. The vector pCGN11123 contains a nopaline T-DNA right border sequence and an octopine T-DNA left border sequence, with an FMV-35S promoter, between the two T-DNA borders, driving the expression of a chimeric EPSP synthase gene containing a chloroplast targeting sequence from the *Arabidopsis* EPSP synthase gene (gi:16272) linked to a synthetic EPSP synthase coding region (U.S. Pat. No. 5,633,435), the 3' UTR from the pea rbcS E9 gene, and recognition sites for cre recombinase.

A 745 base pair fragment of DNA was amplified from pMON70650 using the following primers:

```
CP4-Dra
5'-ACTTCACTTGAGCGGAAGCCATAG-3'     (SEQ ID NO: 16)

and CP4-Kpn
5'-TTTAAAACAATGGCGCAAGTTAGCAG-3'.  (SEQ ID NO: 17)
```

The CP4-Dra primer causes a single nucleotide substitution in the 5' UTR of EPSP synthase that eliminates an NcoI restriction site. The NcoI site was removed to facilitate later cloning. The product of the PCR reaction was purified according to standard methodology well known in the art and cloned into pCR2.1 Topo according to manufacturer's instructions (Invitrogen). The resulting plasmid was named pDMRUEZ033297. The sequence of this clone was determined using standard sequencing methodologies as set forth by PE Applied Biosystems.

A 737 base pair fragment containing the altered portion of the EPSP synthase gene was removed from pDMRUEZ033297 by digestion with KpnI and Dra I and ligated in place of the same size fragment of the vector pCGN11123. The resulting plasmid was named pDMRUEZ033298. A 3149 base pair fragment containing the *E. coli* uidA gene, and the napin 3' UTR was removed from pMON69802 by digestion with NotI and Asp718I. Prior to gel purification, the NotI and Asp718I overhangs were blunt ended using Pfu polymerase according to the manufacturer's instructions (Stratagene). The fragment was ligated into a NotI digested pDMRUEZ033298 vector backbone. Prior to ligation, the NotI overhangs were blunt ended using Pfu polymerase (Stratagene) according to the manufacturer's instructions. The resulting plasmid contains the nopaline T-DNA right border sequence, the *E. coli* uidA gene, and the napin 3' UTR followed by an expression cassette with an FMV-35S promoter, between the two T-DNA borders, driving the expression of a chimeric EPSP synthase gene containing a chloroplast targeting sequence from the *Arabidopsis* EPSP synthase gene (GenBank identifier number gi:16272) linked to a synthetic EPSP synthase coding region (U.S. Pat. No. 5,633,435), the 3' UTR from the pea rbcS E9 gene, and recognition sites for cre recombinase, followed by the octopine T-DNA left border sequence. This plasmid was named pMON65424. DNA sequence analysis confirmed the integrity of the cloning junctions.

Figure 7:
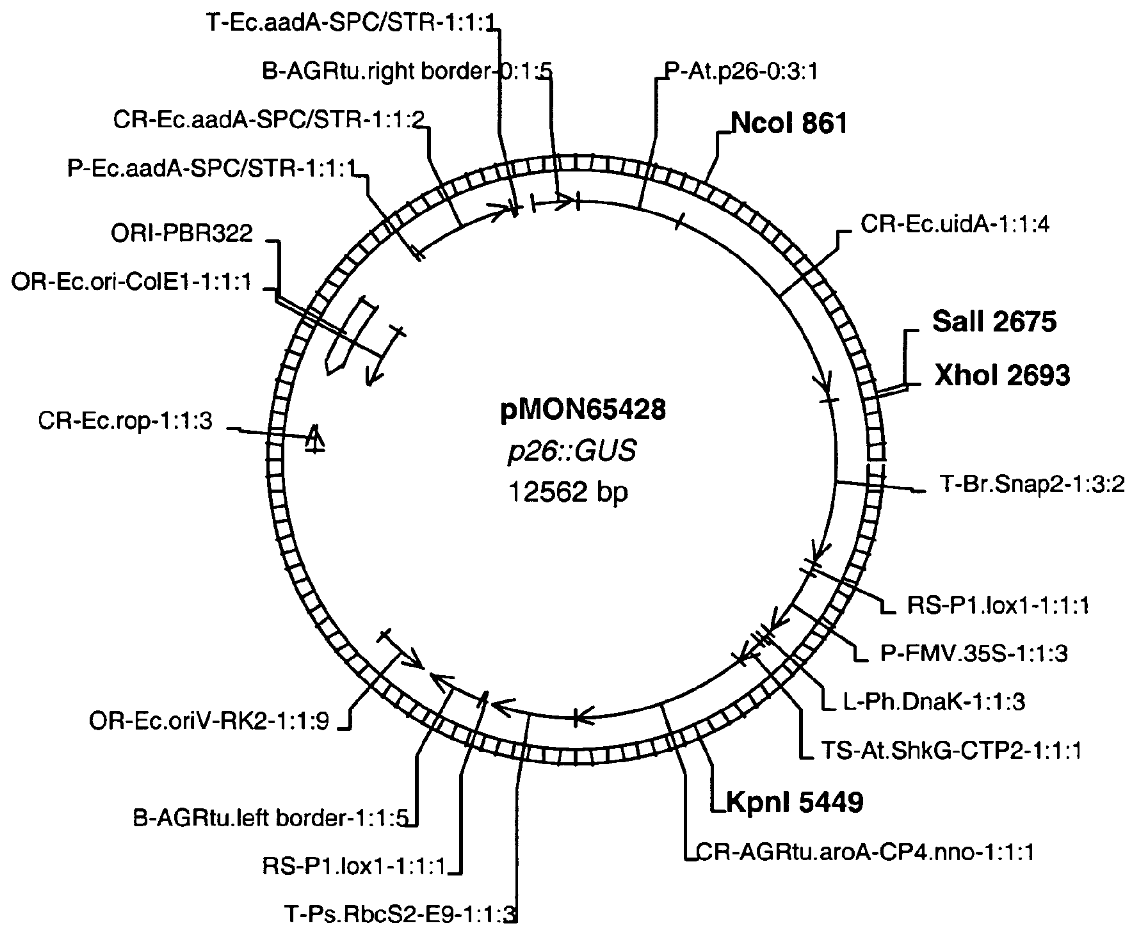
FIG. 7 is a schematic representation of pMON65428.

An 820 base pair fragment containing the p26 promoter sequence was removed from pMON69804 by digestion with SmaI and NcoI (FIG. 2, [SEQ ID NO: 2]). The fragment was ligated into a PmeI-NcoI digested pMON65424 vector backbone. The resulting plasmid was named pMON65428 (FIG. 7). The nucleic acid sequence was determined using known methodology and confirmed the integrity of the cloning junctions.

Canola Transformation

The vectors pMON65428 and pMON65422 are introduced into *Agrobacterium tumefaciens* strain ABI for transformation into *Brassica napus*. Canola plants are transformed using the protocol described by Moloney and Radke in U.S. Pat. No. 5,720,871. Briefly, seeds of *Brassica napus* cv Ebony are planted in 2 inch pots containing Metro Mix 350 (The Scotts Company, Columbus, Ohio). The plants are grown in a growth chamber at 24° C., and a 16/8 hour photoperiod, with light intensity of 400 $\mu Em^{-2}$ $sec^{-1}$ (HID lamps). After 2½ weeks, the plants are transplanted into 6 inch pots and grown in a growth chamber at 15/10° C. day/night temperature, 16/8 hour photoperiod, light intensity of 800 $\mu Em^{-2}$ $sec^{-1}$ (HID lamps).

Four terminal internodes from plants just prior to bolting or in the process of bolting but before flowering are removed and surface sterilized in 70% v/v ethanol for 1 minute, 2% w/v sodium hypochlorite for 20 minutes and rinsing 3 times with sterile deionized water. Six to seven stem segments are cut into 5 mm discs, maintaining orientation of basal end.

The *Agrobacterium* culture used to transform Canola is grown overnight on a rotator shaker at 24° C. in 2 mls of Luria Broth, LB, (10% bacto-tryptone, 5% yeast extract, and 10% NaCl) containing 50 mg/l kanamycin, 24 mg/l chloramphenicol, and 100 mg/l spectinomycin. A 1:10 dilution is made in MS media (Murashige and Skoog, *Physiol-.Plant*., 15:473-497, 1962) giving approximately $9\times10^8$ cells per mi. The stem discs (explants) are inoculated with 1.0 ml of *Agrobacterium* and the excess is aspirated from the explants.

The explants are placed basal side down in petri plates containing media comprising 1/10 MS salts, B5 vitamins (1% inositol; 0.1% thiamine HCl; 0.01% nicotinic acid; 0.01% pyridoxine-HCl), 3% sucrose, 0.8% agar, pH 5.7, 1.0 mg/l 6-benzyladenine (BA). The plates are layered with 1.5 ml of media containing MS salts, B5 vitamins, 3% sucrose, pH 5.7, 4.0 mg/l p-chlorophenoxyacetic acid, 0.005 mg/l kinetin and covered with sterile filter paper.

Following a 2 to 3 day co-culture, the explants are transferred to deep dish petri plates containing MS salts, B5 vitamins, 3% sucrose, 0.8% agar, pH 5.7, 1 mg/l BA, 500 mg/l carbenicillin, 50 mg/l cefotaxime, 200 mg/l kanamycin, or 175 mg/l gentamycin for selection. Seven explants are placed on each plate. After 3 weeks they are transferred to fresh media, 5 explants per plate. The explants are cultured in a growth room at 25° C., continuous light (Cool White).

The transformed plants are grown in a growth chamber at 22° C. in a 16-8 hours light-dark cycle with light intensity of 220 $\mu Em^{-2}s^{b-1}$ for several weeks before transferring to the greenhouse. Plants are maintained in a greenhouse under standard conditions. Developing seed is harvested at various stages after pollination and stored at minus 70° C. Mature seed is collected and stored under controlled conditions consisting of about 17° C. and 30% humidity.

Up to 5 siliques are harvested from individual R0 plants at several time points after pollination. Siliques are scored with an 18 gauge needle to allow the staining solution to contact the developing seed. The siliques are incubated for approximately 24 hours at 37° C. in a solution containing 50 mM NaPO4 (pH 7.2); 100 μM potassium ferricyanide; 100 FM potassium ferrocyanide, 0.03% Triton X-100; 20% methanol and 2.5 mg/ml 5-bromo-4-chloro-3-indoyl glucuronic acid (X-gluc). The stained tissue is cleared of chlorophyll by an overnight incubation in 70% ethanol/30% $H_2O$ at 37° C. Stained tissues are photographed immediately or transferred to a solution of 70% ethanoV30% glycerol (v/v) and stored at 4° C. until photographed. Samples were scored positive (+) or negative (−) for blue color.

Six out of 10 lines transformed with pMON65428 have detectable levels of activity in seeds from at least one time point. Ten out of 10 lines transformed with pMON65422 have detectable levels of activity in seeds from at least one time point. No staining is observed in seeds harvested from nontransgenic control plants. The data is illustrated in the tables below.

| | Days After Pollination | | | | | | | | | |
|---|---|---|---|---|---|---|---|---|---|---|
| Construct | 3 | 6 | 9 | 12 | 15 | 20 | 25 | 30 | 35 | 40 |
| p26 Expression in Developing Canola Seed | | | | | | | | | | |
| pMON65422 | + | + | + | + | + | + | + | + | + | + |
| pMON65422 | − | − | − | + | − | − | + | + | + | + |
| pMON65422 | + | + | + | + | + | + | + | + | − | − |
| pMON65422 | + | | + | + | + | + | + | − | + | + |
| pMON65422 | − | − | − | − | − | + | + | + | + | + |
| pMON65422 | + | + | + | + | + | + | + | + | + | + |
| pMON65422 | + | + | + | + | + | + | + | + | + | + |
| pMON65422 | − | − | − | − | − | + | + | − | + | − |
| pMON65422 | − | + | + | + | + | + | + | + | + | + |
| pMON65422 | − | + | + | + | + | + | + | + | + | + |
| Control | − | − | − | − | − | − | − | − | − | − |
| p63 Expression in Developing Canola Seed | | | | | | | | | | |
| pMON65422 | + | + | + | + | + | + | + | + | + | + |
| pMON65422 | − | − | − | + | − | − | + | + | + | + |
| pMON65422 | + | + | + | + | + | + | + | + | − | − |
| pMON65422 | + | | + | + | + | + | + | − | + | + |
| pMON65422 | − | − | − | − | − | + | + | + | + | + |
| pMON65422 | + | + | + | + | + | + | + | + | + | + |
| pMON65422 | + | + | + | + | + | + | + | + | + | + |
| pMON65422 | − | − | − | − | − | + | + | − | + | − |
| pMON65422 | − | + | + | + | + | + | + | + | + | + |
| pMON65422 | − | + | + | + | + | + | + | + | + | + |
| Control | − | − | − | − | − | − | − | − | − | − |

Having illustrated and described the principles of the present invention, it should be apparent to persons skilled in the art that the present invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

I claim:

1. A promoter comprising an isolated polynucleotide sequence selected from the group of polynucleotide sequences consisting of:

a) a polynucleotide sequence comprising the sequence of SEQ ID NO:4; and;

b) a polynucleotide sequence comprising a fragment of the sequence of SEQ ID NO:4 with promoter function;

wherein the promoter is operably linked to a transcribable polynucleotide molecule.

2. A construct comprising the promoter of claim 1, wherein said promoter is operably linked to a transcribable polynucleotide molecule operably linked to a 3' transcription termination polynucleotide molecule.

3. The construct of claim 2, wherein said transcribable polynucleotide molecule is a gene of agronomic interest.

4. The construct of claim 2, wherein said transcribable polynucleotide molecule is a marker gene.

5. A transgenic, seed-producing dicotyledonous plant stably transformed with a construct comprising the promoter of claim 1, wherein said promoter is operably linked to a transcribable polynucleotide molecule operably linked to a 3' transcription termination polynucleotide molecule.

6. The transgenic dicotyledonous plant of claim 5, wherein said plant is a dicotyledonous plant selected from the group consisting of tobacco, tomato, potato, peanut, soybean, cotton, canola, rapeseed, safflower, flax, sugarbeet, *Arabidopsis, Brassica*, sunflower, and alfalfa.

7. The transgenic dicotyledonous plant of claim 5, wherein said transcribable polynucleotide molecule confers altered oil content in the seed to said transgenic plant.

8. The transgenic dicotyledonous plant of claim 5, wherein said transcribable polynucleotide molecule confers altered protein quality in the seed to said transgenic plant.

9. The transgenic dicotyledonous plant of claim 5, wherein said transcribable polynucleotide molecule confers altered micronutrient content in the seed to said transgenic plant.

10. A seed of said transgenic plant of claim 5, wherein the seed comprises said construct.

11. Meal from said transgenic plant of claim 5.

12. A method of making a vegetable oil and meal, comprising the steps of: a) incorporating in the genome of a dicotyledonous seed producing, oil-containing plant a promoter according to claim 1 operably linked to a transcribable polynucleotide molecule conferring altered oil content; b) growing the dicotyledonous plant to produce seeds; and c) extracting oil from the seed to produce extracted oil and meal.

* * * * *

```
                              SEQUENCE LISTING

<160> NUMBER OF SEQ ID NOS: 17

<210> SEQ ID NO 1
<211> LENGTH: 913
<212> TYPE: DNA
<213> ORGANISM: Arabidopsis thaliana

<400> SEQUENCE: 1

gtttgataac tcgtctcttg ttaggatgat tgctagtttg ggtgttgatg agtattatgt      60

gaagcaacaa tggagtttgg tttccgttga gagtaagaag attgttgaag agaagtataa     120

gttgttgcaa gctaaggagt tggaatttgt gttggagaag actaagtttt tgaatgaggt     180

tgcttctatg ttcgttgaag cttcgaagaa caagccatta gatacataga tttatcggtt     240

tttaaaatcg gaatgctatt gccaatgcct tcttttgttt tcgatttagg atttaccctc     300

tctttttttg tcttcttcac tttttatctt tcaatgtaac tttctggtta ttttatcttt     360

gttaaactct gttatggatt tgtagcttaa atatgataaa attgcttaag gccagattct     420

gtgaaacatg gaccagaaca gagcaagtta tgttgaattg actcgtgtaa ttcgtgaaac     480

agaacatagc aagtccaagt tgtgttaaaa actgcagaga atttgacaga ttggtggaag     540

taaaaagcat tcttttgcaa ctcattttaa gatcggcaaa gaaaaaattg aagtaacaga     600

accttactgt aacactattc gttactctaa agctgtgtta tattgtttag acagaaataa     660

tcaaactctt gtgataattt ggtagatgat aacaaatcag aactcagaag gtcaatcttt     720

ttttattctt aggtgaagac aagttggtta tttcaaagat cacgtgctta ccttctaaaa     780

cagccttatt gatctactgt tgtacctaat gagcaaggac tatttgcaaa tctttttact     840

tcttatatag aagtctcaag acgataaact cataacaact aaatctctat ctctgtaatt     900

tcaaaagtac aac                                                        913


<210> SEQ ID NO 2
<211> LENGTH: 813
<212> TYPE: DNA
<213> ORGANISM: Arabidopsis thaliana

<400> SEQUENCE: 2

atcaaacgtc aaaacatgta ctcccaaata tattttattg gaatatagtt ttggagatat      60

ttttacctgg ggggagatgg aaccaaaata agatctagaa atgtgattgg ctaacgaaag     120

aagcacaata agttgacaag tgacagtgac aatttatccc tcgacaacaa cacacattca     180

catatatctt tttattttat tatttttctg tgtgtcttta aagtttacag cacaagtagt     240

ttctaaatct tataatcaat tttcattgat aaacagaaat ttaaaatatt taaatagaca     300

aataaatgat caaatctata tttctataca agagttaatt cacaaaaatt tgttgtgaaa     360

caaactcttt ctatatttct atacaagagt taacatattt ctatataagt tattgtaaag     420

atcaaaatat gaaaattatg gtataaatgc atagacacat atatacgtgc cctattaaaa     480

gaggcagcga gaagataata taggaggaag aggaagagga agaagatggt gaagaagaga     540

gttaatgcaa ctgcaagaag atagtaacta atcagcaccg tccattttttg tcatctaatt     600
```

ctttcttact tggccgcaac ttccaaccac atcacacact ctttctattc ccttatatat 660
tcccatctca aaagttcttg gagacacata aacattaaaa aaagaaaaag aaaaaaacta 720
taaacataaa cgccaatcgc aactttcttg tctttcaatg ggagagaaag gtttgaagcg 780
gtctggtgtt gcggtggtgg ttgcattact agc 813

<210> SEQ ID NO 3
<211> LENGTH: 2017
<212> TYPE: DNA
<213> ORGANISM: Arabidopsis thaliana

<400> SEQUENCE: 3
cgtgttggaa ggtgagagga aagaaggcag atcgcggatt tcgagagaag gtagattcgg 60
gaactcgaaa acggagttgt ttcctgtaga gtaattgtaa taaatgtcga aagcgaaggc 120
tggttggatc cagagatgaa cagagggaag atgaaatcta cgcgccactt ttggaaccca 180
gttgggaaga atcgtgtaga tcaagcaact tacgggagag tcaccattct gattagcttc 240
gatgaaatcc gatagagctt tatcgccatt acgttcgaag tgtaccaacc cggttttgga 300
cgtcgtcggt gttggagatg actccgtcgt cgaatccgtc ggagaaagta aggaaagaga 360
gattttcgac gttgttgtgg tttgggatca tagagcggtg aatgacagag agacacgtgg 420
cgaaagttac acgtgcgcca gttgttttga tgagccgacg agcaaaacgg agagatgggt 480
tcacgtgacc ttgcgccgga aacgttacca gtagaaaatg cggttgcgcc attttttgaa 540
gtgactttct taatacgtac gaggtgtgtc tcctcgtgga tttgtgctgt tatatgtata 600
taaatggaaa atatattaga tgagagtaat gggatttcat ttggggtcat gtgacatgag 660
ataacatgtt ttaccgcttt tggcgtgatc cacgacgtac gccatgatgg agatcataat 720
aagtatcatg ctgaatatac tatataattt atttataaaa aaaatagaac gaaagaaaaa 780
gtatcatgct gtcaaaaaga aaaaaaatat catattttta tagagaaaaa actcgaaaaa 840
tatctgttta atatctatag ttgtttgaat aatatctaaa ttaattttat gtttttaaat 900 gctttttttaa ttcaaacatt caaattcatg attattatat tttaacggat gttctaactg 960
tggttgaaat ttaactcatg atattcacga aatgtataat ctattttcta aagtttacaa 1020
atatattagt gtaatctaat gggtaaatgt ggattgattc tcttcataaa tctaagttcg 1080
gaatcccccc ttctttccta attaatccaa atttattaag atagtcaatc ccctctttgt 1140
cctaattaat ccaaatttac taagatagtt agtcaatcca cgtttaacca ccatactaac 1200
ctaatatatt tgtaaagttt agagaataga tagtatatat atttataaat accatgagtt 1260
aaattttaat tatagttaga acctcccatt aagtccaaaa tttaaataaa cgaaagcttt 1320
taaatttggg aaaatttaat aatatatgta ttaaatggca aataaaagtt agatgagagt 1380
ttttttaaat tttttattat aaaataattt tttgcatgaa attgttttta agataaaatt 1440
ttgacataac caagtattat tttccgccac gaattgagtc tacgagagat gtcctgtctt 1500
taaacctcgt aaagttttgg tcttacccaa cccaataccc acaaaggtaa acgaccatac 1560
cggttaataa tattctaacc ggtttataag tttacataaa tcatttacta atccgcgtgt 1620
aattaagttt tatgaaatgt ggttattttg taggtcacgt gaaatttatt aattttttag 1680
tacttgtttt tctttttttgg gttcaactag ttactttttt cctttgacat caaaattatt 1740
gtagacgagt ggtccatata tagatggtga aatgaaatga atattgagta ataaataaat 1800
atagaaagtg aacaaaaaaa attagtggaa aaggtaactg gaaagaaaag gcttattggc 1860
ttggcaagat tccataagtt tatttcacca aaaaggaaag agtacttggc cttgctctct 1920

```
ctctctttta aaatggtaaa ctggtaaaga taggagactc aatttctagt tcatcaaaac   1980

atatttggcg ttattatttc tgtggtcact tgaatac                             2017


<210> SEQ ID NO 4
<211> LENGTH: 705
<212> TYPE: DNA
<213> ORGANISM: Arabidopsis thaliana

<400> SEQUENCE: 4

aagcttttaa atttgggaaa atttaataat atatgtatta aatggcaaat aaaagttaga     60

tgagagtttt tttaaatttt ttattataaa ataatttttt gcatgaaatt gtttttaaga    120

taaaattttg acataaccaa gtattatttt ccgccacgaa ttgagtctac gagagatgtc    180

ctgtctttaa acctcgtaaa gttttggtct tacccaaccc aatacccaca aaggtaaacg    240

accataccgg ttaataatat tctaaccggt ttataagttt acataaatca tttactaatc    300

cgcgtgtaat taagttttat gaaatgtggt tattttgtag gtcacgtgaa atttattaat    360

tttttagtac ttgtttttct tttttgggtt caactagtta ctttttttcct ttgacatcaa   420

aattattgta gacgagtggt ccatatatag atggtgaaat gaaatgaata ttgagtaata    480

aataaatata gaaagtgaac aaaaaaaatt agtggaaaag gtaactggaa agaaaaggct    540

tattggcttg gcaagattcc ataagtttat ttcaccaaaa aggaaagagt acttggcctt    600

gctctctctc tcttttaaaa tggtaaactg gtaaagatag gagactcaat ttctagttca    660

tcaaaacata tttggcgtta ttatttctgt ggtcacttga atacc                    705


<210> SEQ ID NO 5
<211> LENGTH: 88398
<212> TYPE: DNA
<213> ORGANISM: Arabidopsis thaliana

<400> SEQUENCE: 5

gatcgtaaag ggaaacgata tgtctacgat ggtttgtata tggttgaaga atattgggtt     60

gagagagatg ttagaggtaa gagtgtgtat aagttcaagc tttgtagaat tcctggtcaa    120

cttccattga cttgatatta gtataaaata aaaactgatg atgatggtat aataagattt    180

gagggaaaaa aaaatattat tgaattgtag agcgtttttg ttaaataaaa atagaggact    240

aaagcttctt ttttatttta ttttattatt gtaatatatt catcaaaaga aaagtgaaag    300

gtattaataa gtggaagtcc taacaataac taataagtga aaggttataa atcagacttt    360

taagtgtaga gctaactggt tttttttttt gtaattatca aattacctta aagttaatat    420

atataaattt aaaatatcaa tactttctta cactattaga aacagatgga gaaagattct    480

ggtaaggtgt cagatttcta tttactgtgt ttttggacaa aaaaacaaag gttcgagtca    540

atttactgtc gtgaaaaaat gtctatttat tactatattg taatctcttt tttttttttt    600

ccttcgacta tattgtaatc tctttgatat atatgtggta gccattcaaa agaataagaa    660

aaaaatttaa ttgctatatt gtgattttgg attctagatt ttccgatagc taaatataaa    720

acatgtattc tcagaatctc gctgcaatat tatattaaga ctagatttta acccgcagta    780

caccgtgggg ctataatttt tagaaaaaat caaaatgtaa tatacttaat tgattaacat    840

tattatataa cctattattt tgtatttttt gaatttaata tgtggtacaa cgggcaaatt    900

gtttttatta gtataggcaa taatgttaac ttttacgatc ttttttgtat taaagttaat    960

aattttatat aagtacaata aaaaaactaa tgctgataaa atattaaaat aagatttaaa   1020
```

-continued

```
ccgtgttatt acttttggtt gatgatatta taaatatgta ttaatatcga tccaaacccg   1080
tcccaccata taactctcat caaatattac tttttataag tttaaatatt attaatgttt   1140
ataaagttaa aatatttcaa taatatattt caaaaattaa tacttttttg ccttttatgt   1200
aatgacattt tttgtaattc ttactaaaac aaaataagtc tacaaaatgt aattcaatat   1260
tttaaatgca gataatgtta taaataacta tttagtttaa tcataatttg taattgatat   1320
gtacttgagt ttttggatta cctgtatttc acgtcattta atagcctaaa ttgggtagtt   1380
ttgtaacatt atttgaaaca ataatattat cttaatacat gtacatttta ctaactgaaa   1440
aatatgagat tgattatttt tataacacgg aaaatatgag atagattttt tatattacac   1500
tgaaaatgaa tgattcaaaa ctaaaaatca tagtgtaata tagtttagcg tagaaaataa   1560
ttaaaaggat tttatttatt tattttgttt cctaaatttt agtttagact cagaaaacaa   1620
ttgtttaact tccttagaag atgataaaca tatatggaag atttgaatct ctattcatat   1680
atatttaaaa atcagtaatg tcaatataat taaaggatag attagaagaa attctcttga   1740
atgctaaata attcatttgt tatttataaa cgaaatatta aatgctgtaa aaaatgaaat   1800
attaaataaa tatggaaaga aaatcctacc ttaaaagatt gtgtattatt gaaatcaatt   1860
tttattacag caaattaaaa ccaaaaatta ataaatactt aagagaaatt ttaggaatga   1920
tttcgtttga aataatggtg gagttaatat agagagattt taggcaatat ttttgttagg   1980
taaatatttg atttaaaatt tctgcataaa ttcagtggca ttgagtcgta aataagtcca   2040
agtccaagat ttatttgtta aaatggctgc aaaaaatgtat atatagattt gcctcataat   2100
caaaaccttt ttactgctta aaaacaaaac aaaaaaaatc cttttaaaaa caaatgtaaa   2160
agtccttttt attctaatta aatctaccga gtataaaagt ttttttttcc aaaaatgtaa   2220
atatttccta aaagtgaaaa cgatttagct ttacaatcta tgattataaa cctataaaga   2280
tggaaatata ctttacttta catatatcca ttatggaagt ttgtttactt acaaaaaaata   2340
tgaatccctt tgggaaatgt ttttacacaa catattattt tccccacata aatgcacatt   2400
atgaatggaa ataaaaagta aattttatat tatttttctt atcaattaag taatttccaa   2460
atttgaattt aaagcatgat ttatatggaa agccaataac tttaacaaaa acaatatttg   2520
gaaaaataat atttcattaa ttaagattat cttcttccac tataaaaaga gttttaattg   2580
catagaatca ttcacttcat aaatatttag agcagtcaca tttgaaatct ctcctctctt   2640
attcttattc ttattcttat tcttattctc ctaaacgtgt atctatctat ggagctaatc   2700
agtcatacaa gttgatacat attttcttaa taacgtcgag tcgggtaagt aacttttgtt   2760
ttttttctta atatcataga atgaaagatt ctaaactatc gctagagttt tctataaatt   2820
ttttagatta ttttttttca taatctctta aaagttttca aacaatctct ttattttaat   2880
gatattttca tgattttatt ttgtgaagaa aagtctataa aatcatatac caataatata   2940
atattttaat tcatcaacaa tcaatttttt ttttaataac acaaaacttt tattgattta   3000
tgaatccttt tattgtgcac tcattgatgt agatgattat ttttcttttc aacttatttt   3060
caaacaaatc cttaatagtt tttagattta ggccgtgaat ggttgcggtt tttaaaatgg   3120
ttttacttag tttttttcat attctatttt acaatcattc ataaattaga aaaagtggtt   3180
ccctaaaata gagaatttag attttgagag tttttataga tttggaagca ctcttcaaaa   3240
aacttttaag agattttcag tgtttgtcat gaatgtgact atatttctct tttgactaac   3300
ttctaatttt gtttagttaa ttatttagtt tcttgcaaaa tccaaaagct gaaatttaaa   3360
aaccaaaatc taacgtcaac aaaaaaaatc tcaaaaccaa aaactaaaat cttaaaacca   3420
```

-continued

```
taaacattca tagctttaaa ccagtgttct agaaagagac ataaacttag acgacaaccg   3480
cctaaacttg catatgactc gttttggtgt attttactaa ttttcaacta aatttgtcta   3540
catatatata tacattgtta taaacgttta taaatcgttg gatataaatt aaataaatat   3600
tttatctaaa ttgtgtttac aaattaaaac ttttctatta taatagatat ttttacataa   3660
ttttatgtat aatatcatat ttataaatat gttataaatg cttaaaccaa gtaaaattgt   3720
ctaggcctct attagatgtt ttaggtacat gaactaggta aacgcctgtg tagcgtttaa   3780
cgctttttta aacatgtttt cacttttttt aattcttttg tacatattcg ttttctggtt   3840
tctattagat gttttaggtg gatgcactag gtcaccgtcg acttagcttc ttagaacaaa   3900
tttttctatt tgtttttaac atattacttt tgtggtttct atttattata cctaaataat   3960
atagtaaata aataaacatt aaaacctaaa aactattgcc caatagttga ataaaaatag   4020
gaaaacccac cacatagtat aatactaaat gcaaataact atttatagca aaagaaattt   4080
gaaatttcta taactataac tagtaataaa gtagatgaga acaaaactta aatgctatgg   4140
aaaaaactta caccaccact actaacgctc cacgtaatca ttaaagttaa ttagtcgcta   4200
atcattcgtt ttgggtattt aatattttaa agttataagt tataaccgaa acaattaacg   4260
tagttaatgg ctccattgaa aaacagattt aaaactcaaa cacacacaat taaccaactt   4320
aagtactgtt cagtgactca tcgtttttcg agcctcagag attatcacaa gaagaagaat   4380
ccagagtccg ccgggaaaaa aaaaaaaaaa aacaataaga agattacaaa aacaaagaat   4440
tactccgttc atcttcgcta ggttctgttt caggttcagt gaattttttt tggttcttct   4500
cttcttccag tgtatacttt gttccctgct ctgtatttca tagttttctt catttctgtt   4560
ccttgttttt tttttttttg cgaattcttc gtttaaagtt cgctttttct gacaaattta   4620
tacacctttt tcgttttttt ctgagactca agcattcttt gatctttcgt tttcttgaat   4680
tttgtgtttt gtagttgaaa ttgcttcgaa ctctctggaa ctttagggtt tgagatcgat   4740
tttcctaata acggttcgtg ttttttcaat ctcgatgctt ttacagaaaa taacggttcg   4800
aatttcaaaa ttcaaaattt tcactctccg tcatcttcgt cttttaccat ttgtgttatc   4860
cctaattgtt acagttttaa gatttagccc tagttttact gtgttcacac ttgcgccgta   4920
taaatgctct tactttaatt gtcattttca gccataatct tggaattaca ttgtgggatc   4980
tttctagatt atgtgtgaga acatagaaga ttaagatagt ttctgaattt ggatagatta   5040
gtgattttgt gaaacaattg tatatatgca ggatgatgat gactcaaagg atctctcctt   5100
ctaataagcg tcggagagtc tcttttgtta gagattttcc tcaatttagt gttaaagatg   5160
aaagtgacat tggtggtgat gatgttgcaa ccataaaaga gaacttggat ggtaaagaag   5220
atagtaactg tgttggtgtc gcttatcgcg atcaccatag gcctaaagaa gaatcgtttg   5280
attcgataat gaagaaagct ggctttaatg tagctaatgg taatcttggg aatggaaagt   5340
ttcctccatc taagaggaat gttcctttac cttgtgaagg taaagtgcaa cctcttagcg   5400
tggaggaagg tattaaacta atggcttatg aaagccaaag aagacgttgt tttggtaagc   5460
ctttggtatc aaccaaagtt gtgcagaaac atagatactc acctgcgaag aagaagttga   5520
gtaatgcaac tgcgttaaga gtaagacact caccgatgaa gaagttgagt aatgcatcaa   5580
gactaagagc aaatgctcat agaccgactc aacataaaga tgaaagacgg tctggagtcc   5640
tctcggttat acaacgaaac cggctttcga aagatcttac cccacgccag aaggttcaag   5700
aagtgttgcg tattttcaca cttgtgtttg atgagctaga tcgtaacaag gcagcaagaa   5760
```

-continued

```
gaggtggatc agagactgcc aagagcagga tagattacca aacttggact attctgaggg   5820
aaatggggat gcaagttaac tctcaaaaga ggattggatc agtccccggg atcaaggttg   5880
gagataaaat tcagttcaaa gcagcactca gtgtaatcgg tcttcatttt ggcatcatga   5940
gtgggattga ctacatgtat aaaggaaaca aggaagtagc tacaagcatt gtttcatcag   6000
aaggtaatga ttacggggat agattcatca acgatgtgat gatctattgt ggtcaaggag   6060
gtaatatgag gagcaaggat cataaagcaa tcaaagatca gaagcttgtt ggtggaaatt   6120
tggctttagc taatagcatt aaggaaaaga ctccggtgcg agtgatccgt ggcgaaagac   6180
gattggacaa cagaggaaag gattatgtgt atgatggttt atacagggtg gagaagtatt   6240
gggaagagag gggacctcaa ggtaacattt tgttcaagtt taagcttaga agaacttgtc   6300
aaccttatgt ggacttttga aagggatagt gtgagataat gaaactttag tttttggttt   6360
tttggtaaga tagtacttac ttaggtccgt gacctgtaat atcaaaccaa ctatagtgtg   6420
gtttaggata actttcttt ctgacagtag taggttcagg atcttgtgtt gtacaaattg   6480
aatgatcctt ctgatgtctt cataactaat gatccttctg tttctaaact tcataaatgt   6540
tacaccttt tgttaatatt atattctaat gatgtaaagt tacttcgcaa atcttggatt   6600
tcttagtttc ataatccggt aaagcagaag aacttcaata agttccttaa acttgttttt   6660
tcagatatgg taatatgggt ggaaacatga ctttgaaacg tttatataga atcctttcca   6720
acattttaat ctaatcagaa aaaggcaaaa tatctaattg gtgagaatcc acagcaaaat   6780
gagaaaccta caaggtttag tcacagacag ctaaaaacca aaccaaatta aagaaaaaag   6840
cgccaaagtt tacgaaggaa acttaaagcc cattgacttc aatatctcaa cacagctctg   6900
acttttatca accttgtcct tgtcttcctt aaccttgtca ccggagtttc gaagcagagc   6960
ttcaatgatt tctttaaaag gtataatctc ttctttctct ttctctttct tcttctttct   7020
tccatcttct ttccatttcc caccacccca ttcgtacgac ggctccatcc acggcggcaa   7080
cactctcctc gctgctgctt caccggcgac tgttgatgtg gaacctaatt tcttgtccga   7140
aaccctagtt tcaatctctt ttggtggatt caatctcgca tcgtcagact ctggtgaagt   7200
gggaacagaa accattacga ttccttcttc cggattcacg ggaggagata aatgccaatc   7260
ttctaaaatc tctgaactct ctgtatctga acgtttctcc attctaaaaa gcttcggaat   7320
tcgaaatcgg cgaaactgtt aaaaaggaag agactttctg cttttctgtt tgatttgaca   7380
caattcagta aacttgttta gtatcggacc tttttgggct ttatgagctc taaaattaaa   7440
atgccttatg gactgttttg atttgaaaga ttagagacaa ttcagagaac ttgtttattg   7500
ttggaccttt ttgggcttta aaggaaaata tgttatgggc tttaacggaa tatactttat   7560
gggaaagatt aaagacaatc cagagcattt gtttgatatt ggaccttttt gggcttttaa   7620
gttggatctt ttggacccaa ttcagatttg ttttataatt tgggcattca cttcattcac   7680
ttaatgatat tgattatttt tttgttaagt acagatttat catttttttt tctcagattt   7740
atcattttta atgactcttg aaatcttgta cccaaatttt tttaatagaa tcttaaaata   7800
catgacctta tatcagtatt agatttaaat tttctttgaa aagttgagaa accaatgacg   7860
gtattaatct attttgaaaa cacatggatt tttttctata tatttatata tataattcat   7920
tgacggtatt atatatatat atatatatgg taatttgatt cattcattca tttgaagtat   7980
gataaaaaaa agttgataca cccaaattac actaattaat atcatcaata cacaacacat   8040
ataataaata aatatagaaa agatttacgc tttcaaaaac gagaaccata ttcactatta   8100
ttatttttct tcaaaataaa tctcattaga gattgtcatt tttgcctatc atattcatat   8160
```

-continued

```
attggatgaa actccaaagt tatctaatct tgacaatgat actagatatc ctctctagga   8220
gtatgaatga tgatgtgatt tcatgagaag agagaaaata aaaatcaata caaagatttg   8280
tttctggact agtttgagat aattgagatc gactcatcac atttcatatc agaatggatt   8340
gcaaataaat atctatttta ttaattagtt aatgataatt aatagatagg aaaagaaaat   8400
tttaaattca agaactacaa ggataataac acatgcattt taatttatcg caaggtgttc   8460
tttggacgca tcggcccaat cccttccgtt tctgtaggca tagagcatta caattgccag   8520
caccacaatc tatttcggtt aaagcctcct cacaacgttg ttgttgttgt tgcccttcaa   8580
tttcattcac catcatccct acaaaaaaat ttgtttcaat agcataaaat atcaattata   8640
ttttttttaa acataaaata catgatttta taatagatta agagcatgct aaatatataa   8700
aaagaaacct agaataagaa tgatgaagaa agcagaaatg atggatttag tcatttttgt   8760
gtgataattg gagtttctga attacaatta taatgacaat agttgtagtg tacactgaaa   8820
tatcacaaac aagattatat atatatatat atatatatat atatataata aagatatatt   8880
tttacaaatt tgattgatga attttggtag gtaaattatt taaaaatctt gtcatctata   8940
gttaataatc tctatatctc ttttttaaaa acaaatccaa tttttcccta acaattgata   9000
ttctagtgtt tcctcaaatt aaaaattcat gatttcaata aaatataatc attactaaaa   9060
tatatcttac ttacttagca aagtaataaa atataatcat tactaaaata tatcttaaaa   9120
attctgcagt tactgctctc tgagagtttc gattctgttt tcttaccgta atctttcttc   9180
aattgttgtt aacttgctat tactaatatt ttttgtttac gactttgaga ctcttcacat   9240
aaagccttag tgattttctg atgaagtaat cttatgcata tattcatgag aagacactac   9300
catattcata aatttaaaca aaagctcata tgctcaagtt ttcatttaaa gacctggtgg   9360
ctaattatac ctttcattta agtgatgcaa tgatcgataa aataattgta acagaattcc   9420
ttcacaaacg ggtaaacaat acaaaggatt agccatcttc aataaagcac aaagaggatt   9480
gaaaaagtgg acaagtaaaa ccaatgatga aagggtctct tgggtcaaaa atgtacataa   9540
tttataactg aaaaaaagaa gaaaatttga tggaagaaac gtgtggaaca ttaggagaaa   9600
gaaagagagg gatataaata acccaaattt agaagattta aaatacccga aaatatgtga   9660
atctgttttg attcggctgt tacatatatt gagatgatag gcgatgtgtt gaagctcaag   9720
agttgttatg tgggagaagc taaggtaagt tttaggatga aaccgatgat gagtccgatg   9780
agtccaacca tagctgccaa cttcaaggat agcccatttc cgctgttcct ctggtttctc   9840
cgcctcctta ccgtttcctg caatgtcgtt caaaaacatt ttaggcagta tcctttgtta   9900
ttaagcactg ttatgttcac atgattttgt ctgaatggta atatgattgc aagcattaac   9960
caatgctaaa ctatcaagga aaaggttcat ggaagcgtac caattcatgt tgcagctgtt  10020
gtgtttgctt aacggctgca tctcgctctt ccttcagccg ctgtatagtc tgttcataca  10080
tattgatggt ataaacgtcc agaaagagga ttaaaacaag acacgaatta atctttctta  10140
aattatgata tgaatgtggc cacttgtgag gttctgtgag atacatttgt tcaccttatg  10200
aagaaaggta taataataac ccaaacaaaa aattaaagct ttgaaaacca gcgtatgtct  10260
cactgtccca accaatcaac tcagtctgtc attacagtat ctatagcttg aaaaccaaaa  10320
gtgcgaatac tagaaagtct aaaatttgat tgaaactttg aataataatt cttgcagaca  10380
ggtatcacaa aaaagggact attcataagg tgtctgtcta tgcaagaggt ccatggtacg  10440
tcaacatact aagtaaatca ttaccacatg cagattaaat aatataggtg ggtactcaca  10500
```

-continued

```
gagatggttt ccgagctttg tccatcacca tttgttgctc cggattcaga ggatctttgg  10560
gttgtagacg gggtaatata agagactttg agcttacatt ctgttaatgt ctttccactg  10620
tccttggtga actagacaca caagtattgc atatataatg tcaatttgtt ttccaaaaac  10680
tgcagaaaca agaagaatct taataaaaaa agttttaaac ttggatttct tacagtgtct  10740
tgaggaagtt catccacatc agtgtgtgga ggtacaatgg tactttgcag gagaaatttg  10800
tctttgcact gcatatctgg aggatactct cgttgcgctt gtagagtaac tataattaag  10860
aagatcttaa tcatctccat gttcaagttt taaactgcta atgaaagaag ttagagtatg  10920
aggaattact atacctctaa tgatgcaaga gtcccatggc tgaatgacac cagtgttagg  10980
tcttacaaaa tacttctttg gagatgttgt tttcacctga ttgatgaagc caaaaacaca  11040
aaagaaagaa gccattgtaa caaacgaaat aacttgatca caagacaaag catatgaagt  11100
tggtggtttg atgcagaaat taccttgaaa gcaacatagt tctctgtttt attggcaact  11160
ttaagatcac agtagctttg cttctcaagt tcaactgaaa caaaatcaaa aattccaaat  11220
gtcatccaaa ggaagaccct ccaaaaagtt tcaaacagca attttcttaa taaccaagag  11280
aatcagcctt atctaaagtc agaacctcaa aagctcaaag aagttaacaa aaacttgatg  11340
ctggtgtatg taaacaagag gaaaacaagc attgatgata cacacaattt cgaaatctct  11400
agagaacaaa aagatggtaa attcgagaga agccttttct cattcacatt tcacaaatta  11460
agaatagata tccctagaat taaccaagta tagatgagac aaatgcatgc cattgattaa  11520
cgaagagagt gtagaagaat gcttacagag aaatttgagt tcatcaggtt gaatggagat  11580
aagctgattc tcgccaacgc cggtcatctt tttttttgt ttgcttaaag ctacgacgac  11640
aaaagtttca caatcaaatc tctattgaaa aaagtataca acaacatcaa aaaatcgaag  11700
ccctaatcca aacaattccg attttatcta actttttcc agaaaaggta aaaagagggg  11760
aaaaactgag aaatgaagag aggaaaaaaa gacggatcaa acctgaagaa aacaaaagtc  11820
acggtcccaa cgatgaggga ggaagaagct gcttattttt ttctctggct ctcccgataa  11880
tcgctctcca ccaatatccc aaaactctcc tcctatctct ctcctctcgt tctattcgtg  11940
gtaacaaagg caaaagaaga gagagaaaga gaaacgggga agacgaaacc caaaggcgct  12000
tcgtggagcg gccacgtgaa gtcgaagcaa agtttccgta cgattttcct ccggcgtcgt  12060
ctccgggaac tgcggggaag aagaaagagc gaaagagaga gaagagaggg aaaaatgtga  12120
cacgtgtgaa aacagttgtg cattgtaaga gacgaaaaaa caaaggttaa aagcgacagg  12180
ctggaaaaaa gaggatgatg acgtggcaga tattgattgg tgtttgattt tatatagtgg  12240
ctaaaaaggc tataatgagc tttcagggtg gtaggccatt tttcgtctct cacgattgat  12300
gatattttaa atttatttct ccgtgtccat taatgattga ttgttagcaa gtaattaatt  12360
atcggacata aaagtcatca tacagaggaa agagacaaga aaaatactca atcattcgtt  12420
tcttttttcc tgctttagct ggaaaattca tttacatgaa tgaattacat gattttacat  12480
gtaaaaaatc tattttgaaa agcaatttca atgattcaaa agttttattt taatgattaa  12540
atcagtcata tttctgaaaa agaatactaa agggtccaga ttctacatac tcaagatcaa  12600
aacaatcaac attgatttac ttttcttaaa ttactgttac tgtaaattac atgaaaagaa  12660
atgaaatcca aaagacgaaa caaacaaaca attattacaa gagaaaagag agtagctagc  12720
tacctttgga gattgaagac aacacaagac aagactggtg ttgggtttgg tgatcattta  12780
aaagttgaga gacgaggaag tttgtccctc agatagtaaa gtcttgctct tctcactttc  12840
ctgtgactta ccacttttat ctcctttatg ttgggagagt atctgttaaa ttcaaaacac  12900
```

-continued

```
acatcacatc agatacatat tctaaaccaa gatcaaaaca tattacttga ttgtgtagat  12960
tagtatctgt tcaagatcaa aacatatcag ttacatatta cttcattgta gaatcagcca  13020
atagtactgg aaagttcata gggactagta tgttatgata acggctagac tctagagtga  13080
ttaagattaa aggttggtgc gcgtttctgt agtaaataag cacaaagctt ggtgacctat  13140
aatgctaaga cttccagcat ttatgtacta gttcctatag tatcatactt ggagtagcaa  13200
ttatttcctt ttttcgtgaa gaaagctaat acatatgatc agatatagaa ttgtaaatct  13260
cttaagttct caagaagcga agactatgac tgttcacgat aaaagaagct aattccggtt  13320
tgttttagag ttcctaaaat ctctctcaaa gccaaaagac tccttaacaa ggtcaaagac  13380
ccttaactct gactatctaa tactatttac atttatactt atcaatatac ccgagtaagt  13440
gtgtgataat aggatagtta aggaagaata aacttacatg ggaaagacga tttcaacacc  13500
aatgcctgca ataatcctcc ggatacggat agtagtgtgg atgcctgcat tttgtctaga  13560
catcacaata cctttgtaga tagatagcct acgtttgttc tcaggaactt cctgtaaaat  13620
caaacccacc atgtcgtatc aaaatcttgc agttaaatgc ataaattgca taagattata  13680
cggggacaat gagttttacc agtttgattt ctacaatatc cccagtccta agtccaggaa  13740
ccggtcttac agtctctgca acctcaatag ctttcttgtt cagtagctac agaaacaaaa  13800
agcaaatcaa catttcattt ctccaatgcc taaaagataa ctgatgattt aagaacagga  13860
gccaaaacaa ctacagtatc agacatgtat aatcagattc agagccaaaa caaaacacta  13920
gacaatctca tagaatcaca ttggataatg aactaacccc catgatatct ccgagcttga  13980
ctctcgtctt ccacggaggt ttagcttcct ccgccgcaac agtggcttct ccttctcctt  14040
ccgcttcagt ttcaacagca ttctccacaa cagcctcagt ttcaccttca gtactctctt  14100
cagctttagc gataaactct tttctcttct tggaatcgat ggcgaaacca aaattggagc  14160
tcgaatgatt gagaaaaacc ctagaaactg atagtcttga gttcactgat gatgctcgtg  14220
gtagaattga agaaacccct aaattcttcg acgagaaaga aggggttctc ggtatcatat  14280
gcaatgcctg gttccataaa tggtagataa atacagaatt caaagaagca taagtatgaa  14340
aatgtgattg agcgtgagag agtgaagaag aagaacctga ggaagaagat gagagctcgt  14400
cgccatgttt gcacaaccca aactcgaaac cagagtaaag aagagcctta tcgcttatcc  14460
gctccgtgta tttcaattta tgggccattt actaatttta tgggcctaga catttaggcc  14520
catattcaat tgatataaca agaaacccat taccaaagct ggttctacca gtctaccacc  14580
acgaaccaag gcttgtccaa gtacactaat gtagaaccaa aaatggttta aataaagagt  14640
ttctgttaca aacaaatgta tgtttatgtg tccttaaatt gatagctcta aataatctac  14700
tttgggcctt ttaaaagtta tgattgacga ataaatttct gctggagttg aaatattatt  14760
ctatgtgact atgttgtata ttcaagtcgt ctacatgttc acgttacatt gacttacacc  14820
gcaagcgatg aaaagctatt atatgttagt ttaatcagaa taccaaaaag ataataatca  14880
aaatattcca tcttctttct ttgtgaaacg aatatatatt ctcttacagg tggtttaatt  14940
aaaagcttga caacagtacg taatattagc atacatataa aaagttacat taattggata  15000
cgaaatttta atctcctaaa gatagttatt ctccgattgt atagaatcaa aaaagaaaag  15060
aacaaaaatc gacaaagaag aagaaaaaag attgattgat tcttttgtcc tccacgcatc  15120
tctctgagtt ggctcggcca cgtcagcatt caaacatcaa aaccaaaacg catttaaatg  15180
tcgaaaagag tgggtccctt tttttctttt ttcttaaccg tgtcattgac aaaaagagca  15240
```

-continued

```
cttaataagc caaagccaca tagaagaaaa aaaaaagaac attcacgtct ctctcgtttt  15300
tttggccgac gacgatcgct gaattgactg ccggagattc ctttaatcgt cagattctcg  15360
ttgagggata atgaatcctg aatagtaaga aacttgtctt ctcgttgttt catgtatcta  15420
ttgtttcgga tcgatccgcg ttttttattt tttgatgtgt ttggtgattt ggtttttgtt  15480
cgattttgct ttggatcttt gttggttgtt aggtttgtga attgaatcta cctaattttg  15540
ctcgtttaag gtattttgta ttagaatttt gtatagattt ggattttcgt tccatggatc  15600
ttatacaggt cagatccgag gaaatttgat cgagatctgc aatttctgtt tactgttgta  15660
gttgaaattc gcgagtgtga cacaattttc cctttgatct cattagcata ttgtatatag  15720
atgttcttgc gtttttattt cctgacccga attttcatga gtttatgagc ttcactgaga  15780
ttggtgttta ccgttctgtt gttgcagtga ctatctgttc aagcttctgc ttattggtga  15840
ttctggtgtt ggaaaatcat gcttgcttct aagatttgct gtaagtattc ccacaattct  15900
ggattcatca tctctggtag ttactttta acattgtgta cacacaaaaa tttgaggatc  15960
acatcttgga gttcaatacc tgttgctcaa gactcaaaac tcaaaagtca ttactccatt  16020
ggattagctt agttctcact atggtatcat tgttactcct ttgtgttctt atttcctgat  16080
atcttgaatt ttatgtggac aggatgattc ttacctggat agctacataa gcaccattgg  16140
tgttgacttt gtaagcacct tcatttgctc atcactcatt tatatacagg aatcagaata  16200
ataagtgtta acctttacta atgatatcat gcagaaaatt cgcacagttg agcaggacgg  16260
aaagaccatc aaactccaga tcgtaagtgt tcttcagcta gatatgcaat cataatctgt  16320
taaaattttg gaaagagcag atagttactc ttgttttggt aatcgcctgt gtatacagtg  16380
ggacacagca ggccaagaac gtttcaggac aatcactagc agctactaca gaggagctca  16440
tgggatcatt gtatgtactc ttactctaac caaccaatca tcttcttgtt aaataacaca  16500
tcctatacct cttgctcaca attgcctatc tttgcaggtc acttatgatg tcacagacct  16560
agagagcttc aacaacgtca aacaatggct gaatgaaatt gaccgttacg ctagcgaaaa  16620
tgtgaacaag ctactggttg ggaacaagaa cgatctcact tcacagaaag ttgtatccac  16680
tgagacagct aaggtaattt tataataaac taggtgaact ctctatccac gtaaaccttg  16740
tcttaaagag aataacattt ttgttgtctc atctccttgt cccacaggct tttgcagatg  16800
aacttgggat cccattcttg gaaacaagtg ctaaaaatgc aaccaatgtg gaagaagctt  16860
tcatggctat gactgctgca attaagacaa ggttagaaac taaattttac ttgtgaagtc  16920
attaaccctt tacttccata cttaaaaggt tttgttgttt tcgcagaatg gctagccaac  16980
cagctggagg tgccaagcca ccaacggtcc agatccgtgg acagccagtg aaccagcaat  17040
caggctgttg ttcttcttga ttcaattagt caccactcct ctttcgatca tcacaccatt  17100
atgatcattt gtttgcattg catgttagac ttctccaaat taacaactct ttggatcctt  17160
ttgcttgttt ttcatttgct ttcttttgat ccgattcttt tctgatgtac gttgaagttt  17220
gaaacccata acttctatat agtaaaaggt cttttatgca aataatgtag agcactcttt  17280
aatgccttcg acgattctaa atcatcgctc aagtatgaaa gatactagat atcgtgctat  17340
tagaaatata cttcatttat gatgtacgaa aagaaagatc gaatgtgtaa taccaaaatt  17400
agagagaaaa atatcttaat aattttttc ataacttaaa aaacgtaata gtttcgcaga  17460
aaagaccttc agaaagtgta acaaaaaatt ataaaactaa caaaattcaa ccaaagagaa  17520
acgaaagaca gagatagcga ggctgaagga ccaggggtct ttactagccc aacgaaggga  17580
actgagctgt gtctccaatc gccggagctg cagcttcttt tgcatacctt tggtttcctc  17640
```

-continued

```
cttcaccacg accaccgcga cctcctcttc cgcgggagcc tccacctctc ccgttgtacc  17700
tctttccatc agccggcttc aagaactcat taatgctcaa cgactacaaa atcacccaaa  17760
atcactcagg taaaaaaatg acacaaccca aaagaaatca tgaagtgaga acagaaagaa  17820
ctaagacctt tttggccttc tcagtagcat ctttgcgttt ttccttgtca gatccctgaa  17880
acaataaaat accaagtatt aactattgct ccgttacagt gaagggaata gataaactga  17940
acagtagatg attttctgac cagcttgatg aagatttctt catcggtgtt cttcttgtta  18000
gagagctgtt gcatggactc aaacactttg gtgtcaactt tcctttcctc aacctttgtg  18060
gcttgcagag ccttcttctt ctcctccaga attttctcat actcttctag agtcatctcc  18120
tatatgacaa aaccatatca gttcaaaatg ttagcaaaca ttctacttca aacttaacta  18180
aacctcaaaa gatgtttcaa gagctgtaaa tgattgtacc ctggcttcag cttcttcagc  18240
ttctttctgt gctttctctt ccgcagtgag ttctttcttt gcttcagggg tttcatcctc  18300
acctccttgc ttctcagcaa cagggctctt ctcaacctct gtggtaggtt cctcagacgt  18360
tctaatataa gaacaacaaa agtttataaa caacctaaag ttaaagtcat atggataatt  18420
aaagtgaaga caaggatgct tacggaggga tatcatcttc agtagtgccc cagtttccac  18480
gacctccacc attacgtttc atgccagtac tatcaaacat caagttaaca taaatgaatc  18540
acaaacagaa gaagtcaaac aaagtagtaa ctaaagtagt ggacagaaca aaaagaaagc  18600
ttacccatga cctgtcctgc tatggcggtc ataattcctc ggtgggcgtt caacatcacc  18660
agattccccg ttggcaactc caccacggcg aggtccttca cgaccaccgc caacacggta  18720
tccaccaaca gacccaccac ggcttgctcc atcagcatct tcagaaggtc tcctgtatcc  18780
tccagaaaat ccattctcat ttccaggagc atcattgttc ctgttgtccc ggttgtatcc  18840
accattaccc ctgccacggg aaaatccacc acgtccacca gtcccaccac gacctccttg  18900
aggagcattc ctcgactccc tcactacatt cataacaaaa agctttcaat atatatactt  18960
atcctaatct aacaaagtat taagctttac cctaatctaa caaagcagta gagaaacaaa  19020
ataagatacg gaagaaacta acaaagcagc aaatgaaaaa agcacacaca tttgactatg  19080
gatctttcat gacaaccata aacaaacttc actagaacta atcaatcaaa cactagacaa  19140
aacacagctg aatctaaatc tgttaagtat caacataaag gaaagaactt ttacctgctt  19200
gagaaggagg agccggcttg gttgggaact tagcggcctt aggaggctga acagcagcag  19260
cagctttctc gactttctga gacaaagcca cagcgagctg gcttggatcc tcagcatcat  19320
ctcctagaag atcgaaaggg ttcaaagacg ccatcaccag tctggtaaga tcgagttagg  19380
tacaagtcac aggagaaatt ggtttacttt gatgggttta tagagaggga aatcagtaat  19440
tcatggcgat atacagaatc agaaaaaaga ggtacttgaa gagagattat tcggacagag  19500
ctgtttgtgt ttaagagata gcgaaacaag aaccctaaga aaagatgcgg cagtgagaga  19560
gagaggtgcg acttaaaaac ctaatctata aacccttcct gagttattat tctctgcggc  19620
gggtgctatt taactgtgtt ctggtcctct ctttatctat ccgtgggcta caaactggtt  19680
aagcccatta acaataataa atatcagctc tcgttggtta aagcccatta atgaaaagaa  19740
tattcgttct tagtccatta agagaataac tgggtttcaa tactgaatcc tctaggcgag  19800
acacggtttt tctcattcta aacctttatt gggttcaaag ttttatgtgc ttcaaaaatc  19860
aaagatataa attgattgct taaatgaatt ttctctagca gagcctttgc ttgtcgacct  19920
tagacagctt catcttctca agagtatcaa acagaaacat ttacaagtga ttacacactt  19980
```

-continued

```
aagctcacaa catttacaac aaaaaaaaat ctaaaataga taggttatta tttattgtcg  20040
cgctactgtt gatggatttt ggttttagta attgttacct cttcgatcaa gttttggcta  20100
cttagcaata tagaactcaa attgagttaa gagattgtat taggggatat ggtgtaatac  20160
tttaataaag ccgtgaatgt catgtaagaa atgaaactag attgaaaaat taacactcac  20220
ggctttatta aagtgtctat tttgtttatg gattgaagat atatggctct gtttagtaac  20280
taatttacat cacgggaaca cttttacttg gtgcctcaac atttatagca aaactattca  20340
actacaaaac acacaagatc aaacttatga aaccaataac tcatcaacac gtgtctcatc  20400
accaacctca cacttcacct gcaccacctc cgacgtcaga ttctctgctt ttctccttcg  20460
tttcaacttc ccgttttcag acgacgacgt agaagaggac gacgacgacg acgacgaaga  20520
agatctctta gacgtgatcc gaaccgggtc aggttcaccg gaattaaccc tcaacggaaa  20580
attcaataaa gcgcgggaac cacgcatcct aaaagcagct atatcgtaag ctaaagccgc  20640
atcttccgcc gtctcaaacg tccctaacca aaccctagct ccattcttcg ccggatcacg  20700
tatctccgcc gcgaatttcc cccacggtct ctgcctcact cctctgtaat gcttcgcctt  20760
cactgccgtc tccgtaaccg gtatcgcttt ctttggtttc tcctccatcg ccgtaaagtt  20820
ctcagttggc tcgactttaa ccgccggaaa atcaaaaaga cagctcaagt ccgatgatga  20880
cgtgtcaaaa tggaaggcat ctttgaggag tccgtacacc aacatgtcct ctgaatcatt  20940
ctctttcaat ggcaaacctc cccaactctc tgtgaaacac gaactcggtg ttgactcatt  21000
gagtcgcagc tcgttctctc ctcctcctcc tagcaagtga cgtgttatcg actccaacaa  21060
agcgtagtcg gattctatat tgcactgtcc gtacattttc agagaaacta actatagagt  21120
tttttttgtt ttgttgattg atttatcaaa tatctgaact tttttctatg tggaaggtgg  21180
ttaagaggtt tatatagagg gtacgaggtt cacgaacctg gaaaaaaaga aaaagttttt  21240
catgtttttc caaatttgtt ttagtttagt gggtaattaa aaaatatgaa agttgtggat  21300
ttttcgttac tacgaaggtt cgtgaattaa acacgtgcgc tttatccaca gatatcacaa  21360
tgaagaaggg tcaagatgac gtcatgtggt catgacattt ctggaagaaa gatgctgatt  21420
tggttttgtc tctcaacttg tcccttgttt tgtcgttcgg ttttgaatac gattccccggt  21480
tttattaggc aaaactagtg tttaattagt ttgttaatcg aaaaccaagg tcttaattca  21540
ttatactttg ttatatcgac ataaattttc aactaaactt atatttcatc gccttacact  21600
agagtaataa tttttgctta agtatacttt attagatagt attggcaagt atattatatg  21660
tttaattaca tgaaatctaa gcttagatct tgttatggtg gtgaatgaaa aatcttaacg  21720
aggtgggcca taattatatg aatggggaca ctgaaagtgt ctgcaaaaat cgggatacat  21780
ttctcctggt caccaaccaa ttcatatcat catctttccc tttcaccttt catttttact  21840
aatttctaat ttagaatttt cctaattgcc aatgtcatgt ttattttagt actttttgat  21900
acaagatttc atgattaaga aattcattag tgccacttta gtcaataaat atggagtagt  21960
gaaatcatag tgataaagtt ttcatgcaaa gctcaattta caaaccacag tttaatccat  22020
atttgttgca tttcttttct ttcttttttg aaaatataac agccttagat ctttttgtac  22080
accaatgatt tggaattttg tggataatta ttgaatttcc atctctttct attggctaaa  22140
agtcaataac aacaataagg ctcaaagaca aattaatggt gggtctctca cgtatgtcca  22200
cttgcaaaag ggacctcctt cacggaagca tagtttagtc aatagtcact caaactctct  22260
aaaaattagt ttactatata tttttaatct atattcgatt ccaagagtag ttttggttca  22320
aacacatcat tctggtcaga tggttatttc aattttgctg tttttgagtg tatatatgat  22380
```

```
gttatgtttg taaacaaatg aaacttttaa ttgattacaa gaacatgaat agctctaaat  22440
atgattaaaa acgaatttat ttatttcttt ggtaaaagaa taatgataat atacttatgg  22500
atccaatcag gttaagttcc gttttgcaat taaatacttt gattaattaa atatgaaagt  22560
agtagttgaa ctttcgtttt tatgtttgaa ctccgcagct aatcctcaaa ttatctcttt  22620
ggacgtttca catacatcca cttttgctgt atcttaggaa tatattgttt tcatattgtt  22680
tcttgtttct ttatgatttg ggtttatata attttcaaat gtcatgatga tcatcattta  22740
atcttagttg ttttagtcac atcttattat gcttattatt agtcggtgat agtttaattt  22800
taagacgtaa atcatctatt ctcatattat gctagaacaa actttttctt tgtgcaacct  22860
cctagaacat atagtcgcct attatccatg gatcccagat actcctccaa gaccaccgaa  22920
aggtttaatt atggatagga accctttggt ctacgttaac accttgattg acttccagac  22980
gaagaggtgg aaagtagatc gtctacggga gttgttcccc cccccccccc cccgaggata  23040
ttactttgat tttagggata aaaccgaggc taaatgtctc gcgagatgga tatagttgga  23100
cattgactaa gttcggtaat tatactgtca agacaagata tgaagctgcg agagccctct  23160
ctcgcccgtc ttgcgaccac cctcttcagg gacctagtgt tacggcacta aaggcgcaag  23220
cgtggaaatt aaaaactaca cgaaagctaa agcattttgt gtagcaatgt gtgtcagagt  23280
gtttagcaac ttgtcaacgc ctatattttc gccatattgg tagagataaa aaatgtccta  23340
gatgtggggc ggatgaagaa accatcaatc atttaatatt tgaatgtccc ccggcaagac  23400
aagtctgggc gctatccggt attccctcct ctccatctag gtttctttcg tcttctatat  23460
acaataatct cgattatctg tattggagag cgaatgagat tggagcttgt gaggagagct  23520
tacgggtctt tccatggata atgtggtata tttggaaagc gcgaaaccga aaaaatttcg  23580
aaagtatttg cgtgcaacct caagacactt tagacttagc aatacatgag gaagaagtat  23640
ggaggcgagc caataggaga gaagagcaac cagaaggtac caagccaagt ttggaagggc  23700
aacatataga tatggcttcc ccaatctgct tcattgatgg gtcttggcat ataactgatt  23760
cgcggagcgg tcatgggtgg attttgaccc gtggggaaag attgcttcat ttaggattga  23820
agggttcacg tcgttgttta tcaccgcttc atgcagaact agacacatta gtttgggctt  23880
taaagtgctt agtagactta tcaatcaagg aagtccttgt taagacggat tgctctgatc  23940
ttctcactat ggttaatacg ccggaggagt ggcccatttt tgcatcagag ttaaaagatt  24000
tcgagtattt taagaatcaa cttgtatctt ttaatattat gcatgttccc cgtactagta  24060
atatccgagc agattatctt gcgaaatgtg caagaactcg cggattctat ttttcccatg  24120
taagttcaac ggttctcgat tggctctctt taaacgagag cgcttatcca tagaataata  24180
tatagagttt taacccggaa aaaaaaaata ctcgcctata gtttgcttta aaaaaaagtt  24240
tcttccaacc aacaaaagca ctcacctaat cttacaactg tgatttttga ccaatgtttt  24300
tgttcatatc tcttcaaaaa aaaatttata ctataatgag cattataata tattttctat  24360
cacatattat tgtgcagaaa ttaagtatca agttaaaggc aagttttagc aaaaacacga  24420
tttacggaat tagcaacatt tacacggacg atcgcatatt tcagacaaga caaatacaga  24480
ggataaaata tcataaaagg gaaaatgacg acacaaatta tgtaggcagt gattggtaca  24540
cattgttagt ttttttaaa atattactat gtttttgcca aaaaaaatta cgaatcagag  24600
caatcatgca taaaaattag aagaatagcg taaatatttt tctcttttct attcacacct  24660
ttactcgctt ttctattcat tttcttattt ttcctctcaa ttactccaaa aacataccaa  24720
```

-continued

```
ttagagttta gattcatgat gtaattgacg aaaaaaatca cccatatgat tagttacact  24780
atatccgaac actaatattc ataaatttag tgtctcggat ttatgcatac aaacttttca  24840
tggaagatgc ttctcattta caagctgatg ataaaattga tcttacattt tttaacaatg  24900
aaatgtcttc tattttttgt tatagccaaa ataactcagc tttcagttat atataatcta  24960
cagtttagtg tattttgtta actttaatcg attcctaatt cattttaatc aacacatcta  25020
tatgtaggca attggatgca aaaggtacac aaaacaatgc aaaaggaagg atcaaaggaa  25080
agatgttata tgacacgtca gcagtattca aaagtttgaa gttgaacaaa tctagtcatg  25140
tttgactttg accactgact tttcaaacct atcttttatt agtagcaaac tcagttccat  25200
acgtgcaaac aacctcacac gtgcgttccc accgcaatgt ttgaggtttt cttcaacaga  25260
agacgatatt tcttattatt ataacgttag attgagaatt caaagattct cgacaaatga  25320
atggtaactt ttttctataa gaatcacaat aattagtttt agttatacaa ttttataatg  25380
ttggagtaat tgtcacatag atgattggtt ggtgataata gttgtttatg tatgattgat  25440
caattaaact tataattttc cattggaata atattttctt gacctttaaa tttggaatgt  25500
agatttatat ggaaaaagta gataatcatt tttgtgacgc taattaaata tgttgtccca  25560
taacgacaga aaaaaaaaaa tgaaacaaaa atagagacca gattggttca agaaaacgac  25620
acacagttta ggatgctaaa aaagctttgt tagtaccata tgattgttat attgtttatt  25680
ggttccttaa taatgtattt agacgtcaaa aaatgttttt gtattgatat gtgacctcat  25740
aactggttag ctgcttaggg ccattagatt agagttttga ttgtttcaaa tgtcaaatct  25800
tacagtccgt caaattttat ttgatgtgaa gtaagtgagt tgataaatgg gactactttc  25860
tccagttggc tagggtcgac tgctaataac atttctccaa ggaattaatc tcaacgggct  25920
tgttgctcag gcaacaattt ataggaatag agattgaacg aaataattaa cagattacac  25980
aacaatgttt cctctacttt aagcaagcaa tcttcaaggc tatattgatc gactgattcg  26040
agacgcaatc gtcttgtcaa gaagaaccac aaaaactatg atgatatgta atgcaaactt  26100
gactcgtctt tgagtaacac ttcttcatct agtccaatcg tcgcagggtt tcttttaatt  26160
tatttattta ttatcttctc ttttggtaag aaagagcttc tttaatttgg ttaaactttt  26220
tttttttggt taagtacaaa acttctcatt ccttaataaa attgatatct atattataaa  26280
atatcaaatt ttgtaaaaca aaaataatta agagtagtgt ttcacaacaa caacaaatta  26340
aaaagactac tatataaatt aaaaagacta cttggctttc tagaaattat taaatataaa  26400
tttttatatt aaatctctga tttgctatat catttattaa aagtgtgaac tttattttgt  26460
ttcattgtaa caagtaacaa catgactttc tagaatctag tgagtgagtc gttgattcat  26520
tctacaaacc agttaatgca ccgcgtaaat tcttttcacg tgcatggtgc agtgcatgaa  26580
gatggatcaa attaaatacg aaaccaaaca taattcaata gtatatcatc ttttaaaatt  26640
tgtatgatta ataatctctg tcaataaaag gccgcatgca ttgacttgac tctttcagtc  26700
ttgtcttgct tactaattaa accctccata atgcatcaac ctaatcataa ccgaaaattt  26760
tctgagttgt atttggttag actttaatgc tttactatca ttttagttac gtttgtgttt  26820
acctcgcaaa aaatcttcta gaaggataat ataatactac aatacaatgt tggcattatc  26880
cattactgag cggtgtgaaa ttggttttga ttgtttaaca tatgagttaa aatttgttcg  26940
caatattggc aaattagcat cggatatgct attgtataag aaaacgctta tttttggagt  27000
gcgcgtctac ctgtaactgt ataaactacg taacgaacct ttgaacgcag agtgaatgtg  27060
agtctctgtg acacgactta aagcttaatc agaagcagat tattggacct tatggagact  27120
```

-continued

```
ttatcaagat tagctaatga aggttactat atatgaaact ttgaagtaat tgtttgcagc  27180
cttttgggat caataaacca taaaagcatt ggttttgttt tctctatcta tatccaattc  27240
cggaaagtag aaaactggat tagtaaaaat catattcaca cattgcgaag aaaaactatg  27300
tgcgcgcgga tacgttggga aaatctgcgc atggtttaaa gttttgcttt cagtcaatta  27360
taattcgttt tttatactcc ctctgttcca agatacttga tattttgggt ttttgcacaa  27420
gaattaagaa aagtaacttt tatattttta attattcttt tagttagttt aataatatta  27480
attttacttc tctcatttca ttattggtta caaacaaaaa taataatgat agtttttcaa  27540
aacatcaatt ttggtggaac aaataaaaaa actcaaaata tcaaataact tgaaacagag  27600
ggagtagtta attaaaaaaa gatatttcac actttgactt ggcgaagcct cataacaatg  27660
aagttatgta tgaactatat atgaagttag aaacaatgga aaacagcttg taaatattca  27720
ttgttgtata tatgtttttt tgggtcaatt tggtgcatga acaaaaaataa aaacgtagat  27780
gaaaaccgga tattttggtg ttaacatttg catttgaact tcgtgaaaga cggataaaag  27840
ctcatttttg ttctttatta tatggctgct attagtacac agagttgaac tttagaatac  27900
taaaaatctc gacatctttt attttatttt tgtcaagcat cgacatcttt tctgttcaag  27960
aaaacgaccg caatagtcga ataatataac tcttggacta gttaatatat atttgcgata  28020
gattttcgat ctcacttata tcttataacc aagagacaaa aacaatattg cagtcaagta  28080
caaaacgaaa acaatcacaa tgtcgactat agatgagtcg gtcattcgat ccaacggctc  28140
tgagtccacg aaacacgcaa ccaagtggtg ctctctttta caccaaatca tattataaaa  28200
aacttaaaag aaagagagga tggttcgttg gctccttctt gttccttaat taattcaaat  28260
tatattcatc acctccattg aataagtcca tttcacgaca aagtcaccaa tgcttctttt  28320
acatgtatat atacttcttt ccactccctc ttctctactc aaatcaaatc ttcttccttc  28380
tctgttttct taagcttttt gaaaatttta tcaatggcga ctcctaacga agtatctgca  28440
ctttggttca tcgagaaaca tctactcgac gaggcttctc ctgtggctac agatccatgg  28500
atgaagcacg aatcatcatc agcaacagaa tctagctctg actcttcttc tatcatcttc  28560
ggatcatcgt cctcttcttt cgccccaatt gatttctctg aatccgtatg caaacctgaa  28620
atcatcgatc tcgatactcc cagatctatg gaatttctat cgattccatt tgaatttgac  28680
tcagaagttt ctgtttctga tttcgatttt aaaccttcta atcaaaatca aaatcagttt  28740
gaaccggagc ttaaatctca aattcgtaaa ccgccattga agatttcgct tccagctaaa  28800
acagagtgga ttcaattcgc agctgaaaac accaaaccgg aagttactaa accggtttcg  28860
gaagaagaga agaagcatta cagaggagta agacaaagac cgtgggggaa attcgcggcg  28920
gagattcgtg acccgaataa acgcggatct cgcgtttggc ttgggacgtt tgatacagcg  28980
attgaagcgg ctagagctta tgacgaagca gcgtttagac tacgaggatc gaaagcgatt  29040
ttgaatttcc ctcttgaagt tgggaagtgg aaaccacgcg ccgatgaagg tgagaagaaa  29100
cggaagagag acgatgatga gaaagtgact gtggttgaga aagtgttgaa gacggaacag  29160
agcgttgacg ttaacggtgg agagacgttt ccgtttgtaa cgtcgaattt aacggaatta  29220
tgtgactggg atttaacggg gtttcttaac tttccgcttc tgtcgccgtt atctcctcat  29280
ccaccgtttg gttattccca gttgaccgtt gtttgattag tttttttga gtttttgaac  29340
gatgtgtatg ctgacgtgga cgtacacgta ggtgcatgcg atgaaaaaaa catctatttg  29400
ttcatatttt tgcgtttttc tatttgttca ttctttttca caattcacaa tacattattt  29460
```

-continued

```
cagttaatga ttacggataa tttagcttta cgttaattta ttatgagtac tagaagaaat  29520
cggagtaatt caacatatag attatactag tataaatgtc aattgcattg acattaattg  29580
aggaattata gtagaaccta gtataaaaag aatgattcaa acatgagata ttgaccggcg  29640
ttatgtgaag ttgttcagac aataaatgca taaccgtgat tctgtctgaa caagtcgatt  29700
cttaggataa aaaatggata aacttagtca aaatatttcc cacgtggtta gacttttgct  29760
tagttacatg acgaatgtga aagccatcca tgcatgtatc cagaagaata tatcttgcac  29820
ggcgaattct ctacgtattt tagtatttta gatttgacga catctaattt tcttttggta  29880
tttcgggttt gacatctaat ctgctaagaa ccttttctta taatcgaaga attttgttgg  29940
gtcgtcttgt aagatattat tttcagtaca cactatctaa tcattcatca aggtcactaa  30000
tgggccttgt ggtctaaact ttgaatatat actttcacct atgaaatcca gaagttctgg  30060
ctgggtaagt tctaaaccaa cctatcttat acatcgaaac acaaaagata attggaacta  30120
caaacaaact ttacccaaaa attattagtt tgtttttatc tccgtagatg aaattgggtt  30180
ttctaaatcg ttttcgaaga tgaacgctaa tcaaacaaaa gtggtataac acagtttgtt  30240
acgaaatttt gttaggaaaa taaatgaagt atgtgttttg cgtcgacctc aaaataaaat  30300
acatattaaa tcttgcatgc taatattatt gtatagaata ccaatcaggt aagaatcgct  30360
cgtcatcata cgactattca atatccaaac atatttattt ggaaaacccg accacgaata  30420
atggttagct ttacatcatt atccacacat actcaaatgg ttaaattttc tagaattgta  30480
atggaagaca caatgttatc acgaatgagg atcatcatgc acttcaggtt acctaattat  30540
cctacgtgga caatacctaa tccttccatg attttcaatt attgcagata atttttctga  30600
acgtcatcat ttcccataac gaataatcat ttcctcaatc aacgcaaacc taactatcta  30660
tgtcatttac atgtttatgt ggtaaaaatc tgcttagaat aagtaaacct tcacatatat  30720
attgtaacaa aataattgag gttaatgtta ttcaatgcga aaaaatgtaa acacttgcta  30780
atgagtcgta ataaccctat attatttttc caaaacatgt ttctattgaa gttacaaatt  30840
aagtttccac tctatttgga tggagcgtac tagtcgtaga cacggagagc ttccaagtcc  30900
atcggatcaa cttatcaaac ttatcgacct tttggtccac aacaagatat cttttgtcca  30960
tcttcatcat ggctctcgca agaggatggg ttacatatat ggtttgcttt attgcttaat  31020
agggattaat ttctctaata cttttgatta gcttttcgca aacatttttc agcataagga  31080
cgcatctgac gtacaaatta aaaatccaaa tgaactaaaa tacttttaaa cagaaaggac  31140
aaggaatcta agccatcaag gcccatctcc acgtagctcc agcaacgaca agatgcttta  31200
ttatcccatt ctcgtggata cttgtgtgag atacacgctt cagataaatc aacggacgaa  31260
attgtaaaaa gcgtgaggaa gagagagcct ctttccaaag gagagggatt ggatcattga  31320
gatatatccg tttatccatc cttgaactcc tgaagattcc ttcgcacaga caactctctc  31380
gaacatgtta aagattctct gatacctaac tattgattcc tttttccctg catttttcgt  31440
tcactatttt tgcttataac tttttgtact aaaattaaaa atcatgccac catcctgtat  31500
ttcatatcca aaagctttgg attattttat aatatatcat tggcttgatg tgattgatat  31560
ttaccaaaaa tctattctag tttctttttg taacaccaaa tgttatttaa aatttgtatt  31620
ggaaaaatga ttcatttata taagttatta tatccctctt aaaaattgta taaaatctct  31680
aagacattat taattgtaaa agatagacac aacacgtagc tatatgtcta tatccaaaaa  31740
taaaacacgt agctatatgt aatattataa aaatgtacat atattattag ggttgtaata  31800
tttggtcggt tgaaaattga aatcgcagct caattggaaa ttcacgtgta ttttgtcttt  31860
```

-continued

```
gattgtaaga tattaaaact gttcttcgct ttccttttct catttctcac ttaaccactc  31920
gatccacttt aaaccacaca ttataagtgt gcctcaaaaa aatctaacat tactctctca  31980
acacatctct ctttcttctc catttccttc ttctctttca ttctcttatt taagatttaa  32040
atctgctcaa atgcttgtaa acaaatttca agttctttaa acgatttcct tttcaagaaa  32100
aatccttctc cttcttcttt ttaccacata gatcttcttg atctacaatg gattctgttt  32160
ctctttctga ggttactgtc attaaaggaa caacacattt gggttttatg cacagtttca  32220
gacagccatt ttgtggtgtc aaaatatctc caaagttcta tttatccaaa ggtaaataat  32280
aacaccttaa aatcacttcc tcttcacaac aagaatcttc attgtctttt ttaaaaattg  32340
tttttttttt tttgcatttt ggacgagaag ttgatggacc aaaggcaata tcttcgagca  32400
gcaacacaaa gagtcaattt gtttatggag gaggaagcat agctgcaact tcagattcag  32460
gttataagat gaatggagta aacctaaaaa gcagaacatt gatgagttct gcagttaaag  32520
aaagatcatt acttgatgct tatgatgatg agtatggtgg agtaatagta gatcatggaa  32580
aattaccatc aaacccttat gctttcgctt ctatgcttcg agcttctcta tccgattgga  32640
gaagaaaggt aaaaacgata aaccctataa aagtcttaaa ccctttttgtt tttgtacata  32700
tgtaaatttg ggggaaattt ttgtagggaa agaaaggagt ttggttaaag ttacctgtgg  32760
aacaatcaga attagtccca atagctataa aggtaagcaa taagaaaatg gttcttgatc  32820
ttgtttgata aagcagagat ttgtttatgc aagttaatga ttttttgtgg attgattttg  32880
caggaaggtt ttgagtatca tcatgcagag aaaggatatg taatgttaac atattggata  32940
ccagaggagg aacctagtat gcttcctgca aatgcttcac atcaagttgg tgttggaggt  33000
tttgtattaa atcaacataa agaggtatca atatatgaat gattattctc tcaagtctca  33060
acacttaaag tagagtaggt aaaaagaaga gttacctgaa ttttttttta aatctcatta  33120
ggtgcttgtg gtacaagaaa agtattgtgc tccttcgatt actggtctat ggaagttacc  33180
aacagggttt attaatgaat ctgaagagat tttctctggt gctgtaagag aagtcaagga  33240
agaaactggg gtaattaaat ccgagaagat tagtatatag tataaatctt gattctgttt  33300
aaaaattcgc aagatcataa ccatgtatgg cattgtgttg tgttattcag gtagatacag  33360
agttctcaga ggttatagct ttcagacatg ctcacaacgt tgcatttgag aaatctgatc  33420
tgttcttcat ctgtatgttg agaccactct ctgataagat aatcatcgat gctcttgaga  33480
tcaaagccgc aaaggtaaat gtaacaagag tctttattag aatgctccag ttgtacatgc  33540
tacaagacgg tcctgattac aatgattgtt gtgtttttca gtggatgcca ttggctgaat  33600
ttgtggagca accgatgata agaggagaca aaatgtttaa aagagtgatt gaaatatgcg  33660
aggcgagatt aagccatcgg tactgcggtc tttctcctca tcgacttgtc tctacttttg  33720
atggcaaacc ttcttctctc tattacaacg ttgttgatga tgatcatgat ccttcccact  33780
ccaattgtag cactgagttt tatagataga cgggtaaaac agaaccaaat caagtggttc  33840
gattctgtat atacttattc tcatgtaatg tatgttgtta tttgatactc tctcttcagt  33900
atagtaaata gtaatagatc ctctgcaaaa tccatgtagc atcgaaccgg tactctcagt  33960
agactataca ataaaaagat ctgttcaaat aaataaccgg tgggtcaaca caagtttaaa  34020
caatattcaa actcttggac tgacatattc aacgcatata atataatgta aaccaagttg  34080
taattttaat tcatagaaga agacattatt gcaatggact aattcaacta aaccaagcta  34140
gccaaacatg tcaagatcct gtgcaaaata tctgcttctc tctcaaaccc tgagcacaat  34200
```

-continued

```
agataacata caattgtggt ggaacatgga aacgttttca ggaatttgac aagacaaaac 34260
aaatgacaag ttgtggaaac atacaagaaa taagaacgta cgggacaaag tgacaggaaa 34320
aaatagctct tgccctcctc cactatccca ttcaaagcct tatatatgag atcatcatcg 34380
attttcttat aatggacgtt gatgaagatt cgggcagttt tctatatcga ctttgttcag 34440
cttcagtttt ggaaaagaga cttgactccc atagatgctt cctagttcct tcaaataatg 34500
tagacgaagg acttgtagct cttgaaaagg atcaacccca acaccttgag ctttctcttt 34560
gtttattaat tctgtcatct taggcgagga ttccacgctt agagactcga gatttgcagc 34620
atacatcagc catgtcaaat cctttagatg tatgcatgag tttattacca cagctgagag 34680
atccttgaac catggattgc ttggagtgat ttcactggat gatgtggatg gagaatactg 34740
gtctcttctc ttaccttccc attctgttcc cgactctgtg atatcgcagt ttaccatttc 34800
aagtttgtgg agactactca acgtaccaat ggctgcaaat gatactttaa gtccttctag 34860
atatataccc tgcgtcatcc ctgccaatct tgtgcttcct agaaactctt ccaaaacaga 34920
atcgttattc acagtaacgg tcaaaagttg taaacccttc aactgctcca agatcttgag 34980
caagcagcaa tctaatgcag cagcagaacc ataaaatctg agaacctgca actttgtaa 35040
ttctgaaatc agaccgacgc ttcgaagatt ggaagtggac tccaaattca agtgaatcaa 35100
tttactcaag actcctaaac cttccggcag atgctttata ctcgtccctg ataagttgag 35160
aagccgcaaa gaaaccaacg ccgagattcc ttttggcaac tcggtgattt ggaagttcca 35220
agatagatcc aaaaccacca gagtcgacat gaccagaaag aatttaccaa caatatctac 35280
caacctgtta ttttgaagga acaaggttac aagatttgtc tggtcaggaa attcaggatc 35340
gtctggtatg ttcttaatct cattgttgaa cagagacatc tttgtcacag ttgtccaatc 35400
ggtgacatca ggcagttggc ttaaaccagc atctgttttc acaacatatc tttctccatc 35460
cctaaattca gatactatcc acaatgccat atcacggatc atatcatgca tatacacttt 35520
cttattagac tctaataaca aacctgcccc aacaagatta tcgatgatct catagcctcg 35580
atcttttgct ctctctcttc cgtctttttc atctatgaaa ccctcaccta tccaatactc 35640
taccagctca tcttgtttga tataatatgc cttgggaaat aaagcacaat acagaaaaca 35700
cttggcattt tttgttttca aataatcata gctcaacttc aaaacttgaa atattccctt 35760
ctctgtacct ttcatctcac tccgataaga ctccaaagta tcgagtgcac gacgccattg 35820
aatcacagta gatttagatg ccatagtctt tcttataact tcaagtgcaa ggggtaagcc 35880
acaacactta gccacaatct tttttgcaat atcagaaatt tcatttaacc cgtcgcaatg 35940
gaccttcata tcgaacaaat cccatgcgtc attctccgac aaacattgaa cttctatgtc 36000
ctcatttgcc ctcataactg aacagacatc cttagaacga gtagtaaaca cgactttgta 36060
ttttttaccg agcactggga tgcctattgc tgttaaactc acatcctccc ataagtcatc 36120
taataacagc acgaaccggg gcttcatatc tcttagtacc ctgcttattt cactagcttt 36180
cttccctctt gagtatgtag accaattatt gtcacagatg tgtaatcttt ccccgatggc 36240
atcttgaatc ttcccgacat ctgcatcttt agacgattca acccaaataa caacatcata 36300
atcatcactg acttcaacga acttgttgtt aattagagtg aggagggtag ttttgcctac 36360
gcctcccata ccgaagattc ccaacattct gttttcatct tttctaagac tttcccaagt 36420
cttttcaagc gtcgtatcaa gaccgactgt ttgttggcaa agtctcactt ctaccacagg 36480
aggaggaggt tgctcagtca cttcttgaaa atctttaccg gagagacttt taacttcagt 36540
caacttcttg aataccttct cgcctaggtt gcaggttgag aaccagcacc cagatgttga 36600
```

-continued

```
cagacgtcga cgtacagctg aagcattctg agaagaagca tcccgagcgg acgcaacatc  36660
cattaactgt ttggtgtttt cctcaatgat ttcgacttgt gaaagccacg tagccactat  36720
agctagccgt tgaccaccct taagctcacc agcattgact ctgtttacaa catcttcttt  36780
ttctgcttta agctcatcaa aagcactctt caacaagaca agattttcct tcaacatgca  36840
aatgttaccc acctttacac acaagtaaga caaagcagac ttataacatg gctcaactac  36900
ctgccaacag caattcattg tgctcaagat tgagaaagag aactaagatg agagtagcaa  36960
atttaaaaca gatctttgta cagaacagga tgtctgaatc gggggagtag aaatagggaa  37020
acagaacttt gtgcaggacg aactagagag accagagaaa aggaagagac cagagaaatg  37080
gagagatgat gaaagaagaa aaataatgga gagaggaaaa gaactagaga aaaaagttat  37140
gtggaatgcc tttaatatcc ctaccccacc cgcatgttgt agaatttttt gtaacaacaa  37200
tgatgactaa aaggtgtact gtgtctgtgt ggtaggtaac gttattggtt cattgattta  37260
caaatccata tataattacg caacatgtgc taagatattg acgtggtttg gtgtcagcta  37320
agagacaaat attggttcac tgattaataa attcatatgg gtttgaactc atacatagaa  37380
taatatggtt gttcttaaat ttaaaaacat ccacaaaacc aggttagaca aacaaaaatg  37440
actaacaaag cataaacgaa tactatatgt ccaccaacca tatgcaaaac gaaagaaaaa  37500
aacaatgaaa tccatgaata aagatttata aaatgaaaga tccacaaaag tatcaccaca  37560
agccacgtaa ctcccatatg cattaaaaca tatcaaattt aatttcaaat agtaaccaaa  37620
aaatttcatt ttgtaaccaa aaaatcaaat taaaatttta aaagggaagg gcaatattgt  37680
caacccacaa agccaaaggg gaaagtggct gaaaaattca gtctcaattc agttgactcc  37740
taaacacaca aaatgggaaa taatttctca gttgaatctc catctttggc gccgttcctg  37800
tgtgggaaac gcaagtattt atacaacctg gagagaaatc tagaggcttt gcataaagta  37860
atgcaagacc tcaacgcaat gagaaacgat ctgttgaaga ggctgtcgaa agaggaggag  37920
ataggtctac aagggctaca agaagtcaaa gagtggattt caatggtgga agagattgaa  37980
cctaaagcca atcggctgct tgatgaaagt gtctctgaaa ttcagagact atcaaggtac  38040
ggctattgtt ctctgatccc tgcgtcgacc tatcgttaca gtgaaaaggt acttacgact  38100
atggaaggag ttgaaactct gagatctaag ggagtcttcg aagctgtcgt tcacagagct  38160
cttccgcctc ttgtgataaa gatgcctcca attcaactta ctgtttctca agcaaagttg  38220
cttgatacgg catgggctcg tctaatggac ataaatgttg ggactttggg tatttatggt  38280
aggggtggag taggcaaaac caccccttctt actaaactca gaaacaagtt acttgtagat  38340
gcatttggtc ttgtgatctt tgttgttgtg gggtttgaag aggtcgagag catacaggat  38400
gaaattggta aaagattagg cctccaatgg agaagagaaa ccaaagagcg caaggcagct  38460
gaaatattgg cagtcttaaa ggagaagaga tttgtgttgt tactggatgg catacagagg  38520
gaattggatc ttgaggaaat tggagttcct tttcccagcc gagataatgg atgcaaaatt  38580
gtattcacca ctcaatctct ggaagcatgt gacgaaagca agtgggttga tgctaaggta  38640
gaaattacat gtttgagccc ggaagaagca tgggatttgt ttcaagagac tgtcggagag  38700
aacacgttga gaagtcatca agacatacct aagctcgcaa gagtagttgc tagtacatgc  38760
cgtggtttgc cccttgctct taatctcatt ggtgaggcca tgtcaggaaa aaggactgta  38820
cgcgaatggc gttacacaat tcatgtcttg gcttcatcca cagccgaatt tccagatatg  38880
gaagatggga ctcttcccat tttaaagtct atctatgata atatgagtga tgagatcatc  38940
```

-continued

```
aggttatgct tcctttattg tgctctgttt ccagaaaatt tggatatagg aaaagaagat  39000
ctggtaaact actggatatg cgagggaatc cttgcaaaag aagatagaga ggaagctgag  39060
atccagggat atgaaattat ctgtgatttg gttaggatgc gattgttgat ggagagtgga  39120
aatggaaatt gtgtaaagat gcatggtatg gttcgtgaaa tggccttgtg gatagcatct  39180
gaacactttg ttgtggtagg cggtgagaga atacatcaga tgctaaatgt caatgactgg  39240
cggatgatta gaagaatgtc agtgacgtct actcaaattc agaatatatc agattctccc  39300
cagtgttccg agcttacaac cctggtcttt cgaagaaacc gacacttaaa atggatctca  39360
ggtgctttct ttcagtggat gacaggactt gtagtcttgg atctatcatt taatagagaa  39420
cttgctgagt tgccggaaga agtttcaagc ctggtgttgc tgcggtttct caacttatca  39480
tggacatgta taaaaggatt gccccttggt ttaaaagagc ttaagagttt gatacacttg  39540
gatttggatt acacatctaa tcttcaagaa gttgacgtga tagcaagttt attgaatttg  39600
caagtactga gattatttca ttctgtttct atggatctca agttaatgga ggatatccaa  39660
cttttgaaga gcctgaaaga gttgagtcta acagtgagag gatcttctgt tttgcagcgg  39720
ttactaagta tccagcgatt agcaagttct atccgacgtt tacatctaac tgaaactaca  39780
atagtcgatg gaggaatatt atcgttgaat gctatattca gtctttgtga gcttgatatt  39840
ttgggatgta atatcctgga gataaccatt gattggagat gcaccatcca aagggaaata  39900
attcctcaat tccagaacat acgcacaatg actattcatc ggtgcgaata tcttagagac  39960
ttgacatggt tgctattagc ccgtgtgtctt ggtgagctaa gtgtatctga atgtccgcaa  40020
atggaagaag taataagcaa agataaagct atggccaagc tgggtaatac gagtgagcag  40080
ccctttcaaa atctaactaa gctcgtctta gatggtttac ctaaactgga gagcatctac  40140
tggactcctc tacccttccc agttctggaa tatttagtga taaggcgttg tccagagctg  40200
agaagacttc cattcaactc tgagagcact ataggaaatc aagttgaaac gataattgag  40260
gagcaagtga taaaaatagt tgaatgggag gatgaagcta caaaacaacg tttctcccat  40320
ttcaataaca ggtatcttct tccttatcct acattttctt ctctattttt ttcgataagg  40380
tttcttaaat ctataaaagc ttggccatga ataactagca tcttcccacg ggaatgtcac  40440
ttaccatctt cttaattttt tatatatttc aatgtcactc ttattattca tagaatctgg  40500
aaagctgatt tgataagatt ttgcaatggt gatccttatt ttgattgatc attgtttgtt  40560
cgaattatgt aacaaacgaa cggagtgcag agactttgta cagatggctg aagatccgaa  40620
gatggatggt ttgacatcgg agtcacatcc aattcaaacc atagacctgg tcgggactac  40680
aggaagtgga gaaactgcca ctgcaaacaa catccaagga aagaaggtgg tccaatcggg  40740
aacacacgca actgttgtta ccatggaatg ccagacatat aaagttttca caccagattg  40800
ccccatcaac aatatgattg acactcctgg tacgaatttc cttttatgtt atacctaact  40860
aaattatcat gcgtgggaag aaaaaataca aattttctaa taagtaaggt ttgtacttta  40920
cgtatacaat tagaatagga tccacgtaaa atgtgtattt ctaattttct atatagttta  40980
aaattaaaaa gtgacaaaac taataatgct gaaccaaata ttataatgta tataactatc  41040
aatactattt tcaattatat aattgatatg attttgtgtc actaccatac gcatatgaca  41100
tatatattta ttatttatat gaacacaaac tctcattcat taaactagtg actaaagttt  41160
actttgctca caaaagagtt gatttaaacg ttttcacaaa caccatccgg acgtaaaatg  41220
tgtaatggaa catacataga gaccaaataa ttataaattt ataatagata atgcttctat  41280
gtatatgtat gtttgtatgt aagattacgt catctcaggt gaactattgt tgagtttttg  41340
```

-continued

```
atattgaaca ctggttaaaa gtcattgaga ctgtgtctct gatgctagaa agtccttcat  41400
ttgatgctaa aaagactttg ggatccgagt tttgtttctg actgtgtcat attttctgac  41460
tttgggaact ggatttaggc aagaggaagg tgaaggagat gctttttaat ttgaacgatg  41520
aggcaagaat tattgggatc tcagggatga tcggttcagg gaaaaccatt cttgccaagg  41580
agcttgcgcg ggacgaggag gtccgaggta atcagttttg ccctttgtta tgtctgaaac  41640
tatccattgt taatatgctt gggccatctt tgaagtcttt tgagcagttt atgttgttgc  41700
tcagtggcat gtttactggt ttatttggat gatcatgcat ttatctctgt atgttccatt  41760
gtgtcatgtt catctccggt gaactgttga tgagtcgtat agttgagttc ttgatattag  41820
aatctgttaa gagtcggaga gactgttcct ttgatgctaa aaaagcttta atacaggcca  41880
ttttgcgaac cgagttttgt ttctgactgt gtcacaatct cccaatcttg aggagctgag  41940
atcccttata cgggattttc ttactggtca tgaggctggc tttggtaccg ctcttccgga  42000
atccgttggt catacacgga agctagtgat ccttgatgat gttaggacaa gggaatctct  42060
agaccagctg atgttcaata ttcctggaac cacaacgctt gtggtctcac agtctaaact  42120
cgtagatcct agaaccacct atgatgtaga gttattaaat gaacatgacg caacatctct  42180
gttctgtctc tctgctttca accagaaatc agttccttca gggttcagca aaagtttggt  42240
caagcaggta atgggtctgc tacaagtgtt acatgcatag tagtaatatt ctttgtactt  42300
tcagtactca tcttgactct atttgttagg ttgttgggga gtctaaaggt ctacctttgt  42360
ctctgaaagt ccttggcgct tcattaaacg atcgacctga aacatattgg gcaattgcag  42420
tggagaggtt atcaagaggt gaacctgttg atgaaactca tgagagtaaa gtgtttgctc  42480
aaatcgaagc aactctagaa aatctcgatc caaaaaccaa agagtgtttc ttggatatgg  42540
gtgctttccc tgaaggcaag aaaatccctg ttgatgttct catcaacatg ttggtcaaga  42600
tacatgatct tgaggacgca gccgcctttg atgttcttgt tgatctagca aataggaatc  42660
ttcttactct cgtgaaagat ccaacgtacg gttatagaac tctttatgtt ctcatctctt  42720
gtagccactt ttataatttt aaccattctt aactaattta ccgtggataa tgttgcaggt  42780
ttgtcgctat gggcactagc tactatgata tattcgtgac gcagcacgat gttttaagag  42840
atgtagcact tcatcttacc aatcgtggaa aagtaagtag aagagaccgc ttattgatgc  42900
caaaaagaga gaccatgctt cccagcgaat gggagaggag caatgatgag ccatacaatg  42960
cacgagtggt ttccattcac acaggcaaga atttgttatg caacgatctt ctaatgaatt  43020
aattcggttc gtcactagaa tcataaggta ttaatatgga tttctttaca ggagaaatga  43080
ctgagatgga ctggtttgac atggatttcc ccaaggcaga agttctgata gtaaacttct  43140
cttcagacaa ctatgtattg cctcctttca ttgctaagat gggaatgctt agggtgttcg  43200
tgattataaa caacggtacc tctccagcgc atctacatga cttccccatc cctaccagtt  43260
tgaccaatct aaggagtctc tggcttgaga gggttcatgt ccctgaactc tctagcagta  43320
tgataccctt gaaaaacctc cacaagctat atctgattat ttgcaagatc aataacagtt  43380
ttgatcagac agccatagac attgcccaaa tcttcccaaa attgactgat atcacaatag  43440
attattgcga tgatcttgcg gaactacctt cgaccatctg tggaataacc tctctcaact  43500
ccatcagcat aacaaattgt cccaacatca aggagttacc gaagaatata agtaagctac  43560
aagcccttca acttttgagg ctatacgctt gcccagagct aaaatctctg cctgtggaaa  43620
tctgtgaatt gccaagacta gtgtatgtcg acatctctca ctgtctcagc ctaagttctc  43680
```

-continued

```
ttccggaaaa gataggaaat gtaaggacac ttgagaaaat cgacatgaga gaatgtagct  43740
tatcgagcat accaagttcc gcagtttcat tgacttccct atgctatgta acatgctata  43800
gagaggcttt gtggatgtgg aaagaggttg agaaggcagt tcccggactt cgtattgaag  43860
ctactgaaaa atggttcaac atgacttggc ccgacgagta gtaggttctt aattctccct  43920
ccgagctttt gaaaatgcat gttgtattat tatttattaa ctcgattagg acccctgtat  43980
gatatacgat tttattaata catgttttgc tcttataacg tcaatatata aattatatgt  44040
tgattttaag tattaaaagt ttctatttgg aatctcaaag atatgttttt aaagattcac  44100
ttataagtaa taacaaacaa acaaaaacta tttagcttaa tggtaaaaag catgagtcta  44160
tatagagaag ggttcataat ttaaaattag tttgaatgtt gtttgttatt aagtgagata  44220
cattttaaaa taatttagtg agataaatat atcgttaata ttatgcatgt gctgattatt  44280
atatgaccaa ttatatgacc catcaatagt tgtcaacatt ttcttggtgg atcgacgagg  44340
acgaacccaa tgatttagaa acagggatga tatataacaa gtaagtatag tcgcaagtgt  44400
ccctgatcta tagtcataca aggtaaggcc cactgctgaa aagagaagtg gcggtcggat  44460
ttaaaacaat acaagtgaag tagtgtatcg agccctttgt aacatgagat tgtatagatc  44520
ccagtaagag atggtagatt tttaatctga gataagaaac tatctctatt tggaaatcag  44580
agaatacttt agcaggggag agggatggga gctacctcga gggcatcaag ttcttcaaaa  44640
ctggagaatc atctttgatt tggatatcag aaagagaaga tatatctatg gttatagtgg  44700
ctgagacaaa cgattctctc tcccaaggat cattgggact gccttggcca tctggactgc  44760
aaggtataaa caggaagaaa taaaaacaac aaaaatatca aggatatagc actaccaata  44820
tgataaatgc attgacaaaa tcagtctttt aagtacaaaa atacttttgg tgaagggaaa  44880
actaataaag gaaacttgtg ctattgaagc ggacaaacag ctacccacac accattgtgg  44940
gggaattttg agaaacagat ttgagacttt ttattgttga tagtaacata tacataatgc  45000
tctagcttct tctttctatg cgacgaatca acaatattgt ccatgctatc aacaatacaa  45060
ataatagcta aaaccccaaa aatcataaaa ctaagcaaca agctaatctt cttcagtttc  45120
agagcaagaa tcaaaatgta cagtatttaa aagagctaga cagactttaa cgtagaagaa  45180
aagaatcaat ctccagagcc ttccttagtc atctctgctt cctttttttg catcttcacg  45240
taatgttggt tatgcgattt aacttgttat ggattcctag tctttacaaa ttctctagat  45300
atgacctccc aagctcctgg ccctttcgac tttagtcctt caagaaagag tctgaaaacg  45360
tacaccaaag taaatggata atcagatgag agattcatca tatgatctat atttaccaaa  45420
ttagcaactt taaacaatta atgcctaagc aaagccaaga cctccatcta acattcatca  45480
tcttaaatta gcaagaagac aacttactcg tgttcttggg ctgaccaacg agttcccttc  45540
ttcgccacta tcggcgtcgc tgaacgtggt gagtactcgg gcacaacatc tctgccggat  45600
tcgataacag caatatcttg gagcagctta tcgtagtggt atttgatctc atccaccgac  45660
gttctcattt gtgcagcgat aatctccagc tttgccggcg aatccgggac ttgcacgagt  45720
gcaacctcga aagctttgtt ctcctcccaa gtccacttca tcgtaccagc cattgtagcc  45780
aagaaaagaa agaaaaagaa ttgagagaga gagagagaaa gatcgagcga gtgtaacgac  45840
gtggagttga atctgttacg taacaagaat ctttgcgatt tatatcttta tacagcaaca  45900
acacattaaa ccaagaaatg aaccaagatt acatcttaat taattcataa accggacatt  45960
ccagagccct taaccggaat tatattagta tatcactata tacatgttaa taatagcctt  46020
gataaaataa tagcaaaaca gattagcctt ttagtttttg acgtcatgca tgcacttgtg  46080
```

-continued

```
ggtctgtgaa aatctcgcgt tttctcgtgg aaaagtggat cgcttacaaa acctcaagat  46140
atcttttttt ttttttcaac ttgaacctca aggtatctaa gcctttaaac aaactctctt  46200
ctacgtttta taatcaacag aaaaatgtta aaatataaaa cttcaaatac aaattaacaa  46260
ttatcaaact agccaaatgt tatatttcaa acatcattgt tcattgactt tttacatgtt  46320
ttcaaatatt tactttaata caaaataaac aaaatactag tggcgtataa aatatcataa  46380
aacacgagca aatatcggag gatactagaa aacatataaa gttgaaaata aactaactcc  46440
gtgtataaag aggaagaagt tatcttatga ctagaaaata tatatatata tatatatata  46500
taatattaaa agtgagagca cgggtcggag caaacaataa aaccctaatt aacaatcaaa  46560
gccacctgat agagatgaga aacacattga tgttgtcgga ccttccagga gatttgttag  46620
aggagatact ttgtcgcgtt cctgccacat ctctgaagca gttacgatct acttgcaaac  46680
aatggaacaa tttattcaac aatgggagat tcacaagaaa acacttggat aaagccccaa  46740
aggattttca gaatctcatg ttgagcgact ctagggtatt ttcgatgagt gtcagtttcc  46800
atggaattcc atctgtagag gccacatgtg aacttagcct aatcgactct ttttctagtt  46860
ttgaagataa attcgagatt tctcaagtct ttcactgtga cggcttattg ttatgcaccg  46920
acgcagacaa cactagaatc gtggtttgga acccgtgtac tggtaaaact aggtggattg  46980
aacccaataa tcgttgctac tactatgctt ttggatccta cttggacaaa tcctacggta  47040
atagctacaa aatattgagc tatagtggtt atggctacga gaaccaagaa ctcgcaatct  47100
atgagattaa ctctcaatca tggaggtttc ttgatgtcac tcgtgactgc atcctcgaaa  47160
gatatactga ttacggtgtg tctttgaagg gacatactta ctggtttgcg tcagatgaga  47220
aagagaaaaa tctcagcgta tttctagtca gttttgatta tacaactgaa agatttagac  47280
gtctacgtct cccgtatcag tgccctgatt ataacactgc gtctttatcc gttgttagag  47340
aagagaaact tgcggtgttg ttacaacgcg aaaatacatc aaggacagag atatgggtga  47400
caagtaggat tggtgagacc aaagtggtgt cgtggagcat ggtcttagca gtggatttcc  47460
cgtccgaact attcattttg tctggcataa gtttcttggt cgatgcggag aaaaaattcg  47520
tcgtatgttg tgataattac ttcggagagg atgaatacga taccaaaaac ttggttcaca  47580
ttgttggaga gaacaacaaa gtgagagaag ttaatttcgg agtatccgaa tcatcttggc  47640
catttttgtt taattatgtt ccaagtttga ttcaaatctg ggaaggtgta ggaggcaaaa  47700
gaaagagagt cgaataagta agcttcacgc aaacctgttt ttttttttc cttctcaccg  47760
ttatctttgg tcatatctag ttatgttttg actaacaaat gtttcataca tacttgttgc  47820
attactttaa gacagttttt ttttttttaa tagtttcgtg atcaaaaaag atctgcatta  47880
atgccgcctc cagcaacatg gggtttcat tcttcttttc ttaacacata caaagacaga  47940
aaaagcaatt aacctaatga agagaccaaa caaacataat gaagagctac gtgtacgttc  48000
caagtctagt tccccttcca ggataagatg gttgtttcgt gtttctaagc ttaattggta  48060
tgtgattgtt catcttctgc catcatatat gatagtgcat atgtattgaa attgactttg  48120
gtttttgtga tacaacctgg acacgtttta ggtctttgtc cacagttgta tcagtttcgg  48180
tcatgtttgt ggtatcaaca aaactaagat acacacattc caagtataca tgacaaattt  48240
cactctatgc tacaaataac caaggtttgt actaaaatcc aaatacaaag aatttggatg  48300
aaccttacag aagctatatg gaacattcta acttgatata cttaatttga ataaacaaaa  48360
aaagaagtca ttatttagtt attgaatact ttttttccct tgaccttaca gattactgat  48420
```

-continued

```
taccatatac atacatatat gtgaattttt gaagaagaca acattgcatt tgtaacatac  48480
attgcaaatg agtaacaatg accaacaaca ttaacagatt gtttaccaag acttacagta  48540
aatgtacaat gttcagtttg tatagatagg gtccttatat atgctgagtc aaagatgtca  48600
atcctaaagg aaaggaagac gagtaacggc attccccac aaacgctatc atctgcttat  48660
ttcttttcgg atgaaggtgg caacattttc ttggtggatc gacgagaaag tatctgaagc  48720
cgcactttaa ggtgagtgcc gagattctac cgcgagttga taactctata ctagctctaa  48780
ctctacacat aaacataaca cacaaactta tacaaagata aacgtaacac acaaatatct  48840
gaacagagat tcaattgtca tacacataag caaaaacagc aagaattgtg aaccagagtg  48900
atccacatgt gtatttcaca tatctgagtc gatctctaat accctctcgt ggtgtaccat  48960
atatttggat taaactaaat gatagcatat ttttgtaaat tatcttaaaa ataaaaattt  49020
aattactttt ttttagtaaa aatataagtc tatgtaccgt gattaatata tctagttaat  49080
taacaaagtt gataactatt ccgttattat tacactttgc aatgtcgatc acatcaataa  49140
acgcattgtc cctttccctt ttcgtatccg ccggaaaaaa ataacgtctt ttttttttc  49200
ttccaatctc tctgtctctc tccccaattc ccagattctc atgtaagctc tctccaagga  49260
tttgatttct gtataatgtt tgcgaattga gactaagagc cctctcgatt tcgatttttg  49320
ttcgtctgga tcctttgcgt taggtttttt cttctcgtat aattagggct tccgatttgt  49380
ttacccttag ttcattttct ctaaattttg gtttttgatt gatgggtttt cttgatttag  49440
caatttttaa gatttacttg aaagattccg taattttgtt ctgattcgga ttctttgatc  49500
tgtgctcact agctctctac caaagcagct tccttttctg atccctagtg ttcaattatg  49560
tgaacagatt gtttacttta gcttctcttc cttttcattc tagttttgca gagattttag  49620
gaggaacatg attgtttgaa ttgggagaga cattggttcg tgtaaaatgc gggtgcttgg  49680
tttgagctca agcttatgct ctggtgagga taaggaagaa gaagagatta atggagaagg  49740
ctctctcacg cctgtttatc tcaacgtcta tgatctaact cctgtcaaca attatctcta  49800
ttggttcggc cttggcatat ttcactctgg cattgagggt aattgtggct tcttctctat  49860
tacttacttg acctaactaa atttttcttt gtcattgctt tctatttgct ttcatccata  49920
tctggtttat catgttatca aagtacttct agccttgaat aggaacaatg atattcctca  49980
attgttctcc acaagttgtg atttattatt cattaggtga aaatggtgtt tattatatta  50040
gctatggaat acattattag aaggaaaaag tggaacaagt tttgaggaat ctagaatgga  50100
atgctttttc aaatcctgcc ttattgtctg aagcattctc tttcaataat tagaacttgc  50160
ctgatgagtt atataactgt acttctgctg aaactgttat tgttgctaaa tgttcatcta  50220
atgtggagtt ttttttcact ttgccatgtg tactactagc tcatggtttc gaatatggat  50280
atggagctca tgagtattcg agcagtgggg tatttgaggt tgaacctagg agctgtccag  50340
gtttcatctt taggcgctca gttttgttgg gaaccaccag catgtctcgc tctgatttcc  50400
gctccttcat ggagaagctt tcgagaaagt atcatgggga cacataccat ttgattgcca  50460
aaaactgtaa ccatttcact gaagaagtat gcttgcaggt aacaggaaag cctattcctg  50520
gatggattaa taggatggct cgagttggta agataacttt cttattccag cttattattt  50580
ctttactggt tcttgttgtt tggcatatct ttttacatgg ttgcttgttc ttgaattttt  50640
tcaggttcgt tctgtaactg tatccttcca gaaagcatac agctctcatc ggttaatcat  50700
cctgaagccc tcgagttctc tggtaagtta atcatgttcg ctcttcttca cctaaaaaaa  50760
actgcaatag gcatttggat ttcggataaa ccagttgtgt ttcatctcca ttgtagatga  50820
```

-continued

```
taacgatgga tcagaagaat cagttgcatc ttctgtgtca tacgaaacag atggagaagg  50880
atcggatcat catctcataa cagcaccaaa cagcgatatt gcgtatctac aggacagacc  50940
agtgagactt gcccgtgagc tcctccaaga accaaccgat gatacatctc cgcagtactt  51000
gttgaagcgg tcctgatcat cacaagcatc aacaacttgt gttgtctgta aacagtgagg  51060
caatgggtcc atatattgag tattctttgg atctataagt gtaaaaaaag atttaagatt  51120
taaatcagaa cccatctgag atgttggatt gtagtgtaag atttagagac aaatggtgtg  51180
acaaaaattg tgccttcttc ttctcccaat gtgagttcac atttcagtgt cataattcgt  51240
aagatttgcg agactaataa ttagttttga tttttctatt caatttacag acagttaatg  51300
gttatggatt ttcagacatt ctttgttctt cggttcactc ttcgcagcta tattttattg  51360
gaggcggtaa cataacttat tgggctagcc tgggaaaata attatacatt gggcccatta  51420
ttttaaataa ccttcatcgg cccagtttgt gtgtaaacag ttatgatcag atccagaccg  51480
tccaaaaata gggaggggtg actctcgaac acgatgctct gaagactgaa aaaggcgtaa  51540
actttttca cctggctagg gttcttggtc gtcgttaact ggtacgtttc aatggtctct  51600
ctgtactatc atttctgcga aatgggtctt ctctttggag gctaatcgac gttgtgctta  51660
atctaattgc tcttttaggt tgtttagagg aatatatcac aggttttcaa ttagattgat  51720
ctgcttagtt ttgtaatcag tgtaggttac cagtgaatca tgaacttccg ttagggttat  51780
aagctctctg tttcttttcc tgacttatca atgtcactaa tttagatttg atgcgtagtt  51840
tagcttttga agatcaggga actgaatata tctggtttaa ggaagctttg aatttctgc  51900
ttgccatgga cattcgactt atcagtattt ttgtacattt tggttaatgt ttatcgaatt  51960
ggtttgatca gtctgtggat tttaacttta caagttaaga tgctattctt ttaggtctag  52020
ttgataggtc atggatttgt tgttatatgg agtctagaca ttttgccact gctttagtgt  52080
tcttagcttc taagggtttc gttgatatat tgtactgggt ttatcgtttc caggcatcta  52140
gtatggcttt ctgcactaaa cttggcggtc actggaaaca aggggtaaat gttccagtgt  52200
catcaatgct cggttctctt cgctacatgt ccacaaaact ttatattggt ggtaagtata  52260
acttcctatc agattgtttc attttcttac tcttcgcagc tgtggatgtt ttctttctct  52320
tgtatagcag tttaaatgtt ttggtcactt ttataatttt ggtcccaggc ctgtcccctg  52380
gaactgacga gcactccttg aaggacgctt tctctagctt caatggagtg acagagggta  52440
tgccctggat cttactatct ttcttttcac tgttctacaa tagaacgtgg ttttgtttgt  52500
gctagttaat gtataaacca ttcaaggatg tgtggttgga ttgaagccgt cctattcatc  52560
attataccat gaatgattga tggtgatgac catttttagt atggtatttg tgttttgctt  52620
tggtttgcct cgggacttaa ctctcttgtt gagtacagtt aatatattca gtcatttcat  52680
tacttgcgta tttaaccaga accttgccgt atcttttttc tgtgcagcaa gagtcatgac  52740
aaacaaagtg accgggaggt ctagaggtta tggatttgtt aacttcataa gcgaggattc  52800
tgccaactct gctatttcag caatgaatgg acaggttaga aatctaaaga atcattgatc  52860
tatctattta cctatcatgt caattgctgt gttgtatggt taatcttccc cttttgttgg  52920
ttttgggatg gtgaaatagg agctgaatgg gtttaacata agtgtgaacg ttgcaaaaga  52980
ttggccaagt ttgccattgt ctttggatga gagtatagaa gaagctgaga agaaagaaaa  53040
taagatgatg agccgatctg tatggaaaga tccattcgtt gatgcgttcc tgatgaagaa  53100
gaagaatgca gctctgaaca ggaaaatatg gtcaaggaga tcgacgattc ttcccgagta  53160
```

-continued

```
tgttgattcg gcggtgagaa tctacaacgg caaaactcat gtgcgttgta agatcacaga  53220
ggggaaagtt gggcataaat tcggagagtt tgcgtttaca agaaaagtga agaagcatgc  53280
taaagcaaag tagcatcttt gagaatgaat tggtcagctg cttgaaagga ttgtgttgaa  53340
aagccaaaaa cgaatcaaat caataaattc tcaataggta aaactcatta gctcacatga  53400
tcatgtagac gaatattgag ctttagaaag tctttagttt tcttgtcgat ttcgtatttt  53460
tggaccacaa aagtgccaat gttattttgg aattcgatta acaaatatca attgtggagc  53520
ttcaataacc aaacgaacga tgcacctcca tagtgcttgt tcaagaactt gtattgttta  53580
tatacagaag caagccaatg gggccatgtt gagtattcta ttcgatctaa agatgtaaaa  53640
gaagattgaa aatgaaatga gaatccagtt taaggtgttg ttggatggta ctagtgatat  53700
tagaggcaaa tggtgtgaac ttgttgacaa aattgtgtct tcttctctct ttgagttcac  53760
atttcagtgt cataattcgt aagatttgcg agactaataa ttagtacaag aatttattaa  53820
tcaatattcg tcgttactgg ttatggattt gatatgttta ctcagaaact gtcgtctagg  53880
cttgaaggga tttattattc agttcacatt ttcatgcaat ggagccctca caagacctgt  53940
aataagacga gttctatttg taagtttttt atgatttata aaaagctcag aaattcattt  54000
atagtctata gcttttatgg tttacatctt gagctgaaaa attaaaactt ttgcttgtag  54060
atattataac ttacataagc tatgaattat atatataaat ttgtatttcg gagctaaaaa  54120
tgttataatt ttattcatag atttcatact tctatgttgc ttacctaaaa tgttaattca  54180
accatatatt ttgagtgtta aggggggtgta aaagcatatg gaattatttg tgttaaaatg  54240
acaaatcctc tgttattcaa tcatcaatat taaaaagttt tataaaaatc cattgttatt  54300
gaaataatga ttccaaaaaa gtaccatcaa atccagtatt atggaaatat tataaccact  54360
ggatttttga atgactttaa ggtggtttat aagattttaa catgttttgt tttttggaat  54420
ttggaagaac tttagaacaa atcataacat ttaatctaaa atcacccaaa aattcatcta  54480
aaaactcatt aaaattcgaa tcattcaaac tatatggttg gataacatag aatttgtcat  54540
ttcaacacca atcatttcaa tgtgatttat tgattatatt ttttatcata gagagagcaa  54600
aaatctctgt caatggcaag taggtaccaa gtagtggcat gagagagtga tgtctggatt  54660
tattgatttc tttggtagct tatacttcca tatgtttcct tatttaattt ttcattccaa  54720
atatgggaca aagttataac aaatagtatt cgatatcaaa cgtcaaaaca tgtactccca  54780
aatatatttt attggaatat agttttggag atatttttac ctggggggag atggaaccaa  54840
aataagatct agaaatgtga ttggctaacg aaagaagcac aataagttaa caagtgacag  54900
tgacaattta tccctcgaca acaacacaca ttcacatata tctttttatt ttattatttt  54960
tctgtgtgtc tttaaagttt acagcacaag tagtttctaa atcttataat caattttcat  55020
tgataaacag aaatttaaaa tatttaaata gacaaataaa tgatcaaatc tatatttcta  55080
tacaagagtt aattcacaaa aatttgttgt gaaacaaact ctttctatat ttctatacaa  55140
gagttaacat atttctatat aagttattgt aaagatcaaa atatgaaaat tatggtataa  55200
atgcatagac acatatatac gtgccctatt aaaagaggca gcgagaagat aatataggag  55260
gaagaggaag aagaagaaga tggtgaagaa gagagttaat gcaactgcaa gaagatagta  55320
actaatcagc accgtccatt tttgtcatct aattctttct tacttggccg caacttccaa  55380
ccacatcaca cactctttct attcccttat atattcccat ctcaaaagtt cttggagaca  55440
cataaacatt aaaaaaagaa aaagaaaaaa actataaaca taaacgccaa tcgcaacttt  55500
cttgtctttc aatgggagag aaaggtttga agcggtctgg tgttgcggtg gtggttgcat  55560
```

```
tactagccat ggttcatgtc tctgtttcag ttccgttcat aatgcttcat gggatctcag  55620
ctcaatgttc taatgctagg gatgctaact tcacacagct tctcactaac ctctctggct  55680
ctcctggctt ttgcttgtaa gtcaatccac aaaatagttt atgcgttttg ataaccaaaa  55740
gatcgggaca tgtagaagaa gagttatgta ttcttgctat ctataagacg ataacgtcca  55800
aagtggctca actatgttga tggatttgtt ctaatgaatc cagagaaatt ggaaatggag  55860
ttgccgattc atggttaatg ccgcttacac gacaagcgga aatagcgtgt gagaaggtga  55920
agcaaatgaa agagttgagt caaggataca acattgttgg aagatctcag gttcttgata  55980
cactttcttg aaaatcctaa aataggttct tgatcattat ttacatagtg tttaagtttc  56040
atggatgttg attaataatg gaacagggga acctagtggc tcgaggcttg atcgagttct  56100
gtgacggtgg ccctccggtt tacaactata tatccttggc cggtcctcat gctggcatct  56160
cctctgttcc tatgtgtggt gtaagttttt tttataaatc ttttttctct aaatattttt  56220
tctatgattt taatttaatc aatcaatcac agtaacaaca ttgtcttttt cttgttaaag  56280
tctggtttat tctgtaagtt agcagatgag ctaatcaagg gagatatcta tagcgacttc  56340
attcaagtat aaatctcttt ctgtcttttt taggattaaa tcctcagtag ttacaaatta  56400
attaacatat atctttaata accctgcagg atcatcttgc tcctagtggt tatctcaaaa  56460
ttcctactgt atgtctactc accaaatata ttttgatgat aaaaaaacta cttcaaaatt  56520
tgagatatca caaaatcttt gtttttgatt tatcaggata tgacaaagta cttgggaagc  56580
tctaagtatt tacctaagct taacaatgag ataccagacc aaagaaacca aacttacaaa  56640
gaccgtttca ccagtttaca taacttggtt cttatcaagg tttggtctcc taaaaaccat  56700
ctagactttt caattatctt ttgattcctc tcttgatgat tcggtttttg tttgttttac  56760
agtttcaggg cgacaaggtt atagttccaa aagattcatc ttggttcggg ttttatccgg  56820
atggtgaatt cgaacctctt ctctctgctc aacagacaaa gctctataca gaggattgga  56880
tcggtctgaa aacattggat gatgcgggaa aagtgaagtt tgtgagtgta gccggtgaac  56940
atatcagaat ggtagatgaa gatgtcgtca aacacgttgt accttatctc caggaccaac  57000
cgtcttcggt gcaaagcttc aaccgcaaga cgaagcagcc cttgcatgct taaaaatagc  57060
aaataccaca atagttatac ttattcatgc aatatatgtc gaaaaagctt agtgatgatt  57120
ttgtagaatc cttattctta tagaaatata tacatactta tctgaaaaat cgaattaatc  57180
agtagagaaa cgactcatga gatcttcatc accacatttg tatcaaggct tcaatggttt  57240
tctcaacatg agaaacttcc aatctcattt ttttttgttt ttgttgttgt agaagtctcc  57300
caaaatgact cgaagttttt tcctttttgg ttctttagtc tcaccaaatt acatattatt  57360
tttaaataat ctaacaattc tccaaatatc ctaaaaacta attcatatct ctccaaatct  57420
aaaatttcct aaattccacc aaattttcta aaatcatgaa tccaatacac tccctgattc  57480
aaatctctcc aaatctaaaa tttcctaagt tccaccagat aatgaatcca atacacaccc  57540
ctaagagagg caacgcggag atgtcattag aggaggaact aggaagcaga gcgttaatgc  57600
aaaatgttac caaaaacgtt aatgcaagat atcaactgat cagcaccgtc catttcaaac  57660
tgagaatgta aaaaccaatc acaatcgtac attttttcat ctagttcttc gttcttggcc  57720
acaacgtcca accacatgac gctctttcta ctcactttat atattcccat ctcaaaagtt  57780
cttggagaca caaaatatca taaacatata aacgccaatt agaacttttt tacttgtggc  57840
ggtttacaat ggagaaaggt ttgaagcgat cttgtgttat ggtggtggtt gcattcttag  57900
```

-continued

```
ccaaggttga tatctcagtt tcagttccgt tcataatgct tcacggaatc gcatctcaat  57960
gttctgatga tacaaatgct aacttcacac agcttctcac taacctctct ggctctcctg  58020
gcttttgctt gtaagtcaat ccacaaaata gtttattcgt tttgataacc gaaagatcgg  58080
gccatgtaga agagttgtgt attcttgcta tataagacgt gcaaagtgac tacttatttt  58140
tgttttatat agcatgaaca agatgatgta tttggtttga tctgattctt gttttttttt  58200
tggtaatgga atccagagaa attggaaatg gagtaataaa ttcaatgttc ttgccactta  58260
cacaacaagc agaaatagca tgtgagaatg tgaaggaaat gaaagagttg agtcaaggat  58320
acaacattgt tggaagatct caggttcttg atacactttc ttgaaaaccc taaaataggt  58380
tttttgatca ctataacacg tttcagtttc atggatgttt gatgaatgat ggaacagggg  58440
aacctagtgg ctcgaggctt gatcgagttc tgcgacggtg gacctcctgt tttcaactat  58500
atatccttag ctggtcctca tgctggcatt tcttctcttc ctaggggtct ttgtggtgta  58560
agcttttttt atttttcctc aaattatcta aaacttttat ctgtaattta attttaatca  58620
atcaaggtaa caacaacgat tgttttgttt tgtttctttt cttttaagtt aacgtccgat  58680
ccagcatgta agaaatttaa tgagttgatc aagggagctc tctatagcga gaccattcaa  58740
gtatatatat ctctttctct atatatatca tgattaaaga ctcaattaga aaataataaa  58800
aaatcttcaa tgactctgca ggatcatctt gctcctagtg gttactacaa aatccctaat  58860
gtaagtccat tcaccatttg tttataagaa aacttgcaaa atcaacaaat aagtgattga  58920
tgatcaaaac aacaacataa agttttaaca aaatctttgt ttttctttta tttattctca  58980
ggatatgaaa cagtacttgg aaagatctaa gtatctacct aagcttaaca acgagatacc  59040
aaaccaaaga aaccaaactt acaaagaccg tttcaccagt ttacacaacc tggttcttgt  59100
caaggtttgg tctcatcaaa accatctaga cttttcaact atcttctcat tcctttcttg  59160
atgactctgt tttttttttt tacagtttca ggacgatgag gttattactc caaatgattc  59220
aacttggttt gggttttatc cggatggtga gttcgaaact cttctctctg ctaaccagac  59280
aaagctctat acagaggatt ggatcggtct gaaaacattg gatgatgctg gaaaagtgaa  59340
gtttgtgagt gtacccggtg gacatgtcag aatggcagaa gaagatgtcg tcaaatacgt  59400
tgtaccttat ctccagaacc aacagcctgc cgcacaaagc ttcaaccgca agaccaagga  59460
gcccttgcat ccttaaaaca gagcaaaaac ctcaattgtt atacttatac ttagcaaaaa  59520
aaaattgtta tacttgttca tgcaatatcg aaaaagccta gtgatgactt tgtagaacaa  59580
gaatccttat tattgatata ttgatatata catacctata tgaattgtcg aattaatccg  59640
ttgagaaacg acgaatgagg tcttcatcac cagttttctt caagacttca atgattatct  59700
caacatgaga aacttccaac taatctcatt ttcttatcaa gcatcggttt cacaagctta  59760
tagctagcag cttcccaaga aagcccattt ataaattaac tttggccaat cttttgcaac  59820
atcttcaata tacataaact aaccaatata atgcatcttc tcgatgcttg ttgaagcagt  59880
attgatcaga gtcatcaata acttatattg tctgcttaca gaagtgagtc aatgtgtcca  59940
ttgtaagtat tatttctatc taaaaaatat ttagagattt tattctttac agaaggagca  60000
aatttatttg tatatttagt tgtcaaatta aaatttagtc tatacattat acaaggcgca  60060
agtttgtgga tttaagaatt atataaaaac ttgaaatata tagtttttat gcattctcct  60120
cttgtgtaat acataaacca aatatgagat aggttaatct gtatttcaga taatattaaa  60180
ttccaaacaa tatttttact tgttataaga aggcaattaa tatctctctg ttaatggcaa  60240
gtggtaccaa gtagtattaa actattaatg caatggaaga gtactgttgg aaattataat  60300
```

-continued

```
cctctatcac acattcaaac agatctcctg aaatcttctc ttccaaactt gtacttctct  60360
gatccaaatg taggctccaa aatatagaca tttaccattt actaagtcca caactccttt  60420
cttgtctcct tcaaaaatga ctcttgtgta accatcatat gactccgaca gttcggcatt  60480
gccatgatga gagcttaaaa attcaccttc ctgagcattt caagtcttca ctcccttagc  60540
ttgacctgaa ccaagataaa atgcctttgt cgtcccgtaa tatccatcct gctttggacg  60600
gcatcatagt tacattcgat ccatcctatt tacaatgtta ttttagtatt aaaaacatga  60660
caataaattt gttgttaaac atattcaaat acaatatgat tggatttata agtaattgta  60720
atatgaaatg tccttagtaa tatgttaaaa aatacataga tacacacacg tactaaaaga  60780
ggcaacgcgg gagatgtcat tagaggaaga actaggaagc agagcgttca tgcaaaatgc  60840
taccaaaaac gttaatgcaa tatctcaact aatcagcaca gtccatttca tactgagaat  60900
gtaaaaacca atcagcatcg tccatttttt catctaatta tttgttaact cttaattggc  60960
cacaacttcc aaccacatga cgctctttct attcccttta tatattccca tctcaaatgt  61020
tcttggagac acaaaatatc ataaacatat aaacataaac gccaatcgca gcttttgtac  61080
ttttggcggt ttacaatgga gaaaggtttg acgatgtctt gtgttttggt ggtggttgca  61140
ttcttagcca tggttcatgt ctctgtttca gttccgttcg tagtgtttcc tgaaatcgga  61200
acacaatgtt ctgatgctcc aaatgctaac ttcacacagc ttctcagtaa cctctctagc  61260
tcacctggct tttgcatgta agtcaatcca caactctttc gtccttttga taatccaaag  61320
attatggcta tttatgtgtt cttgatactt aagacgtgca aagtgactat ttatgatgat  61380
gtctttggtt tgatctgatt cttgtttttt ttttttggta tggaatccag agaaattggc  61440
gagggaaatc caataggcgc ttcatggtta ataccactta cacaacaagc ggaagtagcg  61500
tgtgataagg tgacgcagat ggaagagttg agtcaaggat acaacattgt tggaagagct  61560
caggttcttg aaaaccctaa aatcgggttt tgatcattat atgtacatat tgtttaagtt  61620
tcatggatgt tgatgaatga tggaacaggg gagcttagtg gctcgaggct taatcgagtt  61680
ctgcgaaggt gggcctcctg ttcacaacta tatatccttg gctggtcctc atgctggcac  61740
cgccgatctt cttcggtgta atactgtaag cttttttatt tcctctaaat atcaaatata  61800
tatctttgat ttcattttta atcaatcaat cacagtcaca acattgtatt tttctgttgt  61860
ttttggtttt ccttgttcaa gtctggctta atttgtgaca tagcaaatgg gataggcaag  61920
gaaaatccct acagcgactt tgttcaagta ttgatctctt tctctctctt tacatcatat  61980
gattaagtcg tcaattagaa aattaattaa aatctttgaa tgacttttgc aggataatct  62040
tgctcctagt ggttatttca aaaaccctaa agtatgtctc tattcaccat agtttattag  62100
gaaacttgca aaatcaacaa attagtatct acctaagctt aacattattt tttctgtttc  62160
acagaatgtg acagggtacc tgaaagactg tcagtatcta cctaagctta acaatgagag  62220
accatacgaa agaaacacaa cttacaaaga ccgtttcgca agtttacaga acctggtttt  62280
tgtcctggtt cgcttctctt ctcttaacta ttatagttgt ctactatctt ctgattcctc  62340
tcgtgatgat ttgtttttct tttatacagt ttgagaacga tacggttatt gttccaaaag  62400
agtcatcttg gttcgggttt tatccggatg gtgacttaac acatgttctc cctgttcaag  62460
agacaaagct ctatatagaa gattggatag gtctgaaagc attggttgtt gctggaaaag  62520
tgcagtttgt gaatgtaacc ggtgaccact taataatggc ggacgaagat ctcgtcaaat  62580
acgtcgtacc tcttctccag gatcaacagt ctgccccacc aagactcaac cgcaagacca  62640
```

-continued

```
aggagccctt gcatccttaa aatgagcaaa tagttcaatc gctatactaa ttcatccaat  62700
gtcgaataag ctcagtgatg attgtgtgac acaataatcc ttcttcttat atgaataata  62760
aaagcatact atctgaataa attgaattaa tcaatagaga aacgactcat gagatcttca  62820
tcaccagttt tcttcaaggc ttcaatgatt ttctcaacat gagaaacttt caatctcatt  62880
ttcttgtcaa gcattgattt cgcaagctta gcagcttccc aagaattccc ctgttggcag  62940
agaccgagca aaagaaccgc atgtatatcc gagtctattg ttgatttcac atccttcttc  63000
tcgatttctt gatacagaag gaaacaatcg agataccttt ccaacaaaca taactccctg  63060
aaaacatgac tgcacgcaag accatcaggt ctaaccccgc ggaccaacat cagacggaaa  63120
atcttttcag cctcttccca tcttttcata cggattagcg acacagtagc cgaactaaaa  63180
cactcagaaa gagaaacacc gcctagtttc accaacttat caatcaactt agaaagagcc  63240
ttcacatcct catcattctc caaaaccccc tgaatcaaaa cacaagcagt aacacgattc  63300
ggcatgcacc ctcggtttcc cattctatcc aataccaaca acgcctcttc aaccctcctc  63360
ttctcacaaa acgcttgaat caccaaagta taagtaaccg cattcggact aatcaatcca  63420
ccaccgtctt ctttctccat ctccgccaac aactctaacg ctctctccat atcaccagac  63480
ttgcaaactc cttcaagaat cctagaatac gtcacactgt taagcacgca atcatgctta  63540
ctcatctcct tagctaacct ccaagcgtca tcaatcttac ccgcattgca atacccattg  63600
atcatcgacg tataagtaat cacatctgga taaagaccaa cacaatccat ctcttttatc  63660
aacatatcag ctatattcaa atctccctta tcagcaaaca acctaatcac caaattatac  63720
gcaacagtgt ctgcacatac attaaattca ggaaacttcc ttaataccca caatgcctca  63780
tcagcgagat tcgcttgatt acacagagtc agaacaatcc tcatcgtctt aacattaaca  63840
aagcattctt ctttccgata agattcaata acgtatttga tcaaatctgg ctttgctcta  63900
atcttaagaa tgtcgcaagc tttggtatac atgtaagcac tgtgtctatg gctggataga  63960
gttcctgccc atatgaaaaa cctaagaccc gattgaaatt gatttggatc gcatcttctt  64020
agtacctcgt tgatacaaga ggagtctaat tgtacattag ccgaagctaa ttctttctcg  64080
agattacttg tgcatccttg aagctggccg tataatctct cggcggctga gacagttgtt  64140
aaaaaacgta aagctgagat ttttgagggc tgagatcgta atgaaggaga taccagacga  64200
gaaatcaatg aatttggcat ctgggtcgct ataagtgtag cgattgatga aagatttcgt  64260
taagaaaatc gtaagaatga gacttgagtg agagaaatag gagagtttcg ctttcgcaga  64320
tggaaacgac gacgaaagac taaacgtatg ggccgacata ataatgtagc ccattaagac  64380
ccaataagaa ttgctcatac atctttgtca gatctgaatc ggaaaagcaa ttgaagtcag  64440
attaggtcac aagatttcat gatttcgtta agaacttcaa ataagctaca cttctttttc  64500
ttttcttttt tgagcaactg catataagct acacttatac catgctcaga aactgtgtat  64560
ttatctagaa gacgtttgtg aatttttggt ttaatttaga actcttgtaa gatatcaaaa  64620
aaagatagtt tcataatttt tggttaatat agcaagtttg taactaattt ttgctaattt  64680
aaatcttttt aaggttgcat catacatagg actagttcat gagaaggcca atcatccaaa  64740
attacaatga ccccacacag atagactata taacgataac gaaaaatacc aaaacaccct  64800
tttcccacca ctaaaataaa aaatcacgat cgtggacgca aggcttcaaa attcagccca  64860
tgagccacct gaccagcaca agcaacccac ggattgatag aaacgggcct gtgattgtgg  64920
tgatggttcg atgatgatgg gccacccaca cgctcgcacg aaggacacat gatgagtgta  64980
gttggtggag tcatctgacc gtagaattgt ggagacagct tgagagttcg aagctccata  65040
```

```
gcctctttct gaagtctccg gttctcttcc gttagcttct ctacgcaccg tttcaagtat  65100
tcgcaatcta cctccgtttg ctttaacttg gttctgtaaa accaaatcgg accttgtaag  65160
taaaaacttc tacacaaggg ggtataaatg taattttaca attttggtgt taagacaaga  65220
aaatctcacc tagctcttct gttttggaac cacacttcca cttgtcttgc cgtcaagttc  65280
agcttcttag ccaaagctag cttctgtttc tgtaaattat gataataacc ttggttattt  65340
caaagtaatt acgataatta tcatttgatt cctctgactt ttttacactt acgggattga  65400
gagtgttgtg ttctttgaaa gtctcttcga gaaaagcaga ctgatctttt gataacctga  65460
gcttcttcct cgacgtttcg cccccgtctt cttcttcatc tgaggttcca cgtgagtacc  65520
ctcgatccgg agtgatctcg tcgtgatcgt cgccggagcc aacgccggtt ccggagattc  65580
cttctctctc acttctcttc ccgctaatgg tgcttgagat cgtactgttt ggtgacgaaa  65640
ctcctgtgtc ttcctcgcag ttaaccgttg atggaaaact gttcacgtct atcttgcgaa  65700
gatctgcaaa gagcaatcaa atttaagtt tgagatctgt ttttatttta cttggaaacg  65760
aagaaaagtc tcatacttca attctgaaat ctgttctgtt tctttaaaaa aaaaaacaga  65820
gaagatttaa gtatatacct gatgtaggat cgaatgtttg gttccatggg agtctctgga  65880
gattgtttga taatgaagag ttaggattca gattcatctg aagaggattg tgattttgtg  65940
aaaaccctaa gcttaggctc aaacctagat cttctttgcc catcatcatg ttttttattt  66000
cctttcacaa gaactcaaca gtttcaggaa ttatatttcc ttatgagaat agagaaagaa  66060
agaacacgaa atggtttgtt ctttctgaga tagagatgag aaatggtgtt tgtttcaact  66120
cgaagttagg actctttgtg gaagagaaat agagagagat gtgagatggt aatgaagaag  66180
agaggggatt aatatagtac tttgaatgat gagagatttt gtcaggtggc taattacaat  66240
ccatcattat tgtttctttg tttttggact tgtattactt tatctccaac ttgtgtcccc  66300
cctttggcct ttgccatgtc tttctttttg tactttctca atatttgtgt ttttcttttt  66360
ctttcacaaa catttttagt ttattcctta caagaaccca tgcataataa gatggcagtt  66420
tgtccaaaac aaataagatg gccaatatgt tttcaagtgt acacatgtat atgtgttttg  66480
tgtctgaaga tttaaagcca atgtctttaa aaccaataga aatgtccgga ccactctgag  66540
aaagtaatct acaattaagt gaatcatcaa ggtgcgatgt tttttgtata tggataacgc  66600
aatttgcact acttgtgtta attttcatga tccatatcat gtagtatgtc tcaaagttga  66660
taaatacaat aattctcgta cttcgttttg tcttaatcaa gtacacgtca ttatactcaa  66720
agtacatgta ttatgtggat atcaataaaa gaaagtatag aaaatagtat cttgattagt  66780
tacggcatac cgagctgagt caaatctcca atagtgtagc caattatttg tccaaatatt  66840
ttttaaagag aaaagggaaa atagtatttg aggttggata taatggaata ttgactaatt  66900
ggagtggttg gtacaaaaca caatcaaaaa gaatctgaac ttgttcaaag ttgtggacca  66960
accaacggtt atgaaccaat gatatacgtg tgagatgaat atttgcacat aaatatcatc  67020
atcatggttt ctactttcat caacaatgac attttaaagc tactactttt tttcgtttct  67080
tccgtcagta aaacctttaa atgtttgtgc tttttccttt agaaataaaa atttaaatgt  67140
gagcaatatt ggtcaagtgt gtgtaaatgt ataaccactt tgcgtacagt aacatggaga  67200
taggagcatg tgggtcataa cagcgtgatc gtgcgtgttg tgttgtttcc tcactcgcct  67260
gctccttatc atgtgtaacc atccgcctca atcaatgcta acttgttaat tatttgattc  67320
ctttaactgc tgcctacttt tttatcgtct aatattcctt tcttttcaca aaaactagtt  67380
```

-continued

```
gtagactaac ttcagttttt gtaaatagtt gttttacaat gcctgaagca tgtaaactta  67440
attgttctag taaactacta gtgatcgttg cataatcata attcacaatc caaataaaag  67500
tgtcattagt gtatatgtaa acaataaaaa aatgatggtt tggatatact tttgtaaata  67560
tatttcatgt ttatttagaa aaaaataaca tgtaaactaa aattccaaaa acaatttaat  67620
aatttccgcc taacgtagac atgtatatag tgaaattatg aagagatacg gcaatgagcg  67680
acaataattg agagcaaaaa gatgggtttc gtggtgagag atattatgaa aagtgggacc  67740
caacgcttta cataagatcc gacaagatgt cggagttgtg tttcagtgtg atctggctgt  67800
cccacgtgtt cactctgact tgtgccacac gcactgacca agtgcgttat atccacgcgc  67860
gcatgtttat ttgtaatcat ttacccctca acgaaaaaga gagtccgcaa agcatgatga  67920
ttgatgatca atcatttatt agtgatcctc caatagcttt tatgtaagta ttggcaaaaa  67980
catcgagtgt tcttggtgtt gaggttcgag catgtctaag tttgagttcg gcaccaaggt  68040
aatatatata tcggattcaa atttggtcta ctagtctaac ttttagcact taattgagca  68100
tgaccgcgga tcttgcacta gggtgaaaca attcttaacg agaacatatt caagtagcat  68160
agcttaaatg agaatttcat gttctatccg taatggtgaa tggcttaaat ttctgcattt  68220
agcccctact agcactttgg tatcgttaat ttgtagatat agcaaattga gatatggcgt  68280
ccaaacagca acttgttatt tcacattatt ccgatttttt cagtagagcc tcgtctattt  68340
ggaggtagtg cagaagggta tgagcattct cttacagtct taccttagtt tctcaattta  68400
catgataagt gaaatattga attgaataca ccatttcgat tacttagttt ccttcggaaa  68460
taaaatatat atatattatt tgaaataaaa gctgcaggcc tacatcacag atccaaatcc  68520
aaagttgagt accacaacac aaaacaaaat cataggcaac ggaatatttt aaaagtatgt  68580
gttgtaatca ttttatatgt ttggcaattg cgtaggacta ataatcatgg ttttagttgc  68640
ttaatcatat gtttcatgca tgtgtatatt agctttgaat gttctttaca gcattttggc  68700
tgtagaacga ggtcatcatt ggggatattt tatactctct gttttttcct taacctaact  68760
aaccaattat tctctaaaca aatagtacat tagattttgt ctaattgtcc tctcacatgt  68820
actgagatct gttaactgga atatttgatt attttttaga tttaggaaaa atcaatcaac  68880
atgcataatt atgatcatca cacaaagcag cttattctta ttctagagaa gctcggaatt  68940
tgaggtttgc atcacatgat tgttggactc ttatagtatt ttaaaaataa acactaagct  69000
ttaattatta acgaaaatgc gtatgtgaca gttttgatta ttttttgacg ttaaaattga  69060
ggcttgttat tactaatggt aataatatga tcgatcattg agattcccat gccaaaaata  69120
aagataggga ttataatttc ttcaatgatt ttgtttaaag tcataatttc ttcaatgatt  69180
ataaggataa aaaatgaaaa tcatattgga gaatcttgag agagagcttc gaaagttggg  69240
tggtgcgtaa aatcttatgg gctacccatg tggaattgac gtggcgcaca tattcttatg  69300
cgacccaaaa ccacccactc cagcgaagca cacgtgtgtg tagtgacacc cgcacgtgca  69360
ttccccactt acatatagat ttccagtcaa cggtcaaaca tccgtctctt atttttctac  69420
tcacaagaat aaacgaaatg tttgtttaat gaacgtgtac taattagatt attttcatat  69480
aatcttgaaa atgatgatcc agaagaaaac tattaacctt gaaaatgcaa agtatcacca  69540
agaagaaaaa tcagattatg ctcttctcgg cttataaatc tataatgatg caaagttgtg  69600
aataacttaa acattgttgt tttgtgaccg ttcactctta aattcaaacc acaatctctt  69660
cactcttgtg ttatattaca tcgaccaaaa gtccaaaatt gtcaaatctt gtcgtcgtat  69720
caacaatgtt ccactgtctt atcaaactat acatgtcaca ttatgatttc acaattagca  69780
```

-continued

```
gttagattag ttagttttgt aaaaaaggaa aaatcaagcc agagcggtct gggaaagaag  69840
atagtttctc ttgtacacaa ggatagcctt tttcattgtc tcactataaa catacaaggg  69900
agagaattag ggcatcgaaa gctttcatta taacacaagc aatatccttc taaacccacc  69960
agggcttttt ctccatcaag tccttggaga aaacataacg gaattttgaa ctgtatggca  70020
accattcgac gacctgcgat gctttcttgt tgtttggttt gccttgtacg catttttgta  70080
ttgattctcc aagcttttcg tctgcgttat ctattaacca tctcatcagg tcatcaaagc  70140
tcagagaagc ttcctttgta aacctctcta taatcttagg taataacact ttcttctgca  70200
tctttacaac cacgtttgct ccaagaaact ctctttttga agcatctaat tcctctttaa  70260
cgtttgatgc agtgtaggct tttagctgca atcacttcca tcatgtaatt tcccattaca  70320
agctattctt ttgctcaagt aaaccaacat attctgactg aaatgtgaca aaatttaata  70380
tatgtatgtg aataagatta gtaataaaac gtcaaaagaa gttaccactg gatctgatag  70440
agcaccaatg caaagagcaa aacagacaag tggctctggt ttgtcaaggc taaacattga  70500
ctttacttta tcttcagctg gtttcttcct caaggcggtg gaaataatgg tctcaagcca  70560
ctgcaacata ggattctttc aatgattctt ctttctgttt gaaaaaggat aaggagtaaa  70620
gactcttaca cgtccattcc gtggagtctg gaagcagaag atagagtatt caatggtgtt  70680
tgcattgatg atgtgcccac cgatattata cgcagactgc actagacatt agacaatgaa  70740
acccattagt ctctgctcaa atatgaatct gttctcatgt caagcattga gatcaaagta  70800
gaataccttg tgaaacaaag ctaaccttct gagggaatga gcaggtacac catatgctaa  70860
gtatgccttg agaagatata tagaagatta tcctcataga agcatgaatt agcagatgta  70920
aagggatttt gtatcagatc aatatattct tacatgcatg aggagagcat tgtatatgtt  70980
gatccaaaag gctaactttg cattgccttc catttgattt atagtaactc tctctagttg  71040
ttcaacaagg agcctgcaag ttaaaatcat gagttcttgt gatggaacta aattcagatg  71100
ttgttttcaa aaactgctat tgttggacta acctatagtt gttgatagca tacgttactt  71160
gagaaaatct tttcttgtct gatgagatcc aagatacttc caccatggat ctgcaggacc  71220
aagctctgtc ttcattcata atgttcttgg ggatgatcac attgctagta gatgatcttg  71280
ataggattct cttttcagga tctgctgaca tggcactgca gcagagccag aagtacactg  71340
aagacataca cttgaccata tcttcagaca acttgtttgg gcattggtac aaatgatcct  71400
taagagttct ctgagatgga gacttcactg ttactgaatc ctttaagaag tgggactgac  71460
agaaaaatca acagaatata taaaagttag aagaagtatc aacaatgact aaattagggg  71520
gaagttagtc tttattcatt tacttttgct tgacttgagc aacttgttgt tgaaggaata  71580
cagtttctga actggaactg agaagattgg tcctttttgg aagtttttct actcgaatct  71640
ttaagagtaa ccatagcatg ccacggcttt agagggaaat tattggagga acaaaatgca  71700
tttgaaataa catttgggtc ttgttttctt ggtggctgct ttatatgatg agctggagaa  71760
gaaatgcttg agctttgttc ggaaggtgct ctgcttactg tctgttcaaa tatacttcga  71820
tatagagaaa gcacatgatg ctcgcgattc gtgacctctg cttcaagcaa ctcaatctcc  71880
gtgataagtt catttgcctg aatcatccaa attcacatgt aaaatctaaa gtctcacaat  71940
ttctatttac tcttaagtaa aatgcagaaa tactgaagtg ttttacctga ccagcaaaat  72000
gtctgtgccc tggagacaaa ctgctcgaag cacggcccat tgctctctct aacaccattc  72060
tcatagattt ctcctgttga agacgaaggt gaagctgctc aacctgtgta gccaagtcac  72120
```

-continued

```
aaagatcatt cagatgagat caattcactt tttggacatg ataatgcatg ttaaagacga  72180
ggagatacga aacatgacgc gcttacatcg cgttccaagg atgctctgtc gttagaagac  72240
acattgtttt tagttaacat ctgacaatta tgcagtggtt ttggtctctt gtttgctgtt  72300
gtttgaacag aggatgccta tggaccagaa aaatacaaat caacctcaaa agaaaaaaac  72360
aatcatatga aatacagctt taaagtgtct tacttgcatt ctagtgaagt tgtttgcaga  72420
ttgtgaagct ccattaccag aagtgtgaag atcccgctct gacgacgcac tgggaagatc  72480
ataaacaaga attcgttcta gcctctagga agaaacattc taaacagaaa aagctctaaa  72540
acagacttct ttgcataaca gtctctatct acgtcgtttt catcatagag acgtttaagc  72600
aaacattggt gtgcaagaaa catcgagaga taatctcaaa aacccattaa tggatttaag  72660
ataaagattc aatattagtg aaaagattga gcttaaacta ttgaagcgag agtacctttt  72720
agagcggcca tgtttatgag aatccaggca atgccaagaa tctccgtttc ttctctgctt  72780
gttaccgtct ttattcaaat caaaaccacc catatatctc agccaaaacc ttaaactcag  72840
atgatgaaag taatcaaagt ctccaaaaga atctcagtaa aagaagaaat tgataaagga  72900
gtgaattcaa atgcagcaaa ggagaagaaa gaatgaagaa gtaaatgcag agacgaaaac  72960
tgaaactgta gcttagccca taagaaaggg gaccaggtta gtagtatcag agtgcctgcc  73020
aaaattcaat tacatttcac tttatggttg ttgtattgca tttaattcga tttttttttt  73080
gtctcatttt aaattcatag ttccatttcc ctccttttttt cgagaaatac aacacttcta  73140
ggttaggaaa attcgcataa atagttatac tcttaatttt ctctggtcaa ataatattaa  73200
gaacacgcta cagtaggaca gtgcagtagt taatgttgtc atgtcggtcc gagtacattg  73260
agaatttaat gttccgatat aaatttcctt gttttttccc aattttgaaa agtccgttaa  73320
attttcatat ttattcaacg agacactgta ctttcagttt ccaccgaaaa ataattcatt  73380
actcatcatt tattcaatgt tcgataattt cttggaagca gacagcattt gggcctcgag  73440
atttaaattg gcccaaggtc cacgtttact tgggtcaatc acagtcaaaa cgttttcccg  73500
gggtttctct caatttttttt gtcaaagtct ctcaactttt aaaaatacaa acactgggat  73560
cctccacggc atgcaaaagg atattataat gaagatgaaa tcaaattggt ataaaaagtt  73620
ggagaaaggt ataaacacta tgtatgtggc taaaaatagc tagaaactta taatttaggt  73680
gaaagaagat ttgagtaacg ttgttgttgt tatataataa gatgaaataa tgacaagaaa  73740
tctgaaataa tatgcgaata tgccaccgac gggagaaata cacgtggacg gctgataaag  73800
ctttgtgaag gaatcccaca ataatataag aagatctgac caaaggttcc tttctggata  73860
agccgctctc ctcgtgtcca cgtggcattt tcaaacgtgg gacctcctaa tctatatcac  73920
taaacccatc cactcatatt atctctcttt ctatcatcta aaatccaaaa tgttcgtcca  73980
ttttttttttt tctgttcata aacaaaaact gcattgcctt ttaatttatt cttcttctaa  74040
tccatacaaa tgattatgga actataaatc tataataata atacaattaa ccacaaaata  74100
aaatatatct tagtattata agatatgact tttggagtta gggggtgtct aatacaaata  74160
ttatggtatt tgtaatctta gcaagaaatg aaatcacaat catgtttatc tttcttaaga  74220
taacatattt tactcagtca tgggtctact tttattttca gtttagatta ttaaataaat  74280
aacaatagtt ttgtcgcctt actatatgac caaaaattag attttctcta tgtgtaggat  74340
gttggcattt gtttaccatt tttcttatga taacttatta aacagatgtc atattttact  74400
tatttgtgtt tataactgtt aaaatctagt caagctttct gtatggaacg cgtgaagggc  74460
tattaagata ttttaaaatg ttgaatagtg taattaatct tgtggctaat aatattcatg  74520
```

-continued

```
ccaattgtta atttctggtg gagggttaac acttgtacat aaatacttaa tttttctttt  74580
tgcagttttt gtatagatat ccatccttat ataaatagaa aaatataagg aaattgtaat  74640
gatttagcat aagacaattg gataatcaca aatgcattaa acctattaac tagtctatat  74700
agaaagagtt attagttaca gctatactat ttgtggtggc attaatatat agtaacttat  74760
ttaagatata tgtcataatg ttaaaaagaa atcacagaga aagctgttat tttttttaat  74820
cctaaattta aaactttgga tattgagatt agcctgtaat acatcttttt ccaaaaaatt  74880
tatacaaaaa tggccattaa taattaatag taatagctag ttggacttct tagttcaaag  74940
taattcaaca ttttttctaa aataaatctt ctaataatag aacacgttgg attgactaat  75000
taagtcaaat atgaaatatg gaaaaggaaa aaaatccacc aacgatacac caaataattt  75060
ccgattttta tatatataaa taaacatact aagagcaaaa gaaaaacaaa ctgaaaataa  75120
aaaaaataaa taaataaaaa aaaaaatccg gccagataaa tcgaatttat gtaataaatc  75180
cgaccagata aactgatatt attgtctttc ttccgctcct ttgtctctct atctctttct  75240
cacaattaga ttctgtgctt cttctgcgat caactaagat ccgatccgcg agcgtttcag  75300
acttcgatca gatccgatta agagaagcaa atcgggtcgg gtatgactcg tcgatgttct  75360
cactgcaatc acaatggcca caactctcgg acttgtccca atcgcggcgt gaagctcttt  75420
ggtgttcggc tcaccgaagg ttcgatccgg aaaagtgcaa gtatgggtaa tcttagccat  75480
tacacgggtt ctggatcggg tgggcatgga accgggtcca acactccggg ttctccgggt  75540
gatgtccctg accatgtcgc tggtgatggt tacgcttctg aggatttcgt tgctggctct  75600
tcctctagcc gcgagagaaa gaaaggtatc ttcgtttgat ttctgagatt aaatttttta  75660
tcaaattcca aatttttgta attgagttta ttttgcatca aagtcgttga ttgcattatg  75720
taacaagtgg tgatctggtt tatgtaacaa gattttgatg tgtgtttgat attggttttg  75780
ttgtaggaac tccatggaca gaggaagaac acaggatgtt cttattaggt ttacagaagc  75840
tgggtaaagg tgattggaga ggtatctcaa gaaactatgt gaccactagg acacctacac  75900
aagttgctag ccatgctcag aagtatttca tcagacaatc caatgtctct cgtcgcaaaa  75960
gacgttctag tctctttgat atggttcctg atgaggtttg ttccttcttc attcaaaaac  76020
accattttta tttatattgg agtggttaca aaatgtgttg agatactgat ttaaaggatt  76080
cagaagctta ttaggtggat tggtttgcct tctacatttc aatatgaaaa gttgaagtct  76140
gttggggttc taattgatat gcttgaggat atcattttgt agccaatcct gcttaagcat  76200
tttggtcttc tcatgggaat gtgatcttga aatgtaattc tctttcttta ttctgcttat  76260
gctgtgtgat ttgtccttgt aggttggaga tattcccatg gatttgcaag aaccagagga  76320
agataatatt cctgtggaaa ctgaaatgca aggtgctgac tctattcatc agacacttgc  76380
tcctagctca cttcacgcac cgtcaatctt ggaaatcgaa gaatgtgaat caatggactc  76440
cacaaactct accaccgggg aaccaaccgc aactgccgct gctgcttctt cttcttccag  76500
actagaagaa accacacaac tgcaatcaca actgcaaccg cagccgcaac tacctggctc  76560
attccccata ctatatccga cctacttttc accatattac ccgtttccat tcccaatatg  76620
gcctgctggt tatgttcctg aaccacccaa gaaagaggaa actcatgaaa ttctcagacc  76680
aactgctgtg cactcgaaag ctcctatcaa tgttgacgag cttcttggta tgtctaagct  76740
cagccttgca gagtccaaca aacatggaga atccgatcag tctctttcat tgaagctagg  76800
tggcgggtca tcttcaagac aatcagcatt tcacccgaat cctagctctg atagttcaga  76860
```

-continued

```
catcaaaagc gtgatacacg ctttataaaa gacctgagga agtgatggtc taaaatggga  76920
tctggtttgg ggtttacagg ttagttgttg gtcacagtaa cttaaataag tttttctttg  76980
ttaggttgtt taacttgggt aggatgtttt agttcagctt tgatcattag ggaaaagaaa  77040
aaagaaaaaa aaaagggaga aaaacaaatt attatttttt gcttacattt ctttatattt  77100
gtatgctttt attttgactc taggatgcgt taattttcgt ttaatctgta ctaaaaatta  77160
gaatttatta gttttgaata aataaaatca cagtttgttt atcctctgac caaaaactat  77220
aactggattg aaaacggaaa ttaaaccaag acgaaccgga tttaaccgga ctccagtgtt  77280
gtaagagaaa gtaaacaagt tcccaagcgt ttcgtaagta aaaaaacgaa tgggctaaac  77340
aattagtcta aatgggcctt aaaagagtga ataacgtgtc ataatcagga gcgttaaatt  77400
tagggcgatg agtgtcgaga gtgttcccgc gttcaccgat tcactccact ctttggttaa  77460
aaagtccact gtcatggaaa attaatcgcg gtgatttaca cagatgccac gtggcacgtt  77520
cgctttcttt ttcttcctcg tgttgatttt ttttcttctc ttttgtccct ctttggtttt  77580
tcttttcccc ttcacaaggc gcgatttgag tcgcctcgca tttcaaaccc ttcttctccg  77640
gcgtaaacct ttgctctatc tctcgataaa aacccttgtt tcgttttcac cttcgtattt  77700
agcgatgctt ccacactcct acaccgtcga ttcgctttcg caatcacaag acctagcttc  77760
agctatactc tcagcttcca cgccgtcgag tatctccgct gcttgctctt ccgtcgaatc  77820
gtttcttcag tcgcatacgc ctgatcagtg tcgccatttc ttctctgtta cttttccgag  77880
tttaatctgt aagatcttcg gtttcggcga cacgaccgcg gcatctccgg cacagtcttc  77940
ttcgctgcga ccgaacggtt ggatcgatgt aatctcggcg gccaacgatt tggatttagc  78000
ggagagagta tacaatctct tatcccctag tggaatactc atgagctcaa tcttcgctgt  78060
tgataaatta gctcttgtta agtatgtttt cccgacggaa cgtttaccgg agtatgctag  78120
attcatgctc tccagcgaga aggatcgaat tgcgttatcg aatctgtgcc ccttttttgaa  78180
aggtaaaatt gaggaggatt cagttcgtgg ttcattgtgt gaagttaggc taaatgtttt  78240
tgagtattac atgttttggc tctcttatta tccagtttgt agaggaaaca atgagatttc  78300
agctgtgaat ctgaatccta tccaaaagag aaacaagttt aggctagaga attggacact  78360
tatcaaaggt tttccaggga gtaacaagcg tgattctgat cagaaattgg agtgtaatct  78420
ctacataagg cttctttact cttatttgaa agcatttgtt cctgttttcg acttaaacgc  78480
tcaccagcct tatcgtagtt ctcttttgca ttacggaaat gggtatgatg ggtcagtgat  78540
gacaagagct gagttcttgg tgaatgtttt cgtgcattat tggcttgttg agaatgactt  78600
ctcaccattt cctgttgtta cggctaaatc ttttggtgtg gctcctcctt tccgttctgc  78660
tgtggaggag attccaccta cttgtgggtt ggaagaagta gtgaagttgc ttgtcaagta  78720
tctgaatttg agttgggtta caagtggtgt tgggagtgaa aactacattg agtatggcga  78780
gagtccacgg tggaagacac cgacttcagg atcgtcatcc catgtcgcga atttgagcct  78840
caggccgctc acttcctgga acacccattt acagaggccg ctttatcgtt atatattgag  78900
gagtttcttg ttctgtccca taggaagctc aattaagaat gcatctcagg tgttctccat  78960
ctgggttacg tacctggaac catggatgat cagtttggat gatttctcag tttttgaacc  79020
tgctttaagt ggatctgtaa aagatatgaa aaaggaagat tcttatgaat cacgcgtttg  79080
tggatacacg cctttgtggc agagctatgt gatatccaat tatctctact atagttctct  79140
ggtcatgcat tttattggct ttgcacacaa gttccttcac acagatccag aaataataac  79200
tcagatggct cttaaggttt gatccctggc ttaagctatt ttctcaaatt catgagttta  79260
```

-continued

```
tctgtagaat atggattgca agacttctgt ttgaaatctt aatgtgactg aatggttcta  79320
ctgtgtctcc ctaaataggt gatgagtacg ttgacatcgt caaaagagct tttggttctg  79380
atgaagaata ttgataaagc ctttcactct aaacaaactg gaccaggaaa ctcaaaagtg  79440
aacgaattgt ctagattttc tccatctatc cgtgagcagt tgaaggtatg cctatatttt  79500
tcctcaacac cagttgttat ctgttctccg gtcatagaac gcttttccag tgattttact  79560
cttatgtatc cgccatcctt tgtcttcata cttatttagc tttttcatca taacaccctt  79620
ggaagtttaa caaaagactg taaaatcaat cttttttca cataagtcac ataagtactc  79680
aaactctata ctgaaaaatc atgtttaact gcttgtggaa cttcaggatt gggaagatgg  79740
gttgtgtgag agcaacgctg atggctcata cttgcatgaa aactggaaca aagacttgaa  79800
actctttagt gatggtgaag atggcggaca acaactgctt caggttaatg tcttcctttt  79860
ataacctact gtagtgataa gttaggaata aaaaaatgga agataatctt tgtaggatga  79920
tatcttcaaa tgtacttaaa atagctctat tatggaatga tctagttgac aaatatatag  79980
ataaaccttc agatttactt gtttgttgtt tgtagccttc tatctatatt aacaggagaa  80040
tttgttactt gacaattaga tgagtacgca gtcatcggca atgttgtgag ctattaactt  80100
gggaatttgt tttttgagaa attgttcacg gaaatatact ttgagaacta gttctcctac  80160
atttgttttt cagtaaccta gttgtatcgc atgttttctt gtttccgata ctctacttta  80220
gtttatacga ctcttgaatc ctttagctca taggggggga gtggagctta aaacctgttt  80280
tactttgctg aaggcgtttg ttctttgcat ttgcagctat tcatactgcg ggcagaagcc  80340
gaactgcaaa ctgtatccga taaaaacctc acagaggccc ttaagtgtgt agattcacta  80400
aaatcagcgg tttccaactt ctttggcggg catgtcgtaa aaccaatcgc ttttttccta  80460
gagccggacc atcctcagaa aaaccgtgac gagctcttca agccacgtgg tgctggtaac  80520
caaacagcag gcggtgtgaa gtacaaaggg gactggatga cccgtccggt gtcagaagac  80580
gaggttgcat tgatggctaa actgctaatc aacatgtcta tttggctcaa tgaacgcctc  80640
gggctgaaca aatctgagac gagcaacgac aagaaagaga attcagagtc agtatcatat  80700
gtagatgtat caggggaaga tgtgggaaac gttgcaggac ctggagatgc tgcgaagatg  80760
ctgttgcgag ggatggtgat ggtatgtggc acagtgttgc agctgatgag aagattcggg  80820
attcgagtca atcttcgggt tatggcttca aaaaagtttc tgatgctttt atttctctat  80880
gtcctgtttc ttgtagtcaa aagggtagtc acaaggatga tttggtagat gggtgtccaa  80940
aatgtgttaa aagttgaaga agtaaaagga aatagacact ctaactcgcg tagagcgttt  81000
gataggaatt ggaaagctta tttacgaaac agggactgag ttttttggta atttacatgt  81060
tcgcattaca aattgaagcg tgtctttact tgttacaacc aatgagaatg gtccacgtaa  81120
tcagtctcca cgtgtcatct gccaataaga tccacccatc agcaaaattc atcggtcgtt  81180
cgtcgctgac tatcacaatt ccgaacacca aatttcgaat ttctgccact tgctttgtga  81240
tctgatcgtt cgaaattgac cggagaattc ttctgtgttc ttagatctgt cgcgaatttg  81300
ttaaagctcc tcagaaggtt ttggttacag atcttctctg tggtcttcac cactatggcc  81360
gctccgtttt tttcaactcc atttcagcct tatgtctacc aggtgtgctt cttctctctt  81420
tgatcatttc gctttcaaaa tgatgaggtc gtgttcttct tagttgcaat ttgactaaat  81480
ttgaggttca ttgtaagtag gatttagaga aattccatct ttgattagtt taacttagct  81540
gggagaacgc ataatcgggc caattaggga ttttagatca tgacattgtt ctagtgttgt  81600
```

-continued

```
ctaataagtg gccatttgat gcagagtcaa caagatacta ttacaccgtt ccagattttg  81660
ggtggtgaat cccaagttgt tcaggtacat ttgctttctt aatatagcgt gatcttcgta  81720
tttgtgggtt atatgccata taattttaac ttctctaacc attgctcgta tgttggcaga  81780
taatgttaaa gtcagaggag aaagtcattg ctaagcctgg tacttccact gaataactcg  81840
cttctctact cagttttgta taatggtttc aagtttcaac taattttgtg ttatggtgat  81900
gtagcttcca tgtgctacat gtctggctcc atcgagatgg aaaatacata cactcctgaa  81960
caagaagttg gagttctgca gtggattttg ggcaagagtg taagcagtgt tgttcttcgg  82020
aatactgggc aaaacgacgg gtttgttggt attgctgcac cttatttggc taggattctc  82080
ccggttagtg attttagctt gtccatgttg gcataatcat cttccatttc acccttaatg  82140
tataccgcct gattccttgt tgtttttgtg atctttgttt tccatgtaga ttgatttggc  82200
aatgtttgga ggtgagatct tatgccaggt agagtctttt ttcctagatt ttgaacactt  82260
agctatcagc ttcttcttca ctcagatcaa gctcttacag agtcgcctga ccttttcttc  82320
actttctgta gccagatgca ttcctttgtt ctgtccatga tgtgaaggtt gtcaactccg  82380
ttgaccagag agcaagaaac attgttgccg ctggtgcaga ggtaagaact aagaaggaaa  82440
atacgttgat ttggtttctg atgcaattat tattcttaac aaaattctgc aacccgttgt  82500
ctggcttcta ctcacaaatt gctgttgcag ggatttctga gacaacgcct atctggacaa  82560
ggtcttgctt tcatcctcgc aggtggctct ggtgagattt tatcccaatg aaatgctgtt  82620
tccgttgagg cctcatcccc ttcaataaaa ctgacattta acatcccaaa catgttagtt  82680
gtacaaaaag ttctggaggt aggagaagtt ttctccattg acgtttcctg tattgctgct  82740
ctcacaccct ctatcgatgt ccgaatcaaa aacaatgctc cttttagacg agcactattc  82800
ggggtacatt ttcacatata ctttgtttca atgagaagaa gattcaggtt tttgttttgt  82860
ttctcaactg ttttaatctt tcaacattca aaagggtgat aacgtagtaa tggcgactct  82920
aacggggcct ggcattgtct tcattcaaag cttaccgttt catcggctct cgcagcgtat  82980
tgcaaggtaa agcaaccaac aatccaaatc tccatttatg ttgcaaatat gtttatataa  83040
agtgtgaatg gtttttctgt gacaggtcgg taacgtcgcc aaacatgaga gagaatccaa  83100
aattgctgat acagatagct atatttgcgt tcctagcata cgctgtgatt ttgtcatcgt  83160
tgatcttaac cgaagtttga aagcagagag atagaaagaa ttatccgacc aacaaactaa  83220
cgttgtaatt gttcaaatta tctcgggttt ggactttgga tggatagagt gaagatgaat  83280
tagacacatc tcaaaccatt ttcttttcgt ttactagtga gtttaggcac ttgtgttata  83340
ttgatattgc tcctatatat tgaaaagtga aaacgtagat accgagttga acaaaaattg  83400
gattctttac ttaaatcaca catcaattta aattaattaa tttgattttt tgttttgtta  83460
aataattaat gtctaatgat attattgatt aattttcatc ggatggttaa gaaattggat  83520
taattcaaaa aaaaaaatct ggattaattc gttaccaatg gatcatatag tcaagactca  83580
agagaatgtc tcaatgatat catggactaa ttttcagaaa atggattata gcaggagtta  83640
atagttttcc aaaaacattg aactgtcaaa aacagtaaac atgctcaagc aaaaattcac  83700
aattttgaaa acagcgaaat gtcataggtg ttaacacacg aatttcaaca atatacaata  83760
ctccgttttt tccgtttact ttttaaacta ttcgaattac tcatggatac ggatcttacg  83820
atacgatgaa tacatttacg ttataagaag tgactacaac cattcttaaa catgtttacg  83880
attcgcacat aagatctctc aaatcagtga agctagacca acaagaataa atttgatatg  83940
aatcgtcgtc aaaacaaaca ctaaatttct cactgtaaat tcgctggtct catagattaa  84000
```

-continued

```
gaataaagta gttacgaaat cgaattccac tacaaaaatt aaaaaagaat tcgatgacaa  84060
aagaactctc tctctttgtt cgttacagca aaacaagaag attctcattc tctgtttttg  84120
attatacaaa aaaaaaaaaa aacatgtttg aaaatccatg tcaagctcga gatctctccc  84180
cctttccacg ttttgagtat cggagtttat cttcactcac atcactaacc accaccggtg  84240
gtgatcgcgc gtaccttgac ggcttcctct tgaaatgcct atcttcatca ctagattcat  84300
aatctgctac ttctatttcc ttccgactac tgtgtcggtg aactgatgtt cccacggcgg  84360
ctgcggcaga ggcggaagca gatggatccg taacagaagt agaagaagag gaaggcacct  84420
ttcttcgttt accagaagat gtttcttcct ccggaaaact tatccgagcg aatacgctag  84480
acttaagatt attctcgatc tctgctttag tagcagggac tggtggctcc gatgaaggcg  84540
gttccgatct cttgcggtgg tgatgttggc tgcgttcggt ttcaccacgg tggtggcgat  84600
gatctcggct tctgtcttca tcgcgacggt cgcgagtacg gtcgtgttca cgatctacgt  84660
cttggtgacg tgacctctca cggtcgcgtt gccgatctcg ttcatcagga taacgctcgg  84720
attttctctt ggagtcgcga gacggggaaa tgtttttacg cgtaggcgga tgctctgggg  84780
atagtctctt ctccggtcgt ctccggcgat cgtaatcgtg gattggtggt ggaggtgctt  84840
gtctctgtaa aacaattgtt agcccaaatt attataataa aatatgtatt gaattcggcc  84900
cacaaataaa aaggaaatgg gctcaatagc ccagttaccg tcgtcacctt tcggttccta  84960
cgcctactat tttgcatttt aggcttttta gccatctacc cttctatttc ttttcctttt  85020
tattcacagc ccttagtttc tgataaaccc caattttata tttcagaaaa ttacgttaga  85080
aaccaatata ttttccccta gttttcttca agtttttttt tttttttttt tgggttttca  85140
aaataagcaa aatgagggaa tcagggaaga gaatttggag ccattttctg atataataat  85200
aacatataac caaaagtaaa tgggagagag cgaagcacag gtgaacaaag aaaagaagaa  85260
agagagagcg agaggggaag atgagtcaaa caaaaggaga catacagatt tattagggtt  85320
gatggatgat gcagaggctg aagtaccgtt gttcatcatc attctgctat tctctccatc  85380
cctaaacatc ttcccactgt atatacaacc aaacaacaac caatgtttag gttttagcat  85440
atccttgttt gaatctgtag taaaaataga gtgagtgttt tctttttacc cttcaggtcg  85500
tctctcgttt tcacgttttc ttaacatctc agcgtttcgg gcttcggctt catctctgcc  85560
catcatagca cgttggagat tcattcggtt tcccatttca gctaggtccc tgcgcatgca  85620
cagaaagttc catcatgaga cttgttgaga aagctttatt gctcttcttt gatagagtga  85680
gtgttttacc tatggggtgg tggtatatta gggaacccaa atccttgtgc catgaatgga  85740
tctggatgca tcatattcat acccccacca aatcccatgt ccattgggtt taatccgtaa  85800
cccataaatg gaggcattgc gcctggaaac gggcctccaa atccattgaa gccagggtga  85860
aagccattga agccaggttg aacaccgttg aagcctggtt gtacgccatt gaagccaggt  85920
tgcatgccgt tgaagtactg cggacctggt cccatttgca tcatatagtc agggcctgct  85980
agatctggca caggattcca ttgcatgtct gcaataaatc acataaacaa accatctttt  86040
agacctccca ttcgattcac atagacttcg aaactgacaa tgtattgcct tcagcgtagc  86100
aaagaaagct tttaccattc ccaggcactc ttggtttctt tttcttcttt tttcctgtat  86160
agagacaata agtacgtatt acattgatga atgacaacaa gggttcctca gtaattgaaa  86220
aaaaaaaggt tcatgtgagg tccagcttga ttaatctcag tagggaaatc tgaactggac  86280
tatcagtcac caatcattcg caatgtccag tgaagctaat attagtacat ctttatttta  86340
```

-continued

```
cctggctctc cagcagcaac ctgctgctgc atttcttcct tgggggcttg cgtattcaac  86400
tttgacactg ttgcttcttt cacaatcacg gacccttgag tgctttcaca tgcatcaact  86460
ggcttttcta cattcacttc tgcagatgca cgaggggcac ttgtgatctc tgcaacttcc  86520
attggcgcct ttaaagttga agcatcatta ttgttactaa gtactggttt cttctcgcct  86580
ttagatgcaa cagatgtagt aggagataga gccttgggag gtggacagcg tgcagactcc  86640
aaatctatat tgtccatgat aattcagtag tgaggactaa tcaaacaaag tttaaaaaca  86700
catgaattta aaataatgac ggacctggga tatggccaac gctgcccaca ttctcagtgc  86760
tatcgtttcc agcttccaaa atacggttta tggtatccct gagggtcttg tttggtagaa  86820
ggtcgtcagc aagtacatct gatcttccac aaacacacat tgactttgaa ataatgtgat  86880
ctctgatacc tgaatcagtg aaaaaggata ataatgtaga actggaactg acaacggtca  86940
gaaaaggttt ttgtggaaca gcagaatgca ttaaaagaac ttacacttgt cacagaagct  87000
cttgtaacaa catttgcttg taagcgcagc atctttcatc acttctttgc ataatgggca  87060
ttttagctca ggtggaagtt ctcctacaga acgtgttgtt gatggcaatc cctccatttc  87120
cttctcaaaa gcatccctga atttgttgaa gacacaacaa acatttaaac tataatcaat  87180
atatgtgaag aagtacccaa tagcaacatt cccaaactaa ttcagtacaa cttactcatt  87240
tggtttcaga actgcaactg cgccacttgg caaggaataa gaaccatctg gggtcgccat  87300
caacatggac ttggggatac cagtaggtgg cttaactctc ttaacatcat agttagggtc  87360
tccatttgtg gggcaatgct gaataaaatg tcctgagaca gcaaagaaaa tgctctcaac  87420
acttcttatc tattatatat ccatctacaa aagtgagaga aaaataaaga ttttcagagc  87480
tgacatacca gggatattgc aacgatggca cacataacct ggaggtggcg ttttcctttc  87540
cattcctatc cagccagcaa aaccaaacta agtatcttac aacttgagca aatagaacaa  87600
aaatataaaa tattttgaca gaagtaaatg ttttgtatac tgtattttga cattccagaa  87660
ttcaaccaaa atcaaagaat aaaagtaagt ataagttacc aaaaccacgt ccattcatcc  87720
ttccaggcat acccctccca taacctctac cagctccaaa agtatcttga ccttgtctgt  87780
tacattgaat aaatataaga ggtctgttaa accttctcac aaaatccaac agtttcacct  87840
gcaccatttc tggaagattg cttaccgttg ttgccagtca agtgctggag tgtcaatcag  87900
cgcctgaatt ttgctttctt catctacttt gtcgtctgcg gttgcaagat gaggacgtgg  87960
aataatatgc tgggcatctt gggtatcagg aatggaataa agatcagtcc caaactcgtc  88020
atactcatct tcaggctaag aggtgaatac ggatgacatt agtacttttg tagtagaaga  88080
aaattaggtg cagtcaatgc caacagaagc cgagaaaagt tcactataat caacttacaa  88140
attcagcagc agatggatca gcaacaggaa aattggtggt ttcagcctga acgtcttcca  88200
ctttattctg gattctaggc ctgcaaagtt aagatatttg catcattgag gatcccgaag  88260
tttcttaaat ccgatagtca gacaattaac ttatgtttag ctaaaacgat gcaccagtaa  88320
aatgcaatgc ttttaatatc atgtctattt aagtttaata gctaaataag tagacaaaga  88380
atatagaaac taaagatc                                                88398
```

<210> SEQ ID NO 6
<211> LENGTH: 87394
<212> TYPE: DNA
<213> ORGANISM: Arabidopsis thaliana

<400> SEQUENCE: 6

```
aagctttgaa agctgcaaac acaaatcctt attaaaccga tcaggtcgcg tagcaatcca     60
```

-continued

```
ttgaccaaat ttgataaaag caggacctgc tttctccaga gttcgatgga ggacctcata    120
ctgcagctgt ctgtaacgag gcccgcaagc aaatcccaac aacgccataa taacatttgg    180
agaaaacaaa attgctaaat aaagagctct cccgatcaga acaacaccct tgaccgcaga    240
aaacactaaa gacgagagaa cgatagggaa gtttatcgaa ctcctataag gagaaatgtg    300
tgaaggagaa tagaccacag gatttggaac caccctttgc gcatacgcca cttgtctata    360
ggtaagagcc aataaaccag gtaacaagaa gtgcgaacgg gctaaagaca agctacacgc    420
ttgagcaatc tgacttatcc gaggtaagtt ccaactacga ctcagagtta ctctctgtac    480
aagccttccc caagagactt gagcatgttg cttaactaca ttactcgcaa ctgcaatcga    540
atagctccta cgcgcaagct gatgatgatt actacctaaa aaccttcctt taacattatg    600
aagaagaccc aatgtgtgat atccattact ctgaattctg aattgtggca actttacaga    660
aacattaata gctgttctat tattctgatt cgaaaacaga gttctactaa tcactctaga    720
gatcaaaaat ctgcaaaaga aaccaaaacc aaacccaccc aatgaagatc taatcaaacg    780
aagactttgg agaaaagttc aaaactttat aaacaaaggt tcaattttta aacatagcaa    840
tcaatttaag caatctccgg ctaaaagggc aatcaaaatt aatcggatta gagattcacg    900
agagaccctg aatatgagat tagagacgaa ccttgagatt agggtcatgg cgagaggaga    960
cacgcaaaag gttgagtttt tggaatgatc tttaaaccgt taaacgttgg gagcataatt   1020
tcatcgattt agcgattagg gctgaggaag ctcttccctc gccggaaaaa gaaggttctg   1080
ggttttagga gctgaagaaa gatacggaga aagagaagtc agtgatttgg tgcggagaaa   1140
agtggggccc ataaaaaaaa cctcgtgggc ttcacgctaa aattttattt gtcggcttat   1200
tcgtttattg gattcacttt gacatttcaa tttattttat taattggatg aatgtttttg   1260
aaataaaaag cttggtagat agaaattaaa aatatatgga aaattctact tttccatagt   1320
tttcacagag gtaattcact aatttcgaat tatttattta attattttga cttatttatt   1380
ttatatgaaa acatacttat ctttccgtaa agaaattatc aattgttttt gtgtccattt   1440
tcccaactga aagtgctaaa taatttgttg tgaaaaaata atttcacatt tttataataa   1500
caaaatttaa ttttggtcga tactccctct attcattatt atttgatttt ttagaaaaaa   1560
aattgttttt aaaaagttga tttttaagtt ttctagacac tatttttagt tattattgat   1620
gaattttaaa ctttaagaca aataattatt ggtttagaat tataaaaaaa tctacatcac   1680
aaaaactaat atatttataa ttagttttaa tatgtgtttg tgtgtttttc tagaaaatca   1740
attaaaaaat aacagataga gtaataagta acttgaccag ttaaacaaaa aaaaaaaaac   1800
cttaaaagag aatatggtaa ttgcaaaaga tggagagaca cgattgattt atctgatgtt   1860
aatagttcgg gtagataggc gcaatcactc tctggcccct atgatcccat gatctattta   1920
aaaaaaaatt ggttgtaaaa tcttaaaaca gttgctgcct aagctttagg ttaggttctg   1980
cacatgccct agcttggtgt acactctacc atccctaaat acatccattc catatttcca   2040
tggatctaaa ctctcttttg atagttttag tcttcatgtt gaagtagagc aaataaaaag   2100
gaaagaatag agtgcatcaa gatttcgtca agtattagtc actccaacaa taattcgtcc   2160
tcagcaacta atctaataaa tacgaaattc ataatttaat tcttagtatc cacccataat   2220
tcaagatgtg tactttcttc actaagttcc tcaaacctat ctaacaaaag ctgaggatcc   2280
ccatagtatc atgaaaccta gcagataatt tagagttatt aatgaaatca tttaaaagaa   2340
aaaaaataaa cagtcctaaa tcctaatata aatccaagtc aaagcaagat aaacaatgaa   2400
```

-continued

```
gaagttatta agagatgaga tcacaacagt tgttttggaa tcctctaaag gaagataata   2460
agaagaaaaa atcctctagc tcaggaagag gtttcttcaa tactccttta ctcgacactt   2520
agccactttc cataattttc ttcttctcac agactctcgg ctttctcccc ttagtcctca   2580
atttcctttt catgaactga attgggatct ttaatctatc agaatctacc tttctcttaa   2640
gacattcagg gatacatgaa agggtagtct atgacaggtt tatcatcaca caacctttga   2700
ctcgccatcc caaacatgta tcctaaggca atcccgactg gaacagcaac aacatgccac   2760
tttccacaat cttcatcttc tcccaaactc tagcctttct tcccttagtc ctcatttcct   2820
cttcatgaat tgatttggga tccttaatct accgatacta atacaccatg tacctacatt   2880
gaggaacatt gtatgcacca gcagccatta tgcctcatct tgcttggtaa ttcttgttta   2940
caagacgagc tacaacataa cgaccaacaa atctttccat gaaacctaaa agatttacaa   3000
cgttctccat caagacgtat ttgggcttca agtatagtct atgatattca tgaaaccgtc   3060
acttcattgt ttttttcat cttgaagtgg tttatcttta tttctaaatc ggtgtaaaac   3120
cactaagtcc ctggcatgga agacccccac atacaagatg cacatattcc taaaagaacg   3180
acacaaggtc gaaaagttac gaaaagtggg gaacaagaaa tatttggagg atttacatgt   3240
gtaattaaca tgacttagct tacaagaagt ggcaataaat ttgacttgaa acccttcgtt   3300
acgaattcct taagttttta tttgtatttt ctaatgaaac catatacaga ttagaggaca   3360
acatgagaag gccaaagcag taatttaaaa aaccttaccc caatccatca tacggctccc   3420
aagtatcttc ttctgatttg tattccttct aatacaccta aaaatgatgt aacataagag   3480
aaagttgata tatagttaat cccatgcatg atgactagca tttaaaaaga ggactcttat   3540
aaacaatata cgtgctgatt gtcttgcaaa aaaggcaata gcacgaggtt ttatcttttt   3600
catgtaagct cttttatttt ggactgattt ttttccaaag aaaaccgtac agttctagtt   3660
taaatagata attttatttt accgttcata taaaaaaaaa gccaaaaata aagtaatttt   3720
accaatgtta tctttgtaac actatgtcac aatttaaagg ttacttctgt gattctaaat   3780
atattgggaa caattaacaa acttcataaa ctatatgagc aatttcattc gaatgtttta   3840
tggaaaaaaa ccttcacgta aaagattttc aaaagaaaat ctgtaaatga tatcaatata   3900
taaaggatat caatataaaa cggatatatt ttgattcatg atagtagaga atatataaac   3960
tctttggagg aaaataagcc gtgtgtcttt gtgatactcg gaaacttaaa caatattaga   4020
atcaatgtga tttatttata gaaaaaggaa taaggctttt aagcttcaat caaacgaagc   4080
ttatagctga agatattaag aacttgttgt attcacataa agcaaaaaag atgaaacttg   4140
ttcgtccttt attgtacatc taaaagacta aaaatttatg ctcataatgt tttcttttgc   4200
cttttatatt catattacat tatacatgat cctcctttct tttggcgcat ggcatatttt   4260
gtcaaactct attacaacat tgattctaat cgatctacag ttgaaactag tgaatcgaat   4320
tttcaggtag aagttaaatt tgatttgaaa tgtactcaag tttatgctat ctttctcata   4380
taatatccaa tattttagac tagttatatg ttgtttatgt cgaagattgt tatttgttag   4440
gtacgaaaaa tttatatgag ccaccacata tatagttgta atcgaccatt ttctgtaatt   4500
tattggttaa gatttaagaa gactagaaga gggaccgatg tcactagatt cacaaactta   4560
gcaacttaaa tttacatgaa tccaagttac atattaaacc aatgacaaga gccgaagcac   4620
ctcatgaatc caaaaaatct acgtaggacg gtaacttttg ttgatcctga gacaaaggat   4680
atagccgaat atgagttgca accaaatctt aacttctctc tatcaacgac gataatctta   4740
gttgcaacat gaaaaacatt cataaacaaa catttgccgg ttctccttta gtcgcggaat   4800
```

-continued

```
gatctctttc caatggccag agacatgttg tggtaatcaa gcctagtact tctttaattt   4860
atggttccga gaaccatatt tgaatgtgta gattcaccgt tccatacgtt cactttcgac   4920
cttaactcca ttttcacttt ttagaatctt gaatcctgac tccatgctat gttcttttaa   4980
tttgtttgta ctttggagaa aaccaacatt aatttccaat agggcataat ttgagatttt   5040
gtttttttaat aataaatacg tactaatcat gcatgggact tgttgagtat tttatcgata   5100
ttgagatcta aggtaagaat tctgttcttg cattgcatat atttttgagt ggcatttgat   5160
agattagaca cacatatatg tctttatagt aacatatgaa taatcttttt tctgtaaaca   5220
taaatgatgt tgaatgcaaa tcagtatata tttatcggta tctatactaa aatcatatat   5280
gtatattcaa atcataaagt aggaagcagt gtgggccgct attctactgg cttccactac   5340
tgaatttcca taatatatag ttcttaatcg aaccaacaaa aagttgaatc catatggaca   5400
catatttata catggatatg tacgaacata aatacatgca tgtatccaga aaatgtgcaa   5460
gtttgcaagt ttggacataa atgtaactat gtaagagtaa cggcactatc acaaacaatt   5520
aggttataag tgttggtttt gtgattgtta aaattaaaat ttatgattaa acatgaaaaa   5580
aacaactcta taaaaacaac aaagaacttc atatgacaaa ccaccaatta ttatgttctc   5640
taactttaat aagtgattaa caaagatgtt accaacgaca aaaatatgta tatatatata   5700
ttcaagaaca atgacaggaa caaaaggtta ttcaacataa aaacaaccca tatatgctaa   5760
attcagcaat aaaccccccct taaaatattg aaagaagaag aaaatacatt aaaaattatt   5820
gttatgcttt agagtctcca agctgaattt agcatatgtt cccatccgtc ttgacaacca   5880
caaccctctc tctttaatca cctatatata attaaaaagt gaaatttagg ttaattatta   5940
catatataac atgagagtat gtaagttaat gtttttaaaa atatatctat ctattagttt   6000
atgatagatt attatcccaa attttctaag ccctaaatca ttcttgcttt cgtagttggt   6060
cccctccaac actattgttg cctctgccca cctttgaaga gtcaccttct tcttctccca   6120
tctctacttt ttctccaagt aatgattcaa tctttgatca tgacttgtga attttatttt   6180
cttttatttt tatgctaagc attattaaat aatatcttaa tgctaattaa gaaccgtatg   6240
atatacgtaa ttcaccttct ctacctgaaa ttgttgcccc caaacgttgg tgtccaaaaa   6300
tcggctgttg tttcgttagc caccggaaac gtgcttgata ttgggacgag acatagacca   6360
tgtcctctta gttcgtgatt ctcattttca tcttgactct tcgatttacc agatatctac   6420
atgaatccat actgaaatta gtacttattt aaccatgatt atagcacgaa gactccaact   6480
tggacaaaac taaaacacta gatcgtgtat tgaacctgct gttgttgttg gttcgaggca   6540
ccttgtttca tgtatggagt gcttagaacc tgtatttaaa aaacattaat atgcttaaaa   6600
atttgctcat ttctagggtt ttatgaattc agtgagttag gagagaaatc acaagaaacg   6660
tacagtgact tggtcgtgaa ggaacttgat gtactctata gcttcttgga gaacagatgc   6720
agtatctgtc tgaagtttaa cccaaagata tacaaaataa acaaactaag aagctcaata   6780
cataaccaag ggaaaataaa tgcttttggt tgtatatatt aagccatata aaataaagta   6840
aacacataaa tcattcacct ttccgaaagg tgaaactagt tgttgtaatg aagttatctg   6900
gtcccttaga ttctcttttc tcacctgtta catatacaat ccattttatc caccaagaaa   6960
ttgaattaaa ataaaaggtc ttaaacaaat cttgaaatat gatcatgtac cttgaaagtt   7020
ggcaacggtg aaggcgtggt gactctcggt ttcttcgccg cagattcatt atcctttgct   7080
ctcttcaaag actcactctg agctcttgtc ttcagattct tctcaacaaa aataaataaa   7140
```

-continued

```
taaataaatt caataatata gccacaaaac ttatatagta gcaaaattat tttgacatat   7200
atgagataat ttaccttggt tttgtcctcc aaacgagtag atattatctg cggagtggtt   7260
acaaaattgc tcggcgtcgt gttgtttaag ttagtggttg atgaagaatt ccaaaagggt   7320
cgagagtttg cgttgttaga gaagctgtta attagtccat aagctacttg atgatgagga   7380
tttgtcttat tagcccaaga aagttgagga tcgttgattg aaccacttgt ggtggagaca   7440
aagttgtatg gacttggttc gggatcgtaa aaggttcgta tcaagcttga ggacgaagaa   7500
gttgatggag atgaagaaca agctggatta agtatataag gtgaagtagt tgtggataag   7560
aatccttggc catgatcttg atcttgtgag ctccttatga agcttgagtt taagtcttct   7620
tgtctgaaaa atacaaaaca agaacaaaag agatctcatg attattatta aaaatcttca   7680
atcttgttca tcaagaaagt gaacaaaaaa aattaagtta gggtttttct ttaagaagtt   7740
tacaaaatgg tttggttcca atctgaagaa caatttgagg aaaaccctag acccatcatc   7800
tgcaacgtcg agtccatcgt cacggtactt cctccactgt cagaatccgc ctctcgctgc   7860
ccgaaaacga tgttgttgtt gtccgtacaa gtcatcctag atttgagatg attctcttgc   7920
gagctaaaat cattggaagt gatagccgct ccgaagcatg gtgacaagaa atgatccgaa   7980
ggagacataa cgctccttgg cgagttccac cacgcgccac ctccgccacc acaaatcgat   8040
gccgtagctt taaactcctc cgccatatta agagaatcag aaagttttag tataagcttt   8100
ctactagatc gttgctatac gaaggttaaa gtttttatat atatgagttt gttgtatgtg   8160
atatgaagag cataagtgta aaattttgat atatgtttat gagggtgtgt atgtttatat   8220
aggcaagtac ggacaagtgt gtggaaatta ccggaattta gttgacattt gaagacaaaa   8280
acttatatca tcataacatt cctatgtgat ttttttaatt aaataatctt gattttaaat   8340
tttttcctta agctaaatat tttatttgac agaaagatgt tgtaataata gtgttcctaa   8400
tccctcaatt ttcttctatt attataagaa caactgtctt tgtgagattt gtttctttgc   8460
tgcttagctt ttcgaagaag tgataatgat cctcatttta taaatattta aatatttaat   8520
ttgagattag ataggtgttt ggtactatta tgcaagatgc caaaagggga tactatttat   8580
atatagacat tatatctaac ggtaaccttt gattggttgc catcaaattc tacaaatcga   8640
tcgtttatat taagtggtca gaaatagaaa acatatcacg attttgatta aatcagtttt   8700
tagtaattgt atagacaaaa cacgaaaatg actgattata gtctacgcat gcgtatatat   8760
ataaatgtac ataaatatga aagactaaaa ttttgaaact tgatattttt ttattacttt   8820
catgcttcca tacatgattt ttatcagatc actttagtaa gcttaggaaa aaaaaaaact   8880
aattagtcta tgcaagcgta ttaataattg ttttattatt ttggtaatta taaacgacta   8940
accaattttt gaacaacgtt tcttctaatt aattatccat actttcatac agtaatgatt   9000
atcttgaagt taaaatatat gttttctcaa tcgcatttgc taaaaaaaac tttaaaacat   9060
atatcttcaa ggattagact cacttatttt caaaagtaat attcaaagat tctttcgaga   9120
taaaagttga gtcctaggct agctcgttca ggtttgagtt ttcagtactt gggagggata   9180
tttatacttt aacaggtatt actattacta aaaattagtt ttagatcgaa aaagcgatca   9240
taggaatttt tatttttttta atagacgatc aattgttttt agctcgattg gaaaacgcaa   9300
aattaatggc aaaacctaga gttagcactt gatatgagtt cgatatttat ttcattgtcg   9360
atcggattct ttcggttaaa aatagtacta taaaataaga tttgttcttg tggcttgagg   9420
ctaaagggat aaatggtata tgatgacgat cgtcgatcga tgctgagttt cgatctgtgt   9480
gtcacgtcac cgtttctgga cctattgtgt ttgtgacttt tttcacaatc tctttatacc   9540
```

-continued

```
aaacggtcct tattcttttc aactagcttt ttctaaattc cgtaaatatt ttattcttct    9600
aataaatttg ataagtcaat caattattgc actttaatta caagtcattg ttttgttttt    9660
cttctttctc ttaattcttt ttccatttta tgtgatagac tgatagccac acaaaatatc    9720
aaaaaatgga tttgttgaac ctgataatag taaccagttc tgttctttat gatcattata    9780
cggctcgagg catagtgaac cggctgtgt caccgtccat aaaatataca agttttatca     9840
aacgataggc atagataata aacataattt caccgatatc catgtatata atatttatat    9900
atctatctcc tttcaaaata aaaaaaaaaa ttggacatat tctaagctaa attgtgctag    9960
tatcgttatt acgaaattca aatttacgtt atgtatcttg acaaaaaaaa aattgttatg   10020
aatgcttgaa gaatggtatt tttacgttac atgtaataca aaaaagacac taatcattta   10080
tggtagtcca atgattcaaa aatatatttt gtaattggga gaccattgtt catggttagt   10140
agaagtgaaa gtcttaaatg tattcggcaa aaaaaaaaaa atatcaaatg aaactcgtag   10200
atttttattg ttcatggcta ttcgaattgt gaaaagtctt aaatggtaaa aatatgacac   10260
aaaaatatca aatgaaactg gtaatatttt attggataat ggctattgag gacaaatgaa   10320
gactataaag gccccaattt atctaattat tattaaaata ttaattaaga actaattgaa   10380
tttttttctt aatggtctct ctatgcgaca caatgcattt tgacttaaaa cttaaaagag   10440
ctttgaagca ctgaaataca gagacagtta ggtcagatcc atgcgactga ctagtaagtt   10500
ttcatcgtgc aattaaaatt aattttaata taaactaaga aagtgtcaaa acaaatttga   10560
tcaatttgct taagcccacc agtccactcc gccaaaaatg aaaaaaataa taattcatta   10620
ttgcaacgtg actaactttt tatttattta tgaaaacact tgtttcgttt aggttgatat   10680
cgataaaata aaagttatga aatgaacgtc aaaagaatgt gtcacagcca ccgtatgaca   10740
acataagtta aatccgaaga atctttgtca gcccatcggt tgttttctct aacggtctgg   10800
tcgatcccat cgatatgtac accgacactc ctctaagctc ttgtcggtcg atatttggat   10860
tttattatta tcggacacat atgctaaatt ttatagtccc caatcttatt cagctttctt   10920
ccattttctg tttagtatat tcatggtggc aacatatata gttgaatcaa cgactagttt   10980
tgaaatatac cgcttttcac aatgcaagta tacgaacact ttcggatgtt ggagtaaaac   11040
ttgatcacga acaatgagat tcatgcactc gttgtatgaa aaaaacttag ttgacgaaga   11100
attgctccaa aatacgtatt gctatatacg tatataaagt gatatagaca cgtatatacg   11160
attagaagca atatgaacat gtataaaatt taaagtaggt gaaggaaaac gacaagtagt   11220
caaaaaatag gacccacacg gcaaatatga gtggagactt tgtttggcgc agatagtcgg   11280
ataagtgtca gcgactcatt cttttcttca aaccccaaaa tcaaatcatc atatgtccta   11340
acaatttttt gttttgtatt tggaaaagca catgtttctt tgtttttatg tttatgataa   11400
cattcttttt acacgtaagt aacgtaatgc tgtttttggg actcacggga gctcatatgt   11460
aattattatt ttcatgtagt tcacataagt tcgaaaacta ataaataatt aagttatcta   11520
aaaagagtcc tagtattata tgaatcaaat tctcaaaatg tcccatataa caaattatgt   11580
caacaacata cgtactaatc tcttttgcaa caaactcagc cttaattttt taaacaaact   11640
aaacatatcg aaatttaaaa ggaatacctc atattaaaat atactataat cattaaaatt   11700
gatataaata ttcgatatat tgatatatat aaaccaacaa aaaaacccaa gtaatattgg   11760
aattcaatta atactgttac taaagagtgt atatcatggc gagatgtgtt aaaacttgta   11820
tagttacgta attttttagt gatggtgcgg ataaaaactt cgaaccatta attgtcaatt   11880
```

```
atacagataa tttgctatct catacataaa ctataaaata ttattatgag gcttttaaca  11940
tgcaaaagat attagaacac aaataatgtt ttgttttatt tttattggtt gaaatgaaag  12000
tcactgaaga ataacagtcg aagaatacaa gcgtaacgca tatttctctc atgacatgcc  12060
atttctacat ccgattttac atatcagttg tatttctatt tttatttatc tatcaaattt  12120
ttattgatcg taatattata tatctcatta tctcatacta tgtaggatat atgtcatact  12180
gacgtaagga tgaaatgcag aaaactacaa aaacgaagct tttttttttt gcacgattac  12240
agaacgatga tgatacgatc ggaaaaaatc atcatggccg tgacagacac gtggggtagt  12300
gagctccatg aataaagaaa cgaaattgta ttccttgtag caatgacggt caaaagaaaa  12360
gcgctttaat tagtccactc ctatcttaag ttatggttat taattatgat ttacggtcag  12420
tttaattatt cgcttaatta attacagttt atatgacaaa atcaacataa tgttcttatg  12480
gtttctttgg taatttatca atttaaaatt tattacatgc cactcattct cataatagat  12540
gtcgcaaatg taatatcaca acatttgtag agtgtttgat gacatgacaa tgacatagtc  12600
ataaggtgtg tacatctata ctttgcatct tgtttttctg ttgaaacctg aatttacatc  12660
gaattcaaat atttataaaa tggattgtgt atgatttgct acttcttatt tttcatatag  12720
atatattaat ttacatgtga catataatta cttaacttat atctattata gtattattat  12780
acaactagct aactaaaagt tacaaatatg ttatatactc ttagctgaat cttttgattc  12840
atatatgtta tatattaatt tgtgtccatt tacgatcaat ataagttatt ttgtcatggt  12900
gaaattaagg agttgttaca ttttagattt tacttgtatg tttttttttg ttcacaattc  12960
atgcaatcat ctaactgata aaaacaaatt tggcaataaa ggtaagattt taagtttctg  13020
tgtttgtaat tttgcttggt tatttttatc acgaattcgt ggagcaaaac gaattttggg  13080
acagcaccgt tccaagaacc gtctacatga aaaatattta catgaagtcc ccgatcatca  13140
ttatgcaatt ggttctaccg gtaccacaca ttatcaatac aactggctaa aaactaagca  13200
tggtcagact cttagtaggt ggtgtccaga atactgtggt cgatcaaact aatgtttttt  13260
atgaacccaa aatgttataa acttgacaca caatttcttg gacgccaaac acaaaaatat  13320
gtaaattagt catgtttcct atatcaaaat ttgaatacgt gaccttgagg cgcactactt  13380
ttgagaactc tcatagacac caagagaact acatatgatt aggtaaaaac tgagaattaa  13440
ttgggactga gaaaatatgg aattattcac atgtaataag tcacatttgt tttgtagaca  13500
ttctacaaat tatataacat ctaaatatgg aacagtattt tatggttcat gaacttataa  13560
acatgtaatg atttttttatt tggctaaaac atgtgaaact ggtgatagtt gaaaaagtac  13620
ttataaactt ctaattgtct tctgagaaag taatttaaac aaaaaactgt aatcatttga  13680
cacgctaaaa ttttggttta tgtactactg attagtggtt gaccagtgaa aagtagtagt  13740
cttcttataa gttttacttt ttttttaggt aaagttgact cctagtttat ctcttattca  13800
atttattttc ttgattacaa ttaaaggtca acgcagaact caagatcaat acgactcttc  13860
tagatatcgt gccaagaaca cgacaagagc cgcccccacgc ttttactcta gttttgtcat  13920
tttcatttgt tctttttgtt ttccgaaaaa ttctaataaa tatgaataaa attcaaagtt  13980
agtagtaaaa cccaggatca tttgaaagat caaaaataat ttattctaat cgaagattat  14040
gcctatagtt tttgaagtaa tagttgagat ataaagagag agcgatctct tgctatactt  14100
ggatataaca tttgcaacta aaaagaatat agtttgcaaa tattgttgtt ttataataga  14160
gcatgttatt taagtcaaat tacatacact aataaaactt gaataaaata ataacatttc  14220
actaaccttt gttttttctt taaacatata taaatcactt tctctaacct ttgttatgca  14280
```

```
aaaatatcct acgttcctaa aatacagtta tatgtttaaa actctatacg aaaatgcagt  14340
cattattctt cttgagctat tttgcatccg caactcatca ccttcacact agtataagaa  14400
ggttacaagc tctgatagac tacaacattg ataataaatt gtaatcatct tcatcatttt  14460
taaaataaga ttatatattg cccctatatt aattgtaaga acattttaca aaatctgttt  14520
aaatgttata cagtaattaa taaaaccgtg tataaactat acagtactag tatctttttt  14580
tgttcacttt atagacatag taaattgtac tataattaaa ctttatgtct tttttttcct  14640
atattcgtaa gaacaacacg tagtcaacat taataattat tatttttgtt gccgcaatat  14700
atttcacttg tagtctatga ctaaaaacaa ataaattatt tttaatgaga tgcgaaatga  14760
gataagtatg cttgattgca tcaggccgaa attcggtaaa cttgagaatc tctattactt  14820
atttaatttt catttgttat agattttctc cgtaattttc gttttagtag agaaagcaat  14880
catcataatt tcgcagactt ctaagaaggt ttcgagagaa gaaatgaata aacaacgtca  14940
atgggtttta gagtcttcgg ggtgtggtag tctccatggt cccacttgta agttgtaagt  15000
caattccggt ataagttgcc aaaaactaat acaatttgac tcgttctatt tcttactttt  15060
taggcactga ttttaaaatg taatgaaaac aatatgagtt aacattttac tcggttgaag  15120
tttgtgtatt acatttgtga agtgacatca ggaatgagct ggatttgtga acgagcttct  15180
cgcaaagctg gagatcctga tttgggttat gcatgcatgt ggagtctact agaattgtgc  15240
tatttttaga caaactatta gaccatctcc aacaatattt ttttagtaga agctctaatg  15300
aatttttttaa tattaatttt gaaaatttta tacttaagag gttgtgtaat gattttaatt  15360
tttttatgtg tccaatgcta gacagactct taagttagag ttcttaaaga attcaatttt  15420
tgaaaattat tttagtttaa atgtataaaa aagttgaagt gtatgaaatt tgtgtttaag  15480
ttaaaagata tgaatatgat tcatttggtt acaacacata tgattcattt ggtgtttaag  15540
ttcaagagat ttatttgagt aaaataaaca cagaaatttg taaaacatct tatctaatat  15600
tagcatagag gagaagaaga agatttgtga tacatcttca gtttaatcat ataattgttg  15660
tttctatttt gaaatttcgt gttcaaattc acatgacttt agatttcttt tgttcaattt  15720
atttgattgc actatgccag taagagcatc attattggtt aactcttaaa ttagttctta  15780
ggctaagaat gagatgttct ttgcaatcaa ttacaaaaaa aaaatcctaa gaattaatct  15840
aagagacaac caataatggt gctctaaggc actaaattct ggttttgttc ggttcataac  15900
ttcatattgt aatttgtaac ttgtgtaaga aaactcataa atatctagag tggactggac  15960
tataaatgtt tcttgtttct tatctcggcc catcaaaaac acgaagccca cgataattga  16020
ctaagtcgtt ttatacagct tttgaatttt atgtattcat cagtagtttg accaaaaaaa  16080
aaaatgtact catcaggata aataatttgc gacgtcggtt gtcggacctt ttgaagttta  16140
tacctaattt gatttctatt gattatcgaa tttgtttcgt ttactcagat tcatattcag  16200
cacatacact taagttaagg atgattattt ctaagggttc aaataaggtt gaaatcttca  16260
cattcagttt caaatttgat caaattcata ttgaattata catgtgtatc caatgaattt  16320
ttattgggat ccactcaaat tactagaaca tcttgcttca cttgtcttga cttgataatg  16380
ctctttgaga ttcttgaatc ttaagcctgt ttttttttaa aaaagaacat atttgaatct  16440
gtgttagctg atatagaata agagtaagaa actcgaaata ccagattaag aagtatgaga  16500
gacaaaaata gatggtctgc ctcctgaaca aagaagacaa agacaagaac cggctgcttc  16560
tgattcacct tgaacgatag aaagattaca aaggttcgta ggaaagatat atattatcta  16620
```

-continued

```
ttggttagtt gctaatttgc tataagctct tagtgttttt cttgtaaaat catctatagt  16680
atcataaaac cttcttgaac aacatcgacg ttttgaactg caaacgttaa agattgttaa  16740
aggtccaatg caaggcttgc atgcaactgc atgggcaaac atttttctac ttttgaatgc  16800
tcttcatctt acgatgaggc caacataata aaccttcttt cctacaaaat tttctttgcc  16860
acgtatgaaa agatttattt ttgcaacttt tttaattttt tagaaagagg atcgtgtgga  16920
taaaacgaga agaactacac ttatacactt tcctctttct aaagaagatg caaaaaaaaa  16980
aatgaatctt tgtggtaaaa taaacttcgc aggaaaatgg ggttgttgcg ttggcctcac  17040
cgcaaaatca aaagagcatt gaaaagagaa atcgtgctta aagtgaaaat ttgagaagtt  17100
gtagaatgat atcaaattga gaaccttaac gaagcactta taatgaagca cttgaggacc  17160
ttgagtaacg ttttataaat tgagattttt ctatttattt agatagtata gtctttatga  17220
gataataaat aactttttgt tggtgttgac tgttgaagtt ctacaattca attaagaaaa  17280
cgttatatgt gcattaattc ttgattctca taatgatcat catacggttt tgtttatgta  17340
tatattgatt tttgtataga actgaggaaa tggagatatt ttacttttat aggttttaga  17400
tattttccaa agttttattt ttaacacact tttttattta cagagctacc caaaaacgat  17460
acttaataag cttatataaa tgaaaaatgt tcatcgtcgt acaaagtttt agggagaaag  17520
caagattgat ttaacattgc tactatatag ttcataaact aatataaatt ttaggaagcc  17580
attattccgg actggtatca ttttttttgtg tgttaaaaaa agtttttttt ttctaaaaga  17640
aatggtttat tatatcgtca aagaattcta aatgtaaata gttttatatt tcattcaaat  17700
ttatataaac tttacaaata agcaatgaat tttaccacta cttttttttaa aatacaaaca  17760
aacatgtaat gttaaataca ttttagtgtt attagcgata tgttttcatt gtttttgcag  17820
aacttcggca atccattgtt ggctcaaggt ttggatgact cacatccact aagtctagag  17880
ccattttcca taacaacccc atctttaatg tctccttgcc atatgctatc acactcaaca  17940
cttttggtct ttacattttg cgcatcccat gaatatggag atctattttt tctgcgtaaa  18000
aaattcagac tggtatattt catccaaaat aaatatatta aactgagaat ctattggctg  18060
caagatctat tacttctcac cacacatctc attatcgaaa tatattacaa catcacaagt  18120
ccataatcca ttcacccgat gaagaaaagt taggtggtta atactaatgg ataaggcaat  18180
gtagtgcatc tctgaagtat gctctgaagt tatatatagt gagtttgttg taaattatac  18240
ctcaccattc ttttgttgca ttttcagcaa tagtctgaag aggccgctaa atcatcactt  18300
gatcgatgag ttgtggttat aatgatattt gattttgtat ttgcttggat aattaaaaaa  18360
tttggagggc gagaaaaaaa atcacatata catgtgtgca aaacttgcaa ttaaattatt  18420
agaaaaagag ttttatgcta taatttaatt taaattctat gtcatttatt taaaactgaa  18480
aataataatt ctgctagtga atgaattaaa atgtggagta atgtcggatc attttaactc  18540
tcagatgttc tctctgtttc attattttat ttgatgtttt ggcacaccaa ttaaaataaa  18600
attaaatatc gtttaatttg aaataatttt ttcttctaaa acatcactta atttaaaaca  18660
gaggaagtat tacaagcttt agttggaaat caaaataatt tttaaatatt tattttatgt  18720
aatttctgta cttcatattt caatatagaa actgtgtcat tttcagttcc gtttgggttc  18780
ctttttttgat cccacagccc aagttccttg taccattttt cagacaagac aaaagaataa  18840
cgtctaaatg gaagactgac ttaacgaaac cttttaaaaa gaagtaacga aactattcat  18900
tagcatacta atcaaaatca gtaggcgaaa tttggtgaga agtttacact gtccatgaat  18960
catgataatc aacaacaaca tttataaatt caatacaatt aatgagttac tattggaatg  19020
```

-continued

```
agtctggatt ttttttagat aagtaaaatt tttgcaatct ttatcttgat tagtatttaa  19080
aatcaattaa tttatgtttt aagtgtaaac taaaataagg tagaaaaaag agataaaaac  19140
aataatgtgt gatacactta accatgattg gtactttgga tccactaatt tatgttttaa  19200
gaaaatgata ttccattata atgtttcccg gaaacaaacc gtgatttgcg gatgttacaa  19260
cgtcaattag ttcaacatgg ctttacttaa ggcaaaagac tacaaattca aatagtgaga  19320
ctatacagat aataatatta ttaaaaatta agtggattgt ttttcaaatc attaacatgg  19380
tacaaaaatt atttaaatat atgtatattt gaaataatca caatttttca caaaacacaa  19440
ctcattgcta accagctcat atgctaaaaa agacaactca tttctccact cttttgacaa  19500
aaacagagca ccaaacatta aacccttcaa aaacacaaat ctcaccatca cacgtaaaaa  19560
aagaaaatat gtctatgctt cttcttcttc ttcttcttgt cccattcatt actccatctt  19620
cgcaatcttc cattcgaaac ctcctcgaag ctcgcggttt accaggtggt ttgtttccag  19680
acaacgtgga gagttatagt ctagatgata agacaggaga gctcgaagtt cagctacaaa  19740
atccttgttt cgctcggttc gaaaacagag tatattttga tcgtgtgatt aaagcaaatt  19800
taagctatgg tgggcttgtt ggacttgaag gtttaacaca agaagagctt tttctttggt  19860
tacctgttaa aggcattgca gtgaatgatc cttcttctgg acttgttctc ttcgatatcg  19920
gtgttgctca taaacaaatc tctcgttctc tctttgaaga tcctcctgtt tgttatcctc  19980
ctggtgagtc aaagtttgtt cctcaaaacg ttttagtgtt taatgccaag tgttttattt  20040
attggtaaca tatatatgat cttgaacaga atatttttgt agtaataatt gtatgttttt  20100
atttgtagga tctataatgg agaagttaga aaaaagcaag atggatattc agctcaagag  20160
atgaatgagt tttttttttt ttggggttgt gtaagattca aaactcaaac ttgtctcttt  20220
gaaacttgaa caaaaaatgt gtttttttct ttcttctttt acctttttgt tcggggttgt  20280
ttgggaaacc gtggaaagtg tcgggagata tgtgtaaaat ctggaaagaa gggaggaaaa  20340
ttttggaact ttgtataaat tatggggtcc ataaagtaat caatttttgtc acttgtcaat  20400
tatttttctt ttctttatat agagggaata tagagtactt tagatatttg tttaactttt  20460
gctttaattt ttgaggaatg atgttttcgt ttaatcatta tcctctagca taatcattga  20520
catagaatta ttctttgaat ggaagctcaa agctgcattt gttaccaaac aggcaatcac  20580
agctgttaac ctaaacacaa ctgacggatt ataaaattct agcactgaaa tacctattta  20640
aaactttcac tcatttttac acaagaagtt taaaaaaaaa aaaaatcagg tagatatttc  20700
gggtaaaata aatactccca tttgtaccaa aataaatgat gtttaacttt tttacacaaa  20760
gatcagaagt tattatattt ttttccgaaa taaaaacgta atttatttat ttatacatat  20820
tcaataaatg ataaaataaa atataaatag tcataaggaa aaaatataaa aattttgcat  20880
agaaaaaaaa gaacacgggt caatttcaaa ccaccaatta ttctgatatc acagatgtca  20940
atacgcgtca gagtgtgata tatgttagtt atatgcgatt ttagtaacat ttttggaatt  21000
ttcagtgttg aatatcacat gtatatcgtt gatcaaatta ttttagtaaa catgttttca  21060
ccagttttat ttgaatttat agtcatttca ccaattgatt ctagaatata tttaaaattc  21120
ttaaatgata taaaggtagt tgaaattaga taacctaaca ttttttatgt taaccaaact  21180
ttttaattaa aaataatata tttataggca caacctattg taaatttttt aatttacata  21240
gttttaagta aacgagataa aagaatcagt tggtgatctt caaatcggat aaagtgttat  21300
gagtgtatag gagattttga tacaaattga attctttttg gagtcatata ttttgtctat  21360
```

-continued

```
gctcaccaca gcatcggaag atcttccatc acaaaacagt tcacatttgt ggtggacacg  21420
agagatgaag aatctgtctc aaggtttaat cactgtggta ttatatagta aaaattttat  21480
gatgatatta aatcatgatt ttggctatgt taaaatttga ggtttttggt tctaaggatt  21540
ttttttgcta gatttatgtt aatatctaaa gtttaagaaa tttgataata attatagtta  21600
cgtgacataa ttcaaattta tgatgaacta catttactat atatagccct cgagataata  21660
atgttataca tttatttagt agatatatta ttagataatt caaaacttaa attacattat  21720
tttgtttata tatttcatat tatgttaaag tttaattgat aaatgatatt tttacgaaaa  21780
atttgtataa tactaaagat aaattttaaa aacatcaatt tcgttttatt tttattaata  21840
gtacataaag aaaaataaat aaattaaatt aatttgtgac tattttggta tatgatcaat  21900
gctcgtcttt ttaagtagta atcgtgtctg ttacaggtga atgaacccaa caaaaatctt  21960
cgacgagcat cttctgcttt cttcatctct gaatgatcaa tttctagaat cagatcggat  22020
atttcgatga agaatcgttc tttagggttt tgggcgatcg gggttttgct catcggaagc  22080
ttgatcggag ctacggaagg ctcgattcat gagtacaaca acgaaaagtt cactgcaaaa  22140
ttcaatgctc gcttcttcca tggtggtagc gaaggtcttt acgcttccaa atctcaagat  22200
ctaaactctt cttcttcttc tgataattct tttaaaggca agtcctttat aaggtcagtt  22260
tcactctttc tgaatcagct tcataattca aagtttgtgc atttggaatc gtactgattc  22320
aaagtttgtt ccttttaggt ttgatgatgt aacatttgtg aggacaaagg aatctgctag  22380
taaacagaat gcaatgcagt caacttcagg attagtggaa gcaattatac ttgaggtaaa  22440
agaccgtgat agaatcggtg gtacttttct caaatccgaa gtgatttgtt gcacgccgga  22500
gctagctgat actggatctt gtagtcttgg ggaagttatc attaagagag agtctaatga  22560
tgttgagtgg ccaagacaga tcaagacatt ctttaaaggg aataagactg aagttaacat  22620
gtcccctgaa actgtggtta tcaataagac tgggatgtat tatctttatt tcatgatatg  22680
tgacccggaa ttggatggta ctaggatcaa ggggagaaca gtttggaaga accctgatgg  22740
ttatttacct ggaaaggttg ctcctttaat gaacgttttt ggctttatgt cgttagcgta  22800
tattttgctt ggtctagttt ggtttgtgag gtttgttcag ttttggaagg atataattca  22860
gttgcattat catatcactt tggttattgc tcttggtatg tgtgaaatgg ctgttcgata  22920
ctttgagtat gttaatttta actccactgg gatgaggcca atggatgtta ccctatgggc  22980
ggtgaccttt tcttctataa agaagacgct ttctaggctt cttcttctgg tagtctctat  23040
gggttatggt gttgtaaagc ctacccttgg tggtataacc tcgaggatac ttctacttgg  23100
agtcatatat tttgttgcaa cagaggctct tgagttggtt gagcatttgg gaaacatcaa  23160
tgacttttcg ggaaagacga tgatagtttt ggttattccc gtggcattac tggatgcttg  23220
ctttattctg tggattttct catcattggc aagaacactt gagaaacttc aggtaagata  23280
ccacacttat atcgaatatt ggatactcat gatccgtcac attattatat cagaaggatg  23340
tatatatacc ataggctttc atgggtttta accatgttat cgtacttaga ttccaattta  23400
tgcagcctat tcgagggaaa atcatataca attgctgctt aagccatcta tgacgatcca  23460
gttcttcgta ctcttttttt cagctgctta tctgtctaaa tttcactaca gattaagaga  23520
aacatggcca agcttgagct ttataggaac ttcaccaatg cactcgctat ctctgttctg  23580
ctctctatcg cttggattgg ttttgaggta acaaatcgct actctagtga ctgtgtctcg  23640
tgtataacat gaaaccccta gtcagaggag tgtaactgaa atcaaattct tctatgtgtc  23700
tgtatcagct atacttcaac ggaactgacc ctctaatcga actctggcga atggcgtgga  23760
```

```
tcattccagc tttttggaat ttactctctt atggtctgtt agcagtcata tgcatccttt  23820
gggctccatc aaataatcct acaaggttct aatacttcca ttagcgttta ctcaaatgtt  23880
ttggactccg atggtcccaa tgggtcaact gccaaagatg tcaagattca agacacttat  23940
ttgctcttca ccgagagatt atcattttgc actcagctta cctctaattg gtttaaacct  24000
ttcaggtact catacttagc ggaaacaggg gatgagtttg aagaggaagg tatctcattg  24060
acaggtagtg gaattaagag tacagaagat gttgaaagga atgaacttct atttgggctt  24120
ccagacgacg ttgaagaggg caaacgtgag taagctccag atagcaagcg ttagatagtc  24180
catacctcgc cgagtagttt ttagtgtatg taaccttatg tcttttatcc gttgtacctg  24240
agtaagttgt ttactgacct ttaaggactt gtttaccaga tcgaagttct tttagtctta  24300
tagaaagatt tacagactgc ttatttccag agcgtcaaag ggaacttttt tacattagag  24360
acttgagata ttcgtcggga agtcgttgat catcatcata gctgtacatt aaaggaactg  24420
ttcttgcaat gttgagacaa gcttttgaga atgatcttga gaatggacat ggattcagac  24480
actccctgtt caagcgtttc catgctctag atatcttctg ggcaacatgt gttcttgctt  24540
catcaacagt tgatcccttg tactcgttca ggtaacactc tacatatgat ccatcagttc  24600
catcttggtt ctcatcctgt taaacaacaa aaaccatatc taagattcga tatcaagttt  24660
cagattctct ctagtcacat tagttatcag tagttcaata taaccttggc acttccgaga  24720
tcatcccaga gcctgagaat tgtagctgca gatgatacaa tccccgggtt actctctatt  24780
agttcgactt tctcttttgt tagttcttcg cctaacaaga tataggcatg aagcatcact  24840
aaatgaacac ctgaactcac aaccccattc ttcatatact cttcagtggt gggtaagtaa  24900
cccgaattaa accactttgc ttctaccaag aatgctttac acaaacttgc ccactgagaa  24960
acaaagacat catattttta gtagggtttg aaccagttga gctatatgat acaaaatata  25020
tatacacatt acgttttgaa tgataattac cgattgtcga agagcgtatg tcgggttcca  25080
accatgtgat ttgtagatct tcatgctaat ctccgttgtg atcatatcta gagcttcaaa  25140
acaaaccctc atgtatttgg gtagcgtctt aagcccctta tgatcccatc tagacgaatg  25200
atttcattat gtttgacaga atgttaatca agaaaatgta taaagtaatt tgtatgtacc  25260
tctcaacaac tcgtgtgaag atggttagtt cttctagctc cccatagaca tcgaaaatgt  25320
catctataac ataaacaagc gatattggtt tggtaagatc aagcctttgt tcggttaagg  25380
tcggatcttg aagaattttc atggaccacg tatgccattt taacggctgg cttcttgcct  25440
tctccacatc tttttctaaa ccaagttctg tccaccatct gaaacatcaa aaaccataca  25500
aaaacaaaat cgtatatcgg aattcaatta ttttcgacaa aaagttaaca ttgatcttca  25560
gggagtatca tcattgattt tacttaaatg tttgagacat ttctccttga gtcaatgact  25620
ttagcctaat ggaatcgatc tccgccactc gtaatagaga ctgtaaccat tctggatctt  25680
cttgacccgc gattttgatc atgcttgtga acctcttgga cgttaatcct cttacggttt  25740
tgtggcgagg ttgcgccaaa gacttcatta tctcttgctt ttgatgactt tctctacctg  25800
agcaaagttc attaaggcgg ctatatgtga attctctcgc accgtcgagt gtttcttcac  25860
cttctacacg gagctcagaa gcttcaaaca attctgttag acccttgacg tcattttta  25920
ctacgtcttt aaatccaccc ttcttgtcta ggatgttttt gaaaataact aaatgtttta  25980
taaaaattgt aacagtaaat acgcatatct catacgagca atatagtaag taaatatata  26040
tatataacat cacatacttt cttgaacata gtgaccctct tgtctcagca atcgaaagcg  26100
```

```
aagcgctatc tcatggagat caccgttgaa ttggaggcct tctttgtaaa tcatgtgaag  26160
ggtttgctcg atctcttgtc gaaaatggag atcaatgcct aaactttgaa tgacatcgat  26220
catctccagg ttctcggatg gaacatctac gtttgcactt agtatattct tgatcttctt  26280
gatattcaac tcgtgtaaat attcctacgt acaagaacaa acacattctt agttctgaaa  26340
acagcatgag caacaaaaag taagcagaat atatatacta aggatgtctt attatgaaac  26400
tgcttcgaag ggttagaaac tgaagcatgg acgtttctca agatcgatct tttagcagta  26460
tttgcaggcg acaaagaatc gaccgtattg ggaaatttgg atatcagaaa cgttggagaa  26520
ttgtttggat aagcagaaac aaaacaagaa cgtgaactta ttttggtagc tattaaggcc  26580
atgatgtatg aacttaagtt ttgttttgtt tttgtatgaa cttaagcttt taatgagaat  26640
ggtgttaaac ttcaaacgaa atgctctata catatagcga ttatggatta taaaggagtg  26700
gtggatgtag catttagggg acggggccat gcataataaa attcgttatc aactatgttt  26760
tgtatatata tatataattt gtatcatgtg catactagtg aaaagcatta aacttcaagc  26820
ctcaaccata tataaatgaa ttataaagag tctttgtact aagcttttat ttgaattact  26880
ggagtcgtaa ttttaagatc ttatagaact gatacattcc aataagtttg gctagctaac  26940
attaagatta attgggtaaa tattaaatgc attatgtatc atgtttggtg gcttcactat  27000
atttttcaac ttaatataga aacggtttgt atttattgtt agacaagttc ggaagacatc  27060
aattgtggaa gcaaatccga agaacgtgaa gaaccaaatg atcaacggaa caaaccaata  27120
atgatgactg acactgatat ttttttcca tttttctttc agtttaaaaa gtttcattag  27180
aaaattggta ttacaaaaac aagtacaaag tgcactacaa aacttcagat tttttctttt  27240
aattatataa gccaagttat gtgccatata ctaaagaaaa caaatacgaa aaaatgaatt  27300
taatgatgct tccttgcgat aagctatttt ctattatcat gttaattttt gaaacaattt  27360
tttttatata atgatttgtc aaagtttttc attagttatt tacatattta attgttcaaa  27420
aattaaagat ggaaaaataa ctcaattttc ctaagcaata tattaatgtt agtattcatt  27480
ttagataatt attctagtat aagatttaat taaaccatta gataattttg atgtatttta  27540
tattattaac attcataatt atttgacgtt atttttgaat taaatttctt aactattttg  27600
acagatttga ccaaaaatca caaaaaagaa agttcagttt gattccggcg gtttggaaat  27660
gtaaaagttc agctagatcc atctgaaaat cactaaaatt cagttagtca gcaattcagc  27720
ctgactcagc cagattttc ggttactatt tagaccagtg ttttcacgcc cgacccgaac  27780
cgtccggtcc gaccggttaa cccgtgaccc gaacacgttt ccggtttggg tttagtgcta  27840
aaacccaaca agttcaaaac cgaaaaaacc cacaaaaact cgcaattaac ccgtgacccg  27900
gtgaaccggt tgaaccggcc gagtgtgggt tttaaaaagt tctcttgatt ttacaataaa  27960
atatgggatt ttagacttta ttcaattatt tttaaaaatt tttttcagtt cttaaattca  28020
tttgatgttt tagattttgg tgaagacttt acaataccgc cttaaaattg aatcgaatgg  28080
tgagagagac aatcgagatt agttgtttga attcacgatg ttttattaat ttatttctgt  28140
cattgatgat ctcctaatat atttgttacg gtgttagaca tttagttgga tttcaaattt  28200
ttaaccactt tattattatt gtttgattat atatatatat atatatttgg gtgtaaatga  28260
ttttatattt tgttaaacat aatataattt tatatttgat taaatatgat atgattattt  28320
ttgttttata tttataatac taaatttttt tttatataaa atactctaaa atttctatta  28380
atattaaatt tattaaataa attttaacta attaacccgt ggtccaaccc ggttgacccg  28440
atgacccggt gacccaaaag gtagtccggt tcatcgtccg ggtcgggttt cattgtgtaa  28500
```

-continued

```
atgatatttt ttgtggtcaa agttgagagg tactataacc tttccattta tttttttata  28560
gatttataat caaaagaata taacttatac tttcaattta tttccttata taattagtca  28620
aaagaaacta gaaaataatg tttttaattt cttacctaat tacgtttgaa caatggtaaa  28680
gtgctagtat tatatatttt ttttttggc aaatatatat tatgttatgt acactgtttt  28740
ctctacattt caattttttt tcacattacg aaaatggttg tagcatatat ttaagatttt  28800
gtattacaat tccaaatttt agtggttcca acttgatgtt atgggtaaag aatgttgttg  28860
gtgggaggaa agtttacaca ttccaaacca aattttacac attcttttac caaaaaaaaa  28920
aacatttgca aattcaaagc attatgtttg cagtttttgc tggggaagaa caagctaccg  28980
gccgtactgt gaaacttttg atattagaaa catcaaaaca agaaagtgaa catatcgtgg  29040
gacctatgat catgggcatg atgtatcaag gctaaacttc aaaagaaatg ctcttttata  29100
actattacag tcgttaatgg ggatggggga taacaaacat catcattttc ttttataacc  29160
actacagtcg ttaattaaat aatttaacca atacaaatta attgtaaaac ttcggttaca  29220
ggaatatggt ggtgcatgtg gagaaattta taaaaattaa tttggtcatc tatgttacta  29280
aaacacactt atcttttttg tcaaacgtct taaagaaaat tctacaatta agcattttta  29340
agctgggaaa gtcttatgat agataacttt cgaggaaatg attgtcggaa ccgtgtgagt  29400
gagaacaaaa tacgggagaa aatcatgtgg tgatttgtaa ggtaagtacc aagtttttaa  29460
agcctctcag acatggcgta tcgatcgttg gacagaaata gacccacaga cccgagaaaa  29520
tacatgagac ctactagtag agactcttgg aacattatat tgataataaa taaatggtta  29580
gattggaaac tcaaaacggt acaaggtttt taataaaata gacgaccagt aagcaataaa  29640
tacaaaatag attaaagtcg tagaaaatag ctatatatat ataagtatac aaaaaattta  29700
tgagtatcac ttaaaattgt ttttaggttg atattagacc atctaatatt cataacgtat  29760
aaaaaaaaaa taataataaa aaataataaa gaaaaaacaa ataaatattc attcctccgt  29820
gtttcaattt tcttttagat tttgttctaa tgcgaagcaa aatatatcac taaatttttt  29880
aactgaaact tccattgata tgtaaaagtt tatgttcttt atatcttata tatatatata  29940
tatatatata tatatatata tatatatata tatatatata tatatttggt aggaatcttt  30000
tatatatatt gagaacatat aaaaactgtt gatgttattt cttaggcaga aaaaattaca  30060
tttggttgga ttatttcaca ttgaacgcat tcttatcatt atcataagtc ataacaacaa  30120
catcgtcctc taccaataca tttgccataa gaatactcgg cttcattaca aaacacaaga  30180
caacctagtt gccctgcgga ataacacgcc attagcatga agcaaaacca gtgttttcac  30240
gcccgaccca aaccgtccgg tccgaccggt taacccgtga cccgaacaca ttccggtttg  30300
ggtttagtgc taaaacccaa caagtacaaa accgaaaaaa cccacaaaaa ctcgcaatta  30360
acccgtgacc cggttgaacc ggccgagtgt gggttttaaa aagttctctt gattttacaa  30420
taaaatatgg gattttagac tttattcaat tatttttaaa agtttttttca gttcttaaat  30480
tcatttgatg ttttagattt tggtgaaaac tttacaatac cgccttaaaa ttgaatcgaa  30540
tggtgagaga gacaatcgag attagttgtt tgaattcacg atgttttatt aatttatttc  30600
tgtcattgat gatctcctaa tatatttgtt acagtgttag acatttagtt ggatttcaaa  30660
tttttaacca ctttattatt attgtttgat tttatatata tatatatata tatttgggtg  30720
taaatgattt tatattttgt taaacataat ataattttat atttgattaa atatgatatg  30780
attatttttg ttttatattt ataaaactga attttttttt atataaaata ttctaaaatt  30840
```

-continued

```
tctattaata ttaaatttat taaataaatt ttaactaatt aacccgtggt ccaacccggt  30900
tgacccgatg acccggtgac ccaaaaggta gtccggttca tcgtccgggt cgggtttcaa  30960
aacattgatt ataacatttt gccatgtact actaaaaata aatcaaaatt aaatttataa  31020
aaacaaatta aggaaacaaa atctgtatac atttaattaa acaaaattaa tgtttataaa  31080
taagagtttg ggtttagatt tacaactaaa tgaaactaga tgcggtttgg gttttttatg  31140
gtttagattt tatagttaat tcaatttaag agtttgtaat gaattaatga attttattat  31200
tattagataa taatgactgt tttagtttgt ttaataagat gatatggcaa attttgatgg  31260
gctacttaag aggggggggg ggaataagaa aaataaatgg gttgatttga actagttata  31320
ttttgattgg ctagttaaga ggagggaaca agaaaaacaa attttgattg ttttttttggt  31380
tgatttttag tttaataaaa aaaatgacta gtaatttcat gtgattaact atcaaattct  31440
tacgagattt tgtataataa tgaaaacaaa atataataag aattagagag attgttaaga  31500
ttacccttcc aaggttacct ttttaattct accctttcat ttagttcatt tttatttata  31560
catttttaaa ttattaatga ccattttatc tttatttgaa aatgttttcg gttaacataa  31620
tgaaatattg attttttccg ccaaaaatat tccgacgata cttcttattt aattgtatat  31680
aaaaagatag gttgaacttc ttgccttgtt aaaaacctac agaagccatt atcatgaatc  31740
ggaacaaagg agtgcgtaaa gaataccaca tctctctatt aaaattttag aagcaggcaa  31800
catatgctcc ttttgtctgg cctcatatcc agtgaataat ccacatcatt tcacaaaaag  31860
caatcctcgt gccaacataa ttgatgcaca agaatatgta atatgcatac gtttaacacc  31920
atgtgagccc aaggttgaca acacatattg aagcttgcca agttttctca atctagcaat  31980
agttgattcc gaaagacatt tctattggga gatcgatgag atcgacccaa accgaattga  32040
gacacataga aattacaaac caaaattaag atataattat ggagatattg tggactgtga  32100
atatacgagt ttataaaatt tgatattatg tcttattata ttatttacat ttaagtttat  32160
cattttaaga gaacttagat ttatttcatc tctttataag acaataaatc ttgcatcttt  32220
attctgatga gagtctaaca taattcttcc taaacatttt tattttcttt actctcatca  32280
atttatcggt tactgaaact gtctcaaccc ataggcctac acatcgaaaa cctttccact  32340
tgtgctctct tggagttatc atctatcgct tttggaattg gtatatacat gtactacatc  32400
agtagaggtt accaattaaa cccaaatttg atgaaacaac acgtttacca aatggacccc  32460
gtataacatg tgaaagtatt tggattttct aatattcatt atgttatatt ttcgatttta  32520
gattttattc aatacaaaaa aaagatatca ctcaaacatt taatcaaact atacttttga  32580
ttggtaaagt ttatctattt tgttatttga tcttttatat agatattgag aacataggaa  32640
aactgttgat tattttttca agtagataca tttacatttt cgttggatta tttcagctcg  32700
gacgcattct tatctgtatt ataacaacaa catgatctat taacacattt gtaatgttta  32760
taatgggatt cgtgacaata cacaatgcaa cctatttcat attggcctgg ggcaaaacac  32820
gctggtgtta cgaagcaaat cccatcgttg tcgtgcgagt gcttcgaaag tgcaggacct  32880
aattattaat aaaaatcagt acaatataga cattcattta aaaaaaagga caaaaatatg  32940
ttcataatta taaaatgggt tataagaata cactaacaca ttaaaagtta aatatataat  33000
aatggaacat agaattctta tcttcaaatg aaacaagaat gaaagaggat ggaaactgaa  33060
aaatcaacaa cagtcactat aaaagttttg ctctaaattc taaatggttg gtaaagttta  33120
cctgttgcgt atgttgttgg ttcaccactg cttggggcac ttgcaattgt tgtatgacaa  33180
tgaacataag atatgatgac aataacgctg aaaacaaatg cgattagggt ttttggggtg  33240
```

-continued

```
ttagccattt tttatattct tatttttttt tgtcaatgag gtcttcaata ctttgattga  33300
ttatatatat atatatatat atatatatat atatatatat atattaatac aaatatacgt  33360
aaatggttgt tttcctagtc aaagatgtaa ataacttatg atactataat ttacaattta  33420
ttttcatatg gtcaaaataa atatcttatc ccttcagttt atttctttat agaattgtag  33480
tcaaaataaa atacatagaa tgttttttct taccaagcac tttagaacac cggcattacc  33540
cttactaata tttatgaagt gcataattaa aattaaccat atttcatatc aaaaattaca  33600
tcaaattttc attaaaatat aggttttcat taaacaaatt aataataatc attacaagta  33660
aaatagtaaa cactacggcc atgaatgttt gtagttttta aaatggtttt tggattttgg  33720
tttttggttt ttaatttttg attttcttgg tttttgtttt cggtgtagat tttagtttct  33780
taaaaacttg aatgataatt tgtttagatt ttggttttta tgttaatgaa taatatatat  33840
ttttttaaac aaatctaaaa taaaataaaa aaatgtgatc aatggttttt gagaaagaaa  33900
ctcccataat tatagatttt ggttttcttg aaaaattgtt caaacactca aaaactagat  33960
tccctatttt ttaggaaaac ttgtttttct tttaatctta aatgggtaca aaatagattt  34020
tgtacaaaat agatcttaaa tgggtacaaa atagattttg ggaaaaacta aaaccaaaaa  34080
ctaatttaaa aaccacatcc attcgagggc tactttctta aaacgaacat gctttagtag  34140
ttttcaaaaa tatttaatta atcaaattaa ataaagaaga tttgatatct aatttaacat  34200
attaattttt atttaatcat tgtacttcac cgctcatctt cgtttaattc tacttttctg  34260
aaaaaacaaa tcatcacatc atcttttcgc gtatgctatg atttgaattt ttttgtagga  34320
tgttgtttgt acatcagatg ccttggtctg atggggagtg atcaatgggc tcctctccaa  34380
aatgtttctt cacctttcat gaatcataat acatgatttt gctctttcta cgatcaaaac  34440
ttcctcttta agctcattct tcatgataca tgctccaaac cctaggaaga acctaagtaa  34500
tgcaaaatac acaactgagt tgatataaac cacaaagata tcaacaggta aaagagaaag  34560
ctctgattca aatgtacata tgagtcttct gtgttgttcc atcgacaaaa tatgactaat  34620
gaaaaaactt ccgactctcg tcagtttaca aatcagatga taaacactcg agtaacatga  34680
aggttatgtt acaaatatcc aatgaactgg agagttgaat caacttgaag caagagcgtt  34740
tagcttcttt tcatatagtt ttgcccgtcg aagagcatct aatgcctcag cttgtttccc  34800
tgcacgtttg aaggtcacag cttttacctt ctctgctttg attcgttcct ccaattgact  34860
tctctcttga ttattagtat ttctattact ctccttcact gggtttggtt ttgccgcagc  34920
ttgtgttgtg tctgttttac ttaccggtgg aggattcacg ggattgtcta atccaatagc  34980
tttgagggca gacaggagtt gaggatcgag aaaatcttcc accgctacat cgtccaccgg  35040
ttctggttta gaggatgttg aatcttccaa ttgagcttca agagttttgg cgatttcaaa  35100
ctcagcttca gcttcctgca ttttaccttc cctccgaagc ttcatggctt gacgtttgtg  35160
acttagtgac tcttgctgca gcttaaaacg gtcacgacct gacattgcct ttggagctga  35220
acttgaagga ctattctctt tctctcgagc aggaggatcc tccgttgtgg aaaccatatc  35280
atctcgtccg agcttttcag gagagggatt ttctccttct tgtagtctcc tctccaacaa  35340
ttttgcttct tgcaatgcct ttttggcttc acttatgttt ccttctctct ttaaggcaag  35400
tgccttttc ttatgagcca gaatctcttg tttaagggtg ttctgaggag atgtattttg  35460
aatcgaagct gattgaatat gactgggctc tgactcttca cgtgccactc tttgttcagc  35520
gccgtgattg tttcctgaac gaaagcctga catagtctca gcatttcctt tttctgcatg  35580
```

-continued

```
aatttgagac ctctcagaat gctcaccagt cagcaaatcc atcatacttg gttgctgctg  35640
gccaggttga gaaacaacgc cagaggaacc agatttagca ggggagataa agtctcctaa  35700
caagtcataa ctatcttgag gagcatgaga aacactagca gattttatcg ctttatcctc  35760
catttgcgat ccaactaata aatcaacatc catgtagttt tcaggtttaa ttgcagaagc  35820
tgagcctttc atctccatct tggggggtttc cagttctgct agctgtgcct ccaaaacact  35880
ggccttactg tataattcat cagcatctcc agttttccct tgacgcttga aggcaagtgc  35940
ctttcttttt aagtcaagaa gttctctttg gatttgtccc ttgcttttgg ctgctatccg  36000
tggaccgctt gactgcacag agccgaaaga agcttcttct ttctttggtt cttcatcctc  36060
ccatcccaaa ttcttaagag tcgacaataa cgctgggtcc ttcatatcat tttctgtaac  36120
gctatcatct cctccattga gccgactgtc ggtggcaaga tcattggatc gtttttttcgg  36180
ctgatcactg tcagcatata gattcttgcc tgaatcaatc tccattatct gagcttccaa  36240
tatttgtgtc tggttcagaa cttcctcagc ttcatcaaca ttaccctgtc gtcgcaaagt  36300
taaagccttt cttttcagcc ctaagagttc tcgttgtatt tctgctttag ttctccttgg  36360
tttagtaaca cgtacttcat atgcaccttg agcttctgct gttttccctg gtcgagaatt  36420
tagtgggtca gatttttctg atgaaggacc tgcaggatta ttatcttcat cattccaacc  36480
taagctcttt agcatcgaca agtaattcgg atcatttaac tcctcatctt ttacatccac  36540
ctctccatca tcatccagag aactaatatc aggcagatca tttccttttt cacgagtggc  36600
cttccctgtg gcagctaact ttgacgaatt gtccagctca tcaagctgat tttggagaac  36660
cgctcctttc ttcaattctt cttctgcttc gttaaacttt ccttcccttc tcaaagtaag  36720
tgctttcttt ttcactgcaa gaagttcttt ctgaatcgct agcctgcttc tgggaggagg  36780
tttaagactc gtatccctct ctgccctagt tgtgtcaaca gtttcagagg aagtatcagc  36840
agcctctagt tccttctcaa gtaattttgc cttctttagt gtagccatgg cctcaacgac  36900
atttccagcc cgttttagat taagggcctc tcttttcaat gtctgaattt cagctaaact  36960
ttcatctctg tttttaggag atggtcgaga gtggacattc tcatggtgtc caggatcctc  37020
actccaaccc aaagatttca atgcagcagc gattgctggg tcctccatat cttcatctgt  37080
gacatcatat tcaccatgaa ctccaatatc atctaaattt cccacaaggt tactaatgtc  37140
gaaatcatgg cttccctcgt attgagctaa cagatcatct tctttgtcat catccatact  37200
attaataagt gcagatagct catcatctga tccatcagct ccacccaaaa gttcctgctc  37260
ttccagttcc ctttccaaaa ttttagcctt tttcagttca tctttagctt ccgcaagctt  37320
cccttcacgt ttcagcgtaa gggcttttct cttaagggca attacctgac tcttgtcaat  37380
acccccagtc ttctgaggat tagcacttcg cggaatttca cggagaagag acgaaaattc  37440
gccctccaaa cttatagttg ctggtttctt atcttcatcg tcagaccacc caagctccct  37500
caggtcagct gccaaatcat catttccttt accccccttga cgtagaggct tttgtgattt  37560
gctagattct ttggtagcag ccttgttctg cgtctcagca acatttcgca tagacagttc  37620
ccttttccgg ttccttctta aagatatctc taatgcgtcg gcctctctct caagttccct  37680
ccctctctta aatgctttta gagcttcatc agatttccct tctcctttaa gaattctgta  37740
cttattcttc gcttctactg cttgtttacg caattcttca ggactagcat ccaactccat  37800
acctttatta ctactgctac ttgccatttc tttagaagca ttcctgtctg tgctagacac  37860
agattcagat gaagaagata catcaacatc agagcctaga atctcactga gaacatcatc  37920
ctcattcttt acagtccttt tcgagctacc tcctgaacaa attcacaatc tctttacatc  37980
```

-continued

```
aaaaactagc agataacaca aaagtgtcat aaataagatc actataggta cataaatacc  38040
tttagcagct ctatttttgt aaccatgacg caactcaaac cgtgcagctt cttcaatttt  38100
cttacatggt tcacatatac gcacaggtga gtcaccttgt ccacgtagtg acaacctttg  38160
ctgagtgcag gttccacaga acaatccccc acatctccgg caatgatgct gctcgctcaa  38220
aaaaacaaag ccaacagaaa ctaagaaaaa ttaagcaaat tcaaaggttt ttgggagaca  38280
tagaagaatc cagcaagtca caagtctagt aatacacaaa ccacaaaaca tccagattca  38340
ccaaatttac tcaaaaatat ggaatctatc aaataggcac atcaccagaa accgatcatt  38400
cagtgaagtt ttccgataaa cagattctga attagatctc gaagaagaat cgactaagac  38460
gaaactaaat ttcgatcgaa gaaactaaga atctaaagat cgcgatagca ataagcaagt  38520
accaattgat agagagagta aggaaattaa gagagaggaa gaccttgcga ttgatgaaag  38580
tgaattgaga agaacatcct tgacaatgag aagcatcaac gacccaacta tttcctctta  38640
gagatggctt cggcggtaat ccgatcttct ccaacatttt cccgtctgat tcttcttctc  38700
ctccgccgcg aaacgaactt ggttttgatt ttgatcttac cggaaatgta aaagatcgag  38760
cagatgaaga agaagaagaa gaagaatact tttcctcctc tattgtcaga tataaaataa  38820
ataattttaa ctaatacggt atcgttttag ctaaaacaca taataggact caatatataa  38880
agcaataata attagacatg aaactaattt ttgctttgag acgagaacga agttagaaag  38940
agacaagccc taaagatcgc tttgagacga taaactctta aagtttcgat tcgttcacga  39000
tgatcgtccc tgttcgttgt tttacttgtg gaaaggtttg ttttttcttc tctcttttttg  39060
tacgatttcg atttgttata tatatatgtg tgtgacaaat ctctagggtt tgtagtattg  39120
agatttatga agcttttgtt tatgattttt tgtaggtgat tgggaacaaa tgggacacat  39180
accttgaact tctccaggct gattacgctg aagggtaagc gatatatagt ttatgattag  39240
aaaaagaatc ataatttgtg agaaattttt ttggtgaaca tgagagtgat tgaatcttgg  39300
aattttgaac gttttctgac attttcttag ttgaaatgag agtcatgtaa aagatgaaac  39360
aatagtggaa catgacaata gaatgatttg atggttttgt gtagtcaaag agattgcatg  39420
atcttgtctt gtatgatcat cttgaaagtt tatacatgtt ttagccttgt tactaaaagc  39480
atgaagttag atcattggga tttttcgatt ttcttgtttt aatcgctagt gtaatcttta  39540
gcccgtttgg ttctaggtgt taagctacat gatttggaat tgcgcaattt cgtttttgtt  39600
ttagttgcaa tttgatcatc ttgaagttca tagatgttat cttaagtgtt agtaaagagc  39660
atgatggtag gtgatcactg atatattcca ttctcttgtt tctatctaat cttttagcta  39720
ctttggtttt aggcattatg ctaaaattgc attttgttga actgaaaatc tgaattttgg  39780
ttttggaata cgcagggatg ctcttgacgc gcttggatta gtccgttact gctgcaggcg  39840
tatgcttatg actcatgtcg atctaatcga aaagcttcta aactacaaca gtaatatctc  39900
catacccggt tcttttgcct tgtgttgcct ctgctctatt ctttttgtta acttgcttat  39960
tcgaatactt ctcttttgca gctatggaga aatccgaccc caattaaaaa aagatgctat  40020
aatgaataac aaatcatcaa gagctgaagt gaaggagtga tgcatctcat ccatgtgggc  40080
gtcttaataa aaccacaatg tttcagaaat tttggtttaa tttataacta ggaatgttga  40140
tatttcaatg ttttctgatg ttcttgttcg gttttagaaa tctagacaat ttttcgagcc  40200
aaaaataaag ctcaagcctg tagagtcatc atctattgat ttgtttttgg taatctaatc  40260
ctgataaata gtaaagatca cacatttgat aaggttcaaa tctacaatct agatcacgag  40320
```

-continued

```
taggaagcag ctctttttgt acgatatcaa attggtaatg agaacagagc acataaaaac  40380
aatttgaatg gagctcccat tttataaccg gagaatatca aagtttttta gttacaagtg  40440
gttgtattaa ttcaaggaaa ccatttaaca aaagaaatat aaatatttat attaaatata  40500
cactataatt agttgaatat atatttattt tggatcaaat gtttattaag atatattttt  40560
attataaaaa tttattctga aatatgttta ttgaacaata tactgaactt aacaaaccaa  40620
ggagactttt tttattttat ttttttttcaa acacaaacca aggagacaaa tatgaagaaa  40680
acaaattaca tttgaataga gaggtagagc tatataactc actgaatgct tggaaatatt  40740
gtctattagt ctattacaga ttaagatttt ctaaaagaat ttgagcccgc tgaacccaga  40800
atttgagagt ttggcttaga ctcaaattcg agtttttacc tagtacgcat tcaatatgga  40860
aaatggtgca gcactcaacg caccaataga acacttttgt gtttgtgtct cttaaattac  40920
gttcacatac ttcgcaccaa tctttttcac ggacctcttc ttcccatata gctgtgagaa  40980
agtgtttgtc atgttcatac cttgctctat agggtaatgt agcacacttc atacaaacaa  41040
taaaatcaca tttgatgcaa tttaattgat tatgacgttc tgttttgcat acgcgacata  41100
tgagttttcc gtctcggcct acaaatatga acaatggatg tttatgacct tggaaacaaa  41160
acggctcagc aattgaagca cattttacat ctagagtgaa gatacatccc cttatgcaac  41220
actcatagac aaagccacga caaccacgat tacaagaact gcatccaaaa cgatccatac  41280
catatctact tgcagctttt aatgttagtg gatgaggatg taatgcatgt tgtaatatcc  41340
tgcaaaattt tgcacatgtt tcatggaaga tgaaatcatc acactccaca caagaataga  41400
aattaccttc gaaaataggt aaataacacg cttgacaaag tttttttttcg ttataaagta  41460
tactgacttc gagccggaaa tgatggtcat ggagaaaatg aagtatcact tccttagata  41520
ttatattgaa tgatccaaca tcttgtgtaa tatcatcttt gtctggtaaa ccttcgagat  41580
cttttccatc ccacacattt ttctctagag cacatctcga atgaacagca taatgaccac  41640
acttatcaca agtatatgca ccataatcac cgtcaataat ttgatgaaaa actccacaag  41700
accattcaca tgatcgtaga gaaaaagtgt aggagatacg atggttgtga cgtgatatct  41760
tgatgacgct tggagagtac atacaatcac tatgaaacac aaagttgcat ctgacacata  41820
tgtaggtggg atatagtttt ctcaccaaac cacaaaagtt gcaagttaaa gaagtttgtc  41880
taggaaaaaa agtgagagga tggtcggcat gccttttttgg tgggtctata acaaagggta  41940
ttggcttcac tgcacatact ggatgcatga aaacgttaca tatggtacaa taatatacca  42000
ggaagtttac tcttcttcta cagcataaac aattaatact gtaaagaagg aagtgaaagt  42060
aaagttggag cgaatgctga gggtgataag ggtgtttgat tttaagtgga gactcgacgc  42120
attctttgtg atactttttc gtgcaaatgt cacaaaaata atagtcagtg ccaaaatttg  42180
agtgacggca tatattgcat ccaccatcaa tatcgaattc tttattgttg caccaaaaca  42240
acgggagtac tgaatgatat gtagcacttc ttgtagagaa gacgaactcg gggggaagaat  42300
tgagcgggaa aatattccca gttctatctt taaattttcg tgcacttggg cataaaaaaa  42360
gaggttgaag aagatggtca tcgctgactg cttcaccgga tggagatagg ctatgtgttt  42420
ttggtttggg atgatacttg ggatgatgat attccagaaa taggttacca tccttttcct  42480
cctcatgaaa tccaccgaaa tccatggctt ctcctagtct ttgtttacta tacttctgtt  42540
aagatctttt tttttttatat aaatgcaaaa tactagtttt gagagttttc cactatacat  42600
aagaaaatct gataccaaag gtctccttct acgtttaatt attggatcct taaccgtgaa  42660
aatgagttga attatgttct tttctttgta ttgaatggta attttctttc cacgcaagta  42720
```

-continued

```
aagaatactc ttttccacat agttttcacc cttacggaac ttatatatcc gactcgtcaa  42780
gattttaatt ttacgatcaa ttacaataga gaacaaattg agaccttaac ttaaatggta  42840
actacttttt tagtcagttt ttggtttttg ttatcaaaag aaatcattag tcatccaatc  42900
aagattcttt tacaattgta ctcttagctt tcttctcttc tcgaggaaag aatgattcac  42960
aatggggaaa tgtgaagtag tctttcaggt aatagaattt acaaagcagc ttcctagagt  43020
aatagaatta tcatgtgtgt atgatcaaag aatcttgttt ttcacaagtt catttcaaaa  43080
gtatgtaata tttatgtatc aaaagacatt aaatcaacca acatataata cataattatt  43140
caataccatt ttatagaatg agaatgagac caaagactca tatactcttt gaatccattt  43200
tgacattata aaagtcaagt ttatttagct ttgatcaatc cttttgactc gaagtactct  43260
atcatttgat catacatctc attgatccca tattcgaatc gaaagccttc attgataagt  43320
ttttgcgaag atagtgtcaa tttcggaatc gacaagccct cttcgaatct gccaaatttc  43380
acaaaacaaa aattgattag acaaaagaaa atcgaatttt caattaatat ttttgcaatt  43440
tctgtagaac ataaaggctt actctgacaa cacattgtac ttaggatatc tctgtatgag  43500
aaaatccgca atctctggaa cacttgtgtt gtaagcacag caaatgtagc gaccagaagc  43560
agtttctttc tccgcaagaa acaaatgggc acgagctaaa tcgtctacgt ggacgaacga  43620
gatcgagcca gatagcttct gcatttcctt gagaccggtc acatgcattt ctttccctga  43680
caacaacacc aaatcatctt gattatttat cgtgaaacag aatgggataa aatggtaaat  43740
tcgtgtttac cggtgatgaa agacatcgag agagataagc tactcggagg atcggagagg  43800
agagagtttc cggctataag tgccggaatc acggtaacga gattgatctt attctctttt  43860
gcaaattccc aagctgtctt ttctgctaac accttcgaga ttgggtaacc ctagaaaaga  43920
acagagaggt aagttggttt atgtatgaaa aagccctagc ttgtgtaaca agaaacgtaa  43980
ttacccagtt aaaaggcttc tcctctgtga gaaattcaac gtcagtccag ttttcttcgt  44040
tcatcacgat tccggttcca gaaagattgt tgatggaaac agcagcagct gaagatgtgt  44100
agatcacacg cttgactgat ttcgatttta agcaagattt caacacattg atcactcctt  44160
gtatcgccgg cttgatcatg tctttctgta tattgaaaca aaaacaagat aagcttgata  44220
atgtttctct tatgagtata taaaagcctg cacattctgt tcaagataga cctcgggatc  44280
ttcggattta aagttgatcg gagttgcgac atggaagatg tattcacagc cggagaatga  44340
ggattcgaaa ctgtcttcat cagtcaaatc tgccttgaag atcttcaggt cgccaagctc  44400
ttgaagtttc ctaaggtgag ctattttctt ctcgttttct gcagtttcag aataaaaaaa  44460
atccattaaa cattcaaaat gccttcagag aaaaaagaaa gaagaagaga gtgaagaacc  44520
tggatctcta actgtagtgt taactttgta gccactttga agcaaatgct tgatgagaat  44580
agaggctaag tttcccgtgc caccaatgac acaagccttc ttcgatccgg tgtgtgtaag  44640
agtctggtcc atgattgtac ttttgaaatt acagagatag agatttagtt gttatgagtt  44700
tatcgtcttg agacttctat ataagaagta aaaagatttg caaatagtcc ttgctcatta  44760
ggtacaacag tagatcaata aggctgtttt agaaggtaag cacgtgatct ttgaaataac  44820
caacttgtct tcacctaaga atcaaaaaag attgaccttc agagttctga tttgttatca  44880
tctaccaaat tatcacaaga gtttgattat ttctgtctct aaacaatata acacagcttt  44940
agagtaacga atagtgttac agtaaggttc tgttacttca attttttctt tgccgatctt  45000
aaaatgagtt gcaaaagaat gctttttact tccaccaatc tgtcaaattc tctgcagttt  45060
```

-continued

```
ttaacacaac ttggacttgc tatgttctgt ttcacgaatt acacgagtca attcaacata  45120
acttgctctg ttcttgtcca tgtttcacag aatctggcct taagcaattt tatcatattt  45180
aagctacaaa tccataacag agtttaacaa agataaaata accagaaagt tacattgaaa  45240
gataaaaagt gaagaagaca aaaaaaagag agggtaaatc ctaaatcgaa aacaaaagaa  45300
ggcattggca atagcattcc gattttaaaa aaccgataaa tctatgtatc taatggcttg  45360
ttcttagaag cttcaacgaa catagaagca acctcattca aaaacttagt cttctccaac  45420
acaaattcca actccttagc ttgcaacaac ttatacttct cttcaacaat cttcttactc  45480
tcaaccgaaa ccaaactcca ttgctgcttc acataatact catcaacacc caaactagca  45540
atcatcctaa caagagacga gttatcaaac caatcacatc catcatcacc accatcttct  45600
tcaacttttt taccattagt tgaagaacca ccggcaaaca ccaactcttg cttaacagaa  45660
tcaatcttct tcttcgccac actctttttc gatacaccgt tcgacttaac attagaatca  45720
agagctattc ctttaggtcc ccaaataaac ttagacaatt caaaagcttt cttatcatga  45780
gctttcacaa aactaggttc gttccttcct tctttaccaa tatacttctt ccttaaactc  45840
ctaatcttat ccatgaattg attcttacta acctcaaagc taatcgattt cttcaagaaa  45900
tcgtaaaacg cattagtatc tacataagga gacttccctg tatcagcttt gaaatcaatc  45960
attccttgta acactaagat ttcgtcttct tcactccata gtctttgaaa acctcctggt  46020
ttcttcacac tctcttcatc tttcttcact cgtttcgttg aagtcgtagc agcagcttca  46080
ctcgctggcc gttttgttcc tgatttcatc gccggtaaag ctaaagtagc tgacgacgac  46140
gttggatcct ctttcttctt tagattcact gtgtttaaag cgattgtctt cccagatcca  46200
gaattcggtg gatttgttga ttcagaatcc gaatctgttt cagtctcgga tccagaatct  46260
gaatcagcgg cggtggagac ggcggtggat ttagctggag gagcggcggc ggttgtggcg  46320
gaaggggatt tgattcgaat tttgattggt acgtcttctt cagatgaaga ggaatcgtct  46380
gaagcttcac cagcttcgga agtctcgacg tcatcttcgt cgcttgaagt tgccgttggt  46440
ggatcttcca gtggattgag tttcttcgtc attggaaatt ttcaaggagg caaatcggaa  46500
tccttcaagc agaagagaag agagaagctt tttagggttt gtgaggagag gacggcaaaa  46560
gtgtttggga atataaaggt gttaacttta gtttaaagtg gttgctgtct tccaatagat  46620
attttagggt ttttaatata gggaattaat tattttttttc tctttttctg ttggtcaaag  46680
taatttagta tttttattac ttttgctttg gtaatatttt atctctttct tttggtcaaa  46740
gtaatttagg atttttatta tttgctttgg taaatatttt ctctattttt cttatgtata  46800
accaaaaaaa aaaggcctaa gccaaggcta tggtttttgc ttttagcttt ttccaaaaat  46860
ccattttttta aaccattcaa gattttgagg aaagttgatt ccctatataa attagggaat  46920
ctaattctaa gagtttttac taatttctta acaagatcca aaaatctcat gttatttaca  46980
aaaaccaaaa tctgaaatct aaaatctcct aaaatcttgg cctaaatttc tcttttcagt  47040
atcaaactga agtatgggct ttcaggcttg tacatgctta acttctgttc ttctgttaaa  47100
tgaggtgtaa atccaattgt gtagagccca ttactaggcc cagagaccat tttgacccag  47160
atacaatcag ctcacaaaat agaaaacata acatcatgtg tcgttgaaga aaatatggta  47220
caaggcatga tgggccttgt tgatgaaaat atggttagat tattattaaa tgagcatggt  47280
gaaacattat ataaaggaac gaaagatgat aagtctaccc acattactta ccaccattct  47340
taattatacg tttctttttg cttttgattt tggttcctct tgtattttcg atctaagagt  47400
aatactttag aggaagtaca tacagagaca acctcttaaa caaatccatc ggaaccctaa  47460
```

-continued

```
acatctcctt gtggcagagt tatgactttt tacttccagt gatgaaattt ggttgggatt  47520
atagccacga actcaataga attcttaaga tcatgtgaaa acgttgacaa gatcgtctac  47580
gattttccaa gattctaagt cttctattga tgttcatggc tttaacctga ttttttttt  47640
cctactaaat cgacactcga tggctacctt agaggttaac taaggcacct aagacattca  47700
tggaacgaag ttggctctag cggtgtgtct tagagccaac tctgttccat gtagagatta  47760
ggtttcttag tgatcatgag tctctggctt aaccaactac tcaacaatca agcaacatgg  47820
ttgttggttt gatgtcagtt gaaagccggt tcaagctcaa ggtgttaacg tttttgctgt  47880
tgatcattct tgtaatcttt tctcggattt tgagagagtt ggggtcttat ttttaatgta  47940
accattaaag atgagagtga attttgtaga gaatcaagct tagacgtatt attcactatg  48000
tgagctcgaa ctacttaaga tcgtcttttt cctctgtttt gctctgtttc tgtttctgat  48060
tccgtgtatt attgagtgca tgtgacaaca agtaaagatt tgatcgatta tttcctgcgt  48120
aaagtgacaa tagcaatttc aagaataatg ttataagttt aatgatgaca tggcattatg  48180
gactaataac caaatggatg aaggaacaac caaaagaata tgatgatatg gttatacaca  48240
tctattttga actatttagc aaagaaacca aaactttatt tctgtggtaa tttgaaagtc  48300
atgtaactac agagacaaat cattccaaac atatatccat agctagtcat caacactgtt  48360
caataccatg acaataccaa ccaagaacat aataatcgaa gctcttccat gctcggttat  48420
aaccttttga accacctttt agtcccacga gggaagacac aaaaacaaat aattgcatat  48480
atacttgtgg ttccagtatg ttatatgcct agcaacatgt gttgaatcat agacattgtt  48540
tttttttca tatattgttg atgaaaacag aaccatgaaa taacaagtct tttaacttga  48600
gatatatcaa aaacatatta ttttctgatg gagccaagaa cttgactacg gaaggagctt  48660
gcaaggacgt atagtccatt ggatttaagc caccaataac aattgggtca actgcaatgc  48720
gagcttcaaa atgggtgtag aaggtacata ggcatgatcg gtcttaaaag ttcaagtttt  48780
gtttttcttt tttgtgtgtg tagaaaaata caaagccatg atgggtctta agagttcaag  48840
gggtcaagat caaagtaaga tgtgtatatt caacaccatt agaagcagaa tttcttagag  48900
caaaggtatt gcacgatctt gtatccttgt taacgacaag actgactaat tggctaaagc  48960
tctaatacct attggttgtg gttatgtatt tccctttcat tggctaaata tccgaacgtg  49020
aggaacacca tgactgttgg atgattttga tcatttttca acaagtttct tttgttattg  49080
gtcaataact tttgctacaa atctacttgt gtaattaatt tcttacgtgg ccaaaatgcc  49140
caaaacataa catgtgccgt tcaagaaaaa aaatgctcaa tgcatgatcc ttgtcccaca  49200
aattaccaca ctctagtgct cccacataca accttcgata catgcgagat atggtagaaa  49260
tttattgtgc ctttcatttg aggatattgt aaaataaaat cataaaggaa aaagaggaag  49320
aagaactcat ccggattgta gttatctcca ttatccaaca acaataatcc ggatgaattc  49380
ttgtgttaga gacgtagagt cttggttggg atcagagaaa cggtcttgag atcatggtgt  49440
caaacaaaga tctttcctac aaaattgaaa ctcgatcgag tgctttctca gagtcagagg  49500
tttatgtgta atagagatac acttaaccat tagacccaca cgtagtgcaa gaaccttact  49560
ggtaagaggt cccagaacga tatccattat tttgtagttg gaggccacac caaccgccgc  49620
aatgttccaa tatatcaaag ggattataaa tcataatgag atactagaac attggcgtgg  49680
ttaatgtcat ctccagcaac ccaagaataa tggatatcat tatggcccgt atacacctct  49740
gaccagagca attttcacca tatgttatgg tctgcgacac tagtttctga accaagaaac  49800
```

-continued

```
tagtttagct ttctttcttt tttgacttgt gatcagcaat gaaatcttga tttcttggga  49860
agaaaggaac cgattgtgag acctgatctt tatgttgaga agagtgtcac aagcgtttta  49920
atccaagaac ttctttgttt ttgaataact caaagcattc tatagttcaa atcaatctct  49980
ttctgaatgt agttgccaac gacggcaatt gtggacaaca ctatgacaat aaaactacac  50040
aaacaaatgc atagaattgg atattgaaat ctgaatttag gtccagaaca taacttttat  50100
ttgaccatat attcgaatgc acgagatgtg cattctgaat agtgatttaa aaatcataca  50160
aaagaaagaa atagaaagct tgttaactct aaatgaccaa atggatgaaa gagcaacaac  50220
atggtgatat gatatacaca tgtattatga aacttggtct caacaaggta acttgaaacc  50280
catgtaacga ccagagacat aatcattcca aacatcaaga gctccatagc ttgtcatcaa  50340
cacaatactc aatgccatga cgataccaac cgagaacaca atgatcgaag cccttccata  50400
ctcggttatt accttttgaa ccacctttag tcccacgagt gatgccacaa aacatataac  50460
cgcaaatata cttgcggttc cggtatgttc catgcctagt aataagtatt gaatcgcaga  50520
catcgttgat gaaaaaagaa ccatgaaaga acatgtcgct gcagttacct ataacaatat  50580
aaacagagta tttaaactag agatcgataa acaaaacaga gtattttctg atcgagccaa  50640
gaacttaatt acctcgggag cgataccaac ttggagaaga agaggactaa tgagcattcc  50700
acctccaata ccaaaaacac cacccaaaac tccagctaat agagccatta cagggaacat  50760
acacttgttt gatcttgctc catcatttga tctcaaatct tctacatcct gcaagcacaa  50820
aattgtttta agacattcat cgattctcgt cctttttta aaaactattc aagtgtttgt  50880
tagatttgtt tgaaatctaa cctttactga gacatggtaa tctgattgtt gttggctttg  50940
aacattgtca ctgaagcaga tccagagagt gaagaagaga gttagtggta tttgagacga  51000
tgaaatgagc cagtaggcgt ttccacatgg ctcgatcgat atgattccct gcaaatacaa  51060
atcatgaaat tcttaaaaaa taaaagaaaa tcttgaattt gttcctttca tatatttttt  51120
tatgaagtca catttcaatg tcactgtaga gaaatactgt gttatacttt ctttcttgaa  51180
aatgacataa aaatagtagc cctaagcatc attgaaaggg taaggaatct aaaaaagtgc  51240
aaatcttaaa gaagatccta ggaagaaaaa gacacgtaag tagtgtttgt atttttgatt  51300
ccctttatta ggaccatctc aaaactaaca aacattattg atgacctgtc tttcacgtga  51360
acaagttcgc tatcgctttt catcaaaaaa aaaaaaaaaa gttccctatc gtttttcaaa  51420
cgcatcttta ttcttcacca cgtgattcca aaaaacaaaa aacatataca agactaaaaa  51480
aaaaagatgt catgaaggta gatgagaaaa attcaaacgt gtttcattta cttctcaaac  51540
attaaacata aatcttaacg ttcacctaat tactccatca acgtgatttt gacatatact  51600
ttctctgtat aatcttttac gtctttgaaa tatacctaga taaagcaaaa aatgtaattg  51660
gtatataaaa accaactgaa aaataaagga atatcttaca gaatcatcat tttgacatat  51720
ttttattctc ggtcatagtt ttttcctttt atggtaaaaa aaattacttt ttatcaaata  51780
gttttagaaa gtttggttag aggtattagt gaaatgaaat ttacaagtca gccaattaaa  51840
aataataata actcaatgaa aacaatatta actattccaa aaaaaaaaat cattcaaata  51900
ttatgcaaat aattcttttt ttttctggat aactatgcaa agttgcaagc ctttttggct  51960
ttttctttct tgtttttttt tcctttaatt ttctgtgttt tgtctctagt agtctaaatt  52020
gtcaattcca aatttcaaac ttttaagcag atctataaaa gacattaaat acgattcatt  52080
aaatgcaggc aacattaatt ctaatactaa taatgaaatt aaattaaatt aaatgaaact  52140
ttttagttac ctcgccatat ttgtttcctc gaagaagata aactgcgaag taagaaagcc  52200
```

-continued aaataatgac caaaactcca agcttaatcc atggaaacct ctttggtctc tgataatcct 52260
ccaagagagg caactttaga ctctcaatct tatcttcttc atcatcttct tcaattctat 52320
tcgattctct aatcttcacc atctccgatt ccaatctcca ataataaagt ccatttccaa 52380
aagtcttcaa cgtcgaccac gcaagaaaca cagcgaagag actcgtaatc aaccagttcg 52440
gaaaaacaag attacagatc acaccaatac taactccaag aagcatacat ggttccaata 52500
aaagagctaa atcgaagtcg attagggttt tgccaccaga tttagggttt ctaacgaata 52560
gattgcatcc cacgttagct atagatccac cagtaaccat aaaagctgag aagcttgaag 52620
ctgtctttag atcgagaccg gccacgattg tcattatcgg aacatataaa cctccaccgc 52680
cgattccacc ggcgcttgag attgatgaag ctaggaaaga gagtaagccg gcgatgatcg 52740
ttgatgttgt tagttcgatt cttggttggt tgaattttgt tgaaaaatcg aggtatgagc 52800
ttgttttgtt gaggagttga tcgacgggag aaagaattga aggttcttgt tctgcgattg 52860
atggagtcaa gaagatgatg aaggagagaa ttatagggac gaaattgttt ctcatttttt 52920
tgtttggggg ttttggttaa ctttttaaaa gtttgggaga ttttaggaga tgttgggatt 52980
tttatgtatg ttatttctgt ttataacact ttatatatag ccatatagga gagtgtgtga 53040
tgcttggatt gtcaagtaga aagaaaaaaa aaatatatta aatagaaata gaaatagaaa 53100
tagaaagaag aagataaaaa gagacaaatc aacaattggc aagtggtgag aaaatgaaat 53160
aataccacat agaacttgtg tgggcattat gttatttgct cccaccatta cctattactt 53220
tctcatactt gttaaatatt attatgtaaa accagaataa cttaggagcg agacttttat 53280
ttaaataaga tccactgatc ttaaaagtga gacttttgta ttttttaaaa atatgctaca 53340 gatttttttta tatagttatt atataaaaaa tataaatata attaatatct acaatacttt 53400
tgaaaactgt tagcctcaaa aaaatattat ttcattaaca ataaaatttc agttaaagag 53460
actatataaa tttctaaatc acatttcaat tcaattaaaa actaaattct ttaatctttg 53520
agtgaaatta aagtaaacat atatatagtt ttattttggt ttgtctgctt tttcaacccg 53580
aacagagtat tataactatc aatattagta aatgataagt gatagtattg gttcacttca 53640
tcacttagaa gaacaaaatg ataagtgaat gatttcaatt tctctgattg atactttaga 53700
cagtacctac ctagaaactt ccagacatca tgaacggctc aatactaata gtctggtttt 53760
agcttcttcc aaacaaaaca gttttataag agatattata aaattttgat atattacttg 53820
caacatgctt tatttaacgt tcgtctctcg aaacccatat aggttaaccc acaagccaag 53880
tgtaaaattt tatatctttt ggaaatcccc atgttccgac cacatgcaga cagtttattt 53940
ctctaatgtc aaacccacat gcaaaaaact ataccataaa cctccaaagc cacatgcaag 54000
taaaatttaa ttcttttttg atggggagta aatatactta tgtgttttaa tcgaaagatg 54060
atgaaacgaa tgacgtaatg agtcattctc gtgttatttt cccaaatata tgtctaactc 54120
aagtaagcag gtaattgtca aatcaatgta atagtttata tgaaactttc ctttattcaa 54180
tggcatactt atctttagag tcatgagttg gcgaaaaaat aaacacttat ctgttgtgtt 54240
tcgttttatg tagatcaact tgctctttgc atatacgacc aaattgataa taatataaac 54300
tatatatatg cttatgtata tgtttgcatg taagtataca atgtttgtcg acattattaa 54360
ccagatatta ttggatcctt cacttctacg ccgactaact tgatctagct agtaaccgat 54420
tatataattg aataactatt ttaagttttg aataactatt ttaaatttta cattttctga 54480
tggtattaag tttgaaatgg ttatatagac tcgttgtaag aagatgtagt taatatgaaa 54540

-continued

```
attctccaac gataatcaat tgtctggtgt tatatctttt tgttatagat ttcttggatg  54600
gaaagtttat aatgccggcc aattctaagc tacacaaatg aaaagaaatt atttgtacgt  54660
gacccacact ctaactgcta acctcgcttg aagttggaat agtatctagt attatttttg  54720
ccatctgata gtagattgat cttaaagatt tacctaacta aaagagatcc ttaaatcaag  54780
ctttcaattc ttatttttcc aaaaatataa ctgtcttgtg tgtaagtttt ttattatgtt  54840
ttgtagaaag cctcaagatt gcaatatagt tctgaaattg caacaaattt tgttttattt  54900
ataaccaaga ttaagtaatg gttgattaac ggtaacgttc gattctactc agttttcagt  54960
atacatatat agatcggaaa cttcctacct aatttaaacc aaaaaattga tctaaatatc  55020
aaactatatc gatcttacct aaatataaaa agatttttta tacgtacctg aaaagtggaa  55080
accaaaccca ccatgaaata atttgaactg aaatttaact ttatttggaa aaacaaatgt  55140
atgtattttg attaaaggaa ccaaaattta aaactacaat catatcacgg cgccaaattc  55200
tcctatttaa atatgattac cgtagaagca ttgaaatatt ttataatttg taaactatac  55260
attatcatgc tgctggataa atagtataag gtttaaatac gagactggta tatattaaac  55320
tggagaatat acaactatac aagcattcca taagacatta atctttaggg gtctgataac  55380
ctgaatctag gacaacgaat attccaatta ttggttgtac aactacacaa gataaatttt  55440
aacaaagaat acaagttgtc tgtttacaga tttttatata tagccatatg gagaattaga  55500
tatttcgcta aacctgaaag aagacttaaa tttcttctaa ttttcttatt tttagcaatc  55560
atgatcaggt aagttcttta cattatctag aacaacctag tgtacacaat tttccgatgc  55620
actttcttat attaatcaaa agtgttgtga actttttggt taaagtcgta gtcgtgtatt  55680
cgtaataaca ttattgtaat ctcgaactgt ttcgatatga ttttggctct tggaaagtct  55740
cctgagtcgg gcttgtacta tgatccaata gtaaataatc acttaaaaag caacataaac  55800
gataaaaata tgataagtat gagccggctc taaaagtcac caattttcca ttctcatgat  55860
caaacataat tagcaagtat tatatttgag atctcataat agatcgtacg ttttcattac  55920
ttgttgaaat accaagattt taaaacaaac ttatttagtt tctacaccat caatttttct  55980
aagcttatct aatcgataca acttttaata aatgaaacaa gctgtataag tttattgata  56040
attgttatct ataacatggt gtataagtca ttctggcgcc gaatgataac gcgaactaaa  56100
tacatatttc atataaaaaa attgtttaaa aaaaatatat ataataggag tatctttcaa  56160
gtatatatag ggtttacacg caacacgtat taccatttac caacttgcac tagtctaatg  56220
atattgtgtt gtgatgtatt ggtcaagtga agggggatca atttctataa tacaaaaagt  56280
taacaccaac ggtttggaat tgtccagact tttagtttgt tgaaaagttg tagtttaact  56340
ttaagctcaa aatcattcgt ttatggtata aaagaacaca tgtacaaatt aatttggcaa  56400
cgataaacag atggctaatt aattgtgtgg gtttcaacag tgatcagtac aattgaaatc  56460
tgatttaaac aaacgagttt actttcgtaa atccgattcg gtgttcgtta ttggtgatca  56520
accgtgagat tctctccagt gttaagcgtg ggaatttcta tcgatgcttc tctttggttt  56580
gccttctttt tctttttaat gcaacaacaa caaagagaac acacggaaat taccaagatt  56640
attaccaccg cagctatcac cggagctatg attcttctaa acactttacc tacacacata  56700
aaacaaaact ctatgttata aagactatca aaggaaattt gtttaaatta gcatttcaag  56760
gttcataaaa tatttaaatt catatttaca tacatgtata gcagttgtta taaagagaaa  56820
atttcgtcaa gtacaatata tttaaattac acttccatat catcaaaact accatatctt  56880
agctaaaatt tatataagta cgcttacatg tattatccat agcaatctgt gtaaaaaatg  56940
```

```
ttgattttga taaatagttc caatcgttga caaaagaaag agataaatga tccacgttat  57000
atatataaga tatgttttaa tgttaattaa aaaaaaaata tgatatataa catgaatatg  57060
ttgctccaat cctaagtgtt cgtcaaggaa cacgatgaat attgctaccg atcttttatc  57120
agggtgaata tgaatattag tcggtaaatt cagtttggac aaaaacaaaa caaaagagtc  57180
cgttacttct aattcttgat gattagtcaa acacctaatt atattatcat atgcataagt  57240
tgctattaac cctaatttca catcagttac acttacatgt ttaggtaatt ttcagtgaag  57300
acacaaacat aaatgaaaaa aaattcaaac cctagcgtag aactatattt tatatatatt  57360
tattctcacc taacttgaat gaaaatgatt cgtcggagct aggagtatca ttttctccgt  57420
aaagacgttg tgggggtggt ggaggtggtg gaggtggagg aggagggggt ggtggcgcca  57480
aaaaagtggc tttatatgtc aacatacagt tcgaagagta aaccagagca aaacgtttac  57540
cataacaaca atccttagtc tcattatacg ctgatttcaa gcacctatag caatcatact  57600
gattcagatc gggtgtgcac tgtaccaatc catttagatc gtaaacttct ccaagataac  57660
tgacatgata agtttcttcc gcaaaatatg aagagctcga ataggcttct tgtatcaacc  57720
ggtccatacg atattccacg gtgttaatga aataaaactg gtacaacgtg gtatcgtaag  57780
atgtccatgt aacaaatgga ccttgatcaa gaatcgagaa aatcttacgg ctggagtacc  57840
tgaggaagca ttcttcatac catatgatag cttctttttg gaccggacac catataaaaa  57900
cgtttttgga tgctcttgag atgcatgttt cacaagttga ggacgagata tctccgcgac  57960
atagataact tccgtacact gttgtggttg gggaagaacc cgaggcgtag ctataaaagc  58020
ctttgttgga tgattgagaa tcaagaacgg atattaaagt atctagattg gatttgtacg  58080
aactgttcgg tgtgtagttt cctgatgtgt agcaatagct aaggaggtat gttggttgtg  58140
cattaagggt tttgatgaga agaaaagaga gaaggaagat gagttttgat tgatgaagag  58200
ggagagagaa catcttcgtt tgagtaaact tgttgtgttc ttcaacataa tatcgagcta  58260
taggtctata ttatttgaat tgactcttct tatgtatatc cttttagtag acgatatagt  58320
ttggttcgca tattttcatt tttaaaaaaa ctatacacta ttttgtttcc ctcttctaat  58380
ggtcaacttt gggccaggct gtcctaattt gactttaatg attatgaact tgataatgta  58440
taaataagga cgaggtttca aacttaatat aaaattatat gcatgcctat atgcctttta  58500
gctgattttt tttctataag aaaagtccaa tcccttttac gagtaaattt tttaagtttg  58560
ggaaaactat tgatttgatg aaactaggaa tttattattt taaagtatat cttgaaagat  58620
attaataaag ataaactatg taaaattatg acttaaataa tcgttttact aaagtaattc  58680
gtgtggcaga gatttatttt gaaagatcga attcaaaatt aacataagaa ttttgcccat  58740
tttcttattt cgattttgat tttaataaaa caaaaatcat attactttta gattttagta  58800
cttttctttt aaaatgtacg taatcatttt aacaaaagtt acaaaacgtt tattttcttt  58860
tacaagttca atttaaaatg actaattctt ttctattatg ttgttcatga taatcatatt  58920
atctattgca cagtctcaat ctctcaaatt tcaaataact atctttaata ataagttcta  58980
cgacgtgaca acataagcat aatttttttt tcccaacgta tattaatcaa acgcgtaaat  59040
tgtgcaaata attaggtgac aataagatta tataaagcac taatgtcggc cgtcaacgaa  59100
aacaaaaaaa gaacactaac gtcgagtcat atatagataa tggctagtaa aaacaaaaac  59160
aaatatcgta gaggtcatca ggccgaatgt tacaagttac aaccaaattc aatacacgaa  59220
aaccaataaa atgttccaat aattttttgt aagcattaaa aacaaaatgt aatttcataa  59280
```

-continued

```
tgttaataca tatctatgta aattatgttg gtgacacata cacttttgtt caaatcaagt  59340
gaaataaact ggacatctct tgtctttagt cgcactcaac aacattccat cccaaccgat  59400
ctcaatataa cagcttgcgt acatcttgtg actcttacta tgccatgtgt acaccttaaa  59460
acgtatcatg gaccttacct tcaaacggaa cattatcttc ccttggttcc tgtctcgttc  59520
catctccatc caacggtcct tattcacggc cattgcgggt cgacttaagg ctccgtcgat  59580
cgagctcgtg ttctttgggt cttggtaaaa cggattagta agtttagtcg aaccgatccg  59640
tttctctttg tagtaaacgg atccttccat ggaatcgtag taaatgccga cgttttggtt  59700
cgggttatga gccgttatct tgaagcttat gtgtgacgtc tcgaacccgt cgggcctgga  59760
tagaccagag attgagaacc cgcggatatg gacgcgtggt cggtgtggtt gtagactgat  59820
ccataagatg aaagtgataa tgcctaaaca tagtaaaaga gataagaaaa tggcacatat  59880
gagtttagag actcttgttg tgaggctttc tttaacccga tgaacgatgt tactcgccga  59940
gtggtgacgg gatatgggtc gcgttgatgg gttcgatcga accggtaaag aatcgacctt  60000
gttgtgcatt tttttttgg gggtagattt agtgttagtg ggtcatggga agtaaaatga  60060
tgtaatgtga ggtttatgta gcaatttttt ctaaaagaaa aacattgttg gtagttaaga  60120
agaaagcaaa agataccttg gaaaatatta tggttattac actttgagaa gaaaagaata  60180
gacaactaag tatctaaatt tttaactaaa aagatagagg aaaactaagt agctaaaagt  60240
gcattgcttt tccgtatatg caatgcaaag atttagatgc aatcataaag ttcattaaaa  60300
aatttagacc aaactccttg tccttactag ctagttcctg aaaccaaggc cggcccaatg  60360
cctgaaactt gtaaaatttt taatcgatta attagctatt agctatgtgg attatcaatt  60420
aagttgatat atttgcatgt aattttcttc tctaaaaatc gattaattta ttttgagcgg  60480
atttgaggtt tcttgctgga gggacatact cctgcaaagt gtccatatgt taagagtttt  60540
gctaacatgt gatgtgaagg agtgcttgag aagtatttga tattataaaa aagaaaagtt  60600
ttagaatttt gtgtaagatt tcgaattaac atatgtccta ataccctgtt agaaattttg  60660
aaaaaggccc taagtccaaa attagatttg cttcgagcta gatagaattg aggtacttct  60720
ttatttgatt ttcttgtcaa gtacttcatc ccaactccca agtagcccat atgtccaaaa  60780
ctaattaact ataaatgcat aatttatatg agggtttgta aaaatattct attttcttag  60840
ggtttgtata ggcatctaat ttaacaacta caagttagac tttagctctt agataatagc  60900
ctagttttac aagcaaggat aaaatactca tcttagaaac aactcttaat cattgtagtt  60960
tagcttagtt acttttaaac aaaacaaccc aaatgtatgg gcttgactaa tggcccagta  61020
atggccttct tgactaactc cattttgact ttcttcttcc tcttcccatc atttcttctt  61080
ctttttcatc ttgatttatg atctctgctt ttcatcttct tcttctcact taatcaaaag  61140
actcaattga gtcaattctc aattctcaac agtaacattc tttttttgct acaaaattct  61200
tcaataataa cttcaaaatt atgttatctt agagcttaag tatatattat aaggatactt  61260
tttgtttctt acattgaatt tattgtatct atgatgttct aattatttct tgtgctttga  61320
agactaacat cttgatatat cattttcaga attactttta gaaaattcgg aagtatatag  61380
tagttttttt ttggtaaacc ggaagacgaa agtatatagt tgaaccataa ttcagtacta  61440
atttgtcctc aacttttttt tttttggtgt gttcctcaat cttatttaat agtagcacta  61500
atttcacaaa aaaacgacaa aatgaaatat agatcaacaa taattaatat ggacccatta  61560
atatatacag ttttcaagac taggatgaga caataaaatt gtaaactcta ctaattttag  61620
caatatctat tgtcaaaaat taaacaatct gctatccata ctttcaatac gcatacacaa  61680
```

-continued

```
acaatttatt gtttcgaagc aaacacatat acagcacaaa actttatatt agtattgtct  61740
ttgtatgact attaaaactc gatgttatag tggtaagtat taaaatgtat ataataaaag  61800
aaaaaaccaa aacatatata attatctttc atctaaatag taaaccaaat atataaatat  61860
atagtataat gttttgtaag tttttaaatt cctattattt tgcacgataa gactcaatta  61920
tttaagaaga gaatatacta ctaacgtaaa atctataatg gcccaacaaa attaaatatt  61980
ctaaaaagtc acatttattg ttgaccttca caaaaaaaaa aaactctcaa ttttctgttt  62040
cttataacaa cataacaaac aaaaaaaggc ccaaagagta ttttcctccg aattcgccga  62100
cgactaatca cgagatggcg ccgccggtga cggagcggtg gtgcttagct ttgattcttc  62160
tctttctctc cttgttcgtc caatcttcaa cggcaattta ctgcggtgct gaagattgtt  62220
atgctcttct cgggtttgtt catcagcttc cgatcttcat tttcaaattc agattttgat  62280
ttcgttctct taatcgtttt gcattatcga tttcagagtc gctcaagatg cgaacgcatc  62340
ggatatcaag agatcttatt ataagctctc tcttcaacag taaggatgat tctggatttg  62400
tttagacatt gttcagattt gattttgatt agtgttttgc taatctttgt ttctcaattt  62460
tgatgattcg atttagtcat ccagataaga atccggatcc tgaatcgagg aaactgtttg  62520
ttaaaatcgc cactgcttat gaggtacttc aatattttta tgattctgaa actttggaat  62580
ctggcttagt caatcccatt atatatctct gcgtataatt tcttaggtat gatccagttt  62640
tagcgaatcg agaatcatta cattgggaga tagatttgat agtgtatggt tttttgtta  62700
tagctgagaa taattgaaca tgaaagtttc tcaaaaggat tcgtcttgtt gcagattttg  62760
aaagataata ctactcgggc acaatatgat tatgcaattg aacatccaga agaggttagt  62820
agaccattat tctgagaatt ctcaactgtt attcttggtt tgtgactttg tgtacattgc  62880
ataggtgaaa gatctttgaa aaaaattctg taccgctttg tgtttctttg tatataggta  62940
ttttacaaca ccgctcaata ttaccgcgcg aaatatggac ataaatcggt acgatgttat  63000
tgaatgtttc tgatgacttt tctttcggaa aaccattggc ttttttaact gatgttacga  63060
ctgcctaatg tgtgttctag gatccccgtg ctgttcttgt tggtctattg gtggttttat  63120
ctgcatttca atatctgaac aacgtggcaa ggtataatga ggtacgtatt agagatcggg  63180
attctctcac tatgtgttaa tagtctcaag tagttgttct gtatcgtttt tctgatgcat  63240
gccagaccta tattgttata tatttaagca tcagtactac tcatctatat atcacatgta  63300
tgtgcaatac ctaatcacat gtatgtgcaa tacctaatca catgtatcat agcatctcaa  63360
gaaacgtaga atttgacctc ttgaatgtga ttcatatact ttgttatgag aactttatgt  63420
agcttaaact cttaaagcct ataattagaa attatacaaa cctcggctca ttttcttaat  63480
gagatcttgc attattgttg tgatgcaggc tatagcgacg gttaagcgaa cacctgctta  63540
caaaaataag ctcaaggcat tagaactcga acgcacaggt ggagtaagta acaagaagaa  63600
gggttcaaag cagattgacc agtatgtacc cccagttatt taaattgcct ttttattagc  63660
tgagaatgtg tcgtatcgct gaataaatca taatcattta ttgttttggc aggaaactac  63720
aggaagagct aagcaacgaa cttgacttac aaatcaaagg agctgaaaaa ccatcggtct  63780
gggaacttct cggtgttcga ttcattctcc taccatacac tatcattaag gtttcatttt  63840
cttaaaatac tttcactgtg ccacatttca cagattcctc catatcctac tttcccgaga  63900
tagctgattc aacattctgt tatcttccag cttctagtat ggtacagcag ttgggtgtgg  63960
agatataagg tcaagaaagc tccttattca tgggaagacg catcatacct aacccgaaga  64020
```

-continued

```
tcacttagtg tgcctgccga cgcatgggct aatctaggta tccttctatt ctctaatttc  64080
caacctgaac cgacatattg ataaagattg atgtctaata caatgtgatt aaatctattg  64140
tgcaaattcg atatttttca gatgaatata ggaaggaaga tctggtgcag aaaaggctgt  64200
gggagaagca gaatcttgag aattactttg cagaaatgcg taaagaatcg aagcggagaa  64260
gataggtcac ttgtcgctta ccatgcaacg atacaaaata caattcgagt ttcagagaca  64320
ccatttttac cattatcact ctactttaat gttataagaa cgaaccagtt acaagaagag  64380
acactagtat aattgtacgg taccaggaac caaatctcaa tttgtcatat acaagatgaa  64440
atcatgtctg tcaatggaca tggtccagtt ttgactcagt tttgtttaaa accaatttgc  64500
tccgtggaat gttcaaatct atctttgata cttgaattcg agttctaaaa cgaaacatta  64560
actttatgat cagtcaagaa acacagtgaa gcaacaagat tctgtttggt tatattaaaa  64620
ccggaggaaa ccgatacaaa aaaatacatg agtgagagga tacaacgttg acatcaaagg  64680
gacaaaaact aaaatgtgaa acgcttgcgg atttgtttat acattgcttt gcttgtacat  64740
cttggtgtcc aacacttgct tcccgcacat tgcgcacact cctgcacaac cacgaagagg  64800
caattccatc agttgttaag ttactctata atatcactat ccaaccagag gtaagaattt  64860
agtagagtaa aacagatgta ttaactattt acctttgcta taggcacatg tgtgacagta  64920
tttaccatct tgatgcactt gctgcttgca gatcatacat tttgtggtac aggtactgta  64980
aggtgaccat ctacaaggca aagaaatatc acaatagaaa attagaagca gaacaagagt  65040
aaacaaaact aataactcaa ctcaaaaaag acaacacaaa cattcacagt tacaaatatc  65100
gctagttcca tgagaagttg tacatttact aatgattctt attaaaacct agaggactag  65160
cgaagcggtg gagttctaca ccctagatgg caagagtcca gtagcctaat caactcaaca  65220
gataatacaa acatcccaaa cttaaaaaat ttatcgctat ttccatgaga aattctataa  65280
ttactaatga tttttagaag aacctggagg gatcaactca aaaaagacac tacacgaaac  65340
tacaatacca atatttctta gaagaaacta caggaaacaa aaccaatacc aaactagacg  65400
atacaaacat ccccaaagct acaaattaat cactatttcc atattgcaat tcaaataatg  65460
aaaagtagta aaatgaagat ggataaacat aagaaatgca tacctattct tcttggagag  65520
aagcttattc tcattgattt tacgaccacc accttcagtt acattacgag caccatcctt  65580
ccacttatca ggaactatca ctttcgataa cttcttctca cctaaaatta aaagataaaa  65640
acaaattgag tcaaaaggtt catactttga actaaattag agatcctaca actagggttt  65700
cgatctaaga aaccaaaatc gaatcagaga tcattaaatt tcttcctgaa acatgtaatc  65760
gattaagcta gaaacgaaac gaatcacaaa tcctaacgcc aatagtatag attcaattag  65820
aattaaaacc gatccaagta tagattgatt caattagaat atggaattca aagagaagat  65880
tattgatgga cttacactta tcgcaaacca tcttcttctt ccgagagaga aatatgaaga  65940
aaccctaacg cctaaatcaa ttcgaatggg ttagagttac gacgaaaact tatcggtgtt  66000
gaaattttta tctatgttta aatatatttt ttttcctttt ctggatttgg aaagtcggat  66060
atgtctcgtc aaaactcata gcctcacagg tattttatgc cacgaatcgt aataatccac  66120
gtggtacatc aaccaataaa aacgttccac gtggtacaac cagcgagata ccaagaactt  66180
cgagaccttc ttctccagat agaggctttc cggtaaacgg caaataccct tttccttcac  66240
tttcttcgtc ttctcgaatc tgagagaacg agagatcaac aacaatggcg ctcaaatcaa  66300
aactcgtctc tcttctcttc ctcatagcaa cactatcatc cacattcgca gcttcgtttt  66360
ccgattcgga ttccgattca gatcttctca acgaacttgt atctctcaga tcaacaagcg  66420
```

-continued

```
aatcaggcgt aatccatctc gatgaccatg gaatctcaaa attcctaacc tccgcttcca  66480
cgcctcgtcc ttactcgtta ctcgtcttct tcgacgctac tcaactccac agcaaaaacg  66540
agcttcgtct tcaagagctc cgtcgcgaat tcggcatcgt ctccgcttca ttcctcgcta  66600
acaacaatgg atctgaagga actaagcttt tcttctgtga gatcgagttt tcgaagtctc  66660
aatcttcgtt ccagctcttt ggcgttaacg ctttacctca cattcgtctt gtaagtcctt  66720
cgatatcgaa tctacgtgat gaatctggtc aaatggatca atcggattac tctagattag  66780
ctgaatcaat ggctgagttt gttgagcaac gaactaaact caaggtcggt cctattcaac  66840
gtccaccgct actttcgaaa ccacagatcg gtattatcgt tgcgttgatc gttatcgcta  66900
ctccgtttat catcaaaaga gttttgaaag gagaaactat tcttcatgat actagacttt  66960
ggttatctgg tgctatcttc atttacttct ttagtgttgc tggtacaatg cacaacatta  67020
tcaggaaaat gccgatgttt cttcaagatc gtaacgatcc gaataagctt gtgtttttct  67080
accaaggatc tggaatgcag cttggagctg aaggatttgc tgttggattc ttgtatactg  67140
ttgttggatt gcttttggcg tttgttacca atgtgcttgt tcgagtgaag aatattactg  67200
cacaaaggtt gattatgctt ttggctttgt tcatatcgtt ctgggctgtg aagaaagttg  67260
tttacttgga taactggaag actggatatg gaattcatcc gtattggcca tcgagttggc  67320
gttgattaca tcacacttga ggatctctgt ttcacaaggt aatggcttta gttttggaaa  67380
aacagttatg ggaattgagt aatgatgttt ctggatgttt tgtgtttcga tttgaaatac  67440
ttttgaatcg gtgtagtact actatttcag atggtttaaa actccttact gttacattag  67500
tccattgtta agttatttat ctgaatgagt aacttatata accaagaata tgggatcttt  67560
agtcgattga atataggaac catatttgga aattcaggta ctgtttcttg agatcagtct  67620
aggattgttg ttatttggta cattgacact tttagagttt ctatgtgtct tcagccttgc  67680
gccccttgct tactgcatct attcagaaaa agggactttg tgattgagga tagtgtttct  67740
gtttaagcat tatgggacct tatgttttgt cgttgactgt gtcctcttct cgttttgctc  67800
tctgttttag aatgagtcta agtaaaattt aggttcaagt ataaatttgt gatagagatg  67860
gagtttcgga ttaggtttag ccattcgaca tgacataggc ttgcgcaggt gggaaccaag  67920
tctcttcttg ataggctttt catttgtgta cacacatttt gtgagatcat ttcaacttga  67980
aaattgcaaa gcatgcctct ctgatacatc agtatgactt tgattgtttg tttgcgttta  68040
ttgtgcaatt aatttttttt tcatcaaatg aatttacaat cttcagcagt taaaacagat  68100
tatacttgtt tatggtaaaa aaaaaaaaat gtcacactca cacgcaaaat tgaaaaagtt  68160
tcagatttca ctcgagaaag tgaagtaacc tatgatttgt cttttgtcga atcaaatggt  68220
tgatggaaat tttctttcgt ctttgaattt agttggacaa tctcgactta gttagctcat  68280
tcgatccatt tctagcccac acagaaaaaa tgagcttaat ccatatgagt gtttcacttt  68340
ttctaataag tttttggggg cttctcgact tgggccttga gttttatttg tacgttgtgt  68400
atgggtctaa gtcttgctaa tccacgtttc ttacatattt ctttaggtct ctcatttgac  68460
aatttcgggt cagattgatc ttcgtttgag ttggactggc gcatgttcgg gtttcgacat  68520
attgctatgt ttaatggatt tacgactcta attttaatta accactagta aatttggtat  68580
gtatgcttct tattattaga gcagcccaat cattatcata aaaatagtcc attagcccat  68640
gtgtttaagg tttctttcaa gatagattca gagataaatt tgtgtaatga gaagaagaga  68700
agtaacttta gaattgctga tggtacaact ctcttctcca tctttatatg aaattaatct  68760
```

-continued

```
aataagattt cattagtgct cttggcgaac atttaaatat actctggact aacaaaacaa  68820
aatcactagt ctaccataat ttaggtttgc aaatttttaa agaatactca tttagtaaaa  68880
tttaggtaaa taaatattta aaaactaaat tcattttcga cgaggatatt gaactaaccc  68940
aaaggcacga ggtgtcttga aagtgactaa gcacaaattt tcaacctata taaaaaaaaa  69000
acacagcctg tctcacacag tcacattgta tgttattaca atttaagaca atgacgattg  69060
catatacata aaaattattt atacacacat atatcttgaa aacgtgaagg ccacaactca  69120
aatatctcaa tatgtatagc tttcaaaatc taaatagaaa agagcaaggc taatcatttg  69180
atttgacagc aatataagtt tttgttgcgt cttgtatgga ttatgaatat attattagtc  69240
actaattagc tatggttaat ataacaataa atgacaactt tattgattat tattgataaa  69300
caaagcaaag tcttttgtta actagcataa aagaaaagat gtttagaggc atgtatttga  69360
aaactgtgaa taataaaaat tcatatgatt tggaatttat gttttctaat gatcggatag  69420
ctttatccgt gaacttccca ttttcttgtc tgttttagat ttgtggatct tattttcttc  69480
aaatggtagc aaatcatttg aaaaagcccc acaatatttt gttgcattaa aagaaaaaat  69540
tgtcttcagt tatacgatat tagttatatc ctgatctttg tatgatcatc tattacgcag  69600
ttactataga tttagtgcag actttcaaaa ctataattgt gctttgaaaa tatgagtatg  69660
taaaatcagt tattttagtt ttttcacgtc accttttcag attactatag tttttcaagt  69720
tgttggacca aatcttatga ttgcgttgca tatatacttc catattggtt agttagtgaa  69780
cgaaaaaaat aattaaacac aagaaaacta taccatagtt gaaccaattt ttaaaaataa  69840
aaagaccttt ggactagtat gtagttaacc actatggtgg ttaatttcct tgaacgtcta  69900
agattcgatc ctatctttgc ttcacgggac tataccatat taaggtataa accctatttt  69960
taaactttgt caactagcta tgtgaaccct cttggtgagc ccaaaattag accacttttt  70020
aagaaaaaat ttcagagaaa tatatgcttt tgagtcaaaa tattagatcc atcttcattg  70080
tctatacgat atatttctaa ttagcaaaaa aactttgttt ataaaagaaa acctaaatgg  70140
tagtcatttt attaatatct ttccatacat aaccgataaa aagaaaagat tcattctaat  70200
aaacaaatta aaaaattcac actttttaaa attgacatat tattaagaaa agataggtgt  70260
cttgaggaca tatcaagcgt ttaaatgctt aatcaaaatc taaaacgctt ttaagacgtt  70320
tcaattttta taagaaatat tataaaataa tattaatgaa atatcatgat ttatatatat  70380
atatatatta attaattaca tatttaaagt tgtaagaaaa accaatgatt gtattttata  70440
ttgaaagaaa ttttgtttag ctaaaaggat aaaagtttgc ttcttttttt agtctaataa  70500
tttcttactt tttcaactcc aaattctagt tgttatactg tccaaatcca gtattataat  70560
tgacatcaaa actttataga attaggcata cgcaacattt agttgtatat ataaaagtat  70620
gtattagagt agacgaagaa aatccctaga atgcttatta catgcgattt cgacaacata  70680
tactgctaaa atgccaccaa aatttttgtc tattctttag atataattgt tacaatatga  70740
ttcatttaac attttgttga attgtggagc gaaaatatct tggattcgtt aatcgatcca  70800
atgagcgtgc tagatgcggt ttaaccgaag cggttatgtc gacgatggac cggaaaacct  70860
cctcccattt gagagttgcg gtcatgacca aatttgttat agtgttcttg aatagtatat  70920
tttcagaaaa tttcaagctt attaattatt tgtcgttgtt tcctattaat tattgtttat  70980
aaagctaaca taggaaaatg aaagttgtaa atacattttt attttcttag tttttgagta  71040
aagaagaagt tttgagacta gatttgtaca taatcctctg atcaacgacc aaatcatttt  71100
atatgatatc ttctcaaatg tcactcgaac tgtgtaaaca ttcgtttaat cataacgaaa  71160
```

-continued

```
ccgaaccatc ataattttca cattaaaatg aaccattata aatcatttct gttttttttta  71220
ttttctctaa tcgtttacga aaatttagat ttttaaaaat aaattgctaa attcctaaac  71280
gcattctagt ccaatttttg aacagttgta ttggagtgga tgataactag taaacgaatg  71340
gaattggtag ttgaactaaa actcgtggaa tggatcacct aaacctttaa ctaatttctt  71400
attgtcttat acataacatc ggtaaacaaa actgtaaaca ctattctcct tgtccttggt  71460
cggataagat attcgttttt ctgttttccg ttaaaatata tacaaatttt atatcctcca  71520
ataattgatc aagaatatat atactttcat ttttatttat atattaccac tactctttca  71580
tgtctccttc caatttttct ttgtcttcaa atactattcc aatctcaaac gaaagagtat  71640
tttgtctctt ttctctttct tcttcatttt catcatcctc ttcaatcatc tctgattctt  71700
ttcttctgtt cgattcattg cgttctttac caaattttct tttggtcttg ttaacaatat  71760
catcttacat tttttataga agtgtttcag ttctttataa gtagacagat ttttattgtt  71820
gcgtcggatt cttgagcatg gctacaagat tcaaggggct ttataacaag agcttcaaat  71880
gtttctccga catttttggt aaatagataa aacctctaat cttgtttagt tttatcttta  71940
aatggacatg aataagcttt ctaatgatta caaaatggat taaatttgta gatgtggagg  72000
aggaggagga gatggaaatt ggttatccga ccgatgttcg acacgtgtca catatcggtt  72060
gggatagttc atcaagtagt gcacctagtt gggtaagaca tttttttgca acaattagaa  72120
attatggtgt gtgtttttta attacaacgt taatgtgctc tgtgttgtgg atttcatcat  72180
ttgtactctg ttttgatgtt ttaagatatc agatgagcaa aaaaaataga acgtggatcg  72240
atttaggtta agttttaacc tatttatgga attttgcagc tacatgaatt caagacgagc  72300
aacaatgttt tagagccaaa ctcatcgtgg ccatttcaag gcaagttttt ttctattata  72360
ttcctttttt aaaagaagct ttctgtcaat aataagcaaa tggtttccac gtattactag  72420
tccttattga aatttatatc aaaaaataaa taatttaagc agacctccaa atgtattact  72480
tgatagatgg atgcataaac taatatatgt gtttgacaac atagatccta atgaaatgta  72540
attttaaaaa tatatagatt tgaagtcagc gatggaggca tttggagaag ttgaaagcag  72600
caaagaaatg gaaagagaat caactaaaca aaatctgaag aagaaactct cttcaaaagc  72660
ttctctattg tgtaattcat ggtcaccaag attctcaaga tcaagcaagg tcctggctta  72720
attatttttc attttaattt aatttcccat gccattgttt atataataat atatagagcg  72780
tatagtaaga tatcaatctt aatgttttca ttcgagatac gtatgtcttt tcacaagtgt  72840
gtacaaatta atattcatac tgtcttcgca atgatattgg gatggtttta ctaatttcac  72900
aaattattgt ttcaaaaagt atccattaag aaaactttca caaatctaat gattatgact  72960
tgttttagat ctatattttt gttttcgaat ttcgaagttt ctttgaaaag aatgaatatg  73020
gtgaaaatct agttcagtag ggttgtgaat gtgaaaattt actatacgac attccgtttg  73080
ggacagcggg ggaaattggg atgatcaagg attagtgtat attggtcgta agtgcaacaa  73140
taatcacaat ttattgagtt agtggtttga gtgaagaaca tttgatggtt atgggtttta  73200
aaatgtaatg aacccttgat ttctctattg cacttttgaa agtttttaaa cttcgcagct  73260
caatttttat caagtactta gtaatttata ttatggtgtt tgtaatcatc gaaagtttga  73320
tcaaatgaga tgatgcttaa cagaaaaaaa acaaataatc aaaaaaagaa gttaaaacta  73380
atttagttat aaatggattg aatgacctcc ttcacaaaat ctaaaatatg ataaaatggt  73440
ttcattaatc aagtgatact ggttaagtgg ttcttactta aggaagaatt gcttcttatg  73500
```

-continued

```
tcgccaaaga ggcaaagatc aattcttctt aaacgtgtga tttacaaaat cattttattt  73560
gatcaatcga aatggtgtta tatttttacg ctcattaaaa aaccatgtga gtggactatt  73620
caatagctaa atttactata tacagagatt tttcgggtgg tagaaacccc cgattacacc  73680
tgatttcatt ggcttatatg gccttgtgcc gatatagtag tggacatact ctaaagtctt  73740
gaaaaatgca ccaaaaagct aatactttgt taacatgggc taaacatttt gcctagcata  73800
tatgatccgg cccatttatt aatatgtatc tacatcttta agaagtaacg aatttgtagt  73860
agcaaagaat gaatggaatc gatattgttc agtgaccatg aaattctcat atattgccat  73920
aagcccatac cttttttttta ttatttatac tttttacggt cgaagaaaaa gagaatagta  73980
gcaggattcc tactgcaggc aatgataata aacttataga aattttgaac agcgaaaaga  74040
aaacgacttg agattcaata tcaatcgttg gtgctgtcca attggcaatg aagtaaaatt  74100
tatgaacatt gaattttttt aatttaccta ttaagcttcg atcgtattca acctaagaat  74160
attacatttt ataaaattta acagtaaaaa tatctaattt aagagataat tattaaaaat  74220
tatataaaaa agtgactgac tttttaatct aattttaatt tattaggaga aaatctactt  74280
tgaaaattat tatatatata tatatatata ttgtgaggta gaattttttta tttcttaaaa  74340
aggtttacta ttttaactga acattgtgta aacgatgaac atcataactc gattgtgtcc  74400
aattcatatc taatagttaa atgaatcaac gactcatata tcacggagca aaacgcgcat  74460
gcagaaaaat ccaccaagcg aacaatttgg aaagcgatat ttctgatgaa tcgttgattt  74520
ccccaatatt acgaactttc ctgaaatctt tcctagccgt cgaatatgaa ccaaatttat  74580
tacctgacct ataaacacac acatatgcag gcaaatggac acatgtgttc tatgaatcag  74640
tgttggtgaa gagagagctt gtcgtgtaat gagagttgca tgtgttcaac aactttgtgt  74700
atgttttgta attttcctct tgtgatattt tctacggtga gaattccatt tgcaaggtta  74760
catcaatggg tgaagcctgt acgtccaaca tgtgaccaga ccttctttta tatcaacggt  74820
ccaaattaac attacattaa catacacaaa tatattatat atttaatact attgttcctg  74880
ttcttctttt tattgtcgtt acctcgttag catcaatgac gaatgaaaat gacaaacgat  74940
acattgtgtt gttcgaattc gtgttattgt tgccaaaacg atgtgataat aatggaacta  75000
tgttcattgt attggcgttg cccgctggtt tacaacgatc tatttcatcg atgaattttg  75060
gtaattaacg atataaaatt ttcaatacta aaagacacac ctttttcaac atttcttttt  75120
ataacttatg atgttcccat tccattatat tatagctcaa cttacaaact aacttgtcac  75180
atgtaaatta ctcattgact cgtgacaact attgacggca atattatcaa actcgtggtt  75240
ggaaatattt taagtccaca aaggaggaga aaataaaatt cttgaatatt gaaaattctt  75300
atacctctat gatataaaag aaaataaaat caaagagaag taccacaaaa acaaattttt  75360
agtatttaaa aatgccatta ctttggaaaa ggtcccaaaa tatcacaaaa tctaggctta  75420
ggaagggtct ctaaacgttt attaagaatt actaagccca aaacttgaaa actcctaaaa  75480
ctctttcttc aaatttagac taatcatttt taattctctc caaaatatta gtaacccttg  75540
taaagcctaa acattttagt aaattttatg atttttggtg gtaattttgg aaaataaagc  75600
ataaaatgtg gtattccgag gactgaccaa atttcaaaaa ttcaaataaa tgattaatat  75660
cctaaatcaa tcattatttt ttataattgt ttttgagaaa cttatattaa tactattttc  75720
aggcattttc ttataaatta ccctatggtt ttagtaggca acaaaaagat gaacgtctca  75780
gatttttttg aattcaattt aatcttaaca aaagcgataa atatcaagaa gataattggg  75840
tacgtgtatt gtgtactatt tcaaaattga tatttgcttc cataacgtaa cgtaacgtaa  75900
```

-continued

```
gacccaaaga ttaacacttg gtttcttcat ggtcgtagat tattaaaagt ttataactaa  75960
tgacgacaaa gtttaaacga aaaacaatat tttctcaatt ttcactagtt tttttttttt  76020
attccagaaa attattagta tacaaccaac tatttttacg attataaact tttatttgat  76080
gatattcata atttagaaaa accttaaacg gatcttaatg tcaatatcat cagctcatgc  76140
accgcctctc ggatatgttg acaaaattac cccatacaat ataaaccacc aaaccataac  76200
cacaaagggt atattcgtat attataaaaa tatctgaata gtcgaacttg tcgttacact  76260
caaaaacgaa atctttccct cctctgttct caatctttct ataaattctc ttcttcttct  76320
tcttccattt tcccaacaac acaaagtctc tctctctctg ataaaatctt aaaacccacc  76380
tcgagatcat agtcttcatc aattagccat aaaaaagcac aatgctttct tcaatcaaac  76440
catcttcgtc ttccttctcc accgctatct ccggcagcgt aaggcggtca attcctacaa  76500
agctcaagtt ttctccttta ctcatcatca aaaactgcca taaccaaagc tttaacgcta  76560
atgttgtctc ccatcaaaag cctctacaca tttcatctgc ttcgaatttc aagcgtgagg  76620
tcaaagtcga agcttacgag gccgatcgtt cccgtccact ggacatcaac atcgagcttc  76680
ccgatgaaca atccgcgcag aaactgaaaa tcggaatcta cttcgcaact tggtgggcac  76740
ttaacgttgt cttcaacatc tacaacaaga aagtcctcaa tgcttttcct tacccgtggc  76800
ttacttcgac gttgtctctc gcttgtggtt ctttgatgat gcttgtctct tgggctacta  76860
gaatcgcaga tgctcctaaa actgatctcg agttctggaa aactctgttc ccggtaagta  76920
attagggttt attgtgtgta gttgttgcct caaaagtttc aatctttttt ttttacgatt  76980
gagagctcag tttctggaat actctgtttt tccggtacga attcatgatt tattctgttt  77040
tctggtaaaa agtcatgatt tactctgttt tacggtaaga attttagatt ctctgttttc  77100
atgtaagtat tttatatctt ctctgttttc atgtaagaat ttagtgtact ttcgagcatg  77160
aaactgatct tgagatctgt cttccggtaa tggtttaggt attttcatga tgttgttgct  77220
tgatggattt ataattttgt ttgttgtctg ataatgaaag agtgtgtttt gatcgatgtt  77280
cccgtttttt cttattcttc aaggtcgctg tagcacacac gataggacac gttgcagcaa  77340
cagtgagtat gtcaaaagta gcagtttcct tcacacacat cattaaaagt ggtgaaccag  77400
ctttcagtgt cttagtctca agattcttca tgggagagac tttccctctt cctgtctatc  77460
tctctctctt accaatcatc ggaggctgcg ctctcgcggc catcaccgag cttaacttca  77520
acatcactgg taaaactcac aatcctagaa tattggtttc acatggtgac atttctttga  77580
tttatggtct tatgtgaaac tttgtggaat ttttttgta gggtttatgg gggcaatgat  77640
atcgaatttg gcatttgtgt tccggaatat cttttcgaag aaagggatga aagggaagtc  77700
agtgagcgga atgaactact acgcttgctt atcgatgatg tctcttgtga tcctcactcc  77760
attttctatt gccgtggaag gtcctcaaat gtgggctgct ggttggcaaa atgcggtttc  77820
tcaagtcgga ccaaactttg tctggtatga tctaaaaacc aaatcaataa tctttaattg  77880
tttgttaagt tttatagact ccaactcaaa tgactatgag tggattggta tatattgctt  77940
tagttccctt ctaacttaag atataagatt ctaacttaat gtgttgtttt tgttttttga  78000
atcaataggt gggtagtggc acaaagtgtg ttttaccatt tgtacaatca ggtctcatac  78060
atgtcattag accagatttc gccgttaact ttcagtatcg gtaatacgat gaagcggatt  78120
tccgttattg ttgcatcgat catcattttc cataccccga ttcaaccggt taatgccctc  78180
ggtgctgcca ttgcgatttt tggaactttc ctctactcac aggtaaacaa acaaacttat  78240
```

-continued

```
tcttgtttac ctacctctag tacttggttc tttagtgaac aatttctagt tctaatataa  78300
ttcattgacg ttcttcctat gttctttgca atcattgagc aggcgaagca gtgaggatgg  78360
tttaggaggc agtttttgg gtttgttttg caaaagaaaa tgaaaactaa caaaagagta  78420
gccggggagg agagaacatt ccggtgagat caacatcgga aaatgctttt ccccggtcca  78480
tggatatgaa gaaactggag cttgaagttg atagagtgtt tgcttttact ttttttttca  78540
ttgtctcata atagattctg cacaagacag gctaattcta tattatctat gttttattta  78600
gatgatcgta ataataaaga tatcagtgtc atttcttgat cagaccatct actgaattat  78660
ttttgaggta tctatcagtt gatgcatgtg taatagtttc agaaatcact gaattataaa  78720
tatattgagg tgtgtcgcta ctggcctata tacatatcat attaggccat taggttaaaa  78780
attctactca atccattcct tataattggt ctagttagct atattggtct ctcacacact  78840
ctcttattcc aagaagaaca ttaggaaact ccaatattgg gcctggtcca tgtactcttc  78900
taagttcgtc tatacttgga cactgtctcc attttgtggg ctagggatct acaatccaat  78960
gactgcaaaa tatttacggc atgcaaaact tcttatgaca agtgtgtttg acacacgtct  79020
ctaaaatttc aattatgtgg atgtgcttat ttgtatcaat gcatttcatg cttgcttggc  79080
ttcgtatgga aaaagtatga gccatcataa aaatttgtta aaaaagattc gagtcattta  79140
cattgtttta ggagcctttt ttgatcggtt agggtgctag agaacccatt acatactagt  79200
catctggggg tattagtatt ttgtaagctg ttttaaacga ttccgaattt tgtttctata  79260
ttttgtggtc agatctgatg gcctgaaaat catccccaat aatcaaatct taatgcgcgt  79320
ttaatatttt actaaattat gatcatatta ttttttgcga tctagtcagt agtcactgta  79380
gtgaagttgg tgagacgaca cccacccaaa aggagtacgt aaagcaattc cggcttccaa  79440
ttattttatg ctaatcttgt cggcagatga gatggataca tttatacata tcatatataa  79500
taggttggga aattgttagt ttcgttgata aaataattaa ggttttgact tttgactgat  79560
tctggatttg atttcaggaa atgtaaaatt ttccagattc tgtatgtact ttttgataag  79620
aaatttcaag ttgctgcatg tcaaaaattt caactaatct cttttgtagt gtataaattt  79680
atttactgtc caatagacaa ttgccaccga tcctaaggag caacgtacaa taccaaaagt  79740
ttgcatgcat aataaaagtt catttaaaca taacgtataa taattttcag agtgattatt  79800
gtaactttca aattttcaca taaattttag agtattaaat caaatagcct ttgtaatttt  79860
tgagtaaact aaatgacggt cttttttac tcaaaatcaa ttacaaccct ttaaaatatc  79920
ctaaaagctt tgttttaaaa aagaagataa attatcacaa caagaatata atctaactca  79980
ctacaaaatg taaggccaaa gaagagatac gttcactgat tggacgtgat ggagagagct  80040
cacatctcgt ctggccttat catcatcgta atctattgaa gatatatata tggtaagaca  80100
aattaacttt actcacggat tctattcttt ttacccattc tcggttttgt aacgaacgac  80160
gaaccaccaa ctagacaacg aaacgtccca cttgtttcca ttagttaaat ttgggtaaca  80220
ccaaaatcgc attaacttaa taaaacactg ttccaatatc aaccactgcc atattttctc  80280
ccttattttt ttttgacatc aaaactgatt ttggagaggc tttgaaaccc cgactataaa  80340
tttgatttag gtgttattct gatttatgag tgaatagtta cacagtcgga gtttgaactg  80400
aaagttatag gattacattt ttggtaaaaa attgttgagt cgtatttttg gtagaaaaca  80460
gtaaaattat gttttttgac agaaaattgg aggatagtaa ttttggagga aatcatatat  80520
atgaaaattg gccaactctc tccatatgat tgacacataa tcactttagc atttgacatg  80580
tgtctattaa ataattaatg taagctcttc aacttctaat ttataggtta aagatatatt  80640
```

-continued

```
tattatttaa ttttacatct tattttattt tacgtattta attatactat tactatattt  80700
attttaatat tacatgattt ttcaataaaa ccattttaat agttttctta tactctgaag  80760
tttttttttt ttttttgtaa tccaaactca aagtatgagt gtataatagt cgtggattac  80820
ttaataattt gagtaagtta ttctcttaaa tgaatattta tattttctta aattgatatt  80880
tatataataa atcactaagg gtgaaaaatg cgtaaggagt tccatcatca aattcttagg  80940
tttctagaat ccaacactaa cctctgttaa attggtttaa aacaaacgtt gtttatgaat  81000
tatgtatatg atgcattgtt gagaacgttg ctagaaaaaa atatttttaa tactaaaagt  81060
aattgtttat tgcatgattg aatgattaga taaatataaa ttatatttaa attaaacact  81120
acaaaagaat ccgaaaaaac cgcgacgtag cgcggataat tacctagtag tgttaaaaca  81180
aaattggagg aaattttgga gatcacattt ttaacataaa attagtagaa atatatattt  81240
taattattaa ataaaaaatt aaagtaagcg ctaaatgtca ttaagaaaat tttgtgaaag  81300
gcggaaacaa aaattttaaa agaaaaagaa aggactaatc acatcatcgc cattcaatga  81360
tatagtttga caatgatatg attcattaac taccattcaa taaatcggtt tatgaaatct  81420
aacggttaaa tattagttgg taaagcatga ttaattaaga taatcactca acaatcaatt  81480
caggaccaac gtcacctagc taccaccacg aaggaaaatg ctaatacaag aaccaaatcg  81540
tcttattaac cagttatctt tttctcatgg accacattta aatcgtcacg gcaattaagc  81600
tagattttaa gaaagaataa atgggatact caactaattg ccacaaattt tattactttt  81660
aaaactcggc tgctcggccc aaacttatcc ggtacggatg gatagaccta tcttttatcg  81720
tgtaaagaaa ctcttgggct ccactcttga cgttgctcat tttatctact tttgttggtt  81780
tcttagtgac ctttgacgtt tatttacata gagttgacag atttgaattg acgttttctc  81840
aataatgcag accaaaattt tcacgtttct tacatgtaca tatatatagt aaaacaaatc  81900
tctgaagaca cacaagagaa tcaagaacaa tgaaaaattt aaccagtttc gtaattgtta  81960
tcttactaca aagcttattg tttcatgtat atggtcgtca tcaaagttct tcgaagaaca  82020
ttttagtaga ttcatctcca tttccttctg atttcctctt tggtacagct tcttccgctt  82080
accaggtact tattttgcgt cccactgata atttaatatc agatttattt agtgtatcgt  82140
cattacgaaa tgtttatttt atatataaaa aaattgtgaa tagtatgaag gtgcgttctt  82200
gactgatgga aaaagtttga acaattggga tgtctttacg cataaaaatc ctggtatgta  82260
ttttattttg gtttccattt ggtttatttt ctatttgaaa tagtttaaga ttagtttaag  82320
atttttattt ttttttaatt cacttattct attgacaagt atatatattg gaactgcagg  82380
gaaaatactt gacaagaaca atgcagatag agctgtggac caatataatc gatttttggt  82440
tattttctta tgataattat ttctttctat ttttgttctt gtcaacttct tttatcatat  82500
tatattctca tattatttga tgttgttatt tattttatat tatcttctat gcttaggagg  82560
acatccaatt aatgtctttt cttggagtga acagttatag gttttcaatt tcttggtgta  82620
gaatcttacc tagtaagtcc ttctttagtt aaatcagcag tattattaat actacattgc  82680
attgcatggt aaaaaaaaga aaatattcga ttgcatctca tatactaacc agagttgata  82740
aattaaaata ctgaaactca atcgacgaat agttatttag atttagctta ttatttgtga  82800
gacaggagga agatttggag agattaatta tttggggata aagtattaca acatatttat  82860
cgatgctctc attagtagag gtactttttt gtctttccgg tttataataa tttaagtttt  82920
tttttaaaat attgtaatct cataaagtta atgaaaatac ataattgtat caactaatca  82980
```

-continued

```
ctatccaggg attaaaccat ttgtgacgtt gaaccatgtc gactatcctc aagaactcga  83040
ggaccggttt caaagttggt taaaccccga gatgcagtga gtggttaaat agaattagta  83100
tttttatgaa cccctaatta cttagaatgg caatgaactt ataaacactt tttttttttt  83160
ttgttatttt tgataggaag gaatttggtt atttagccga tatatgtttc aagcattttg  83220
gaaaccgagt taaatactgg accacgctta acgaaccaaa tcaacaatta atcttaggct  83280
atctaacagg taaatttcca ccctctcgtt gctcctcgcc atacgggaac tgtagccagg  83340
ggaattcaga aaccgaacct ttcatagccg cacataacat gatccttgca cacgcaaaag  83400
cggttaacat atacaagacc aaatatcagg taataaaact catacatcaa attaagacct  83460
ggtttcgtga gttatcgata taaatataat gtttttgcag aaagaacaaa agggaagcat  83520
tggcattgtg gtacaaacat catggtttga acccattagt gattccaatg cggataaaga  83580
agctgctgag agagctcaat cattttactc taattggtat gttatattac tatatatgtt  83640
gagatcatat ttgtagatat gaagtatagt acttcaccca catatggaat atatattgtt  83700
ttatctattt gtattctaac atgtactagg attctagatc ccgttatata tgggaaatat  83760
ccaaaagaaa tggtagatat tcttggacca gccttgccac aattttcgag caatgaagtg  83820
aagaacttag agaagtcgag ggcagatttc gttggtatta atcactatac aagttacttc  83880
attcaagatt gtttgacctc tgcttgtaat actggacatg gagcttttaa ggccgaagga  83940
tatgctctca agttagaccg gaaaggcaat gttactatag gagaacttgt aagtacattc  84000
attcagtttc ttatattcaa tattttacga ctatattcaa atgttttagt aaattttatt  84060
gtttattgac catgtttcta ttgttagacc gatgtaaatt ggcagcatat tgatcccaca  84120
ggattccaca agatgctgaa ttatttaaaa gataggtacc caaacatgcc aatgttcata  84180
actgaaaacg gtacaagacc tcaaatttga tcaatgatcg agtcatcaac catatttgaa  84240
attatcatga aaaattatta ttaatggctt gaaggttttg gagacttgca aaaacctgaa  84300
acaacggata aagaacttct aaatgataca aaaaggatcc aatacatgag tggatactta  84360
gaagctttac aagcagcaat gaggtaaata atttatgtaa atttatgcag aaatccaatt  84420
cttaaaatca tgcattcaaa tagtctttaa accaattttt atctaatgaa aatttactaa  84480
ttctatataa gttgtgaatt gttttggtag ggatggagca aatgtgaagg gttattttgt  84540
gtggtcacta ttagacaatt ttgagtggtt gttcggatac aaggttcggt ttggtctatt  84600
ccatgtggat ctaacaactc ttaaaaggtc accgaaacaa tcagcttcat ggtacaaaaa  84660
ttatatcgaa gaacacgtga atcgaagaga tatcgtagat aattattaaa cacatttatt  84720
tttaattcgt attcactgcc aaagaaagtc aaaaattaca aaagcattta aaattgatac  84780
ttatcattgt tgttgattgt tgaatgatta aatttgtctt ttcctcctaa aagtgaatgt  84840
ttaatgtgtt acatgattat ttgtctaatc ttgcacaata attctattag cttaagatgt  84900
tgaagaacac gtgagaagag aatttaggtt ttttttttgg tcaaaggaag aatagtaatt  84960
cgtattccta agtaaagaaa gtcaaactag gaaagaattt atgtaacttc gttaaatgaa  85020
tgattaatgg ttttctttac cttaaagtga atgtttaatc agtgttacgc gccatacgga  85080
agtaattgtc taatcttgca caatcattca acacgttttc aaagaaaact ttttttgttc  85140
tctatgatga taatagtgtt aaatcaaaag tagtacaaaa gtaaactaaa cttattttag  85200
attaaaaatc accgaaaaaa ctaaacacgc gttagaaagc atttgacatc acctccaaat  85260
ttaatttcac gcaagcaagc gtttctaaga tatggattct aaacgctata tcactgtttt  85320
ttgtaagata aattcttctt aattttttca ataaaaaaat ttaaaattaa aaataaaatc  85380
```

```
ataaactaac tgataatgac caaaggaacc ataaacacct agaaaattat atttctgtgt  85440

tttctatctg cggtttaacg tcagtaacat ctaggaaagt tattttacga aagtgaactt  85500

ggtttttgtt tgattgaaat atgtttcaga ctttcagaag aaaaaaaaag atacttattt  85560

aaaatatgtt aagattttag ttcacttcaa attatgtaaa catgctgatt tttttttttt  85620

tttttttttt tttttttgca atcatccttc aatattgtct gcgaaacagt caagtttcaa  85680

gtacgattca caacattttt caaaaaattt attcattcat ttcactccca aaacttttta  85740

atttacaaaa ctacccgtac acgtatattg gttgaataga aatttttga atatttatta  85800

tattttgagt tacatataga ctatgattta atcaaataca caatgagtcg ttaaacaatc  85860

taaagaaaaa gacacacgaa caaactgata acatagataa catataagca aaataggtcg  85920

gaatcaacaa ttacatatat aaatggttgc gtggttaatg atttcatttg gtattttcac  85980

gacaagatcg tttctaggta catagaagtc aacttcgttg ccatataaac tgtataacac  86040

ttagtcatac aatctggttt atttatcaag ttcaaaaatt taatttaatc aaaatatttg  86100

tttgcgaaat tttcaatcga gaattaaaaa attaaaaaaa gttgcgtggt tgagttaatc  86160

gtttggtctc catcgctgat atcttcaatt tctctgaatt aatcttcaca tagctgtata  86220

aagacctaga aaagaaaaca gatatactag taaccaaact tagaatcaag aaagaaaaaa  86280

acagctatag agttgaataa gaagaagaag aagatgacat tttttaaacc aattagaatc  86340

atcaattttt tattcctatt tttcatattt cttgtggtat acgcaaccgt gttctgcaaa  86400

ttttgttcag acactggaaa cttcaaaaga agtaagttga ggtacgaaac ttccgatgat  86460

agttatgaag ctaggagtag ccatgtcacc aaccatatcc tcagccgccg caacaccaac  86520

cccttcacca aatgggtcaa cgttctccgc cgcactagca cttcttgtac gaaaccgtaa  86580

gtttcttctt tttacttgaa tttatataaa cgtatgaatt agtcgtgtgt ttgccaaaaa  86640

agaaaagaaa aagaattagc cgtgtcatag aattgtaaat tatggcgacg gatgatataa  86700

tatttaacac gtgagtagta ttgaagacat ttattaaaga atatgtttgt tgttaaaaag  86760

taagatatca gtaattaatt aatgtttcac actgtcaata acataaaata tgtgattttg  86820

aattcgaagc atagtaacaa caatattaaa aactattacg ccataaacta tagccatagt  86880

atttttattt atacttattt atactttcta acttccaaat ttttatattt tatataataa  86940

tcatcaacgc tatatatcta gaaagtaaaa ccagtaaaat ctaacgtacg aaattagatg  87000

gagttgttag gcacatttca tatattaaaa ttttaatgat tttcttttaa actttatgat  87060

atttaaagca tgtacatatt cttttttggg ttataatata tgtaaaaatt tggtatgctt  87120

tgtctatagt tgtaaccaaa ttgatgcata gtttatgata tttaatagtt tcgaatatat  87180

tcagtaggta gaaattgggg aatttttaaa aagttgacaa gactgcccca aaatcgcaat  87240

gatgcattta aaatattctg caattttttc atataaatat agacacgtat agataagagt  87300

gcacacaaaa ccacagacga catacacgag aaagaaaaaa aaccaaaatg aaaacttttg  87360

ccaactttgc aattctgttt ttattacaaa gctt                              87394
```

<210> SEQ ID NO 7
<211> LENGTH: 26
<212> TYPE: DNA
<213> ORGANISM: Artificial
<220> FEATURE:
<223> OTHER INFORMATION: primer

<400> SEQUENCE: 7

```
atcggcaact ccatttccaa tttctc                                          26


<210> SEQ ID NO 8
<211> LENGTH: 27
<212> TYPE: DNA
<213> ORGANISM: Artificial
<220> FEATURE:
<223> OTHER INFORMATION: primer

<400> SEQUENCE: 8

tagcatccct agcattagaa cattgag                                         27


<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9

gtttgataac tcgtctcttg                                                 20


<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10

ggtgtgtgta agagtctggt cc                                              22


<210> SEQ ID NO 11
<211> LENGTH: 28
<212> TYPE: DNA
<213> ORGANISM: Artificial
<220> FEATURE:
<223> OTHER INFORMATION: Primer

<400> SEQUENCE: 11

ccatggttgt acttttgaaa ttacagag                                        28


<210> SEQ ID NO 12
<211> LENGTH: 24
<212> TYPE: DNA
<213> ORGANISM: Artificial
<220> FEATURE:
<223> OTHER INFORMATION: Primer

<400> SEQUENCE: 12

ccatggttat tcaagtgacc acag                                            24


<210> SEQ ID NO 13
<211> LENGTH: 17
<212> TYPE: DNA
<213> ORGANISM: Artificial
<220> FEATURE:
<223> OTHER INFORMATION: Primer

<400> SEQUENCE: 13

cgtgttgagg tgagagg                                                    17


<210> SEQ ID NO 14
<211> LENGTH: 39
<212> TYPE: DNA
<213> ORGANISM: Artificial
```

-continued

```
<220> FEATURE:
<223> OTHER INFORMATION: Primer

<400> SEQUENCE: 14

aggcggcgcc taaaccatgg tccgtcctgt agaaacccc                         39


<210> SEQ ID NO 15
<211> LENGTH: 39
<212> TYPE: DNA
<213> ORGANISM: Artificial
<220> FEATURE:
<223> OTHER INFORMATION: Primer

<400> SEQUENCE: 15

agtcgactca ttgtttgcct ccctgctgcg gtttttcac                         39


<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16

acttcacttg agcggaagcc atag                                         24


<210> SEQ ID NO 17
<211> LENGTH: 26
<212> TYPE: DNA
<213> ORGANISM: Artificial
<220> FEATURE:
<223> OTHER INFORMATION: Primer

<400> SEQUENCE: 17

tttaaaacaa tggcgcaagt tagcag                                       26
```